(12) United States Patent
Bandman et al.

(10) Patent No.: US 7,112,426 B2
(45) Date of Patent: Sep. 26, 2006

(54) HUMAN CAMP-DEPENDENT PROTEIN KINASE BETA-CATALYTIC SUBUNIT

(75) Inventors: Olga Bandman, Mountain View, CA (US); Danniel B Nguyen, San Jose, CA (US); Narinder K Chawla, Union City, CA (US); April J A Hafalia, Santa Clara, CA (US); Monique G Yao, Carmel, IN (US); Ameena R Gandhi, San Francisco, CA (US); Rajagopal Gururajan, San Jose, CA (US); Li Ding, Creve Coeur, MO (US); Chandra S Arvizu, San Jose, CA (US); Henry Yue, Sunnyvale, CA (US); Mariah R Baughn, San Leandro, CA (US); Catherine M Tribouley, San Francisco, CA (US); Michael B Thornton, Oakland, CA (US); Vicki S Elliott, San Jose, CA (US); Yan Lu, Palo Alto, CA (US); Craig H Ison, San Jose, CA (US); Janice K Au-Young, Brisbane, CA (US); Y Tom Tang, San Jose, CA (US); Yalda Azimzai, Oakland, CA (US); John D Burrill, Redwood City, CA (US); Gregory A Marcus, San Carlos, CA (US); Kurt A Zingler, San Francisco, CA (US); Dyung Aina M Lu, San Jose, CA (US); Preeti G Lai, Santa Clara, CA (US); Jayalaxmi Ramkumar, Fremont, CA (US); Bridget A Warren, Encinitas, CA (US); Liam Kearney, San Francisco, CA (US); Jennifer L Policky, San Jose, CA (US); Kavitha Thangavelu, Sunnyvale, CA (US); Neil Burford, Durham, CT (US)

(73) Assignee: Incyte Corporation, Wilmington, DE (US)

( * ) Notice: Subject to any disclaimer, the term of this patent is extended or adjusted under 35 U.S.C. 154(b) by 260 days.

(21) Appl. No.: 10/288,798

(22) Filed: Nov. 1, 2002

(65) Prior Publication Data
US 2003/0207299 A1    Nov. 6, 2003

Related U.S. Application Data

(63) Continuation of application No. PCT/US01/27219, filed on Aug. 31, 2001.

(60) Provisional application No. 60/240,542, filed on Oct. 13, 2000, provisional application No. 60/238,389, filed on Oct. 6, 2000, provisional application No. 60/236,499, filed on Sep. 29, 2000, provisional application No. 60/234,902, filed on Sep. 22, 2000, provisional application No. 60/232,654, filed on Sep. 14, 2000, provisional application No. 60/231,357, filed on Sep. 8, 2000, provisional application No. 60/229,873, filed on Aug. 31, 2000.

(51) Int. Cl.
C12N 15/54    (2006.01)
C12N 9/12    (2006.01)

(52) U.S. Cl. .................. 435/194; 435/325; 435/320.1; 435/252.3; 536/23.2

(58) Field of Classification Search ............... 435/194, 435/325, 320.1, 252.3; 536/23.2
See application file for complete search history.

(56) References Cited

OTHER PUBLICATIONS

S. Wiemann et al. "Isoform C beta 2, an Unusual Form of the Bovine Catalytic Subunit of cAMP-dependent Protein Kinase", J. Biol. Chem. 266(8):5140-5146. (Mar. 1991).*

M.D. Uhler et al. "Expression of cDNAs for Two Isoforms of the Catalytic Subunit of cAMP-dependent Protein Kinase", J. Biol. Chem. 262(31): 15202-15207. (Nov. 1987).*

* cited by examiner

Primary Examiner—Rebecca Prouty
(74) Attorney, Agent, or Firm—Foley & Lardner LLP

(57) ABSTRACT

The invention provides human human kinases (PKIN) and polynucleotides which identify and encode PKIN. The invention also provides expression vectors, host cells, antibodies, agonists, and antagonists. The invention also provides methods for diagnosing, treating, or preventing disorders associated with aberrant expression of PKIN.

17 Claims, No Drawings

HUMAN CAMP-DEPENDENT PROTEIN KINASE BETA-CATALYTIC SUBUNIT

This application is a continuation application of PCT application PCT/US01/27219, filed Aug. 31, 2001, and published in English as WO 02/18557 on Mar. 7, 2002, which claims the benefit of provisional applications U.S. Ser. No. 60/229,873, filed Aug. 31, 2000, U.S. Ser. No. 60/231,357, filed Sep. 8, 2000, U.S. Ser. No. 60/232,654, filed Sep. 14, 2000, U.S. Ser. No. 60/234,902, filed Sep. 22, 2000, U.S. Ser. No. 60/236,499, filed Sep. 29, 2000, U.S. Ser. No. 60/238,389, filed Oct. 6, 2000, and U.S. Ser. No. 60/240,542, filed Oct. 13, 2000, all of which applications and patents are hereby incorporated herein by reference.

TECHNICAL FIELD

This invention relates to nucleic acid and amino acid sequences of human kinases and to the use of these sequences in the diagnosis, treatment, and prevention of cancer, immune disorders, disorders affecting growth and development, cardiovascular diseases, and lipid disorders, and in the assessment of the effects of exogenous compounds on the expression of nucleic acid and amino acid sequences of human kinases.

BACKGROUND OF THE INVENTION

Kinases comprise the largest known enzyme superfamily and vary widely in their target molecules. Kinases catalyze the transfer of high energy phosphate groups from a phosphate donor to a phosphate acceptor. Nucleotides usually serve as the phosphate donor in these reactions, with most kinases utilizing adenosine triphosphate (ATP). The phosphate acceptor can be any of a variety of molecules, including nucleosides, nucleotides, lipids, carbohydrates, and proteins. Proteins are phosphorylated on hydroxyamino acids. Addition of a phosphate group alters the local charge on the acceptor molecule, causing internal conformational changes and potentially influencing intermolecular contacts. Reversible protein phosphorylation is the primary method for regulating protein activity in eukaryotic cells. In general, proteins are activated by phosphorylation in response to extracellular signals such as hormones, neurotransmitters, and growth and differentiation factors. The activated proteins initiate the cell's intracellular response by way of intracellular signaling pathways and second messenger molecules such as cyclic nucleotides, calcium-calmodulin, inositol, and various mitogens, that regulate protein phosphorylation.

Kinases are involved in all aspects of a cell's function, from basic metabolic processes, such as glycolysis, to cell-cycle regulation, differentiation, and communication with the extracellular environment through signal transduction cascades. Inappropriate phosphorylation of proteins in cells has been linked to changes in cell cycle progression and cell differentiation. Changes in the cell cycle have been linked to induction of apoptosis or cancer. Changes in cell differentiation have been linked to diseases and disorders of the reproductive system, immune system, and skeletal muscle.

There are two classes of protein kinases. One class, protein tyrosine kinases (PTKs), phosphorylates tyrosine residues, and the other class, protein serine/threonine kinases (STKs), phosphorylates serine and threonine residues. Some PTKs and STKs possess structural characteristics of both families and have dual specificity for both tyrosine and serine/threonine residues. Almost all kinases contain a conserved 250–300 amino acid catalytic domain containing specific residues and sequence motifs characteristic of the kinase family. The protein kinase catalytic domain can be further divided into 11 subdomains. N-terminal subdomains I–IV fold into a two-lobed structure which binds and orients the ATP donor molecule, and subdomain V spans the two lobes. C-terminal subdomains IV–XI bind the protein substrate and transfer the gamma phosphate from ATP to the hydroxyl group of a tyrosine, serine, or threonine residue. Each of the 11 subdomains contains specific catalytic residues or amino acid motifs characteristic of that subdomain. For example, subdomain I contains an 8-amino acid glycine-rich ATP binding consensus motif, subdomain II contains a critical lysine residue required for maximal catalytic activity, and subdomains VI through IX comprise the highly conserved catalytic core. PTKs and STKs also contain distinct sequence motifs in subdomains VI and VIII which may confer hydroxyamino acid specificity.

In addition, kinases may also be classified by additional amino acid sequences, generally between 5 and 100 residues, which either flank or occur within the kinase domain. These additional amino acid sequences regulate kinase activity and determine substrate specificity. (Reviewed in Hardie, G. and S. Hanks (1995) *The Protein Kinase Facts Book*, Vol 1, pp. 17–20 Academic Press, San Diego Calif.). In particular, two protein kinase signature sequences have been identified in the kinase domain, the first containing an active site lysine residue involved in ATP binding, and the second containing an aspartate residue important for catalytic activity. If a protein analyzed includes the two protein kinase signatures, the probability of that protein being a protein kinase is close to 100% (PROSITE: PDOC00100, November 1995).

Protein Tyrosine Kinases

Protein tyrosine kinases (PTKs) may be classified as either transmembrane, receptor PTKs or nontransmembrane, nonreceptor PTK proteins. Transmembrane tyrosine kinases function as receptors for most growth factors. Growth factors bind to the receptor tyrosine kinase (RTK), which causes the receptor to phosphorylate itself (autophosphorylation) and specific intracellular second messenger proteins. Growth factors (GF) that associate with receptor PTKs include epidermal GF, platelet-derived GF, fibroblast GF, hepatocyte GF, insulin and insulin-like GFs, nerve GF, vascular endothe lial GF, and macrophage colony stimulating factor.

Nontransmembrane, nonreceptor PTKs lack transmembrane regions and, instead, form signaling complexes with the cytosolic domains of plasma membrane receptors. Receptors that function through non-receptor PTKs include those for cytokines and hormones (growth hormone and prolactin), and antigen-specific receptors on T and B lymphocytes.

Many PTKs were first identified as oncogene products in cancer cells in which PTK activation was no longer subject to normal cellular controls. In fact, about one third of the known oncogenes encode PTKs. Furthermore, cellular transformation (oncogenesis) is often accompanied by increased tyrosine phosphorylation activity (Charbonneau, H. and N. K. Tonks (1992) Annu. Rev. Cell Biol. 8:463–493). Regulation of PTK activity may therefore be an important strategy in controlling some types of cancer.

Substrates for tyrosine kinases can be identified using anti-phosphotyrosine antibodies to screen tyrosine-phosphorylated cDNA expression libraries. Fish, so named for tyrosine-phosphorylated in Src-transfromed fibroblast, is a tyrosine kinase substrate which has been identified by such a technique. Fish has five SH3 domains and a phox homology (PX) domain. Fish is suggested to be involved in signalling by tyrosine kinases and have a role in the actin cytoskeleton (Lock, P. et al (1998) EMBO J. 17:4346–4357).

SHP-2, an SH2-domain-containing phosphotyrosine phosphatase, is a positive signal transducer for several receptor tyrosine kinases (RTKs) and cytokine receptors. Phosphotyrosine phosphatases are critical positive and negative regulators in the intraellular signalling pathways that result in growth-factor-specific cell responses such as mitosis, migration, differentiation, transformation, survival or death. Signal-regulatory proteins (SIRPs) comprise a new gene family of at least 15 members, consisting of two subtypes distinguished by the presence or absence of a cytoplasmic SHP-2-binding domain. The SIRP-alpha subfamily members have a cytoplasmic SHP2-binding domain and includes SIRP-alpha-1, a transmembrane protein, a substrate of activated RTKs and which binds to SH2 domains. SIRPs have a high degree of homology with immune antigen recognition molecules. The SIRP-beta subfamily lacks the cytoplasmic tail. The SIRP-beta-1 gene encodes a polypeptide of 398 amino acids. SIRP family members are generally involved in regulation of signals which define differnet physiological and pathological process (Kharitonenkov, A. et al (1997) Nature 386:181–186). Two possible areas of regulation include determination of brain diversity and genetic individuality (Sano, S et al (1999) Biochem. J. 344 Pt 3:667–675) and recognition of self which fails in diseases such as hemolytic anemia (Oldenborg, P. -A et al (2000) Science 288:2051–2054).

Protein Serine/Threonine Kinases

Protein serine/threonine kinases (STKs) are nontransmembrane proteins. A subclass of STKs are known as ERKs (extracellular signal regulated kinases) or MAPs (mitogen-activated protein kinases) and are activated after cell stimulation by a variety of hormones and growth factors. Cell stimulation induces a signaling cascade leading to phosphorylation of MEK (MAP/ERK kinase) which, in turn, activates ERK via serine and threonine phosphorylation. A varied number of proteins represent the downstream effectors for the active ERK and implicate it in the control of cell proliferation and differentiation, as well as regulation of the cytoskeleton. Activation of ERK is normally transient, and cells possess dual specificity phosphatases that are responsible for its down-regulation. Also, numerous studies have shown that elevated ERK activity is associated with some cancers. Other STKs include the second messenger dependent protein kinases such as the cyclic-AMP dependent protein kinases (PKA), calcium-calmodulin (CaM) dependent protein kinases, and the mitogen-activated protein kinases (MAP); the cyclin-dependent protein kinases; checkpoint and cell cycle kinases; Numb-associated kinase (Nak); human Fused (hFu); proliferation-related kinases; 5'-AMP-activated protein kinases; and kinases involved in apoptosis.

The second messenger dependent protein kinases primarily mediate the effects of second messengers such as cyclic AMP (cAMP), cyclic GMP, inositol triphosphate, phosphatidylinositol, 3,4,5-triphosphate, cyclic ADP ribose, arachidonic acid, diacylglycerol and calcium-calmodulin. The PKAs are involved in mediating hormone-induced cellular responses and are activated by cAMP produced within the cell in response to hormone stimulation. cAMP is an intracellular mediator of hormone action in all animal cells that have been studied. Hormone-induced cellular responses include thyroid hormone secretion, cortisol secretion, progesterone secretion, glycogen breakdown, bone resorption, and regulation of heart rate and force of heart muscle contraction. PKA is found in all animal cells and is thought to account for the effects of cAMP in most of these cells. Altered PKA expression is implicated in a variety of disorders and diseases including cancer, thyroid disorders, diabetes, atherosclerosis, and cardiovascular disease (Isselbacher, K. J. et al. (1994) Harrison's Principles of Internal Medicine, McGraw-Hill, New York N.Y., pp. 416–431, 1887).

The casein kinase I (CKI) gene family is another subfamily of serine/threonine protein kinases. This continuously expanding group of kinases have been implicated in the regulation of numerous cytoplasmic and nuclear processes, including cell metabolism, and DNA replication and repair. CKI enzymes are present in the membranes, nucleus, cytoplasm and cytoskeleton of eukaryotic cells, and on the mitotic spindles of mammalian cells (Fish, K. J. et al. (1995) J. Biol. Chem. 270:14875–14883).

The CKI family members all have a short amino-terminal domain of 9–76 amino acids, a highly conserved kinase domain of 284 amino acids, and a variable carboxyl-terminal domain that ranges from 24 to over 200 amino acids in length (Cegielska, A. et al. (1998) J. Biol. Chem. 273: 1357–1364). The CKI family is comprised of highly related proteins, as seen by the identification of isoforms of casein kinase I from a variety of sources. There are at least five mammalian isoforms, $\alpha$, $\beta$, $\gamma$, $\delta$, and $\epsilon$. Fish et al., identified CKI-epsilon from a human placenta cDNA library. It is a basic protein of 416 amino acids and is closest to CKI-delta. Through recombinant expression, it was determined to phosphorylate known CKI substrates and was inhibited by the CKI-specific inhibitor CKI-7. The human gene for CKI-epsilon was able to rescue yeast with a slow-growth phenotype caused by deletion of the yeast CKI locus, HRR250 (Fish et al., supra).

The mammalian circadian mutation tau was found to be a semidominant autosomal allele of CKI-epsilon that markedly shortens period length of circadian rhythms in Syrian hamsters. The tau locus is encoded by casein kinase I-epsilon, which is also a homolog of the Drosophila circadian gene double-time. Studies of both the wildtype and tau mutant CKI-epsilon enzyme indicated that the mutant enzyme has a noticeable reduction in the maximum velocity and autophosphorylation state. Further, in vitro, CKI-epsilon is able to interact with mammalian PERIOD proteins, while the mutant enzyme is deficient in its ability to phosphorylate PERIOD. Lowrey et al., have proposed that CKI-epsilon plays a major role in delaying the negative feedback signal within the transcription-translation-based autoregulatory loop that composes the core of the circadian mechanism. Therefore the CKI-epsilon enzyme is an ideal target for pharmaceutical compounds influencing circadian rhythms, jet-lag and sleep, in addition to other physiologic and metabolic processes under circadian regulation (Lowrey, P. L. et al. (2000) Science 288:483–491).

Homeodomain-interacting protein kinases (HIPKs) are serine/threonine kinases and novel members of the DYRK kinase subfamily (Hofmann, T. G. et al. (2000) Biochimie 82:1123–1127). HIPKs contain a conserved protein kinase domain separated from a domain that interacts with homeoproteins. HIPKs are nuclear kinases, and HIPK2 is highly expressed in neuronal tissue (Kim, Y. H. et al. (1998) J. Biol. Chem. 273:25875–25879; Wang, Y. et al. (2001) Biochim. Biophys. Acta 1518:168–172). HIPKs act as corepressors for homeodomian transcription factors. This corepressor activity is seen in posttranslational modifications such as ubiquitination and phosphorylation, each of which are important in the regulation of cellular protein function (Kim, Y. H. et al. (1999) Proc. Natl. Acad. Sci. USA 96:12350–12355).

The UNC-51 serine/threonine kinase of *Caenorhabditis elegans* is required for axon formation. Its murine homolog is expressed in granule cells of the cerebellar cortex (Tomoda, T. et al. (1999) Neuron 24:833–846). The human homolog of UNC-51, ULK1 (UNC-51 (*C. elegans*)-like kinase 1), is highly conserved among vertebrates. It is composed of 1050 amino acids, has a calculated MW of 112.6 kDa and a pI of 8.80. ULK1 is ubiquitously expressed in adult tissues while UNC-51 has been specifically located in the nervous system of *C. elegans*. ULK1 has been mapped to human chromosome 12q24.3 (Kuroyanagi, H. et al. (1998) Genomics 51:76–85).

Calcium-Calmodulin Dependent Protein Kinases

Calcium-calmodulin dependent (CaM) kinases are involved in regulation of smooth muscle contraction, glycogen breakdown (phosphorylase kinase), and neurotransmission (CaM kinase I and CaM kinase II). CaM dependent protein kinases are activated by calmodulin, an intracellular calcium receptor, in response to the concentration of free calcium in the cell. Many CaM kinases are also activated by phosphorylation. Some CaM kinases are also activated by autophosphorylation or by other regulatory kinases. CaM kinase I phosphorylates a variety of substrates including the neurotransmitter-related proteins synapsin I and II, the gene transcription regulator, CREB, and the cystic fibrosis conductance regulator protein, CFTR (Haribabu, B. et al. (1995) EMBO J. 14:3679–3686). CaM kinase II also phosphorylates synapsin at different sites and controls the synthesis of catecholamines in the brain through phosphorylation and activation of tyrosine hydroxylase. CaM kinase II controls the synthesis of catecholamines and seratonin, through phosphorylation/activation of tyrosine hydroxylase and tryptophan hydroxylase, respectively (Fujisawa, H. (1990) BioEssays 12:27–29). The mRNA encoding a calmodulin-binding protein kinase-like protein was found to be enriched in mammalian forebrain. This protein is associated with vesicles in both axons and dendrites and accumulates largely postnatally. The amino acid sequence of this protein is similar to CaM-dependent STKs, and the protein binds calmodulin in the presence of calcium (Godbout, M. et al. (1994) J. Neurosci. 14:1–13).

Mitogen-Activated Protein Kinases

The mitogen-activated protein kinases (MAP) which mediate signal transduction from the cell surface to the nucleus via phosphorylation cascades are another STK family that regulates intracellular signaling pathways. Several subgroups have been identified, and each manifests different substrate specificities and responds to distinct extracellular stimuli (Egan, S. E. and R. A. Weinberg (1993) Nature 365:781–2483). There are 3-kinase modules comprising the MAP kinase cascade: MAPK (MAP), MAPK kinase (MAP2K, MAPKK, or MKK), and MKK kinase (MAP3K, MAPKKK, OR MEKK) (Wang, X. S. et al (1998) Biochem. Biophys. Res. Commun. 253:33–37). The extracellular-regulated kinase (ERK) pathway is activated by growth factors and mitogens, for example, epidermnal growth factor (EGF), ultraviolet light, hyperosmolar medium, heat shock, endotoxic lipopolysaccharide (LPS). The closely related though distinct parallel pathways, the c-Jun N-terminal kinase (JNK), or stress-activated kinase (SAPK) pathway, and the p38 kinase pathway are activated by stress stimuli and proinflammatory cytokines such as tumor necrosis factor (TNF) and interleukin-1 (IL-1). Altered MAP kinase expression is implicated in a variety of disease conditions including cancer, inflammation, immune disorders, and disorders affecting growth and development. MAP kinase signaling pathways are present in mammalian cells as well as in yeast.

MAPKKK6 (MAP3K6) is one of numerous MAP3Ks identified. Isolated from skeletal muscle, MAP3K6 is 1,280 amino acids in length with 11 kinase subdomains and is detected in several tissues. The highest expression has been found in heart and skeletal muscle. MAP3K6 has 45% amino acid sequence identity with MAP3K5, while their catalytic domains share 82% identity. MAP3K6 interaction with MAP3K5 in vivo was confirmed by coimmunoprecipitation. Recombinant MAP3K6 has been shown to weakly activate the JNK but not the p38 kinase or ERK pathways (Wang, X. S. et al. supra)

Cyclin-Dependent Protein Kinases

The cyclin-dependent protein kinases (CDKs) are STKs that control the progression of cells through the cell cycle. The entry and exit of a cell from mitosis are regulated by the synthesis and destruction of a family of activating proteins called cyclins. Cyclins are small regulatory proteins that bind to and activate CDKs, which then phosphorylate and activate selected proteins involved in the mitotic process. CDKs are unique in that they require multiple inputs to become activated. In addition to cyclin binding, CDK activation requires the phosphorylation of a specific threonine residue and the dephosphorylation of a specific tyrosine residue on the CDK.

Another family of STKs associated with the cell cycle are the NIMA (never in mitosis)-related kinases (Neks). Both CDKs and Neks are involved in duplication, maturation, and separation of the microtubule organizing center, the centrosome, in animal cells (Fry, A. M. et al. (1998) EMBO J. 17:470–481).

Checkpoint and Cell Cycle Kinases

In the process of cell division, the order and timing of cell cycle transitions are under control of cell cycle checkpoints, which ensure that critical events such as DNA replication and chromosome segregation are carried out with precision. If DNA is damaged, e.g. by radiation, a checkpoint pathway is activated that arrests the cell cycle to provide time for repair. If the damage is extensive, apoptosis is induced. In the absence of such checkpoints, the damaged DNA is inherited by aberrant cells which may cause proliferative disorders such as cancer. Protein kinases play an important role in this process. For example, a specific kinase, checkpoint kinase 1 (Chk1), has been identified in yeast and mammals, and is activated by DNA damage in yeast. Activation of Chk1 leads to the arrest of the cell at the G2/M transition (Sanchez, Y. et al. (1997) Science 277:1497–1501). Specifically, Chk1 phosphorylates the cell division cycle phosphatase CDC25, inhibiting its normal function which is to dephosphorylate and activate the cyclin-dependent kinase Cdc2. Cdc2 activation controls the entry of cells into mitosis (Peng, C. -Y. et al. (1997) Science 277:1501–1505). Thus, activation of Chk1 prevents the damaged cell from entering mitosis. A similar deficiency in a checkpoint kinase, such as Chk1, may also contribute to cancer by failure to arrest cells with damaged DNA at other checkpoints such as G2/M.

Proliferation-Related Kinases

Proliferation-related kinase is a serum/cytokine inducible STK that is involved in regulation of the cell cycle and cell proliferation in human megakarocytic cells (Li, B. et al. (1996) J. Biol. Chem. 271:19402–19408). Proliferation-related kinase is related to the polo (derived from *Drosophila* polo gene) family of STKs implicated in cell division. Proliferation-related kinase is downregulated in lung tumor tissue and may be a proto-oncogene whose deregulated expression in normal tissue leads to oncogenic transformation.

5'-AMP-activated Protein Kinase

A ligand-activated STK protein kinase is 5'-AMP-activated protein kinase (AMPK) (Gao, G. et al. (1996) J. Biol Chem. 271:8675–8681). Mammalian AMPK is a regulator of fatty acid and sterol synthesis through phosphorylation of the enzymes acetyl-CoA carboxylase and hydroxymethyl-glutaryl-CoA reductase and mediates responses of these pathways to cellular stresses such as heat shock and depletion of glucose and ATP. AMPK is a heterotrimeric complex comprised of a catalytic alpha subunit and two non-catalytic beta and gamma subunits that are believed to regulate the activity of the alpha subunit. Subunits of AMPK have a much wider distribution in non-lipogenic tissues such as brain, heart, spleen, and lung than expected. This distribution suggests that its role may extend beyond regulation of lipid metabolism alone.

Kinases in Apoptosis

Apoptosis is a highly regulated signaling pathway leading to cell death that plays a crucial role in tissue development and homeostasis. Deregulation of this process is associated with the pathogenesis of a number of diseases including autoimmune disease, neurodegenerative disorders, and cancer. Various STKs play key roles in this process. ZIP kinase is an STK containing a C-terminal leucine zipper domain in addition to its N-terminal protein kinase domain. This C-terminal domain appears to mediate homodimerization and activation of the kinase as well as interactions with transcription factors such as activating transcription factor, ATF4, a member of the cyclic-AMP responsive element binding protein (ATF/CREB) family of transcriptional factors (Sanjo, H. et al. (1998) J. Biol. Chem. 273:29066–29071). DRAK1 and DRAK2 are STKs that share homology with the death-associated protein kinases (DAP kinases), known to function in interferon-γ induced apoptosis (Sanjo et al., supra). Like ZIP kinase, DAP kinases contain a C-terminal protein-protein interaction domain, in the form of ankyrin repeats, in addition to the N-terminal kinase domain. ZIP, DAP, and DRAK kinases induce morphological changes associated with apoptosis when transfected into NIH3T3 cells (Sanjo et al., supra). However, deletion of either the N-terminal kinase catalytic domain or the C-terminal domain of these proteins abolishes apoptosis activity, indicating that in addition to the kinase activity, activity in the C-terminal domain is also necessary for apoptosis, possibly as an interacting domain with a regulator or a specific substrate.

RICK is another STK recently identified as mediating a specific apoptotic pathway involving the death receptor, CD95 (Inohara, N. et al. (1998) J. Biol. Chem. 273:12296–12300). CD95 is a member of the tumor necrosis factor receptor superfamily and plays a critical role in the regulation and homeostasis of the immune system (Nagata, S. (1997) Cell 88:355–365). The CD95 receptor signaling pathway involves recruitment of various intracellular molecules to a receptor complex following ligand binding. This process includes recruitment of the cysteine protease caspase-8 which, in turn, activates a caspase cascade leading to cell death. RICK is composed of an N-terminal kinase catalytic domain and a C-terminal "caspase-recruitment" domain that interacts with caspase-like domains, indicating that RICK plays a role in the recruitment of caspase-8. This interpretation is supported by the fact that the expression of RICK in human 293T cells promotes activation of caspase-8 and potentiates the induction of apoptosis by various proteins involved in the CD95 apoptosis pathway (Inohara et al., supra).

Mitochondrial Protein Kinases

A novel class of eukaryotic kinases, related by sequence to prokaryotic histidine protein kinases, are the mitochondrial protein kinases (MPKs) which seem to have no sequence similarity with other eukaryotic protein kinases. These protein kinases are located exclusively in the mitochondrial matrix space and may have evolved from genes originally present in respiration-dependent bacteria which were endocytosed by primitive eukaryotic cells. MPKs are responsible for phosphorylation and inactivation of the branched-chain alpha-ketoacid dehydrogenase and pyruvate dehydrogenase complexes (Harris, R. A. et al. (1995) Adv. Enzyme Regul. 34:147–162). Five MPKs have been identified. Four members correspond to pyruvate dehydrogenase kinase isozymes, regulating the activity of the pyruvate dehydrogenase complex, which is an important regulatory enzyme at the interface between glycolysis and the citric acid cycle. The fifth member corresponds to a branched-chain alpha-ketoacid dehydrogenase kinase, important in the regulation of the pathway for the disposal of branched-chain amino acids. (Harris, R. A. et al. (1997) Adv. Enzyme Regul. 37:271–293). Both starvation and the diabetic state are known to result in a great increase in the activity of the pyruvate dehydrogenase kinase in the liver, heart and muscle of the rat. This increase contributes in both disease states to the phosphorylation and inactivation of the pyruvate dehydrogenase complex and conservation of pyruvate and lactate for gluconeogenesis (Harris (1995) supra).

Kinases with Non-Protein Substrates

Lipid and Inositol Kinases

Lipid kinases phosphorylate hydroxyl residues on lipid head groups. A family of kinases involved in phosphorylation of phosphatidylinositol (PI) has been described, each member phosphorylating a specific carbon on the inositol ring (Leevers, S. J. et al. (1999) Curr. Opin. Cell. Biol. 11:219–225). The phosphorylation of phosphatidylinositol is involved in activation of the protein kinase C signaling pathway. The inositol phospholipids (phosphoinositides) intracellular signaling pathway begins with binding of a signaling molecule to a G-protein linked receptor in the plasma membrane. This leads to the phosphorylation of phosphatidylinositol (PI) residues on the inner side of the plasma membrane by inositol kinases, thus converting PI residues to the biphosphate state ($PIP_2$). $PIP_2$ is then cleaved into inositol triphosphate ($IP_3$) and diacylglycerol. These two products act as mediators for separate signaling pathways. Cellular responses that are mediated by these pathways are glycogen breakdown in the liver in response to vasopressin, smooth muscle contraction in response to acetylcholine, and thrombin-induced platelet aggregation.

PI 3-kinase (PI3K), which phosphorylates the D3 position of PI and its derivatives, has a central role in growth factor signal cascades involved in cell growth, differentiation, and metabolism. PI3K is a heterodimer consisting of an adapter subunit and a catalytic subunit. The adapter subunit acts as a scaffolding protein, interacting with specific tyrosine-phosphorylated proteins, lipid moieties, and other cytosolic factors. When the adapter subunit binds tyrosine phosphorylated targets, such as the insulin responsive substrate (IRS)-1, the catalytic subunit is activated and converts PI (4,5) bisphosphate ($PIP_2$) to PI (3,4,5) $P_3$ ($PIP_3$). $PIP_3$ then activates a number of other proteins, including PKA, protein kinase B (PKB), protein kinase C (PKC), glycogen synthase kinase (GSK)-3, and p70 ribosomal s6 kinase. PI3K also interacts directly with the cytoskeletal organizing proteins, Rac, rho, and cdc42 (Shepherd, P. R. et al. (1998) Biochem. J. 333:471–490). Animal models for diabetes, such as obese and fat mice, have altered PI3K adapter subunit levels. Specific mutations in the adapter subunit have also been found in an insulin-resistant Danish population, suggesting a role for PI3K in type-2 diabetes (Shepard, supra).

An example of lipid kinase phosphorylation activity is the phosphorylation of D-erythro-sphingosine to the sphingolipid metabolite, sphingosine-1-phosphate (SPP). SPP has emerged as a novel lipid second-messenger with both extracellular and intracellular actions (Kohama, T. et al. (1998) J. Biol. Chem. 273:23722–23728). Extracellularly, SPP is a ligand for the G-protein coupled receptor EDG-1 (endothelial-derived, G-protein coupled receptor). Intracellularly, SPP regulates cell growth, survival, motility, and cytoskeletal changes. SPP levels are regulated by sphingosine kinases that specifically phosphorylate D-erythro-sphingosine to SPP. The importance of sphingosine kinase in cell signaling is indicated by the fact that various stimuli, including platelet-derived growth factor (PDGF), nerve growth factor, and activation of protein kinase C, increase cellular levels of SPP by activation of sphingosine kinase, and the fact that competitive inhibitors of the enzyme selectively inhibit cell proliferation induced by PDGF (Kohama et al., supra).

Purine Nucleotide Kinases

The purine nucleotide kinases, adenylate kinase (ATP: AMP phosphotransferase, or AdK) and guanylate kinase (ATP:GMP phosphotransferase, or GuK) play a key role in nucleotide metabolism and are crucial to the synthesis and regulation of cellular levels of ATP and GTP, respectively. These two molecules are precursors in DNA and RNA synthesis in growing cells and provide the primary source of biochemical energy in cells (ATP), and signal transduction pathways (GTP). Inhibition of various steps in the synthesis of these two molecules has been the basis of many antiproliferative drugs for cancer and antiviral therapy (Pillwein, K. et al. (1990) Cancer Res. 50:1576–1579).

AdK is found in almost all cell types and is especially abundant in cells having high rates of ATP synthesis and utilization such as skeletal muscle. In these cells AdK is physically associated with mitochondria and myofibrils, the subcellular structures that are involved in energy production and utilization, respectively. Recent studies have demonstrated a major function for AdK in transferring high energy phosphoryls from metabolic processes generating ATP to cellular components consuming ATP (Zeleznikar, R. J. et al. (1995) J. Biol. Chem. 270:7311–7319). Thus AdK may have a pivotal role in maintaining energy production in cells, particularly those having a high rate of growth or metabolism such as cancer cells, and may provide a target for suppression of its activity to treat certain cancers. Alternatively, reduced AdK activity may be a source of various metabolic, muscle-energy disorders that can result in cardiac or respiratory failure and may be treatable by increasing AdK activity.

GuK, in addition to providing a key step in the synthesis of GTP for RNA and DNA synthesis, also fulfills an essential function in signal transduction pathways of cells through the regulation of GDP and GTP. Specifically, GTP binding to membrane associated G proteins mediates the activation of cell receptors, subsequent intracellular activation of adenyl cyclase, and production of the second messenger, cyclic AMP. GDP binding to G proteins inhibits these processes. GDP and GTP levels also control the activity of certain oncogenic proteins such as $p21^{ras}$ known to be involved in control of cell proliferation and oncogenesis (Bos, J. L. (1989) Cancer Res. 49:4682–4689). High ratios of GTP:GDP caused by suppression of GuK cause activation of $p21^{ras}$ and promote oncogenesis. Increasing GuK activity to increase levels of GDP and reduce the GTP:GDP ratio may provide a therapeutic strategy to reverse oncogenesis.

GuK is an important enzyme in the phosphorylation and activation of certain antiviral drugs useful in the treatment of herpes virus infections. These drugs include the guanine homologs acyclovir and buciclovir (Miller, W. H. and R. L. Miller (1980) J. Biol. Chem. 255:7204–7207; Stenberg, K. et al. (1986) J. Biol. Chem. 261:2134–2139). Increasing GuK activity in infected cells may provide a therapeutic strategy for augmenting the effectiveness of these drugs and possibly for reducing the necessary dosages of the drugs.

Pyrimidine Kinases

The pyrimidine kinases are deoxycytidine kinase and thymidine kinase 1 and 2. Deoxycytidine kinase is located in the nucleus, and thymidine kinase 1 and 2 are found in the cytosol (Johansson, M. et al. (1997) Proc. Natl. Acad. Sci. USA 94:11941–11945). Phosphorylation of deoxyribonucleosides by pyrimidine kinases provides an alternative pathway for de novo synthesis of DNA precursors. The role of pyrimidine kinases, like purine kinases, in phosphorylation is critical to the activation of several chemotherapeutically important nucleoside analogues (Amer E. S. and S. Eriksson (1995) Pharmacol. Ther. 67:155–186).

The discovery of new human kinases, and the polynucleotides encoding them, satisfies a need in the art by providing new compositions which are useful in the diagnosis, prevention, and treatment of cancer, immune disorders, disorders affecting growth and development, cardiovascular diseases, and lipid disorders, and in the assessment of the effects of exogenous compounds on the expression of nucleic acid and amino acid sequences of human kinases.

SUMMARY OF THE INVENTION

The invention features purified polypeptides, human kinases, referred to collectively as "PKIN" and individually as "PKIN-1," "PKIN-2," "PKIN-3," "PKIN-4," "PKIN-5," "PKIN-6," "PKIN-7," "PKIN-8," "PKIN-9," "PKIN-10," "PKIN-11," "PKIN-12," "PKIN-13," "PKIN-14," "PKIN-15," "PKIN-16," "PKIN-17," "PKIN-18," "PKIN-19," "PKIN-20," "PKIN-21," "PKIN-22," "PKIN-23," and "PKIN-24." In one aspect, the invention provides an isolated polypeptide selected from the group consisting of a) a polypeptide comprising an amino acid sequence selected from the group consisting of SEQ ID NO:1–24, b) a polypeptide comprising a naturally occurring amino acid sequence at least 90% identical to an amino acid sequence selected from the group consisting of SEQ ID NO:1–24, c) a biologically active fragment of a polypeptide having an amino acid sequence selected from the group consisting of SEQ ID NO:1–24, and d) an immunogenic fragment of a polypeptide having an amino acid sequence selected from the group consisting of SEQ ID NO:1–24. In one alternative, the invention provides an isolated polypeptide comprising the amino acid sequence of SEQ ID NO:1–24.

The invention further provides an isolated polynucleotide encoding a polypeptide selected from the group consisting of a) a polypeptide comprising an amino acid sequence selected from the group consisting of SEQ ID NO:1–24, b) a polypeptide comprising a naturally occurring amino acid sequence at least 90% identical to an amino acid sequence selected from the group consisting of SEQ ID NO:1–24, c) a biologically active fragment of a polypeptide having an amino acid sequence selected from the group consisting of SEQ ID NO:1–24, and d) an immunogenic fragment of a polypeptide having an amino acid sequence selected from the group consisting of SEQ ID NO:1–24. In one alternative, the polynucleotide encodes a polypeptide selected from the group consisting of SEQ ID NO:1–24. In another alternative, the polynucleotide is selected from the group consisting of SEQ ID NO:25–48.

Additionally, the invention provides a recombinant polynucleotide comprising a promoter sequence operably linked to a polynucleotide encoding a polypeptide selected from the group consisting of a) a polypeptide comprising an amino acid sequence selected from the group consisting of SEQ ID NO:1–24, b) a polypeptide comprising a naturally occurring amino acid sequence at least 90% identical to an amino acid sequence selected from the group consisting of SEQ ID NO:1–24, c) a biologically active fragment of a polypeptide having an amino acid sequence selected from the group consisting of SEQ ID NO:1–24, and d) an immunogenic fragment of a polypeptide having an amino acid sequence selected from the group consisting of SEQ ID NO:1–24. In one alternative, the invention provides a cell transformed with the recombinant polynucleotide. In another alternative, the invention provides a transgenic organism comprising the recombinant polynucleotide.

The invention also provides a method for producing a polypeptide selected from the group consisting of a) a polypeptide comprising an amino acid sequence selected from the group consisting of SEQ ID NO:1–24, b) a polypeptide comprising a naturally occurring amino acid sequence at least 90% identical to an amino acid sequence selected from the group consisting of SEQ ID NO:1–24, c) a biologically active fragment of a polypeptide having an amino acid sequence selected from the group consisting of SEQ ID NO:1–24, and d) an immunogenic fragment of a polypeptide having an amino acid sequence selected from the group consisting of SEQ ID NO:1–24. The method comprises a) culturing a cell under conditions suitable for expression of the polypeptide, wherein said cell is transformed with a recombinant polynucleotide comprising a promoter sequence operably linked to a polynucleotide encoding the polypeptide, and b) recovering the polypeptide so expressed.

Additionally, the invention provides an isolated antibody which specifically binds to a polypeptide selected from the group consisting of a) a polypeptide comprising an amino acid sequence selected from the group consisting of SEQ ID NO:1–24, b) a polypeptide comprising a naturally occurring amino acid sequence at least 90% identical to an amino acid sequence selected from the group consisting of SEQ ID NO:1–24, c) a biologically active fragment of a polypeptide having an amino acid sequence selected from the group consisting of SEQ ID NO:1–24, and d) an immunogenic fragment of a polypeptide having an amino acid sequence selected from the group consisting of SEQ ID NO:1–24.

The invention further provides an isolated polynucleotide selected from the group consisting of a) a polynucleotide comprising a polynucleotide sequence selected from the group consisting of SEQ ID NO:25–48, b) a polynucleotide comprising a naturally occurring polynucleotide sequence at least 90% identical to a polynucleotide sequence selected from the group consisting of SEQ ID NO:25–48, c) a polynucleotide complementary to the polynucleotide of a), d) a polynucleotide complementary to the polynucleotide of b), and e) an RNA equivalent of a)–d). In one alternative, the polynucleotide comprises at least 60 contiguous nucleotides.

Additionally, the invention provides a method for detecting a target polynucleotide in a sample, said target polynucleotide having a sequence of a polynucleotide selected from the group consisting of a) a polynucleotide comprising a polynucleotide sequence selected from the group consisting of SEQ ID NO:25–48, b) a polynucleotide comprising a naturally occurring polynucleotide sequence at least 90% identical to a polynucleotide sequence selected from the group consisting of SEQ ID NO:25–48, c) a polynucleotide complementary to the polynucleotide of a), d) a polynucleotide complementary to the polynucleotide of b), and e) an RNA equivalent of a)–d). The method comprises a) hybridizing the sample with a probe comprising at least 20 contiguous nucleotides comprising a sequence complementary to said target polynucleotide in the sample, and which probe specifically hybridizes to said target polynucleotide, under conditions whereby a hybridization complex is formed between said probe and said target polynucleotide or fragments thereof, and b) detecting the presence or absence of said hybridization complex, and optionally, if present, the amount thereof. In one alternative, the probe comprises at least 60 contiguous nucleotides.

The invention further provides a method for detecting a target polynucleotide in a sample, said target polynucleotide having a sequence of a polynucleotide selected from the group consisting of a) a polynucleotide comprising a polynucleotide sequence selected from the group consisting of SEQ ID NO:25–48, b) a polynucleotide comprising a naturally occurring polynucleotide sequence at least 90% identical to a polynucleotide sequence selected from the group consisting of SEQ ID NO:25–48, c) a polynucleotide complementary to the polynucleotide of a), d) a polynucleotide complementary to the polynucleotide of b), and e) an RNA equivalent of a)–d). The method comprises a) amplifying said target polynucleotide or fragment thereof using polymerase chain reaction amplification, and b) detecting the presence or absence of said amplified target polynucleotide or fragment thereof, and, optionally, if present, the amount thereof.

The invention further provides a composition comprising an effective amount of a polypeptide selected from the group consisting of a) a polypeptide comprising an amino acid sequence selected from the group consisting of SEQ ID NO:1–24, b) a polypeptide comprising a naturally occurring amino acid sequence at least 90% identical to an amino acid sequence selected from the group consisting of SEQ ID NO:1–24, c) a biologically active fragment of a polypeptide having an amino acid sequence selected from the group consisting of SEQ ID NO:1–24, and d) an immunogenic fragment of a polypeptide having an amino acid sequence selected from the group consisting of SEQ ID NO:1–24, and a pharmaceutically acceptable excipient. In one embodiment, the composition comprises an amino acid sequence selected from the group consisting of SEQ ID NO:1–24. The invention additionally provides a method of treating a disease or condition associated with decreased expression of functional PKIN, comprising administering to a patient in need of such treatment the composition.

The invention also provides a method for screening a compound for effectiveness as an agonist of a polypeptide selected from the group consisting of a) a polypeptide comprising an amino acid sequence selected from the group consisting of SEQ ID NO:1–24, b) a polypeptide comprising a naturally occurring amino acid sequence at least 90% identical to an amino acid sequence selected from the group consisting of SEQ ID NO:1–24, c) a biologically active fragment of a polypeptide having an amino acid sequence selected from the group consisting of SEQ ID NO:1–24, and d) an immunogenic fragment of a polypeptide having an amino acid sequence selected from the group consisting of SEQ ID NO:1–24. The method comprises a) exposing a sample comprising the polypeptide to a compound, and b) detecting agonist activity in the sample. In one alternative, the invention provides a composition comprising an agonist compound identified by the method and a pharmaceutically acceptable excipient. In another alternative, the invention provides a method of treating a disease or condition associated with decreased expression of functional PKIN, comprising administering to a patient in need of such treatment the composition.

Additionally, the invention provides a method for screening a compound for effectiveness as an antagonist of a polypeptide selected from the group consisting of a) a polypeptide comprising an amino acid sequence selected from the group consisting of SEQ ID NO:1–24, b) a polypeptide comprising a naturally occurring amino acid sequence at least 90% identical to an amino acid sequence selected from the group consisting of SEQ ID NO:1–24, c) a biologically active fragment of a polypeptide having an amino acid sequence selected from the group consisting of SEQ ID NO:1–24, and d) an immunogenic fragment of a polypeptide having an amino acid sequence selected from the group consisting of SEQ ID NO:1–24. The method comprises a) exposing a sample comprising the polypeptide to a compound, and b) detecting antagonist activity in the sample. In one alternative, the invention provides a composition comprising an antagonist compound identified by the method and a pharmaceutically acceptable excipient. In another alternative, the invention provides a method of treating a disease or condition associated with overexpression of functional PKIN, comprising administering to a patient in need of such treatment the composition.

The invention further provides a method of screening for a compound that specifically binds to a polypeptide selected from the group consisting of a) a polypeptide comprising an amino acid sequence selected from the group consisting of SEQ ID NO:1–24, b) a polypeptide comprising a naturally occurring amino acid sequence at least 90% identical to an amino acid sequence selected from the group consisting of SEQ ID NO:1–24, c) a biologically active fragment of a polypeptide having an amino acid sequence selected from the group consisting of SEQ ID NO:1–24, and d) an immunogenic fragment of a polypeptide having an amino acid sequence selected from the group consisting of SEQ ID NO:1–24. The method comprises a) combining the polypeptide with at least one test compound under suitable conditions, and b) detecting binding of the polypeptide to the test compound, thereby identifying a compound that specifically binds to the polypeptide.

The invention further provides a method of screening for a compound that modulates the activity of a polypeptide selected from the group consisting of a) a polypeptide comprising an amino acid sequence selected from the group consisting of SEQ ID NO:1–24, b) a polypeptide comprising a naturally occurring amino acid sequence at least 90% identical to an amino acid sequence selected from the group consisting of SEQ ID NO:1–24, c) a biologically active fragment of a polypeptide having an amino acid sequence selected from the group consisting of SEQ ID NO:1–24, and d) an immunogenic fragment of a polypeptide having an amino acid sequence selected from the group consisting of SEQ ID NO:1–24. The method comprises a) combining the polypeptide with at least one test compound under conditions permissive for the activity of the polypeptide, b) assessing the activity of the polypeptide in the presence of the test compound, and c) comparing the activity of the polypeptide in the presence of the test compound with the activity of the polypeptide in the absence of the test compound, wherein a change in the activity of the polypeptide in the presence of the test compound is indicative of a compound that modulates the activity of the polypeptide.

The invention further provides a method for screening a compound for effectiveness in altering expression of a target polynucleotide, wherein said target polynucleotide comprises a polynucleotide sequence selected from the group consisting of SEQ ID NO:25–48, the method comprising a) exposing a sample comprising the target polynucleotide to a compound, and b) detecting altered expression of the target polynucleotide.

The invention further provides a method for assessing toxicity of a test compound, said method comprising a) treating a biological sample containing nucleic acids with the test compound; b) hybridizing the nucleic acids of the treated biological sample with a probe comprising at least 20 contiguous nucleotides of a polynucleotide selected from the group consisting of i) a polynucleotide comprising a polynucleotide sequence selected from the group consisting of SEQ ID NO:25–48, ii) a polynucleotide comprising a naturally occurring polynucleotide sequence at least 90% identical to a polynucleotide sequence selected from the group consisting of SEQ ID NO:25–48, iii) a polynucleotide having a sequence complementary to i), iv) a polynucleotide complementary to the polynucleotide of ii), and v) an RNA equivalent of i)–iv). Hybridization occurs under conditions whereby a specific hybridization complex is formed between said probe and a target polynucleotide in the biological sample, said target polynucleotide selected from the group consisting of i) a polynucleotide comprising a polynucleotide sequence selected from the group consisting of SEQ ID NO:25–48, ii) a polynucleotide comprising a naturally occurring polynucleotide sequence at least 90% identical to a polynucleotide sequence selected from the group consisting of SEQ ID NO:25–48, iii) a polynucleotide complementary to the polynucleotide of i), iv) a polynucleotide complementary to the polynucleotide of ii), and v) an RNA equivalent of i)–iv). Alternatively, the target polynucleotide comprises a fragment of a polynucleotide sequence selected from the group consisting of i)–v) above; c) quantifying the amount of hybridization complex; and d) comparing the amount of hybridization complex in the treated biological sample with the amount of hybridization complex in an untreated biological sample, wherein a difference in the amount of hybridization complex in the treated biological sample is indicative of toxicity of the test compound.

BRIEF DESCRIPTION OF THE TABLES

Table 1 summarizes the nomenclature for the full length polynucleotide and polypeptide sequences of the present invention.

Table 2 shows the GenBank identification number and annotation of the nearest GenBank homolog for polypeptides of the invention. The probability score for the match between each polypeptide and its GenBank homolog is also shown.

Table 3 shows structural features of polypeptide sequences of the invention, including predicted motifs and domains, along with the methods, algorithms, and searchable databases used for analysis of the polypeptides.

Table 4 lists the cDNA and/or genomic DNA fragments which were used to assemble polynucleotide sequences of the invention, along with selected fragments of the polynucleotide sequences.

Table 5 shows the representative cDNA library for polynucleotides of the invention.

Table 6 provides an appendix which describes the tissues and vectors used for construction of the cDNA libraries shown in Table 5.

Table 7 shows the tools, programs, and algorithms used to analyze the polynucleotides and polypeptides of the invention, along with applicable descriptions, references, and threshold parameters.

DESCRIPTION OF THE INVENTION

Before the present proteins, nucleotide sequences, and methods are described, it is understood that this invention is not limited to the particular machines, materials and methods described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural reference unless the context clearly dictates otherwise. Thus, for example, a reference to "a host cell" includes a plurality of such host cells, and a reference to "an antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any machines, materials, and methods similar or equivalent to those described herein can be used to practice or test the present invention, the preferred machines, materials and methods are now described. All publications mentioned herein are cited for the purpose of describing and disclosing the cell lines, protocols, reagents and vectors which are reported in the publications and which might be used in connection with the invention. Nothing herein is to be construed as an admission that the invention is not entitled to antedate such disclosure by virtue of prior invention.

Definitions

"PKIN" refers to the amino acid sequences of substantially purified PKIN obtained from any species, particularly a mammalian species, including bovine, ovine, porcine, murine, equine, and human, and from any source, whether natural, synthetic, semi-synthetic, or recombinant.

The term "agonist" refers to a molecule which intensifies or mimics the biological activity of PKIN. Agonists may include proteins, nucleic acids, carbohydrates, small molecules, or any other compound or composition which modulates the activity of PKIN either by directly interacting with PKIN or by acting on components of the biological pathway in which PKIN participates.

An "allelic variant" is an alternative form of the gene encoding PKIN. Allelic variants may result from at least one mutation in the nucleic acid sequence and may result in altered mRNAs or in polypeptides whose structure or function may or may not be altered. A gene may have none, one, or many allelic variants of its naturally occurring form. Common mutational changes which give rise to allelic variants are generally ascribed to natural deletions, additions, or substitutions of nucleotides. Each of these types of changes may occur alone, or in combination with the others, one or more times in a given sequence.

"Altered" nucleic acid sequences encoding PKIN include those sequences with deletions, insertions, or substitutions of different nucleotides, resulting in a polypeptide the same as PKIN or a polypeptide with at least one functional characteristic of PKIN. Included within this definition are polymorphisms which may or may not be readily detectable using a particular oligonucleotide probe of the polynucleotide encoding PKIN, and improper or unexpected hybridization to allelic variants, with a locus other than the normal chromosomal locus for the polynucleotide sequence encoding PKIN. The encoded protein may also be "altered," and may contain deletions, insertions, or substitutions of amino acid residues which produce a silent change and result in a functionally equivalent PKIN. Deliberate amino acid substitutions may be made on the basis of similarity in polarity, charge, solubility, hydrophobicity, hydrophilicity, and/or the amphipathic nature of the residues, as long as the biological or immunological activity of PKIN is retained. For example, negatively charged amino acids may include aspartic acid and glutamic acid, and positively charged amino acids may include lysine and arginine. Amino acids with uncharged polar side chains having similar hydrophilicity values may include: asparagine and glutamine; and serine and threonine. Amino acids with uncharged side chains having similar hydrophilicity values may include: leucine, isoleucine, and valine; glycine and alanine; and phenylalanine and tyrosine.

The terms "amino acid" and "amino acid sequence" refer to an oligopeptide, peptide, polypeptide, or protein sequence, or a fragment of any of these, and to naturally occurring or synthetic molecules. Where "amino acid sequence" is recited to refer to a sequence of a naturally occurring protein molecule, "amino acid sequence" and like terms are not meant to limit the amino acid sequence to the complete native amino acid sequence associated with the recited protein molecule.

"Amplification" relates to the production of additional copies of a nucleic acid sequence. Amplification is generally carried out using polymerase chain reaction (PCR) technologies well known in the art.

The term "antagonist" refers to a molecule which inhibits or attenuates the biological activity of PKIN. Antagonists may include proteins such as antibodies, nucleic acids, carbohydrates, small molecules, or any other compound or composition which modulates the activity of PKIN either by directly interacting with PKIN or by acting on components of the biological pathway in which PKIN participates.

The term "antibody" refers to intact immunoglobulin molecules as well as to fragments thereof, such as Fab, F(ab')$_2$, and Fv fragments, which are capable of binding an epitopic determinant. Antibodies that bind PKIN polypeptides can be prepared using intact polypeptides or using fragments containing small peptides of interest as the immunizing antigen. The polypeptide or oligopeptide used to immunize an animal (e.g., a mouse, a rat, or a rabbit) can be derived from the translation of RNA, or synthesized chemically, and can be conjugated to a carrier protein if desired. Commonly used carriers that are chemically coupled to peptides include bovine serum albumin, thyroglobulin, and keyhole limpet hemocyanin (KLH). The coupled peptide is then used to immunize the animal.

The term "antigenic determinant" refers to that region of a molecule (i.e., an epitope) that makes contact with a particular antibody. When a protein or a fragment of a protein is used to immunize a host animal, numerous regions of the protein may induce the production of antibodies which bind specifically to antigenic determinants (particular regions or three-dimensional structures on the protein). An antigenic determinant may compete with the intact antigen (i.e., the immunogen used to elicit the immune response) for binding to an antibody.

The term "antisense" refers to any composition capable of base-pairing with the "sense" (coding) strand of a specific nucleic acid sequence. Antisense compositions may include DNA; RNA; peptide nucleic acid (PNA); oligonucleotides having modified backbone linkages such as phosphorothioates, methylphosphonates, or benzylphosphonates; oligonucleotides having modified sugar groups such as 2'-methoxyethyl sugars or 2'-methoxyethoxy sugars; or oligonucleotides having modified bases such as 5-methyl cytosine, 2'-deoxyuracil, or 7-deaza-2'-deoxyguanosine. Antisense molecules may be produced by any method including chemical synthesis or transcription. Once introduced into a cell, the complementary antisense molecule base-pairs with a naturally occurring nucleic acid sequence produced by the cell to form duplexes which block either transcription or translation. The designation "negative" or "minus" can refer to the antisense strand, and the designation "positive" or "plus" can refer to the sense strand of a reference DNA molecule.

The term "biologically active" refers to a protein having structural, regulatory, or biochemical functions of a naturally occurring molecule. Likewise, "immunologically active" or "immunogenic" refers to the capability of the natural, recombinant, or synthetic PKIN, or of any oligopeptide thereof, to induce a specific immune response in appropriate animals or cells and to bind with specific antibodies.

"Complementary" describes the relationship between two single-stranded nucleic acid sequences that anneal by base-pairing. For example, 5'-AGT-3' pairs with its complement, 3'-TCA-5'.

A "composition comprising a given polynucleotide sequence" and a "composition comprising a given amino acid sequence" refer broadly to any composition containing the given polynucleotide or amino acid sequence. The composition may comprise a dry formulation or an aqueous solution. Compositions comprising polynucleotide sequences encoding PKIN or fragments of PKIN may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., sodium dodecyl sulfate; SDS), and other components (e.g., Denhardt's solution, dry milk, salmon sperm DNA, etc.).

"Consensus sequence" refers to a nucleic acid sequence which has been subjected to repeated DNA sequence analysis to resolve uncalled bases, extended using the XL-PCR kit (Applied Biosystems, Foster City Calif.) in the 5' and/or the 3' direction, and resequenced, or which has been assembled from one or more overlapping cDNA, EST, or genomic DNA fragments using a computer program for fragment assembly, such as the GELVIEW fragment assembly system (GCG, Madison Wis.) or Phrap (University of Washington, Seattle Wash.). Some sequences have been both extended and assembled to produce the consensus sequence.

"Conservative amino acid substitutions" are those substitutions that are predicted to least interfere with the properties of the original protein, i.e., the structure and especially the function of the protein is conserved and not significantly changed by such substitutions. The table below shows amino acids which may be substituted for an original amino acid in a protein and which are regarded as conservative amino acid substitutions.

| Original Residue | Conservative Substitution |
| --- | --- |
| Ala | Gly, Ser |
| Arg | His, Lys |
| Asn | Asp, Gln, His |
| Asp | Asn, Glu |
| Cys | Ala, Ser |
| Gln | Asn, Glu, His |
| Glu | Asp, Gln, His |
| Gly | Ala |
| His | Asn, Arg, Gln, Glu |
| Ile | Leu, Val |
| Leu | Ile, Val |
| Lys | Arg, Gln, Glu |
| Met | Leu, Ile |
| Phe | His, Met, Leu, Trp, Tyr |
| Ser | Cys, Thr |
| Thr | Ser, Val |
| Trp | Phe, Tyr |
| Tyr | His, Phe, Trp |
| Val | Ile, Leu, Thr |

Conservative amino acid substitutions generally maintain (a) the structure of the polypeptide backbone in the area of the substitution, for example, as a beta sheet or alpha helical conformation, (b) the charge or hydrophobicity of the molecule at the site of the substitution, and/or (c) the bulk of the side chain.

A "deletion" refers to a change in the amino acid or nucleotide sequence that results in the absence of one or more amino acid residues or nucleotides.

The term "derivative", refers to a chemically modified polynucleotide or polypeptide. Chemical modifications of a polynucleotide can include, for example, replacement of hydrogen by an alkyl, acyl, hydroxyl, or amino group. A derivative polynucleotide encodes a polypeptide which retains at least one biological or immunological function of the natural molecule. A derivative polypeptide is one modified by glycosylation, pegylation, or any similar process that retains at least one biological or immunological function of the polypeptide from which it was derived.

A "detectable label" refers to a reporter molecule or enzyme that is capable of generating a measurable signal and is covalently or noncovalently joined to a polynucleotide or polypeptide.

"Differential expression" refers to increased or upregulated; or decreased, downregulated, or absent gene or protein expression, determined by comparing at least two different samples. Such comparisons may be carried out between, for example, a treated and an untreated sample, or a diseased and a normal sample.

"Exon shuffling" refers to the recombination of different coding regions (exons). Since an exon may represent a structural or functional domain of the encoded protein, new proteins may be assembled through the novel reassortment of stable substructures, thus allowing acceleration of the evolution of new protein functions.

A "fragment" is a unique portion of PKIN or the polynucleotide encoding PKIN which is identical in sequence to but shorter in length than the parent sequence. A fragment may comprise up to the entire length of the defined sequence, minus one nucleotide/amino acid residue. For example, a fragment may comprise from 5 to 1000 contiguous nucleotides or amino acid residues. A fragment used as a probe, primer, antigen, therapeutic molecule, or for other purposes, may be at least 5, 10, 15, 16, 20, 25, 30, 40, 50, 60, 75, 100, 150, 250 or at least 500 contiguous nucleotides or amino acid residues in length. Fragments may be preferentially selected from certain regions of a molecule. For example, a polypeptide fragment may comprise a certain length of contiguous amino acids selected from the first 250 or 500 amino acids (or first 25% or 50%) of a polypeptide as shown in a certain defined sequence. Clearly these lengths are exemplary, and any length that is supported by the specification, including the Sequence Listing, tables, and figures, may be encompassed by the present embodiments.

A fragment of SEQ ID NO:25–48 comprises a region of unique polynucleotide sequence that specifically identifies SEQ ID NO:25–48, for example, as distinct from any other sequence in the genome from which the fragment was obtained. A fragment of SEQ ID NO:25–48 is useful, for example, in hybridization and amplification technologies and in analogous methods that distinguish SEQ ID NO:25–48 from related polynucleotide sequences. The precise length of a fragment of SEQ ID NO:25–48 and the region of SEQ ID NO:25–48 to which the fragment corresponds are routinely determinable by one of ordinary skill in the art based on the intended purpose for the fragment.

A fragment of SEQ ID NO:1–24 is encoded by a fragment of SEQ ID NO:25–48. A fragment of SEQ ID NO:1–24 comprises a region of unique amino acid sequence that specifically identifies SEQ ID NO:1–24. For example, a fragment of SEQ ID NO:1–24 is useful as an immunogenic peptide for the development of antibodies that specifically recognize SEQ ID NO:1–24. The precise length of a fragment of SEQ ID NO:1–24 and the region of SEQ ID NO:1–24 to which the fragment corresponds are routinely determinable by one of ordinary skill in the art based on the intended purpose for the fragment.

A "full length" polynucleotide sequence is one containing at least a translation initiation codon (e.g., methionine) followed by an open reading frame and a translation termination codon. A "full length" polynucleotide sequence encodes a "full length" polypeptide sequence.

"Homology" refers to sequence similarity or, interchangeably, sequence identity, between two or more polynucleotide sequences or two or more polypeptide sequences.

The terms "percent identity" and "% identity," as applied to polynucleotide sequences, refer to the percentage of residue matches between at least two polynucleotide sequences aligned using a standardized algorithm. Such an algorithm may insert, in a standardized and reproducible way, gaps in the sequences being compared in order to optimize alignment between two sequences, and therefore achieve a more meaningful comparison of the two sequences.

Percent identity between polynucleotide sequences may be determined using the default parameters of the CLUSTAL V algorithm as incorporated into the MEGA-LIGN version 3.12e sequence alignment program. This program is part of the LASERGENE software package, a suite of molecular biological analysis programs (DNAS-TAR, Madison Wis.). CLUSTAL V is described in Higgins, D. G. and P. M. Sharp (1989) CABIOS 5:151–153 and in Higgins, D. G. et al. (1992) CABIOS 8:189–191. For pairwise alignments of polynucleotide sequences, the default parameters are set as follows: Ktuple=2, gap penalty=5, window=4, and "diagonals saved"=4. The "weighted" residue weight table is selected as the default. Percent identity is reported by CLUSTAL V as the "percent similarity" between aligned polynucleotide sequences.

Alternatively, a suite of commonly used and freely available sequence comparison algorithms is provided by the National Center for Biotechnology Information (NCBI) Basic Local Alignment Search Tool (BLAST) (Altschul, S. F. et al. (1990) J. Mol. Biol. 215:403–410), which is available from several sources, including the NCBI, Bethesda, Md., and on the Internet at http://www.ncbi.nlm.nih.gov/BLAST/. The BLAST software suite includes various sequence analysis programs including "blastn," that is used to align a known polynucleotide sequence with other polynucleotide sequences from a variety of databases. Also available is a tool called "BLAST 2 Sequences" that is used for direct pairwise comparison of two nucleotide sequences. "BLAST 2 Sequences" can be accessed and used interactively at http://www.ncbi.nlm.nih.gov/gorf/bl2.html. The "BLAST 2 Sequences" tool can be used for both blastn and blastp (discussed below). BLAST programs are commonly used with gap and other parameters set to default settings. For example, to compare two nucleotide sequences, one may use blastn with the "BLAST 2 Sequences" tool Version 2.0.12 (Apr. 21, 2000) set at default parameters. Such default parameters may be, for example:

Matrix: BLOSUM62
Reward for match: 1
Penalty for mismatch: −2
Open Gap: 5 and Extension Gap: 2 penalties
Gap×drop-off: 50
Expect: 10
Word Size: 11
Filter: on Percent identity may be measured over the length of an entire defined sequence, for example, as defined by a particular SEQ ID number, or may be measured over a shorter length, for example, over the length of a fragment taken from a larger, defined sequence, for instance, a fragment of at least 20, at least 30, at least 40, at least 50, at least 70, at least 100, or at least 200 contiguous nucleotides. Such lengths are exemplary only, and it is understood that any fragment length supported by the sequences shown herein, in the tables, figures, or Sequence Listing, may be used to describe a length over which percentage identity may be measured.

Nucleic acid sequences that do not show a high degree of identity may nevertheless encode similar amino acid sequences due to the degeneracy of the genetic code. It is understood that changes in a nucleic acid sequence can be made using this degeneracy to produce multiple nucleic acid sequences that all encode substantially the same protein.

The phrases "percent identity" and "% identity," as applied to polypeptide sequences, refer to the percentage of residue matches between at least two polypeptide sequences aligned using a standardized algorithm. Methods of polypeptide sequence alignment are well-known. Some alignment methods take into account conservative amino acid substitutions. Such conservative substitutions, explained in more detail above, generally preserve the charge and hydrophobicity at the site of substitution, thus preserving the structure (and therefore function) of the polypeptide.

Percent identity between polypeptide sequences may be determined using the default parameters of the CLUSTAL V algorithm as incorporated into the MEGALIGN version 3.12e sequence alignment program (described and referenced above). For pairwise alignments of polypeptide sequences using CLUSTAL V, the default parameters are set as follows: Ktuple=1, gap penalty=3, window=5, and "diagonals saved"=5. The PAM250 matrix is selected as the default residue weight table. As with polynucleotide alignments, the percent identity is reported by CLUSTAL V as the "percent similarity" between aligned polypeptide sequence pairs.

Alternatively the NCBI BLAST software suite may be used. For example, for a pairwise comparison of two polypeptide sequences, one may use the "BLAST 2 Sequences" tool Version 2.0.12 (Apr. 21, 2000) with blastp set at default parameters. Such default parameters may be, for example:

Matrix: BLOSUM62
Open Gap: 11 and Extension Gap: 1 penalties
Gap×drop-off: 50
Expect: 10
Word Size: 3
Filter: on Percent identity may be measured over the length of an entire defined polypeptide sequence, for example, as defined by a particular SEQ ID number, or may be measured over a shorter length, for example, over the length of a fragment taken from a larger, defined polypeptide sequence, for instance, a fragment of at least 15, at least 20, at least 30, at least 40, at least 50, at least 70 or at least 150 contiguous residues. Such lengths are exemplary only, and it is understood that any fragment length supported by the sequences shown herein, in the tables, figures or Sequence Listing, may be used to describe a length over which percentage identity may be measured.

"Human artificial chromosomes" (HACs) are linear microchromosomes which may contain DNA sequences of about 6 kb to 10 Mb in size and which contain all of the elements required for chromosome replication, segregation and maintenance.

The term "humanized antibody" refers to an antibody molecule in which the amino acid sequence in the non-antigen binding regions has been altered so that the antibody more closely resembles a human antibody, and still retains its original binding ability.

"Hybridization" refers to the process by which a polynucleotide strand anneals with a complementary strand through base pairing under defined hybridization conditions. Specific hybridization is an indication that two nucleic acid sequences share a high degree of complementarity. Specific hybridization complexes form under permissive annealing conditions and remain hybridized after the "washing" step(s). The washing step(s) is particularly important in determining the stringency of the hybridization process, with more stringent conditions allowing less non-specific binding, i.e., binding between pairs of nucleic acid strands that are not perfectly matched. Permissive conditions for annealing of nucleic acid sequences are routinely determinable by one of ordinary skill in the art and may be consistent among hybridization experiments, whereas wash conditions may be varied among experiments to achieve the desired stringency, and therefore hybridization specificity. Permissive annealing conditions occur, for example, at 68° C. in the presence of about 6×SSC, about 1% (w/v) SDS, and about 100 µg/ml sheared, denatured salmon sperm DNA.

Generally, stringency of hybridization is expressed, in part, with reference to the temperature under which the wash step is carried out. Such wash temperatures are typically selected to be about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. An equation for calculating $T_m$ and conditions for nucleic acid hybridization are well known and can be found in Sambrook, J. et al. (1989) *Molecular Cloning: A Laboratory Manual*, $2^{nd}$ ed., vol. 1–3, Cold Spring Harbor Press, Plainview N.Y.; specifically see volume 2, chapter 9.

High stringency conditions for hybridization between polynucleotides of the present invention include wash conditions of 68° C. in the presence of about 0.2×SSC and about 0.1% SDS, for 1 hour. Alternatively, temperatures of about 65° C., 60° C., 55° C., or 42° C. may be used. SSC concentration may be varied from about 0.1 to 2×SSC, with SDS being present at about 0.1%. Typically, blocking reagents are used to block non-specific hybridization. Such blocking reagents include, for instance, sheared and denatured salmon sperm DNA at about 100–200 µg/ml. Organic solvent, such as formamide at a concentration of about 35–50% v/v, may also be used under particular circumstances, such as for RNA:DNA hybridizations. Useful variations on these wash conditions will be readily apparent to those of ordinary skill in the art. Hybridization, particularly under high stringency conditions, may be suggestive of evolutionary similarity between the nucleotides. Such similarity is strongly indicative of a similar role for the nucleotides and their encoded polypeptides.

The term "hybridization complex" refers to a complex formed between two nucleic acid sequences by virtue of the formation of hydrogen bonds between complementary bases. A hybridization complex may be formed in solution (e.g., $C_0t$ or $R_0t$ analysis) or formed between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

The words "insertion" and "addition" refer to changes in an amino acid or nucleotide sequence resulting in the addition of one or more amino acid residues or nucleotides, respectively.

"Immune response" can refer to conditions associated with inflammation, trauma, immune disorders, or infectious or genetic disease, etc. These conditions can be characterized by expression of various factors, e.g., cytokines, chemokines, and other signaling molecules, which may affect cellular and systemic defense systems.

An "immunogenic fragment" is a polypeptide or oligopeptide fragment of PKIN which is capable of eliciting an immune response when introduced into a living organism, for example, a mammal. The term "immunogenic fragment" also includes any polypeptide or oligopeptide fragment of PKIN which is useful in any of the antibody production methods disclosed herein or known in the art.

The term "microarray" refers to an arrangement of a plurality of polynucleotides, polypeptides, or other chemical compounds on a substrate.

The terms "element" and "array element" refer to a polynucleotide, polypeptide, or other chemical compound having a unique and defined position on a microarray.

The term "modulate" refers to a change in the activity of PKIN. For example, modulation may cause an increase or a decrease in protein activity, binding characteristics, or any other biological, functional, or immunological properties of PKIN.

The phrases "nucleic acid" and "nucleic acid sequence" refer to a nucleotide, oligonucleotide, polynucleotide, or any fragment thereof. These phrases also refer to DNA or RNA of genomic or synthetic origin which may be single-stranded or double-stranded and may represent the sense or the antisense strand, to peptide nucleic acid (PNA), or to any DNA-like or RNA-like material.

"Operably linked" refers to the situation in which a first nucleic acid sequence is placed in a functional relationship with a second nucleic acid sequence. For instance, a promoter is operably linked to a coding sequence if the promoter affects the transcription or expression of the coding sequence. Operably linked DNA sequences may be in close proximity or contiguous and, where necessary to join two protein coding regions, in the same reading frame.

"Peptide nucleic acid" (PNA) refers to an antisense molecule or anti-gene agent which comprises an oligonucleotide of at least about 5 nucleotides in length linked to a peptide backbone of amino acid residues ending in lysine. The terminal lysine confers solubility to the composition. PNAs preferentially bind complementary single stranded DNA or RNA and stop transcript elongation, and may be pegylated to extend their lifespan in the cell.

"Post-translational modification" of an PKIN may involve lipidation, glycosylation, phosphorylation, acetylation, racemization, proteolytic cleavage, and other modifications known in the art. These processes may occur synthetically or biochemically. Biochemical modifications will vary by cell type depending on the enzymatic milieu of PKIN.

"Probe" refers to nucleic acid sequences encoding PKIN, their complements, or fragments thereof, which are used to detect identical, allelic or related nucleic acid sequences. Probes are isolated oligonucleotides or polynucleotides attached to a detectable label or reporter molecule. Typical labels include radioactive isotopes, ligands, chemiluminescent agents, and enzymes. "Primers" are short nucleic acids, usually DNA oligonucleotides, which may be annealed to a target polynucleotide by complementary base-pairing. The primer may then be extended along the target DNA strand by a DNA polymerase enzyme. Primer pairs can be used for amplification (and identification) of a nucleic acid sequence, e.g., by the polymerase chain reaction (PCR).

Probes and primers as used in the present invention typically comprise at least 15 contiguous nucleotides of a known sequence. In order to enhance specificity, longer probes and primers may also be employed, such as probes and primers that comprise at least 20, 25, 30, 40, 50, 60, 70, 80, 90, 100, or at least 150 consecutive nucleotides of the disclosed nucleic acid sequences. Probes and primers may be considerably longer than these examples, and it is understood that any length supported by the specification, including the tables, figures, and Sequence Listing, may be used.

Methods for preparing and using probes and primers are described in the references, for example Sambrook, J. et al. (1989) *Molecular Cloning: A Laboratory Manual*, $2^{nd}$ ed., vol. 1–3, Cold Spring Harbor Press, Plainview N.Y.; Ausubel, F. M. et al. (1987) *Current Protocols in Molecular Biology*, Greene Publ. Assoc. & Wiley-Intersciences, New York N.Y.; Innis, M. et al. (1990) *PCR Protocols, A Guide to Methods and Applications*, Academic Press, San Diego Calif. PCR primer pairs can be derived from a known sequence, for example, by using computer programs intended for that purpose such as Primer (Version 0.5, 1991, Whitehead Institute for Biomedical Research, Cambridge Mass.).

Oligonucleotides for use as primers are selected using software known in the art for such purpose. For example, OLIGO 4.06 software is useful for the selection of PCR primer pairs of up to 100 nucleotides each, and for the analysis of oligonucleotides and larger polynucleotides of up to 5,000 nucleotides from an input polynucleotide sequence of up to 32 kilobases. Similar primer selection programs have incorporated additional features for expanded capabilities. For example, the PrimOU primer selection program (available to the public from the Genome Center at University of Texas South West Medical Center, Dallas Tex.) is capable of choosing specific primers from megabase sequences and is thus useful for designing primers on a genome-wide scope. The Primer3 primer selection program (available to the public from the Whitehead Institute/MIT Center for Genome Research, Cambridge Mass.) allows the user to input a "mispriming library," in which sequences to avoid as primer binding sites are user-specified. Primer3 is useful, in particular, for the selection of oligonucleotides for microarrays. (The source code for the latter two primer selection programs may also be obtained from their respective sources and modified to meet the user's specific needs.) The PrimeGen program (available to the public from the UK Human Genome Mapping Project Resource Centre, Cambridge UK) designs primers based on multiple sequence alignments, thereby allowing selection of primers that hybridize to either the most conserved or least conserved regions of aligned nucleic acid sequences. Hence, this program is useful for identification of both unique and conserved oligonucleotides and polynucleotide fragments. The oligonucleotides and polynucleotide fragments identified by any of the above selection methods are useful in hybridization technologies, for example, as PCR or sequencing primers, microarray elements, or specific probes to identify fully or partially complementary polynucleotides in a sample of nucleic acids. Methods of oligonucleotide selection are not limited to those described above.

A "recombinant nucleic acid" is a sequence that is not naturally occurring or has a sequence that is made by an artificial combination of two or more otherwise separated segments of sequence. This artificial combination is often accomplished by chemical synthesis or, more commonly, by the artificial manipulation of isolated segments of nucleic acids, e.g., by genetic engineering techniques such as those described in Sambrook, supra. The term recombinant includes nucleic acids that have been altered solely by addition, substitution, or deletion of a portion of the nucleic acid. Frequently, a recombinant nucleic acid may include a nucleic acid sequence operably linked to a promoter sequence. Such a recombinant nucleic acid may be part of a vector that is used, for example, to transform a cell.

Alternatively, such recombinant nucleic acids may be part of a viral vector, e.g., based on a vaccinia virus, that could be use to vaccinate a mammal wherein the recombinant nucleic acid is expressed, inducing a protective immunological response in the mammal.

A "regulatory element" refers to a nucleic acid sequence usually derived from untranslated regions of a gene and includes enhancers, promoters, introns, and 5' and 3' untranslated regions (UTRs). Regulatory elements interact with host or viral proteins which control transcription, translation, or RNA stability.

"Reporter molecules" are chemical or biochemical moieties used for labeling a nucleic acid, amino acid, or antibody. Reporter molecules include radionuclides; enzymes; fluorescent, chemiluminescent, or chromogenic agents; substrates; cofactors; inhibitors; magnetic particles; and other moieties known in the art.

An "RNA equivalent," in reference to a DNA sequence, is composed of the same linear sequence of nucleotides as the reference DNA sequence with the exception that all occurrences of the nitrogenous base thymine are replaced with uracil, and the sugar backbone is composed of ribose instead of deoxyribose.

The term "sample" is used in its broadest sense. A sample suspected of containing PKIN, nucleic acids encoding PKIN, or fragments thereof may comprise a bodily fluid; an extract from a cell, chromosome, organelle, or membrane isolated from a cell; a cell; genomic DNA, RNA, or cDNA, in solution or bound to a substrate; a tissue; a tissue print; etc.

The terms "specific binding" and "specifically binding" refer to that interaction between a protein or peptide and an agonist, an antibody, an antagonist, a small molecule, or any natural or synthetic binding composition. The interaction is dependent upon the presence of a particular structure of the protein, e.g., the antigenic determinant or epitope, recognized by the binding molecule. For example, if an antibody is specific for epitope "A," the presence of a polypeptide comprising the epitope A, or the presence of free unlabeled A, in a reaction containing free labeled A and the antibody will reduce the amount of labeled A that binds to the antibody.

The term "substantially purified" refers to nucleic acid or amino acid sequences that are removed from their natural environment and are isolated or separated, and are at least 60% free, preferably at least 75% free, and most preferably at least 90% free from other components with which they are naturally associated.

A "substitution" refers to the replacement of one or more amino acid residues or nucleotides by different amino acid residues or nucleotides, respectively.

"Substrate" refers to any suitable rigid or semi-rigid support including membranes, filters, chips, slides, wafers, fibers, magnetic or nonmagnetic beads, gels, tubing, plates, polymers, microparticles and capillaries. The substrate can have a variety of surface forms, such as wells, trenches, pins, channels and pores, to which polynucleotides or polypeptides are bound.

A "transcript image" refers to the collective pattern of gene expression by a particular cell type or tissue under given conditions at a given time.

"Transformation" describes a process by which exogenous DNA is introduced into a recipient cell. Transformation may occur under natural or artificial conditions according to various methods well known in the art, and may rely on any known method for the insertion of foreign nucleic acid sequences into a prokaryotic or eukaryotic host cell. The method for transformation is selected based on the type of host cell being transformed and may include, but is not limited to, bacteriophage or viral infection, electroporation, heat shock, lipofection, and particle bombardment. The term "transformed cells" includes stably transformed cells in which the inserted DNA is capable of replication either as an autonomously replicating plasmid or as part of the host chromosome, as well as transiently transformed cells which express the inserted DNA or RNA for limited periods of time.

A "transgenic organism," as used herein, is any organism, including but not limited to animals and plants, in which one or more of the cells of the organism contains heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. The transgenic organisms contemplated in accordance with the present invention include bacteria, cyanobacteria, fungi, plants and animals. The isolated DNA of the present invention can be introduced into the host by methods known in the art, for example infection, transfection, transformation or transconjugation. Techniques for transferring the DNA of the present invention into such organisms are widely known and provided in references such as Sambrook et al. (1989), supra.

A "variant" of a particular nucleic acid sequence is defined as a nucleic acid sequence having at least 40% sequence identity to the particular nucleic acid sequence over a certain length of one of the nucleic acid sequences using blastn with the "BLAST 2 Sequences" tool Version 2.0.9 (May 7, 1999) set at default parameters. Such a pair of nucleic acids may show, for example, at least 50%, at least 60%, at least 70%, at least 80%, at least 85%, at least 90%, at least 91%, at least 92%, at least 93%, at least 94%, at least 95%, at least 96%, at least 97%, at least 98%, or at least 99% or greater sequence identity over a certain defined length. A variant may be described as, for example, an "allelic" (as defined above), "splice," "species," or "polymorphic" variant. A splice variant may have significant identity to a reference molecule, but will generally have a greater or lesser number of polynucleotides due to alternate splicing of exons during mRNA processing. The corresponding polypeptide may possess additional functional domains or lack domains that are present in the reference molecule. Species variants are polynucleotide sequences that vary from one species to another. The resulting polypeptides will generally have significant amino acid identity relative to each other. A polymorphic variant is a variation in the polynucleotide sequence of a particular gene between individuals of a given species. Polymorphic variants also may encompass "single nucleotide polymorphisms" (SNPs) in which the polynucleotide sequence varies by one nucleotide base. The presence of SNPs may be indicative of, for example, a certain population, a disease state, or a propensity for a disease state.

A "variant" of a particular polypeptide sequence is defined as a polypeptide sequence having at least 40% sequence identity to the particular polypeptide sequence over a certain length of one of the polypeptide sequences using blastp with the "BLAST 2 Sequences" tool Version 2.0.9 (May 7, 1999) set at default parameters. Such a pair of polypeptides may show, for example, at least 50%, at least 60%, at least 70%, at least 80%, at least 90%, at least 91%, at least 92%, at least 93%, at least 94%, at least 95%, at least 96%, at least 97%, at least 98%, or at least 99% or greater sequence identity over a certain defined length of one of the polypeptides.

The Invention

The invention is based on the discovery of new human human kinases (PKIN), the polynucleotides encoding PKIN, and the use of these compositions for the diagnosis, treatment, or prevention of cancer, immune disorders, disorders affecting growth and development, cardiovascular diseases, and lipid disorders.

Table 1 summarizes the nomenclature for the full length polynucleotide and polypeptide sequences of the invention. Each polynucleotide and its corresponding polypeptide are correlated to a single Incyte project identification number (Incyte Project ID). Each polypeptide sequence is denoted by both a polypeptide sequence identification number (Polypeptide SEQ ID NO:) and an Incyte polypeptide sequence number (Incyte Polypeptide ID) as shown. Each polynucleotide sequence is denoted by both a polynucleotide sequence identification number (Polynucleotide SEQ ID NO:) and an Incyte polynucleotide consensus sequence number (Incyte Polynucleotide ID) as shown.

Table 2 shows sequences with homology to the polypeptides of the invention as identified by BLAST analysis against the GenBank protein (genpept) database. Columns 1 and 2 show the polypeptide sequence identification number (Polypeptide SEQ ID NO:) and the corresponding Incyte polypeptide sequence number (Incyte Polypeptide ID) for polypeptides of the invention. Column 3 shows the GenBank identification number (Genbank ID NO:) of the nearest GenBank homolog. Column 4 shows the probability score for the match between each polypeptide and its GenBank homolog. Column 5 shows the annotation of the GenBank homolog along with relevant citations where applicable, all of which are expressly incorporated by reference herein.

Table 3 shows various structural features of the polypeptides of the invention. Columns 1 and 2 show the polypeptide sequence identification number (SEQ ID NO:) and the corresponding Incyte polypeptide sequence number (Incyte Polypeptide ID) for each polypeptide of the invention. Column 3 shows the number of amino acid residues in each polypeptide. Column 4 shows potential phosphorylation sites, and column 5 shows potential glycosylation sites, as determined by the MOTIFS program of the GCG sequence analysis software package (Genetics Computer Group, Madison Wis.). Column 6 shows amino acid residues comprising signature sequences, domains, and motifs. Column 7 shows analytical methods for protein structure/function analysis and in some cases, searchable databases to which the analytical methods were applied.

Together, Tables 2 and 3 summarize the properties of polypeptides of the invention, and these properties establish that the claimed polypeptides are human kinases. For example, SEQ ID NO:2 is 95% identical to rat myotonic dystrophy kinase-related Cdc42-binding kinase (GenBank ID g2736151) as determined by the Basic Local Alignment Search Tool (BLAST). (See Table 2.) The BLAST probability score is 0.0, which indicates the probability of obtaining the observed polypeptide sequence alignment by chance. SEQ ID NO:2 also contains kinase active site domains, a phorbol ester binding domain, and a protein-protein interaction domain as determined by searching for statistically significant matches in the hidden Markov model (HMM)-based PFAM database of conserved protein family domains. (See Table 3.) BLIMPS, MOTIFS, and PROFILESCAN analyses confirm the presence of these domains and provide further corroborative evidence that SEQ ID NO:2 is a protein kinase. In an alternate example, SEQ ID NO:4 is 79% identical to *Rattus norvegicus* extracellular signal-regulated kinase 7 (ERK7) (GenBank ID g4220888) as determined by the Basic Local Alignment Search Tool (BLAST). (See Table 2.) The BLAST probability score is 5.3e-171, which indicates the probability of obtaining the observed polypeptide sequence alignment by chance. In another example, SEQ ID NO:4 is 47% identical to *Leishmania mexicana* MAP-kinase homologue (LMPK) (GenBank ID g2131000) with a probability score of 4.2e-70 as determined by the BLAST. (See Table 2.) it has been shown that *Leishmania mexicana* mutants, deleted for LMPK, loose the ability to cause a progressive disease in Balb/c mice. These *L. mexicana* mutants were restored to infectivity in complementation experiments, demonstrating that LMPK is essential for the infectivity of *L. mexicana* in an infected host. Additionally, SEQ ID NO:4 is 48% identical to a MAP-kinase homologue from the human malaria parasite, *Plasmodium falciparum* (GenBank ID g1360110) with a probability score of 5.8e-73 as determined by the BLAST. (See Table 2.) This homologue is closely related to MAP-kinases, which play important roles in eukaryotic adaptative response and signal transduction. SEQ ID NO:4 also contains a eukaryotic protein kinase domain as determined by searching for statistically significant matches in the hidden Markov model (HMM)-based PFAM database of conserved protein family domains. (See Table 3.) Data from BLIMPS reveals a tyrosine kinase catalytic domain signature (See Table 3.) Additional data from MOTIFS and PROFILESCAN analyses provide further corroborative evidence that SEQ ID NO:4 is a protein kinase. SEQ ID NO:5 is 45% identical to *Mus musculus* serine/threonine kinase (GenBank ID g404634) as determined by the BLAST. (See Table 2.) The BLAST probability score is 2.6e-54. SEQ ID NO:5 also contains a eukaryotic protein kinase domain as determined by searching for statistically significant matches in the hidden Markov model (HMM)-based PFAM database of conserved protein family domains. (See Table 3.) Data from BLIMPS_PRINTS reveals a tyrosine kinase catalytic domain signature. BLAST_DOMO data indicates the presence of a protein kinase domain. Additional data from MOTIFS and PROFILESCAN analyses provide further corroborative evidence that SEQ ID NO:5 is a protein kinase. In an alternate example, SEQ ID NO:7 is 53% identical to chicken qin-induced kinase (Qik), a serine-threonine kinase (GenBank ID g6760436) as determined by the Basic Local Alignment Search Tool (BLAST). (See Table 2.) The BLAST probability score is 9.2e-125, which indicates the probability of obtaining the observed polypeptide sequence alignment by chance. SEQ ID NO:7 also contains a eukaryotic protein kinase domain as determined by searching for statistically significant matches in the hidden Markov model (HMM)-based PFAM database of protein family domains. (See Table 3.) Data from BLIMPS, MOTIFS, and PROFILESCAN analyses provide further corroborative evidence that SEQ ID NO:7 is a protein kinase. In an alternate example, SEQ ID NO:8 is 55% identical to human adenylate kinase (GenBank ID g5757703) as determined by the Basic Local Alignment Search Tool (BLAST). (See Table 2.) The BLAST probability score is 0.0, which indicates the probability of obtaining the observed polypeptide sequence alignment by chance. SEQ ID NO:8 also contains a eukaryotic protein kinase domain and a PDZ domain, as determined by searching for statistically significant matches in the hidden Markov model (HMM)-based PFAM database of conserved protein family domains. (See Table 3.) Data from BLIMPS, MOTIFS, and PROFILESCAN analyses provide further corroborative evidence that SEQ ID NO:8 is a protein kinase. In an alternate example, SEQ ID NO:16 is 42% identical to rat serine/threonine protein kinase (GenBank ID g4115429) as determined by the Basic Local Alignment Search Tool (BLAST). (See Table 2.) The BLAST probability score is 7.9e-53, which indicates the probability of obtaining the observed polypeptide sequence alignment by chance. SEQ ID NO:16 also contains a eukaryotic protein kinase domain as determined by searching for statistically significant matches in the hidden Markov model (HMM)-based PFAM database of conserved protein family domains. (See Table 3.) Data from BLIMPS, MOTIFS, and PROFILESCAN analyses provide further corroborative evidence that SEQ ID NO:16 is a protein kinase. In an alternate example, SEQ ID NO:19 is 95% identical to rat nucleoside diphosphate kinase beta isoform (GenBank ID g286232) as determined by the Basic Local Alignment Search Tool (BLAST). (See Table 2.) The BLAST probability score is 3.1e-76, which indicates the probability of obtaining the observed polypeptide sequence alignment by chance. SEQ ID NO:19 also contains a nucleoside diphosphate kinase domain as determined by searching for statistically significant matches in the hidden Markov model (HMM)-based PFAM database of conserved protein family domains. (See Table 3.) Data from BLIMPS, MOTIFS, and PROFILESCAN analyses provide further corroborative evidence that SEQ ID NO:19 is a nucleoside diphosphate kinase. In an alternate example, SEQ ID NO:24 is 52% identical to murine apoptosis associated tyrosine kinase (GenBank ID g2459993) as determined by the Basic Local Alignment Search Tool (BLAST). (See Table 2.) The BLAST probability score is 1.5e-153, which indicates the probability of obtaining the observed polypeptide sequence alignment by chance. SEQ ID NO:24 also contains a eukaryotic protein kinase domain as determined by searching for statistically significant matches in the hidden Markov model (HMM)-based PFAM database of conserved protein family domains. (See Table 3.) Data from BLIMPS, MOTIFS, and PROFILESCAN analyses provide further corroborative evidence that SEQ ID NO:24 is a tyrosine kinase. SEQ ID NO:1, SEQ ID NO:3, SEQ ID NO:6, SEQ ID NO:9–15, SEQ ID NO:17–18, and SEQ ID NO:20–23 were analyzed and annotated in a similar manner. The algorithms and parameters for the analysis of SEQ ID NO:1–24 are described in Table 7.

As shown in Table 4, the full length polynucleotide sequences of the present invention were assembled using cDNA sequences or coding (exon) sequences derived from genomic DNA, or any combination of these two types of sequences. Columns 1 and 2 list the polynucleotide sequence identification number (Polynucleotide SEQ ID NO:) and the corresponding Incyte polynucleotide consensus sequence number (Incyte Polynucleotide ID) for each polynucleotide of the invention. Column 3 shows the length of each polynucleotide sequence in basepairs. Column 4 lists fragments of the polynucleotide sequences which are useful, for example, in hybridization or amplification technologies that identify SEQ ID NO:25–48 or that distinguish between SEQ ID NO:25–48 and related polynucleotide sequences. Column 5 shows identification numbers corresponding to cDNA sequences, coding sequences (exons) predicted from genomic DNA, and/or sequence assemblages comprised of both cDNA and genomic DNA. These sequences were used to assemble the full length polynucleotide sequences of the invention. Columns 6 and 7 of Table 4 show the nucleotide start (5') and stop (3') positions of the cDNA and/or genomic sequences in column 5 relative to their respective full length sequences.

The identification numbers in Column 5 of Table 4 may refer specifically, for example, to Incyte cDNAs along with their corresponding cDNA libraries. For example, 6259135F8 is the identification number of an Incyte cDNA sequence, and BMARTXT06 is the cDNA library from which it is derived. Incyte cDNAs for which cDNA libraries are not indicated were derived from pooled cDNA libraries (e.g., 71899371V1). Alternatively, the identification numbers in column 5 may refer to GenBank cDNAs or ESTs (e.g., g1441460) which contributed to the assembly of the full length polynucleotide sequences. In addition, the identification numbers in column 5 may identify sequences derived from the ENSEMBL (The Sanger Centre, Cambridge, UK) database (i.e., those sequences including the designation "ENST"). Alternatively, the identification numbers in column 5 may be derived from the NCBI RefSeq Nucleotide Sequence Records Database (i.e., those sequences including the designation "NM" or "NT") or the NCBI RefSeq Protein Sequence Records (i.e., those sequences including the designation "NP"). Alternatively, the identification numbers in column 5 may refer to assemblages of both cDNA and Genscan-predicted exons brought together by an "exon stitching" algorithm. For example, FL_XXXXXX_$N_1$_$N_2$_YYYYY_$N_3$_$N_4$ represents a "stitched" sequence in which XXXXXX is the identification number of the cluster of sequences to which the algorithm was applied, and YYYYY is the number of the prediction generated by the algorithm, and $N_{1,2,3}$, if present, represent specific exons that may have been manually edited during analysis (See Example V). Alternatively, the identification numbers in column 5 may refer to assemblages of exons brought together by an "exon-stretching" algorithm. For example, FLXXXXXX_gAAAAA_gBBBBB_1_N is the identification number of a "stretched" sequence, with XXXXXX being the Incyte project identification number, gAAAAA being the GenBank identification number of the human genomic sequence to which the "exon-stretching" algorithm was applied, gBBBBB being the GenBank identification number or NCBI RefSeq identification number of the nearest GenBank protein homolog, and N referring to specific exons (See Example V). In instances where a RefSeq sequence was used as a protein homolog for the "exon-stretching" algorithm, a RefSeq identifier (denoted by "NM," "NP," or "NT") may be used in place of the GenBank identifier (i.e., gBBBBB).

Alternatively, a prefix identifies component sequences that were hand-edited, predicted from genomic DNA sequences, or derived from a combination of sequence analysis methods. The following Table lists examples of component sequence prefixes and corresponding sequence analysis methods associated with the prefixes (see Example IV and Example V).

| Prefix | Type of analysis and/or examples of programs |
|---|---|
| GNN, GFG, ENST | Exon prediction from genomic sequences using, for example, GENSCAN (Stanford University, CA, USA) or FGENES (Computer Genomics Group, The Sanger Centre, Cambridge, UK). |
| GBI | Hand-edited analysis of genomic sequences. |
| FL | Stitched or stretched genomic sequences (see Example V). |
| INCY | Full length transcript and exon prediction from mapping of EST sequences to the genome. Genomic location and EST composition data are combined to predict the exons and resulting transcript. |

In some cases, Incyte cDNA coverage redundant with the sequence coverage shown in column 5 was obtained to confirm the final consensus polynucleotide sequence, but the relevant Incyte cDNA identification numbers are not shown.

Table 5 shows the representative cDNA libraries for those full length polynucleotide sequences which were assembled using Incyte cDNA sequences. The representative cDNA library is the Incyte cDNA library which is most frequently represented by the Incyte cDNA sequences which were used to assemble and confirm the above polynucleotide sequences. The tissues and vectors which were used to construct the cDNA libraries shown in Table 5 are described in Table 6.

The invention also encompasses PKIN variants. A preferred PKIN variant is one which has at least about 80%, or alternatively at least about 90%, or even at least about 95% amino acid sequence identity to the PKIN amino acid sequence, and which contains at least one functional or structural characteristic of PKIN.

The invention also encompasses polynucleotides which encode PKIN. In a particular embodiment, the invention encompasses a polynucleotide sequence comprising a sequence selected from the group consisting of SEQ ID NO:25–48, which encodes PKIN. The polynucleotide sequences of SEQ ID NO:25–48, as presented in the Sequence Listing, embrace the equivalent RNA sequences, wherein occurrences of the nitrogenous base thymine are replaced with uracil, and the sugar backbone is composed of ribose instead of deoxyribose.

The invention also encompasses a variant of a polynucleotide sequence encoding PKIN. In particular, such a variant polynucleotide sequence will have at least about 70%, or alternatively at least about 85%, or even at least about 95% polynucleotide sequence identity to the polynucleotide sequence encoding PKIN. A particular aspect of the invention encompasses a variant of a polynucleotide sequence comprising a sequence selected from the group consisting of SEQ ID NO:25–48 which has at least about 70%, or alternatively at least about 85%, or even at least about 95% polynucleotide sequence identity to a nucleic acid sequence selected from the group consisting of SEQ ID NO:25–48. Any one of the polynucleotide variants described above can encode an amino acid sequence which contains at least one functional or structural characteristic of PKIN.

It will be appreciated by those skilled in the art that as a result of the degeneracy of the genetic code, a multitude of polynucleotide sequences encoding PKIN, some bearing minimal similarity to the polynucleotide sequences of any known and naturally occurring gene, may be produced. Thus, the invention contemplates each and every possible variation of polynucleotide sequence that could be made by selecting combinations based on possible codon choices. These combinations are made in accordance with the standard triplet genetic code as applied to the polynucleotide sequence of naturally occurring PKIN, and all such variations are to be considered as being specifically disclosed.

Although nucleotide sequences which encode PKIN and its variants are generally capable of hybridizing to the nucleotide sequence of the naturally occurring PKIN under appropriately selected conditions of stringency, it may be advantageous to produce nucleotide sequences encoding PKIN or its derivatives possessing a substantially different codon usage, e.g., inclusion of non-naturally occurring codons. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding PKIN and its derivatives without altering the encoded amino acid sequences include the production of RNA transcripts having more desirable properties, such as a greater half-life, than transcripts produced from the naturally occurring sequence.

The invention also encompasses production of DNA sequences which encode PKIN and PKIN derivatives, or fragments thereof, entirely by synthetic chemistry. After production, the synthetic sequence may be inserted into any of the many available expression vectors and cell systems using reagents well known in the art. Moreover, synthetic chemistry may be used to introduce mutations into a sequence encoding PKIN or any fragment thereof.

Also encompassed by the invention are polynucleotide sequences that are capable of hybridizing to the claimed polynucleotide sequences, and, in particular, to those shown in SEQ ID NO:25–48 and fragments thereof under various conditions of stringency. (See, e.g., Wahl, G. M. and S. L. Berger (1987) Methods Enzymol. 152:399–407; Kimmel, A. R. (1987) Methods Enzymol. 152:507–511.) Hybridization conditions, including annealing and wash conditions, are described in "Definitions."

Methods for DNA sequencing are well known in the art and may be used to practice any of the embodiments of the invention. The methods may employ such enzymes as the Klenow fragment of DNA polymerase I, SEQUENASE (US Biochemical, Cleveland Ohio), Taq polymerase (Applied Biosystems), thermostable T7 polymerase (Amersham Pharmacia Biotech, Piscataway N.J.), or combinations of polymerases and proofreading exonucleases such as those found in the ELONGASE amplification system (Life Technologies, Gaithersburg Md.). Preferably, sequence preparation is automated with machines such as the MICROLAB 2200 liquid transfer system (Hamilton, Reno Nev.), PTC200 thermal cycler (MJ Research, Watertown Mass.) and ABI CATALYST 800 thermal cycler (Applied Biosystems). Sequencing is then carried out using either the ABI 373 or 377 DNA sequencing system (Applied Biosystems), the MEGABACE 1000 DNA sequencing system (Molecular Dynamics, Sunnyvale Calif.), or other systems known in the art. The resulting sequences are analyzed using a variety of algorithms which are well known in the art. (See, e.g., Ausubel, F. M. (1997) *Short Protocols in Molecular Biology,* John Wiley & Sons, New York N.Y., unit 7.7; Meyers, R. A. (1995) *Molecular Biology and Biotechnology,* Wiley VCH, New York N.Y., pp. 856–853.)

The nucleic acid sequences encoding PKIN may be extended utilizing a partial nucleotide sequence and employing various PCR-based methods known in the art to detect upstream sequences, such as promoters and regulatory elements. For example, one method which may be employed, restriction-site PCR, uses universal and nested primers to amplify unknown sequence from genomic DNA within a cloning vector. (See, e.g., Sarkar, G. (1993) PCR Methods Applic. 2:318–322.) Another method, inverse PCR, uses primers that extend in divergent directions to amplify unknown sequence from a circularized template. The template is derived from restriction fragments comprising a known genomic locus and surrounding sequences. (See, e.g., Triglia, T. et al. (1988) Nucleic Acids Res. 16:8186.) A third method, capture PCR, involves PCR amplification of DNA fragments adjacent to known sequences in human and yeast artificial chromosome DNA. (See, e.g., Lagerstrom, M. et al. (1991) PCR Methods Applic. 1:111–119.) In this method, multiple restriction enzyme digestions and ligations may be used to insert an engineered double-stranded sequence into a region of unknown sequence before performing PCR. Other methods which may be used to retrieve unknown sequences are known in the art. (See, e.g., Parker, J. D. et al. (1991) Nucleic Acids Res. 19:3055–3060). Additionally, one may use PCR, nested primers, and PROMOTERFINDER libraries (Clontech, Palo Alto Calif.) to walk genomic DNA. This procedure avoids the need to screen libraries and is useful in finding intron/exon junctions. For all PCR-based methods, primers may be designed using commercially available software, such as OLIGO 4.06 primer analysis software (National Biosciences, Plymouth Minn.) or another appropriate program, to be about 22 to 30 nucleotides in length, to have a GC content of about 50% or more, and to anneal to the template at temperatures of about 68° C. to 72° C.

When screening for full length cDNAs, it is preferable to use libraries that have been size-selected to include larger cDNAs. In addition, random-primed libraries, which often include sequences containing the 5' regions of genes, are preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different nucleotide-specific, laser-stimulated fluorescent dyes, and a charge coupled device camera for detection of the emitted wavelengths. Output/light intensity may be converted to electrical signal using appropriate software (e.g., GENOTYPER and SEQUENCE NAVIGATOR, Applied Biosystems), and the entire process from loading of samples to computer analysis and electronic data display may be computer controlled. Capillary electrophoresis is especially preferable for sequencing small DNA fragments which may be present in limited amounts in a particular sample.

In another embodiment of the invention, polynucleotide sequences or fragments thereof which encode PKIN may be cloned in recombinant DNA molecules that direct expression of PKIN, or fragments or functional equivalents thereof, in appropriate host cells. Due to the inherent degeneracy of the genetic code, other DNA sequences which encode substantially the same or a functionally equivalent amino acid sequence may be produced and used to express PKIN.

The nucleotide sequences of the present invention can be engineered using methods generally known in the art in order to alter PKIN-encoding sequences for a variety of purposes including, but not limited to, modification of the cloning, processing, and/or expression of the gene product. DNA shuffling by random fragmentation and PCR reassembly of gene fragments and synthetic oligonucleotides may be used to engineer the nucleotide sequences. For example, oligonucleotide-mediated site-directed mutagenesis may be used to introduce mutations that create new restriction sites, alter glycosylation patterns, change codon preference, produce splice variants, and so forth.

The nucleotides of the present invention may be subjected to DNA shuffling techniques such as MOLECULAR-BREEDING (Maxygen Inc., Santa Clara Calif.; described in U.S. Pat. No. 5,837,458; Chang, C. -C. et al. (1999) Nat. Biotechnol. 17:793–797; Christians, F. C. et al. (1999) Nat. Biotechnol. 17:259–264; and Crameri, A. et al. (1996) Nat. Biotechnol. 14:315–319) to alter or improve the biological properties of PKIN, such as its biological or enzymatic activity or its ability to bind to other molecules or compounds. DNA shuffling is a process by which a library of gene variants is produced using PCR-mediated recombination of gene fragments. The library is then subjected to selection or screening procedures that identify those gene variants with the desired properties. These preferred variants may then be pooled and further subjected to recursive rounds of DNA shuffling and selection/screening. Thus, genetic diversity is created through "artificial" breeding and rapid molecular evolution. For example, fragments of a single gene containing random point mutations may be recombined, screened, and then reshuffled until the desired properties are optimized. Alternatively, fragments of a given gene may be recombined with fragments of homologous genes in the same gene family, either from the same or different species, thereby maximizing the genetic diversity of multiple naturally occurring genes in a directed and controllable manner.

In another embodiment, sequences encoding PKIN may be synthesized, in whole or in part, using chemical methods well known in the art. (See, e.g., Caruthers, M. H. et al. (1980) Nucleic Acids Symp. Ser. 7:215–223; and Horn, T. et al. (1980) Nucleic Acids Symp. Ser. 7:225–232.) Alternatively, PKIN itself or a fragment thereof may be synthesized using chemical methods. For example, peptide synthesis can be performed using various solution-phase or solid-phase techniques. (See, e.g., Creighton, T. (1984) *Proteins, Structures and Molecular Properties,* WH Freeman, New York N.Y., pp. 55–60; and Roberge, J. Y. et al. (1995) Science 269:202–204.) Automated synthesis may be achieved using the ABI 431A peptide synthesizer (Applied Biosystems). Additionally, the amino acid sequence of PKIN, or any part thereof, may be altered during direct synthesis and/or combined with sequences from other proteins, or any part thereof, to produce a variant polypeptide or a polypeptide having a sequence of a naturally occurring polypeptide.

The peptide may be substantially purified by preparative high performance liquid chromatography. (See, e.g., Chiez, R. M. and F. Z. Regnier (1990) Methods Enzymol. 182: 392–421.) The composition of the synthetic peptides may be confirmed by amino acid analysis or by sequencing. (See, e.g., Creighton, supra, pp. 28–53.)

In order to express a biologically active PKIN, the nucleotide sequences encoding PKIN or derivatives thereof may be inserted into an appropriate expression vector, i.e., a vector which contains the necessary elements for transcriptional and translational control of the inserted coding sequence in a suitable host. These elements include regulatory sequences, such as enhancers, constitutive and inducible promoters, and 5' and 3' untranslated regions in the vector and in polynucleotide sequences encoding PKIN. Such elements may vary in their strength and specificity. Specific initiation signals may also be used to achieve more efficient translation of sequences encoding PKIN. Such signals include the ATG initiation codon and adjacent sequences, e.g. the Kozak sequence. In cases where sequences encoding PKIN and its initiation codon and upstream regulatory sequences are inserted into the appropriate expression vector, no additional transcriptional or translational control signals may be needed. However, in cases where only coding sequence, or a fragment thereof, is inserted, exogenous translational control signals including an in-frame ATG initiation codon should be provided by the vector. Exogenous translational elements and initiation codons may be of various origins, both natural and synthetic. The efficiency of expression may be enhanced by the inclusion of enhancers appropriate for the particular host cell system used. (See, e.g., Scharf, D. et al. (1994) Results Probl. Cell Differ. 20:125–162.)

Methods which are well known to those skilled in the art may be used to construct expression vectors containing sequences encoding PKIN and appropriate transcriptional and translational control elements. These methods include in vitro recombinant DNA techniques, synthetic techniques, and in vivo genetic recombination. (See, e.g., Sambrook, J. et al. (1989) *Molecular Cloning, A Laboratory Manual,* Cold Spring Harbor Press, Plainview N.Y., ch. 4, 8, and 16–17; Ausubel, F. M. et al. (1995) *Current Protocols in Molecular Biology,* John Wiley & Sons, New York N.Y., ch. 9, 13, and 16.)

A variety of expression vector/host systems may be utilized to contain and express sequences encoding PKIN. These include, but are not limited to, microorganisms such as bacteria transformed with recombinant bacteriophage, plasmid, or cosmid DNA expression vectors; yeast transformed with yeast expression vectors; insect cell systems infected with viral expression vectors (e.g., baculovirus); plant cell systems transformed with viral expression vectors (e.g., cauliflower mosaic virus, CaMV, or tobacco mosaic virus, TMV) or with bacterial expression vectors (e.g., Ti or pBR322 plasmids); or animal cell systems. (See, e.g., Sambrook, supra; Ausubel, supra; Van Heeke, G. and S. M. Schuster (1989) J. Biol. Chem. 264:5503–5509; Engelhard, E. K. et al. (1994) Proc. Natl. Acad. Sci. USA 91:3224–3227; Sandig, V. et al. (1996) Hum. Gene Ther. 7:1937–1945; Takamatsu, N. (1987) EMBO J. 6:307–311; *The McGraw Hill Yearbook of Science and Technology* (1992) McGraw Hill, New York N.Y., pp. 191–196; Logan, J. and T. Shenk (1984) Proc. Natl. Acad. Sci. USA 81:3655–3659; and Harrington, J. J. et al. (1997) Nat. Genet. 15:345–355.) Expression vectors derived from retroviruses, adenoviruses, or herpes or vaccinia viruses, or from various bacterial plasmids, may be used for delivery of nucleotide sequences to the targeted organ, tissue, or cell population. (See, e.g., Di Nicola, M. et al. (1998) Cancer Gen. Ther. 5(6):350–356; Yu, M. et al. (1993) Proc. Natl. Acad. Sci. USA 90(13):6340–6344; Buller, R. M. et al. (1985) Nature 317(6040):813–815; McGregor, D. P. et al. (1994) Mol. Immunol. 31(3):219–226; and Verma, I. M. and N. Somia (1997) Nature 389:239–242.) The invention is not limited by the host cell employed.

In bacterial systems, a number of cloning and expression vectors may be selected depending upon the use intended for polynucleotide sequences encoding PKIN. For example, routine cloning, subcloning, and propagation of polynucleotide sequences encoding PKIN can be achieved using a multifunctional *E. coli* vector such as PBLUESCRIPT (Stratagene, La Jolla Calif.) or PSPORT1 plasmid (Life Technologies). Ligation of sequences encoding PKIN into the vector's multiple cloning site disrupts the lacZ gene, allowing a colorimetric screening procedure for identification of transformed bacteria containing recombinant molecules. In addition, these vectors may be useful for in vitro transcription, dideoxy sequencing, single strand rescue with helper phage, and creation of nested deletions in the cloned sequence. (See, e.g., Van Heeke, G. and S. M. Schuster (1989) J. Biol. Chem. 264:5503–5509.) When large quantities of PKIN are needed, e.g. for the production of antibodies, vectors which direct high level expression of PKIN may be used. For example, vectors containing the strong, inducible SP6 or T7 bacteriophage promoter may be used.

Yeast expression systems may be used for production of PKIN. A number of vectors containing constitutive or inducible promoters, such as alpha factor, alcohol oxidase, and PGH promoters, may be used in the yeast *Saccharomyces cerevisiae* or *Pichia pastoris*. In addition, such vectors direct either the secretion or intracellular retention of expressed proteins and enable integration of foreign sequences into the host genome for stable propagation. (See, e.g., Ausubel, 1995, supra; Bitter, G. A. et al. (1987) Methods Enzymol. 153:516–544; and Scorer, C. A. et al. (1994) Bio/Technology 12:181–184.)

Plant systems may also be used for expression of PKIN. Transcription of sequences encoding PKIN may be driven by viral promoters, e.g., the 35S and 19S promoters of CaMV used alone or in combination with the omega leader sequence from TMV (Takamatsu, N. (1987) EMBO J. 6:307–311). Alternatively, plant promoters such as the small subunit of RUBISCO or heat shock promoters may be used. (See, e.g., Coruzzi, G. et al. (1984) EMBO J. 3:1671–1680; Broglie, R. et al. (1984) Science 224:838–843; and Winter, J. et al. (1991) Results Probl. Cell Differ. 17:85–105.) These constructs can be introduced into plant cells by direct DNA transformation or pathogen-mediated transfection. (See, e.g., *The McGraw Hill Yearbook of Science and Technology* (1992) McGraw Hill, New York N.Y., pp. 191–196.)

In mammalian cells, a number of viral-based expression systems may be utilized. In cases where an adenovirus is used as an expression vector, sequences encoding PKIN may be ligated into an adenovirus transcription/translation complex consisting of the late promoter and tripartite leader sequence. Insertion in a non-essential E1 or E3 region of the viral genome may be used to obtain infective virus which expresses PKIN in host cells. (See, e.g., Logan, J. and T. Shenk (1984) Proc. Natl. Acad. Sci. USA 81:3655–3659.) In addition, transcription enhancers, such as the Rous sarcoma virus (RSV) enhancer, may be used to increase expression in mammalian host cells. SV40 or EBV-based vectors may also be used for high-level protein expression.

Human artificial chromosomes (HACs) may also be employed to deliver larger fragments of DNA than can be contained in and expressed from a plasmid. HACs of about 6 kb to 10 Mb are constructed and delivered via conventional delivery methods (liposomes, polycationic amino polymers, or vesicles) for therapeutic purposes. (See, e.g., Harrington, J. J. et al. (1997) Nat. Genet. 15:345–355.)

For long term production of recombinant proteins in mammalian systems, stable expression of PKIN in cell lines is preferred. For example, sequences encoding PKIN can be transformed into cell lines using expression vectors which may contain viral origins of replication and/or endogenous expression elements and a selectable marker gene on the same or on a separate vector. Following the introduction of the vector, cells may be allowed to grow for about 1 to 2 days in enriched media before being switched to selective media. The purpose of the selectable marker is to confer resistance to a selective agent, and its presence allows growth and recovery of cells which successfully express the introduced sequences. Resistant clones of stably transformed cells may be propagated using tissue culture techniques appropriate to the cell type.

Any number of selection systems may be used to recover transformed cell lines. These include, but are not limited to, the herpes simplex virus thymidine kinase and adenine phosphoribosyltransferase genes, for use in tk$^-$ and apr$^-$ cells, respectively. (See, e.g., Wigler, M. et al. (1977) Cell 11:223–232; Lowy, I. et al. (1980) Cell 22:817–823.) Also, antimetabolite, antibiotic, or herbicide resistance can be used as the basis for selection. For example, dhfr confers resistance to methotrexate; neo confers resistance to the aminoglycosides neomycin and G-418; and als and pat confer resistance to chlorsulfuron and phosphinotricin acetyltransferase, respectively. (See, e.g., Wigler, M. et al. (1980) Proc. Natl. Acad. Sci. USA 77:3567–3570; Colbere-Garapin, F. et al. (1981) J. Mol. Biol. 150:1–14.) Additional selectable genes have been described, e.g., trpB and hisD, which alter cellular requirements for metabolites. (See, e.g., Hartman, S. C. and R. C. Mulligan (1988) Proc. Natl. Acad. Sci. USA 85:8047–8051.) Visible markers, e.g., anthocyanins, green fluorescent proteins (GFP; Clontech), β glucuronidase and its substrate β-glucuronide, or luciferase and its substrate luciferin may be used. These markers can be used not only to identify transformants, but also to quantify the amount of transient or stable protein expression attributable to a specific vector system. (See, e.g., Rhodes, C. A. (1995) Methods Mol. Biol. 55:121–131.)

Although the presence/absence of marker gene expression suggests that the gene of interest is also present, the presence and expression of the gene may need to be confirmed. For example, if the sequence encoding PKIN is inserted within a marker gene sequence, transformed cells containing sequences encoding PKIN can be identified by the absence of marker gene function. Alternatively, a marker gene can be placed in tandem with a sequence encoding PKIN under the control of a single promoter. Expression of the marker gene in response to induction or selection usually indicates expression of the tandem gene as well.

In general, host cells that contain the nucleic acid sequence encoding PKIN and that express PKIN may be identified by a variety of procedures known to those of skill in the art. These procedures include, but are not limited to, DNA-DNA or DNA-RNA hybridizations, PCR amplification, and protein bioassay or immunoassay techniques which include membrane, solution, or chip based technologies for the detection and/or quantification of nucleic acid or protein sequences.

Immunological methods for detecting and measuring the expression of PKIN using either specific polyclonal or monoclonal antibodies are known in the art. Examples of such techniques include enzyme-linked immunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes on PKIN is preferred, but a competitive binding assay may be employed. These and other assays are well known in the art. (See, e.g., Hampton, R. et al. (1990) *Serological Methods, a Laboratory Manual*, APS Press, St. Paul Minn., Sect. IV; Coligan, J. E. et al. (1997) *Current Protocols in Immunology*, Greene Pub. Associates and Wiley-Interscience, New York N.Y.; and Pound, J. D. (1998) *Immunochemical Protocols*, Humana Press, Totowa N.J.)

A wide variety of labels and conjugation techniques are known by those skilled in the art and may be used in various nucleic acid and amino acid assays. Means for producing labeled hybridization or PCR probes for detecting sequences related to polynucleotides encoding PKIN include oligolabeling, nick translation, end-labeling, or PCR amplification using a labeled nucleotide. Alternatively, the sequences encoding PKIN, or any fragments thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits, such as those provided by Amersham Pharmacia Biotech, Promega (Madison Wis.), and US Biochemical. Suitable reporter molecules or labels which may be used for ease of detection include radionuclides, enzymes, fluorescent, chemiluminescent, or chromogenic agents, as well as substrates, cofactors, inhibitors, magnetic particles, and the like.

Host cells transformed with nucleotide sequences encoding PKIN may be cultured under conditions suitable for the expression and recovery of the protein from cell culture. The protein produced by a transformed cell may be secreted or retained intracellularly depending on the sequence and/or the vector used. As will be understood by those of skill in the art, expression vectors containing polynucleotides which encode PKIN may be designed to contain signal sequences which direct secretion of PKIN through a prokaryotic or eukaryotic cell membrane.

In addition, a host cell strain may be chosen for its ability to modulate expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" or "pro" form of the protein may also be used to specify protein targeting, folding, and/or activity. Different host cells which have specific cellular machinery and characteristic mechanisms for post-translational activities (e.g., CHO, HeLa, MDCK, HEK293, and W138) are available from the American Type Culture Collection (ATCC, Manassas Va.) and may be chosen to ensure the correct modification and processing of the foreign protein.

In another embodiment of the invention, natural, modified, or recombinant nucleic acid sequences encoding PKIN may be ligated to a heterologous sequence resulting in translation of a fusion protein in any of the aforementioned host systems. For example, a chimeric PKIN protein containing a heterologous moiety that can be recognized by a commercially available antibody may facilitate the screening of peptide libraries for inhibitors of PKIN activity. Heterologous protein and peptide moieties may also facilitate purification of fusion proteins using commercially available affinity matrices. Such moieties include, but are not limited to, glutathione S-transferase (GST), maltose binding protein (MBP), thioredoxin (Trx), calmodulin binding peptide (CBP), 6-His, FLAG, c-myc, and hemagglutinin (HA). GST, MBP, Trx, CBP, and 6-His enable purification of their cognate fusion proteins on immobilized glutathione, maltose, phenylarsine oxide, calmodulin, and metal-chelate resins, respectively. FLAG, c-myc, and hemagglutinin (HA) enable immunoaffinity purification of fusion proteins using commercially available monoclonal and polyclonal antibodies that specifically recognize these epitope tags. A fusion protein may also be engineered to contain a proteolytic cleavage site located between the PKIN encoding sequence and the heterologous protein sequence, so that PKIN may be cleaved away from the heterologous moiety following purification. Methods for fusion protein expression and purification are discussed in Ausubel (1995, supra, ch. 10). A variety of commercially available kits may also be used to facilitate expression and purification of fusion proteins.

In a further embodiment of the invention, synthesis of radiolabeled PKIN may be achieved in vitro using the TNT rabbit reticulocyte lysate or wheat germ extract system (Promega). These systems couple transcription and translation of protein-coding sequences operably associated with the T7, T3, or SP6 promoters. Translation takes place in the presence of a radiolabeled amino acid precursor, for example, $^{35}$S-methionine.

PKIN of the present invention or fragments thereof may be used to screen for compounds that specifically bind to PKIN. At least one and up to a plurality of test compounds may be screened for specific binding to PKIN. Examples of test compounds include antibodies, oligonucleotides, proteins (e.g., receptors), or small molecules.

In one embodiment, the compound thus identified is closely related to the natural ligand of PKIN, e.g., a ligand or fragment thereof, a natural substrate, a structural or functional mimetic, or a natural binding partner. (See, e.g., Coligan, J. E. et al. (1991) Current Protocols in Immunology 1(2): Chapter 5.) Similarly, the compound can be closely related to the natural receptor to which PKIN binds, or to at least a fragment of the receptor, e.g., the ligand binding site. In either case, the compound can be rationally designed using known techniques. In one embodiment, screening for these compounds involves producing appropriate cells which express PKIN, either as a secreted protein or on the cell membrane. Preferred cells include cells from mammals, yeast, Drosophila, or E. coli. Cells expressing PKIN or cell membrane fractions which contain PKIN are then contacted with a test compound and binding, stimulation, or inhibition of activity of either PKIN or the compound is analyzed.

An assay may simply test binding of a test compound to the polypeptide, wherein binding is detected by a fluorophore, radioisotope, enzyme conjugate, or other detectable label. For example, the assay may comprise the steps of combining at least one test compound with PKIN, either in solution or affixed to a solid support, and detecting the binding of PKIN to the compound. Alternatively, the assay may detect or measure binding of a test compound in the presence of a labeled competitor. Additionally, the assay may be carried out using cell-free preparations, chemical libraries, or natural product mixtures, and the test compound(s) may be free in solution or affixed to a solid support.

PKIN of the present invention or fragments thereof may be used to screen for compounds that modulate the activity of PKIN. Such compounds may include agonists, antagonists, or partial or inverse agonists. In one embodiment, an assay is performed under conditions permissive for PKIN activity, wherein PKIN is combined with at least one test compound, and the activity of PKIN in the presence of a test compound is compared with the activity of PKIN in the absence of the test compound. A change in the activity of PKIN in the presence of the test compound is indicative of a compound that modulates the activity of PKIN. Alternatively, a test compound is combined with an in vitro or cell-free system comprising PKIN under conditions suitable for PKIN activity, and the assay is performed. In either of these assays, a test compound which modulates the activity of PKIN may do so indirectly and need not come in direct contact with the test compound. At least one and up to a plurality of test compounds may be screened.

In another embodiment, polynucleotides encoding PKIN or their mammalian homologs may be "knocked out" in an animal model system using homologous recombination in embryonic stem (ES) cells. Such techniques are well known in the art and are useful for the generation of animal models of human disease. (See, e.g., U.S. Pat. Nos. 5,175,383 and 5,767,337.) For example, mouse ES cells, such as the mouse 129/SvJ cell line, are derived from the early mouse embryo and grown in culture. The ES cells are transformed with a vector containing the gene of interest disrupted by a marker gene, e.g., the neomycin phosphotransferase gene (neo; Capecchi, M. R. (1989) Science 244:1288–1292). The vector integrates into the corresponding region of the host genome by homologous recombination. Alternatively, homologous recombination takes place using the Cre-loxP system to knockout a gene of interest in a tissue- or developmental stage-specific manner (Marth, J. D. (1996) Clin. Invest. 97:1999–2002; Wagner, K. U. et al. (1997) Nucleic Acids Res. 25:4323–4330). Transformed ES cells are identified and microinjected into mouse cell blastocysts such as those from the C57BL/6 mouse strain. The blastocysts are surgically transferred to pseudopregnant dams, and the resulting chimeric progeny are genotyped and bred to produce heterozygous or homozygous strains. Transgenic animals thus generated may be tested with potential therapeutic or toxic agents.

Polynucleotides encoding PKIN may also be manipulated in vitro in ES cells derived from human blastocysts. Human ES cells have the potential to differentiate into at least eight separate cell lineages including endoderm, mesoderm, and ectodermal cell types. These cell lineages differentiate into, for example, neural cells, hematopoietic lineages, and cardiomyocytes (Thomson, J. A. et al. (1998) Science 282: 1145–1147).

Polynucleotides encoding PKIN can also be used to create "knockin" humanized animals (pigs) or transgenic animals (mice or rats) to model human disease. With knockin technology, a region of a polynucleotide encoding PKIN is injected into animal ES cells, and the injected sequence integrates into the animal cell genome. Transformed cells are injected into blastulae, and the blastulae are implanted as described above. Transgenic progeny or inbred lines are studied and treated with potential pharmaceutical agents to obtain information on treatment of a human disease. Alternatively, a mammal inbred to overexpress PKIN, e.g., by secreting PKIN in its milk, may also serve as a convenient source of that protein (Janne, J. et al. (1998) Biotechnol. Annu. Rev. 4:55–74).

Therapeutics

Chemical and structural similarity, e.g., in the context of sequences and motifs, exists between regions of PKIN and human kinases. In addition, the expression of PKIN is closely associated with neurological, brain, immune system, diseased, developing, myometrium, smooth muscle cell, thyroid, nervous, reproductive, lung, gastrointestinal, developmental, tumorous, and cardiac tissues. Therefore, PKIN appears to play a role in cancer, immune disorders, disorders affecting growth and development, cardiovascular diseases, and lipid disorders. In the treatment of disorders associated with increased PKIN expression or activity, it is desirable to decrease the expression or activity of PKIN. In the treatment of disorders associated with decreased PKIN expression or activity, it is desirable to increase the expression or activity of PKIN.

Therefore, in one embodiment, PKIN or a fragment or derivative thereof may be administered to a subject to treat or prevent a disorder associated with decreased expression or activity of PKIN. Examples of such disorders include, but are not limited to, a cancer, such as adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus, leukemias such as multiple myeloma and lymphomas such as Hodgkin's disease; an immune disorder, such as acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, autoimmune polyendocrinopathy-candidiasis-ectodermal dystrophy (APECED), bronchitis, cholecystitis, contact dermatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scleroderma, Sjögren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, and trauma; a growth and developmental disorder, such as actinic keratosis, arteriosclerosis, atherosclerosis, bursitis, cirrhosis, hepatitis, mixed connective tissue disease (MCTD), myelofibrosis, paroxysmal nocturnal hemoglobinuria, polycythemia vera, psoriasis, primary thrombocythemia, and cancers including adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus, renal tubular acidosis, anemia, Cushing's syndrome, achondroplastic dwarfism, Duchenne and Becker muscular dystrophy, epilepsy, gonadal dysgenesis, WAGR syndrome (Wilms' tumor, aniridia, genitourinary abnormalities, and mental retardation), Smith-Magenis syndrome, myelodysplastic syndrome, hereditary mucoepithelial dysplasia, hereditary keratodermas, hereditary neuropathies such as Charcot-Marie-Tooth disease and neurofibromatosis, hypothyroidism, hydrocephalus, seizure disorders such as Syndenham's chorea and cerebral palsy, spina bifida, anencephaly, craniorachischisis, congenital glaucoma, cataract, and sensorineural hearing loss; a cardiovascular disease, such as arteriovenous fistula, atherosclerosis, hypertension, vasculitis, Raynaud's disease, aneurysms, arterial dissections, varicose veins, thrombophlebitis and phlebothrombosis, vascular tumors, and complications of thrombolysis, balloon angioplasty, vascular replacement, and coronary artery bypass graft surgery, congestive heart failure, ischemic heart disease, angina pectoris, myocardial infarction, hypertensive heart disease, degenerative valvular heart disease, calcific aortic valve stenosis, congenitally bicuspid aortic valve, mitral annular calcification, mitral valve prolapse, rheumatic fever and rheumatic heart disease, infective endocarditis, nonbacterial thrombotic endocarditis, endocarditis of systemic lupus erythematosus, carcinoid heart disease, cardiomyopathy, myocarditis, pericarditis, neoplastic heart disease, congenital heart disease, and complications of cardiac transplantation, congenital lung anomalies, atelectasis, pulmonary congestion and edema, pulmonary embolism, pulmonary hemorrhage, pulmonary infarction, pulmonary hypertension, vascular sclerosis, obstructive pulmonary disease, restrictive pulmonary disease, chronic obstructive pulmonary disease, emphysema, chronic bronchitis, bronchial asthma, bronchiectasis, bacterial pneumonia, viral and mycoplasmal pneumonia, lung abscess, pulmonary tuberculosis, diffuse interstitial diseases, pneumoconioses, sarcoidosis, idiopathic pulmonary fibrosis, desquamative interstitial pneumonitis, hypersensitivity pneumonitis, pulmonary eosinophilia bronchiolitis obliterans-organizing pneumonia, diffuse pulmonary hemorrhage syndromes, Goodpasture's syndromes, idiopathic pulmonary hemosiderosis, pulmonary involvement in collagen-vascular disorders, pulmonary alveolar proteinosis, lung tumors, inflammatory and noninflammatory pleural effusions, pneumothorax, pleural tumors, drug-induced lung disease, radiation-induced lung disease, and complications of lung transplantation; and a lipid disorder such as fatty liver, cholestasis, primary biliary cirrhosis, carnitine deficiency, carnitine palmitoyltransferase deficiency, myoadenylate deaminase deficiency, hypertriglyceridemia, lipid storage disorders such Fabry's disease, Gaucher's disease, Niemann-Pick's disease, metachromatic leukodystrophy, adrenoleukodystrophy, $GM_2$ gangliosidosis, and ceroid lipofuscinosis, abetalipoproteinemia, Tangier disease, hyperlipoproteinemia, diabetes mellitus, lipodystrophy, lipomatoses, acute panniculitis, disseminated fat necrosis, adiposis dolorosa, lipoid adrenal hyperplasia, minimal change disease, lipomas, atherosclerosis, hypercholesterolemia, hypercholesterolemia with hypertriglyceridemia, primary hypoalphalipoproteinemia, hypothyroidism, renal disease, liver disease, lecithin:cholesterol acyltransferase deficiency, cerebrotendinous xanthomatosis, sitosterolemia, hypocholesterolemia, Tay-Sachs disease, Sandhoff's disease, hyperlipidemia, hyperlipemia, lipid myopathies, and obesity.

In another embodiment, a vector capable of expressing PKIN or a fragment or derivative thereof may be administered to a subject to treat or prevent a disorder associated with decreased expression or activity of PKIN including, but not limited to, those described above.

In a further embodiment, a composition comprising a substantially purified PKIN in conjunction with a suitable pharmaceutical carrier may be administered to a subject to treat or prevent a disorder associated with decreased expression or activity of PKIN including, but not limited to, those provided above.

In still another embodiment, an agonist which modulates the activity of PKIN may be administered to a subject to treat or prevent a disorder associated with decreased expression or activity of PKIN including, but not limited to, those listed above.

In a further embodiment, an antagonist of PKIN may be administered to a subject to treat or prevent a disorder associated with increased expression or activity of PKIN. Examples of such disorders include, but are not limited to, those cancer, immune disorders, disorders affecting growth and development, cardiovascular diseases, and lipid disorders described above. In one aspect, an antibody which specifically binds PKIN may be used directly as an antagonist or indirectly as a targeting or delivery mechanism for bringing a pharmaceutical agent to cells or tissues which express PKIN.

In an additional embodiment, a vector expressing the complement of the polynucleotide encoding PKIN may be administered to a subject to treat or prevent a disorder associated with increased expression or activity of PKIN including, but not limited to, those described above.

In other embodiments, any of the proteins, antagonists, antibodies, agonists, complementary sequences, or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of PKIN may be produced using methods which are generally known in the art. In particular, purified PKIN may be used to produce antibodies or to screen libraries of pharmaceutical agents to identify those which specifically bind PKIN. Antibodies to PKIN may also be generated using methods that are well known in the art. Such antibodies may include, but are not limited to, polyclonal, monoclonal, chimeric, and single chain antibodies, Fab fragments, and fragments produced by a Fab expression library. Neutralizing antibodies (i.e., those which inhibit dimer formation) are generally preferred for therapeutic use.

For the production of antibodies, various hosts including goats, rabbits, rats, mice, humans, and others may be immunized by injection with PKIN or with any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, KLH, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to PKIN have an amino acid sequence consisting of at least about 5 amino acids, and generally will consist of at least about 10 amino acids. It is also preferable that these oligopeptides, peptides, or fragments are identical to a portion of the amino acid sequence of the natural protein. Short stretches of PKIN amino acids may be fused with those of another protein, such as KLH, and antibodies to the chimeric molecule may be produced.

Monoclonal antibodies to PKIN may be prepared using any technique which provides for the production of antibody molecules by continuous cell lines in culture. These include, but are not limited to, the hybridoma technique, the human B-cell hybridoma technique, and the EBV-hybridoma technique. (See, e.g., Kohler, G. et al. (1975) Nature 256: 495–497; Kozbor, D. et al. (1985) J. Immunol. Methods 81:31–42; Cote, R. J. et al. (1983) Proc. Natl. Acad. Sci. USA 80:2026–2030; and Cole, S. P. et al. (1984) Mol. Cell Biol. 62:109–120.)

In addition, techniques developed for the production of "chimeric antibodies," such as the splicing of mouse antibody genes to human antibody genes to obtain a molecule with appropriate antigen specificity and biological activity, can be used. (See, e.g., Morrison, S. L. et al. (1984) Proc. Natl. Acad. Sci. USA 81:6851–6855; Neuberger, M. S. et al. (1984) Nature 312:604–608; and Takeda, S. et al. (1985) Nature 314:452–454.) Alternatively, techniques described for the production of single chain antibodies may be adapted, using methods known in the art, to produce PKIN-specific single chain antibodies. Antibodies with related specificity, but of distinct idiotypic composition, may be generated by chain shuffling from random combinatorial immunoglobulin libraries. (See, e.g., Burton, D. R. (1991) Proc. Natl. Acad. Sci. USA 88:10134–10137.)

Antibodies may also be produced by inducing in vivo production in the lymphocyte population or by screening immunoglobulin libraries or panels of highly specific binding reagents as disclosed in the literature. (See, e.g., Orlandi, R. et al. (1989) Proc. Natl. Acad. Sci. USA 86:3833–3837; Winter, G. et al. (1991) Nature 349:293–299.)

Antibody fragments which contain specific binding sites for PKIN may also be generated. For example, such fragments include, but are not limited to, $F(ab')_2$ fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (See, e.g., Huse, W. D. et al. (1989) Science 246:1275–1281.)

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between PKIN and its specific antibody. A two-site, monoclonal-based immunoassay utilizing monoclonal antibodies reactive to two non-interfering PKIN epitopes is generally used, but a competitive binding assay may also be employed (Pound, supra).

Various methods such as Scatchard analysis in conjunction with radioimmunoassay techniques may be used to assess the affinity of antibodies for PKIN. Affinity is expressed as an association constant, $K_a$, which is defined as the molar concentration of PKIN-antibody complex divided by the molar concentrations of free antigen and free antibody under equilibrium conditions. The $K_a$ determined for a preparation of polyclonal antibodies, which are heterogeneous in their affinities for multiple PKIN epitopes, represents the average affinity, or avidity, of the antibodies for PKIN. The $K_a$ determined for a preparation of monoclonal antibodies, which are monospecific for a particular PKIN epitope, represents a true measure of affinity. High-affinity antibody preparations with $K_a$ ranging from about $10^9$ to $10^{12}$ L/mole are preferred for use in immunoassays in which the PKIN-antibody complex must withstand rigorous manipulations. Low-affinity antibody preparations with $K_a$ ranging from about $10^6$ to $10^7$ L/mole are preferred for use in immunopurification and similar procedures which ultimately require dissociation of PKIN, preferably in active form, from the antibody (Catty, D. (1988) *Antibodies, Volume 1: A Practical Approach*, IRL Press, Washington D.C.; Liddell, J. E. and A. Cryer (1991) *A Practical Guide to Monoclonal Antibodies*, John Wiley & Sons, New York N.Y.).

The titer and avidity of polyclonal antibody preparations may be further evaluated to determine the quality and suitability of such preparations for certain downstream applications. For example, a polyclonal antibody preparation containing at least 1–2 mg specific antibody/ml, preferably 5–10 mg specific antibody/ml, is generally employed in procedures requiring precipitation of PKIN-antibody complexes. Procedures for evaluating antibody specificity, titer, and avidity, and guidelines for antibody quality and usage in various applications, are generally available. (See, e.g., Catty, supra, and Coligan et al. supra.)

In another embodiment of the invention, the polynucleotides encoding PKIN, or any fragment or complement thereof, may be used for therapeutic purposes. In one aspect, modifications of gene expression can be achieved by designing complementary sequences or antisense molecules (DNA, RNA, PNA, or modified oligonucleotides) to the coding or regulatory regions of the gene encoding PKIN. Such technology is well known in the art, and antisense oligonucleotides or larger fragments can be designed from various locations along the coding or control regions of sequences encoding PKIN. (See, e.g., Agrawal, S., ed. (1996) *Antisense Therapeutics,* Humana Press Inc., Totawa N.J.)

In therapeutic use, any gene delivery system suitable for introduction of the antisense sequences into appropriate target cells can be used. Antisense sequences can be delivered intracellularly in the form of an expression plasmid which, upon transcription, produces a sequence complementary to at least a portion of the cellular sequence encoding the target protein. (See, e.g., Slater, J. E. et al. (1998) J. Allergy Clin. Immunol. 102(3):469–475; and Scanlon, K. J. et al. (1995) 9(13):1288–1296.) Antisense sequences can also be introduced intracellularly through the use of viral vectors, such as retrovirus and adeno-associated virus vectors. (See, e.g., Miller, A. D. (1990) Blood 76:271; Ausubel, supra; Uckert, W. and W. Walther (1994) Pharmacol. Ther. 63(3):323–347.) Other gene delivery mechanisms include liposome-derived systems, artificial viral envelopes, and other systems known in the art. (See, e.g., Rossi, J. J. (1995) Br. Med. Bull. 51(1):217–225; Boado, R. J. et al. (1998) J. Pharm. Sci. 87(11): 1308–1315; and Morris, M. C. et al. (1997) Nucleic Acids Res. 25(14):2730–2736.)

In another embodiment of the invention, polynucleotides encoding PKIN may be used for somatic or germline gene therapy. Gene therapy may be performed to (i) correct a genetic deficiency (e.g., in the cases of severe combined immunodeficiency (SCID)-X1 disease characterized by X-linked inheritance (Cavazzana-Calvo, M. et al. (2000) Science 288:669–672), severe combined immunodeficiency syndrome associated with an inherited adenosine deaminase (ADA) deficiency (Blaese, R. M. et al. (1995) Science 270:475–480; Bordignon, C. et al. (1995) Science 270: 470–475), cystic fibrosis (Zabner, J. et al. (1993) Cell 75:207–216; Crystal, R. G. et al. (1995) Hum. Gene Therapy 6:643–666; Crystal, R. G. et al. (1995) Hum. Gene Therapy 6:667–703), thalassamias, familial hypercholesterolemia, and hemophilia resulting from Factor VIII or Factor IX deficiencies (Crystal, R. G. (1995) Science 270:404–410; Verma, I. M. and N. Somia (1997) Nature 389:239–242)), (ii) express a conditionally lethal gene product (e.g., in the case of cancers which result from unregulated cell proliferation), or (iii) express a protein which affords protection against intracellular parasites (e.g., against human retroviruses, such as human immunodeficiency virus (HIV) (Baltimore, D. (1988) Nature 335:395–396; Poeschla, E. et al. (1996) Proc. Natl. Acad. Sci. USA. 93:11395–11399), hepatitis B or C virus (HBV, HCV); fungal parasites, such as *Candida albicans* and *Paracoccidioides brasiliensis;* and protozoan parasites such as *Plasmodium falciparum* and *Trypanosoma cruzi*). In the case where a genetic deficiency in PKIN expression or regulation causes disease, the expression of PKIN from an appropriate population of transduced cells may alleviate the clinical manifestations caused by the genetic deficiency.

In a further embodiment of the invention, diseases or disorders caused by deficiencies in PKIN are treated by constructing mammalian expression vectors encoding PKIN and introducing these vectors by mechanical means into PKIN-deficient cells. Mechanical transfer technologies for use with cells in vivo or ex vitro include (i) direct DNA microinjection into individual cells, (ii) ballistic gold particle delivery, (iii) liposome-mediated transfection, (iv) receptor-mediated gene transfer, and (v) the use of DNA transposons (Morgan, R. A. and W. F. Anderson (1993) Annu. Rev. Biochem. 62:191–217; Ivics, Z. (1997) Cell 91:501–510; Boulay, J -L. and H. Récipon (1998) Curr. Opin. Biotechnol. 9:445–450).

Expression vectors that may be effective for the expression of PKIN include, but are not limited to, the PCDNA 3.1, EPITAG, PRCCMV2, PREP, PVAX, PCR2-TOPOTA vectors (Invitrogen, Carlsbad Calif.), PCMV-SCRIPT, PCMV-TAG, PEGSH/PERV (Stratagene, La Jolla Calif.), and PTET-OFF, PTET-ON, PTRE2, PTRE2-LUC, PTK-HYG (Clontech, Palo Alto Calif.). PKIN may be expressed using (i) a constitutively active promoter, (e.g., from cytomegalovirus (CMV), Rous sarcoma virus (RSV), SV40 virus, thymidine kinase (TK), or β-actin genes), (ii) an inducible promoter (e.g., the tetracycline-regulated promoter (Gossen, M. and H. Bujard (1992) Proc. Natl. Acad. Sci. USA 89:5547–5551; Gossen, M. et al. (1995) Science 268:1766–1769; Rossi, F. M. V. and H. M. Blau (1998) Curr. Opin. Biotechnol. 9:451–456), commercially available in the T-REX plasmid (Invitrogen)); the ecdysone-inducible promoter (available in the plasmids PVGRXR and PIND; Invitrogen); the FK506/rapamycin inducible promoter; or the RU486/mifepristone inducible promoter (Rossi, F. M. V. and Blau, H. M. supra)), or (iii) a tissue-specific promoter or the native promoter of the endogenous gene encoding PKIN from a normal individual.

Commercially available liposome transformation kits (e.g., the PERFECT LIPID TRANSFECTION KIT, available from Invitrogen) allow one with ordinary skill in the art to deliver polynucleotides to target cells in culture and require minimal effort to optimize experimental parameters. In the alternative, transformation is performed using the calcium phosphate method (Graham, F. L. and A. J. Eb (1973) Virology 52:456–467), or by electroporation (Neumann, E. et al. (1982) EMBO J. 1:841–845). The introduction of DNA to primary cells requires modification of these standardized mammalian transfection protocols.

In another embodiment of the invention, diseases or disorders caused by genetic defects with respect to PKIN expression are treated by constructing a retrovirus vector consisting of (i) the polynucleotide encoding PKIN under the control of an independent promoter or the retrovirus long terminal repeat (LTR) promoter, (ii) appropriate RNA packaging signals, and (iii) a Rev-responsive element (RRE) along with additional retrovirus cis-acting RNA sequences and coding sequences required for efficient vector propagation. Retrovirus vectors (e.g., PFB and PFBNEO) are commercially available (Stratagene) and are based on published data (Riviere, I. et al. (1995) Proc. Natl. Acad. Sci. USA 92:6733–6737), incorporated by reference herein. The vector is propagated in an appropriate vector producing cell line (VPCL) that expresses an envelope gene with a tropism for receptors on the target cells or a promiscuous envelope protein such as VSVg (Armentano, D. et al. (1987) J. Virol. 61:1647–1650; Bender, M. A. et al. (1987) J. Virol. 61:1639–1646; Adam, M. A. and A. D. Miller (1988) J. Virol. 62:3802–3806; Dull, T. et al. (1998) J. Virol. 72:8463–8471; Zufferey, R. et al. (1998) J. Virol. 72:9873–9880). U.S. Pat. No. 5,910,434 to Rigg ("Method for obtaining retrovirus packaging cell lines producing high transducing efficiency retroviral supernatant") discloses a method for obtaining retrovirus packaging cell lines and is hereby incorporated by reference. Propagation of retrovirus vectors, transduction of a population of cells (e.g., CD4$^+$ T-cells), and the return of transduced cells to a patient are procedures well known to persons skilled in the art of gene therapy and have been well documented (Ranga, U. et al. (1997) J. Virol. 71:7020–7029; Bauer, G. et al. (1997) Blood 89:2259–2267; Bonyhadi, M. L. (1997) J. Virol.

71:4707–4716; Ranga, U. et al. (1998) Proc. Natl. Acad. Sci. USA 95:1201–1206; Su, L. (1997) Blood 89:2283–2290).

In the alternative, an adenovirus-based gene therapy delivery system is used to deliver polynucleotides encoding PKIN to cells which have one or more genetic abnormalities with respect to the expression of PKIN. The construction and packaging of adenovirus-based vectors are well known to those with ordinary skill in the art. Replication defective adenovirus vectors have proven to be versatile for importing genes encoding immunoregulatory proteins into intact islets in the pancreas (Csete, M. E. et al. (1995) Transplantation 27:263–268). Potentially useful adenoviral vectors are described in U.S. Pat. No. 5,707,618 to Armentano ("Adenovirus vectors for gene therapy"), hereby incorporated by reference. For adenoviral vectors, see also Antinozzi, P. A. et al. (1999) Annu. Rev. Nutr. 19:511–544 and Verma, I. M. and N. Somia (1997) Nature 18:389:239–242, both incorporated by reference herein.

In another alternative, a herpes-based, gene therapy delivery system is used to deliver polynucleotides encoding PKIN to target cells which have one or more genetic abnormalities with respect to the expression of PKIN. The use of herpes simplex virus (HSV)-based vectors may be especially valuable for introducing PKIN to cells of the central nervous system, for which HSV has a tropism. The construction and packaging of herpes-based vectors are well known to those with ordinary skill in the art. A replication-competent herpes simplex virus (HSV) type 1-based vector has been used to deliver a reporter gene to the eyes of primates (Liu, X. et al. (1999) Exp. Eye Res. 169:385–395). The construction of a HSV-1 virus vector has also been disclosed in detail in U.S. Pat. No. 5,804,413 to DeLuca ("Herpes simplex virus strains for gene transfer"), which is hereby incorporated by reference. U.S. Pat. No. 5,804,413 teaches the use of recombinant HSV d92 which consists of a genome containing at least one exogenous gene to be transferred to a cell under the control of the appropriate promoter for purposes including human gene therapy. Also taught by this patent are the construction and use of recombinant HSV strains deleted for ICP4, ICP27 and ICP22. For HSV vectors, see also Goins, W. F. et al. (1999) J. Virol. 73:519–532 and Xu, H. et al. (1994) Dev. Biol. 163: 152–161, hereby incorporated by reference. The manipulation of cloned herpesvirus sequences, the generation of recombinant virus following the transfection of multiple plasmids containing different segments of the large herpesvirus genomes, the growth and propagation of herpesvirus, and the infection of cells with herpesvirus are techniques well known to those of ordinary skill in the art.

In another alternative, an alphavirus (positive, single-stranded RNA virus) vector is used to deliver polynucleotides encoding PKIN to target cells. The biology of the prototypic alphavirus, Semliki Forest Virus (SFV), has been studied extensively and gene transfer vectors have been based on the SFV genome (Garoff, H. and K. -J. Li (1998) Curr. Opin. Biotechnol. 9:464–469). During alphavirus RNA replication, a subgenomic RNA is generated that normally encodes the viral capsid proteins. This subgenomic RNA replicates to higher levels than the full length genomic RNA, resulting in the overproduction of capsid proteins relative to the viral proteins with enzymatic activity (e.g., protease and polymerase). Similarly, inserting the coding sequence for PKIN into the alphavirus genome in place of the capsid-coding region results in the production of a large number of PKIN-coding RNAs and the synthesis of high levels of PKIN in vector transduced cells. While alphavirus infection is typically associated with cell lysis within a few days, the ability to establish a persistent infection in hamster normal kidney cells (BHK-21) with a variant of Sindbis virus (SIN) indicates that the lytic replication of alphaviruses can be altered to suit the needs of the gene therapy application (Dryga, S. A. et al. (1997) Virology 228:74–83). The wide host range of alphaviruses will allow the introduction of PKIN into a variety of cell types. The specific transduction of a subset of cells in a population may require the sorting of cells prior to transduction. The methods of manipulating infectious cDNA clones of alphaviruses, performing alphavirus cDNA and RNA transfections, and performing alphavirus infections, are well known to those with ordinary skill in the art.

Oligonucleotides derived from the transcription initiation site, e.g., between about positions −10 and +10 from the start site, may also be employed to inhibit gene expression. Similarly, inhibition can be achieved using triple helix base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature. (See, e.g., Gee, J. E. et al. (1994) in Huber, B. E. and B. I. Carr, *Molecular and Immunologic Approaches,* Futura Publishing, Mt. Kisco N.Y., pp. 163–177.) A complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. For example, engineered hammerhead motif ribozyme molecules may specifically and efficiently catalyze endonucleolytic cleavage of sequences encoding PKIN.

Specific ribozyme cleavage sites within any potential RNA target are initially identified by scanning the target molecule for ribozyme cleavage sites, including the following sequences: GUA, GUU, and GUC. Once identified, short RNA sequences of between 15 and 20 ribonucleotides, corresponding to the region of the target gene containing the cleavage site, may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding PKIN. Such DNA sequences may be incorporated into a wide variety of vectors with suitable RNA polymerase promoters such as T7 or SP6. Alternatively, these cDNA constructs that synthesize complementary RNA, constitutively or inducibly, can be introduced into cell lines, cells, or tissues.

RNA molecules may be modified to increase intracellular stability and half-life. Possible modifications include, but are not limited to, the addition of flanking sequences at the 5' and/or 3' ends of the molecule, or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

An additional embodiment of the invention encompasses a method for screening for a compound which is effective in altering expression of a polynucleotide encoding PKIN. Compounds which may be effective in altering expression of a specific polynucleotide may include, but are not limited to, oligonucleotides, antisense oligonucleotides, triple helix-forming oligonucleotides, transcription factors and other polypeptide transcriptional regulators, and non-macromolecular chemical entities which are capable of interacting with specific polynucleotide sequences. Effective compounds may alter polynucleotide expression by acting as either inhibitors or promoters of polynucleotide expression. Thus, in the treatment of disorders associated with increased PKIN expression or activity, a compound which specifically inhibits expression of the polynucleotide encoding PKIN may be therapeutically useful, and in the treatment of disorders associated with decreased PKIN expression or activity, a compound which specifically promotes expression of the polynucleotide encoding PKIN may be therapeutically useful.

At least one, and up to a plurality, of test compounds may be screened for effectiveness in altering expression of a specific polynucleotide. A test compound may be obtained by any method commonly known in the art, including chemical modification of a compound known to be effective in altering polynucleotide expression; selection from an existing, commercially-available or proprietary library of naturally-occurring or non-natural chemical compounds; rational design of a compound based on chemical and/or structural properties of the target polynucleotide; and selection from a library of chemical compounds created combinatorially or randomly. A sample comprising a polynucleotide encoding PKIN is exposed to at least one test compound thus obtained. The sample may comprise, for example, an intact or permeabilized cell, or an in vitro cell-free or reconstituted biochemical system. Alterations in the expression of a polynucleotide encoding PKIN are assayed by any method commonly known in the art. Typically, the expression of a specific nucleotide is detected by hybridization with a probe having a nucleotide sequence complementary to the sequence of the polynucleotide encoding PKIN. The amount of hybridization may be quantified, thus forming the basis for a comparison of the expression of the polynucleotide both with and without exposure to one or more test compounds. Detection of a change in the expression of a polynucleotide exposed to a test compound indicates that the test compound is effective in altering the expression of the polynucleotide. A screen for a compound effective in altering expression of a specific polynucleotide can be carried out, for example, using a *Schizosaccharomyces pombe* gene expression system (Atkins, D. et al. (1999) U.S. Pat. No. 5,932,435; Arndt, G. M. et al. (2000) Nucleic Acids Res. 28:E15) or a human cell line such as HeLa cell (Clarke, M. L. et al. (2000) Biochem. Biophys. Res. Commun. 268:8–13). A particular embodiment of the present invention involves screening a combinatorial library of oligonucleotides (such as deoxyribonucleotides, ribonucleotides, peptide nucleic acids, and modified oligonucleotides) for antisense activity against a specific polynucleotide sequence (Bruice, T. W. et al. (1997) U.S. Pat. No. 5,686,242; Bruice, T. W. et al. (2000) U.S. Pat. No. 6,022,691).

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections, or by polycationic amino polymers may be achieved using methods which are well known in the art. (See, e.g., Goldman, C. K. et al. (1997) Nat. Biotechnol. 15:462–466.)

Any of the therapeutic methods described above may be applied to any subject in need of such therapy, including, for example, mammals such as humans, dogs, cats, cows, horses, rabbits, and monkeys.

An additional embodiment of the invention relates to the administration of a composition which generally comprises an active ingredient formulated with a pharmaceutically acceptable excipient. Excipients may include, for example, sugars, starches, celluloses, gums, and proteins. Various formulations are commonly known and are thoroughly discussed in the latest edition of *Remington's Pharmaceutical Sciences* (Maack Publishing, Easton Pa.). Such compositions may consist of PKIN, antibodies to PKIN, and mimetics, agonists, antagonists, or inhibitors of PKIN.

The compositions utilized in this invention may be administered by any number of routes including, but not limited to, oral, intravenous, intramuscular, intra-arterial, intramedullary, intrathecal, intraventricular, pulmonary, transdermal, subcutaneous, intraperitoneal, intranasal, enteral, topical, sublingual, or rectal means.

Compositions for pulmonary administration may be prepared in liquid or dry powder form. These compositions are generally aerosolized immediately prior to inhalation by the patient. In the case of small molecules (e.g. traditional low molecular weight organic drugs), aerosol delivery of fast-acting formulations is well-known in the art. In the case of macromolecules (e.g. larger peptides and proteins), recent developments in the field of pulmonary delivery via the alveolar region of the lung have enabled the practical delivery of drugs such as insulin to blood circulation (see, e.g., Patton, J. S. et al., U.S. Pat. No. 5,997,848). Pulmonary delivery has the advantage of administration without needle injection, and obviates the need for potentially toxic penetration enhancers.

Compositions suitable for use in the invention include compositions wherein the active ingredients are contained in an effective amount to achieve the intended purpose. The determination of an effective dose is well within the capability of those skilled in the art.

Specialized forms of compositions may be prepared for direct intracellular delivery of macromolecules comprising PKIN or fragments thereof. For example, liposome preparations containing a cell-impermeable macromolecule may promote cell fusion and intracellular delivery of the macromolecule. Alternatively, PKIN or a fragment thereof may be joined to a short cationic N-terminal portion from the HIV Tat-1 protein. Fusion proteins thus generated have been found to transduce into the cells of all tissues, including the brain, in a mouse model system (Schwarze, S. R. et al. (1999) Science 285:1569–1572).

For any compound, the therapeutically effective dose can be estimated initially either in cell culture assays, e.g., of neoplastic cells, or in animal models such as mice, rats, rabbits, dogs, monkeys, or pigs. An animal model may also be used to determine the appropriate concentration range and route of administration. Such information can then be used to determine useful doses and routes for administration in humans.

A therapeutically effective dose refers to that amount of active ingredient, for example PKIN or fragments thereof, antibodies of PKIN, and agonists, antagonists or inhibitors of PKIN, which ameliorates the symptoms or condition. Therapeutic efficacy and toxicity may be determined by standard pharmaceutical procedures in cell cultures or with experimental animals, such as by calculating the $ED_{50}$ (the dose therapeutically effective in 50% of the population) or $LD_{50}$ (the dose lethal to 50% of the population) statistics. The dose ratio of toxic to therapeutic effects is the therapeutic index, which can be expressed as the $LD_{50}/ED_{50}$ ratio. Compositions which exhibit large therapeutic indices are preferred. The data obtained from cell culture assays and animal studies are used to formulate a range of dosage for human use. The dosage contained in such compositions is preferably within a range of circulating concentrations that includes the $ED_{50}$ with little or no toxicity. The dosage varies within this range depending upon the dosage form employed, the sensitivity of the patient, and the route of administration.

The exact dosage will be determined by the practitioner, in light of factors related to the subject requiring treatment. Dosage and administration are adjusted to provide sufficient levels of the active moiety or to maintain the desired effect. Factors which may be taken into account include the severity of the disease state, the general health of the subject, the age, weight, and gender of the subject, time and frequency of administration, drug combination(s), reaction sensitivities, and response to therapy. Long-acting compositions may be administered every 3 to 4 days, every week, or biweekly depending on the half-life and clearance rate of the particular formulation.

Normal dosage amounts may vary from about 0.1 μg to 100,000 μg, up to a total dose of about 1 gram, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind PKIN may be used for the diagnosis of disorders characterized by expression of PKIN, or in assays to monitor patients being treated with PKIN or agonists, antagonists, or inhibitors of PKIN. Antibodies useful for diagnostic purposes may be prepared in the same manner as described above for therapeutics. Diagnostic assays for PKIN include methods which utilize the antibody and a label to detect PKIN in human body fluids or in extracts of cells or tissues. The antibodies may be used with or without modification, and may be labeled by covalent or non-covalent attachment of a reporter molecule. A wide variety of reporter molecules, several of which are described above, are known in the art and may be used.

A variety of protocols for measuring PKIN, including ELISAs, RIAs, and FACS, are known in the art and provide a basis for diagnosing altered or abnormal levels of PKIN expression. Normal or standard values for PKIN expression are established by combining body fluids or cell extracts taken from normal mammalian subjects, for example, human subjects, with antibodies to PKIN under conditions suitable for complex formation. The amount of standard complex formation may be quantitated by various methods, such as photometric means. Quantities of PKIN expressed in subject, control, and disease samples from biopsied tissues are compared with the standard values. Deviation between standard and subject values establishes the parameters for diagnosing disease.

In another embodiment of the invention, the polynucleotides encoding PKIN may be used for diagnostic purposes. The polynucleotides which may be used include oligonucleotide sequences, complementary RNA and DNA molecules, and PNAs. The polynucleotides may be used to detect and quantify gene expression in biopsied tissues in which expression of PKIN may be correlated with disease. The diagnostic assay may be used to determine absence, presence, and excess expression of PKIN, and to monitor regulation of PKIN levels during therapeutic intervention.

In one aspect, hybridization with PCR probes which are capable of detecting polynucleotide sequences, including genomic sequences, encoding PKIN or closely related molecules may be used to identify nucleic acid sequences which encode PKIN. The specificity of the probe, whether it is made from a highly specific region, e.g., the 5' regulatory region, or from a less specific region, e.g., a conserved motif, and the stringency of the hybridization or amplification will determine whether the probe identifies only naturally occurring sequences encoding PKIN, allelic variants, or related sequences.

Probes may also be used for the detection of related sequences, and may have at least 50% sequence identity to any of the PKIN encoding sequences. The hybridization probes of the subject invention may be DNA or RNA and may be derived from the sequence of SEQ ID NO:25–48 or from genomic sequences including promoters, enhancers, and introns of the PKIN gene.

Means for producing specific hybridization probes for DNAs encoding PKIN include the cloning of polynucleotide sequences encoding PKIN or PKIN derivatives into vectors for the production of mRNA probes. Such vectors are known in the art, are commercially available, and may be used to synthesize RNA probes in vitro by means of the addition of the appropriate RNA polymerases and the appropriate labeled nucleotides. Hybridization probes may be labeled by a variety of reporter groups, for example, by radionuclides such as $^{32}P$ or $^{35}S$, or by enzymatic labels, such as alkaline phosphatase coupled to the probe via avidin/biotin coupling systems, and the like.

Polynucleotide sequences encoding PKIN may be used for the diagnosis of disorders associated with expression of PKIN. Examples of such disorders include, but are not limited to, a cancer, such as adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus, leukemias such as multiple myeloma and lymphomas such as Hodgkin's disease; an immune disorder, such as acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimiune thyroiditis, autoimmune polyendocrinopathy-candidiasis-ectodermal dystrophy (APECED), bronchitis, cholecystitis, contact dermatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scleroderma, Sjögren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, and trauma; a growth and developmental disorder, such as actinic keratosis, arteriosclerosis, atherosclerosis, bursitis, cirrhosis, hepatitis, mixed connective tissue disease (MCTD), myelofibrosis, paroxysmal nocturnal hemoglobinuria, polycythemia vera, psoriasis, primary thrombocythemia, and cancers including adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus, renal tubular acidosis, anemia, Cushing's syndrome, achondroplastic dwarfism, Duchenne and Becker muscular dystrophy, epilepsy, gonadal dysgenesis, WAGR syndrome (Wilms' tumor, aniridia, genitourinary abnormalities, and mental retardation), Smith-Magenis syndrome, myelodysplastic syndrome, hereditary mucoepithelial dysplasia, hereditary keratodermas, hereditary neuropathies such as Charcot-Marie-Tooth disease and neurofibromatosis, hypothyroidism, hydrocephalus, seizure disorders such as Syndenham's chorea and cerebral palsy, spina bifida, anencephaly, craniorachischisis, congenital glaucoma, cataract, and sensorineural hearing loss; a cardiovascular disease, such as arteriovenous fistula, atherosclerosis, hypertension, vasculitis, Raynaud's disease, aneurysms, arterial dissections, varicose veins, thrombophlebitis and phlebothrombosis, vascular tumors, and complications of thrombolysis, balloon angioplasty, vascular replacement, and coronary artery bypass graft surgery, congestive heart failure, ischemic heart disease, angina pectoris, myocardial infarction, hypertensive heart disease, degenerative valvular heart disease, calcific aortic valve stenosis, congenitally bicuspid aortic valve, mitral annular calcification, mitral valve prolapse, rheumatic fever and rheumatic heart disease, infective endocarditis, nonbacterial thrombotic endocarditis, endocarditis of systemic lupus erythematosus, carcinoid heart disease, cardiomyopathy, myocarditis, pericarditis, neoplastic heart disease, congenital heart disease, and complications of cardiac transplantation, congenital lung anomalies, atelectasis, pulmonary congestion and edema, pulmonary embolism, pulmonary hemorrhage, pulmonary infarction, pulmonary hypertension, vascular sclerosis, obstructive pulmonary disease, restrictive pulmonary disease, chronic obstructive pulmonary disease, emphysema, chronic bronchitis, bronchial asthma, bronchiectasis, bacterial pneumonia, viral and mycoplasmal pneumonia, lung abscess, pulmonary tuberculosis, diffuse interstitial diseases, pneumoconioses, sarcoidosis, idiopathic pulmonary fibrosis, desquamative interstitial pneumonitis, hypersensitivity pneumonitis, pulmonary eosinophilia bronchiolitis obliterans-organizing pneumonia, diffuse pulmonary hemorrhage syndromes, Goodpasture's syndromes, idiopathic pulmonary hemosiderosis, pulmonary involvement in collagen-vascular disorders, pulmonary alveolar proteinosis, lung tumors, inflammatory and noninflammatory pleural effusions, pneumothorax, pleural tumors, drug-induced lung disease, radiation-induced lung disease, and complications of lung transplantation; and a lipid disorder such as fatty liver, cholestasis, primary biliary cirrhosis, carnitine deficiency, carnitine palmitoyltransferase deficiency, myoadenylate deaminase deficiency, hypertriglyceridemia, lipid storage disorders such Fabry's disease, Gaucher's disease, Niemann-Pick's disease, metachromatic leukodystrophy, adrenoleukodystrophy, $GM_2$ gangliosidosis, and ceroid lipofuscinosis, abetalipoproteinemia, Tangier disease, hyperlipoproteinemia, diabetes mellitus, lipodystrophy, lipomatoses, acute panniculitis, disseminated fat necrosis, adiposis dolorosa, lipoid adrenal hyperplasia, minimal change disease, lipomas, atherosclerosis, hypercholesterolemia, hypercholesterolemia with hypertriglyceridemia, primary hypoalphalipoproteinemia, hypothyroidism, renal disease, liver disease, lecithin:cholesterol acyltransferase deficiency, cerebrotendinous xanthomatosis, sitosterolemia, hypocholesterolemia, Tay-Sachs disease, Sandhoff's disease, hyperlipidemia, hyperlipemia, lipid myopathies, and obesity. The polynucleotide sequences encoding PKIN may be used in Southern or northern analysis, dot blot, or other membrane-based technologies; in PCR technologies; in dipstick, pin, and multiformat ELISA-like assays; and in microarrays utilizing fluids or tissues from patients to detect altered PKIN expression. Such qualitative or quantitative methods are well known in the art.

In a particular aspect, the nucleotide sequences encoding PKIN may be useful in assays that detect the presence of associated disorders, particularly those mentioned above. The nucleotide sequences encoding PKIN may be labeled by standard methods and added to a fluid or tissue sample from a patient under conditions suitable for the formation of hybridization complexes. After a suitable incubation period, the sample is washed and the signal is quantified and compared with a standard value. If the amount of signal in the patient sample is significantly altered in comparison to a control sample then the presence of altered levels of nucleotide sequences encoding PKIN in the sample indicates the presence of the associated disorder. Such assays may also be used to evaluate the efficacy of a particular therapeutic treatment regimen in animal studies, in clinical trials, or to monitor the treatment of an individual patient.

In order to provide a basis for the diagnosis of a disorder associated with expression of PKIN, a normal or standard profile for expression is established. This may be accomplished by combining body fluids or cell extracts taken from normal subjects, either animal or human, with a sequence, or a fragment thereof, encoding PKIN, under conditions suitable for hybridization or amplification. Standard hybridization may be quantified by comparing the values obtained from normal subjects with values from an experiment in which a known amount of a substantially purified polynucleotide is used. Standard values obtained in this manner may be compared with values obtained from samples from patients who are symptomatic for a disorder. Deviation from standard values is used to establish the presence of a disorder.

Once the presence of a disorder is established and a treatment protocol is initiated, hybridization assays may be repeated on a regular basis to determine if the level of expression in the patient begins to approximate that which is observed in the normal subject. The results obtained from successive assays may be used to show the efficacy of treatment over a period ranging from several days to months.

With respect to cancer, the presence of an abnormal amount of transcript (either under- or overexpressed) in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding PKIN may involve the use of PCR. These oligomers may be chemically synthesized, generated enzymatically, or produced in vitro. Oligomers will preferably contain a fragment of a polynucleotide encoding PKIN, or a fragment of a polynucleotide complementary to the polynucleotide encoding PKIN, and will be employed under optimized conditions for identification of a specific gene or condition. Oligomers may also be employed under less stringent conditions for detection or quantification of closely related DNA or RNA sequences.

In a particular aspect, oligonucleotide primers derived from the polynucleotide sequences encoding PKIN may be used to detect single nucleotide polymorphisms (SNPs). SNPs are substitutions, insertions and deletions that are a frequent cause of inherited or acquired genetic disease in humans. Methods of SNP detection include, but are not limited to, single-stranded conformation polymorphism (SSCP) and fluorescent SSCP (fSSCP) methods. In SSCP, oligonucleotide primers derived from the polynucleotide sequences encoding PKIN are used to amplify DNA using the polymerase chain reaction (PCR). The DNA may be derived, for example, from diseased or normal tissue, biopsy samples, bodily fluids, and the like. SNPs in the DNA cause differences in the secondary and tertiary structures of PCR products in single-stranded form, and these differences are detectable using gel electrophoresis in non-denaturing gels. In fSCCP, the oligonucleotide primers are fluorescently labeled, which allows detection of the amplimers in high-throughput equipment such as DNA sequencing machines. Additionally, sequence database analysis methods, termed in silico SNP (isSNP), are capable of identifying polymorphisms by comparing the sequence of individual overlapping DNA fragments which assemble into a common consensus sequence. These computer-based methods filter out sequence variations due to laboratory preparation of DNA and sequencing errors using statistical models and automated analyses of DNA sequence chromatograms. In the alternative, SNPs may be detected and characterized by mass spectrometry using, for example, the high throughput MASSARRAY system (Sequenom, Inc., San Diego Calif.).

Methods which may also be used to quantify the expression of PKIN include radiolabeling or biotinylating nucleotides, coamplification of a control nucleic acid, and interpolating results from standard curves. (See, e.g., Melby, P. C. et al. (1993) J. Immunol. Methods 159:235–244; Duplaa, C. et al. (1993) Anal. Biochem. 212:229–236.) The speed of quantitation of multiple samples may be accelerated by running the assay in a high-throughput format where the oligomer or polynucleotide of interest is presented in various dilutions and a spectrophotometric or colorimetric response gives rapid quantitation.

In further embodiments, oligonucleotides or longer fragments derived from any of the polynucleotide sequences described herein may be used as elements on a microarray. The microarray can be used in transcript imaging techniques which monitor the relative expression levels of large numbers of genes simultaneously as described below. The microarray may also be used to identify genetic variants, mutations, and polymorphisms. This information may be used to determine gene function, to understand the genetic basis of a disorder, to diagnose a disorder, to monitor progression/regression of disease as a function of gene expression, and to develop and monitor the activities of therapeutic agents in the treatment of disease. In particular, this information may be used to develop a pharmacogenomic profile of a patient in order to select the most appropriate and effective treatment regimen for that patient. For example, therapeutic agents which are highly effective and display the fewest side effects may be selected for a patient based on his/her pharmacogenomic profile.

In another embodiment, PKIN, fragments of PKIN, or antibodies specific for PKIN may be used as elements on a microarray. The microarray may be used to monitor or measure protein-protein interactions, drug-target interactions, and gene expression profiles, as described above.

A particular embodiment relates to the use of the polynucleotides of the present invention to generate a transcript image of a tissue or cell type. A transcript image represents the global pattern of gene expression by a particular tissue or cell type. Global gene expression patterns are analyzed by quantifying the number of expressed genes and their relative abundance under given conditions and at a given time. (See Seilhamer et al., "Comparative Gene Transcript Analysis," U.S. Pat. No. 5,840,484, expressly incorporated by reference herein.) Thus a transcript image may be generated by hybridizing the polynucleotides of the present invention or their complements to the totality of transcripts or reverse transcripts of a particular tissue or cell type. In one embodiment, the hybridization takes place in high-throughput format, wherein the polynucleotides of the present invention or their complements comprise a subset of a plurality of elements on a microarray. The resultant transcript image would provide a profile of gene activity.

Transcript images may be generated using transcripts isolated from tissues, cell lines, biopsies, or other biological samples. The transcript image may thus reflect gene expression in vivo, as in the case of a tissue or biopsy sample, or in vitro, as in the case of a cell line.

Transcript images which profile the expression of the polynucleotides of the present invention may also be used in conjunction with in vitro model systems and preclinical evaluation of pharmaceuticals, as well as toxicological testing of industrial and naturally-occurring environmental compounds. All compounds induce characteristic gene expression patterns, frequently termed molecular fingerprints or toxicant signatures, which are indicative of mechanisms of action and toxicity (Nuwaysir, E. F. et al. (1999) Mol. Carcinog. 24:153–159; Steiner, S. and N. L. Anderson (2000) Toxicol. Lett. 112–113:467–471, expressly incorporated by reference herein). If a test compound has a signature similar to that of a compound with known toxicity, it is likely to share those toxic properties. These fingerprints or signatures are most useful and refined when they contain expression information from a large number of genes and gene families. Ideally, a genome-wide measurement of expression provides the highest quality signature. Even genes whose expression is not altered by any tested compounds are important as well, as the levels of expression of these genes are used to normalize the rest of the expression data. The normalization procedure is useful for comparison of expression data after treatment with different compounds. While the assignment of gene function to elements of a toxicant signature aids in interpretation of toxicity mechanisms, knowledge of gene function is not necessary for the statistical matching of signatures which leads to prediction of toxicity. (See, for example, Press Release 00–02 from the National Institute of Environmental Health Sciences, released Feb. 29, 2000, available at http://www.niehs.nih.gov/oc/news/toxchip.htm.) Therefore, it is important and desirable in toxicological screening using toxicant signatures to include all expressed gene sequences.

In one embodiment, the toxicity of a test compound is assessed by treating a biological sample containing nucleic acids with the test compound. Nucleic acids that are expressed in the treated biological sample are hybridized with one or more probes specific to the polynucleotides of the present invention, so that transcript levels corresponding to the polynucleotides of the present invention may be quantified. The transcript levels in the treated biological sample are compared with levels in an untreated biological sample. Differences in the transcript levels between the two samples are indicative of a toxic response caused by the test compound in the treated sample.

Another particular embodiment relates to the use of the polypeptide sequences of the present invention to analyze the proteome of a tissue or cell type. The term proteome refers to the global pattern of protein expression in a particular tissue or cell type. Each protein component of a proteome can be subjected individually to further analysis. Proteome expression patterns, or profiles, are analyzed by quantifying the number of expressed proteins and their relative abundance under given conditions and at a given time. A profile of a cell's proteome may thus be generated by separating and analyzing the polypeptides of a particular tissue or cell type. In one embodiment, the separation is achieved using two-dimensional gel electrophoresis, in which proteins from a sample are separated by isoelectric focusing in the first dimension, and then according to molecular weight by sodium dodecyl sulfate slab gel electrophoresis in the second dimension (Steiner and Anderson, supra). The proteins are visualized in the gel as discrete and uniquely positioned spots, typically by staining the gel with an agent such as Coomassie Blue or silver or fluorescent stains. The optical density of each protein spot is generally proportional to the level of the protein in the sample. The optical densities of equivalently positioned protein spots from different samples, for example, from biological samples either treated or untreated with a test compound or therapeutic agent, are compared to identify any changes in protein spot density related to the treatment. The proteins in the spots are partially sequenced using, for example, standard methods employing chemical or enzymatic cleavage followed by mass spectrometry. The identity of the protein in a spot may be determined by comparing its partial sequence, preferably of at least 5 contiguous amino acid residues, to the polypeptide sequences of the present invention. In some cases, further sequence data may be obtained for definitive protein identification.

A proteomic profile may also be generated using antibodies specific for PKIN to quantify the levels of PKIN expression. In one embodiment, the antibodies are used as elements on a microarray, and protein expression levels are quantified by exposing the microarray to the sample and detecting the levels of protein bound to each array element (Lueking, A. et al. (1999) Anal. Biochem. 270:103–111; Mendoze, L. G. et al. (1999) Biotechniques 27:778–788). Detection may be performed by a variety of methods known in the art, for example, by reacting the proteins in the sample with a thiol- or amino-reactive fluorescent compound and detecting the amount of fluorescence bound at each array element.

Toxicant signatures at the proteome level are also useful for toxicological screening, and should be analyzed in parallel with toxicant signatures at the transcript level. There is a poor correlation between transcript and protein abundances for some proteins in some tissues (Anderson, N. L. and J. Seilhamer (1997) Electrophoresis 18:533–537), so proteome toxicant signatures may be useful in the analysis of compounds which do not significantly affect the transcript image, but which alter the proteomic profile. In addition, the analysis of transcripts in body fluids is difficult, due to rapid degradation of mRNA, so proteomic profiling may be more reliable and informative in such cases.

In another embodiment, the toxicity of a test compound is assessed by treating a biological sample containing proteins with the test compound. Proteins that are expressed in the treated biological sample are separated so that the amount of each protein can be quantified. The amount of each protein is compared to the amount of the corresponding protein in an untreated biological sample. A difference in the amount of protein between the two samples is indicative of a toxic response to the test compound in the treated sample. Individual proteins are identified by sequencing the amino acid residues of the individual proteins and comparing these partial sequences to the polypeptides of the present invention.

In another embodiment, the toxicity of a test compound is assessed by treating a biological sample containing proteins with the test compound. Proteins from the biological sample are incubated with antibodies specific to the polypeptides of the present invention. The amount of protein recognized by the antibodies is quantified. The amount of protein in the treated biological sample is compared with the amount in an untreated biological sample. A difference in the amount of protein between the two samples is indicative of a toxic response to the test compound in the treated sample.

Microarrays may be prepared, used, and analyzed using methods known in the art. (See, e.g., Brennan, T. M. et al. (1995) U.S. Pat. No. 5,474,796; Schena, M. et al. (1996) Proc. Natl. Acad. Sci. USA 93:10614–10619; Baldeschweiler et al. (1995) PCT application WO95/251116; Shalon, D. et al. (1995) PCT application WO95/35505; Heller, R. A. et al. (1997) Proc. Natl. Acad. Sci. USA 94:2150–2155; and Heller, M. J. et al. (1997) U.S. Pat. No. 5,605,662.) Various types of microarrays are well known and thoroughly described in *DNA Microarrays: A Practical Approach*, M. Schena, ed. (1999) Oxford University Press, London, hereby expressly incorporated by reference.

In another embodiment of the invention, nucleic acid sequences encoding PKIN may be used to generate hybridization probes useful in mapping the naturally occurring genomic sequence. Either coding or noncoding sequences may be used, and in some instances, noncoding sequences may be preferable over coding sequences. For example, conservation of a coding sequence among members of a multi-gene family may potentially cause undesired cross hybridization during chromosomal mapping. The sequences may be mapped to a particular chromosome, to a specific region of a chromosome, or to artificial chromosome constructions, e.g., human artificial chromosomes (HACs), yeast artificial chromosomes (YACs), bacterial artificial chromosomes (BACs), bacterial P1 constructions, or single chromosome cDNA libraries. (See, e.g., Harrington, J. J. et al. (1997) Nat. Genet. 15:345–355; Price, C. M. (1993) Blood Rev. 7:127–134; and Trask, B. J. (1991) Trends Genet. 7:149–154.) Once mapped, the nucleic acid sequences of the invention may be used to develop genetic linkage maps, for example, which correlate the inheritance of a disease state with the inheritance of a particular chromosome region or restriction fragment length polymorphism (RFLP). (See, for example, Lander, E. S. and D. Botstein (1986) Proc. Natl. Acad. Sci. USA 83:7353–7357.)

Fluorescent in situ hybridization (FISH) may be correlated with other physical and genetic map data. (See, e.g., Heinz-Ulrich, et al. (1995) in Meyers, supra, pp. 965–968.) Examples of genetic map data can be found in various scientific journals or at the Online Mendelian Inheritance in Man (OMIM) World Wide Web site. Correlation between the location of the gene encoding PKIN on a physical map and a specific disorder, or a predisposition to a specific disorder, may help define the region of DNA associated with that disorder and thus may further positional cloning efforts.

In situ hybridization of chromosomal preparations and physical mapping techniques, such as linkage analysis using established chromosomal markers, may be used for extending genetic maps. Often the placement of a gene on the chromosome of another mammalian species, such as mouse, may reveal associated markers even if the exact chromosomal locus is not known. This information is valuable to investigators searching for disease genes using positional cloning or other gene discovery techniques. Once the gene or genes responsible for a disease or syndrome have been crudely localized by genetic linkage to a particular genomic region, e.g., ataxia-telangiectasia to 11q22–23, any sequences mapping to that area may represent associated or regulatory genes for further investigation. (See, e.g., Gatti, R. A. et al. (1988) Nature 336:577–580.) The nucleotide sequence of the instant invention may also be used to detect differences in the chromosomal location due to translocation, inversion, etc., among normal, carrier, or affected individuals.

In another embodiment of the invention, PKIN, its catalytic or immunogenic fragments, or oligopeptides thereof can be used for screening libraries of compounds in any of a variety of drug screening techniques. The fragment employed in such screening may be free in solution, affixed to a solid support, borne on a cell surface, or located intracellularly. The formation of binding complexes between PKIN and the agent being tested may be measured.

Another technique for drug screening provides for high throughput screening of compounds having suitable binding affinity to the protein of interest. (See, e.g., Geysen, et al. (1984) PCT application WO84/03564.) In this method, large numbers of different small test compounds are synthesized on a solid substrate. The test compounds are reacted with PKIN, or fragments thereof, and washed. Bound PKIN is then detected by methods well known in the art. Purified PKIN can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding PKIN specifically compete with a test compound for binding PKIN. In this manner, antibodies can be used to detect the presence of any peptide which shares one or more antigenic determinants with PKIN.

In additional embodiments, the nucleotide sequences which encode PKIN may be used in any molecular biology techniques that have yet to be developed, provided the new techniques rely on properties of nucleotide sequences that are currently known, including, but not limited to, such properties as the triplet genetic code and specific base pair interactions.

Without further elaboration, it is believed that one skilled in the art can, using the preceding description, utilize the present invention to its fullest extent. The following embodiments are, therefore, to be construed as merely illustrative, and not limitative of the remainder of the disclosure in any way whatsoever.

The disclosures of all patents, applications and publications, mentioned above and below and including U.S. Ser. No. 60/229,873, U.S. Ser. No. 60/231,357, U.S. Ser. No. 60/232,654, U.S. Ser. No. 60/234,902, U.S. Ser. No. 60/236,499, U.S. Ser. No. 60/238,389, and U.S. Ser. No. 60/240,542, are expressly incorporated by reference herein.

EXAMPLES

I. Construction of cDNA Libraries

Incyte cDNAs were derived from cDNA libraries described in the LIFESEQ GOLD database (Incyte Genomics, Palo Alto Calif.) and shown in Table 4, column 5. Some tissues were homogenized and lysed in guanidinium isothiocyanate, while others were homogenized and lysed in phenol or in a suitable mixture of denaturants, such as TRIZOL (Life Technologies), a monophasic solution of phenol and guanidine isothiocyanate. The resulting lysates were centrifuged over CsCl cushions or extracted with chloroform. RNA was precipitated from the lysates with either isopropanol or sodium acetate and ethanol, or by other routine methods.

Phenol extraction and precipitation of RNA were repeated as necessary to increase RNA purity. In some cases, RNA was treated with DNase. For most libraries, poly(A)+ RNA was isolated using oligo d(T)-coupled paramagnetic particles (Promega), OLIGOTEX latex particles (QIAGEN, Chatsworth Calif.), or an OLIGOTEX mRNA purification kit (QIAGEN). Alternatively, RNA was isolated directly from tissue lysates using other RNA isolation kits, e.g., the POLY(A)PURE mRNA purification kit (Ambion, Austin Tex.).

In some cases, Stratagene was provided with RNA and constructed the corresponding cDNA libraries. Otherwise, cDNA was synthesized and cDNA libraries were constructed with the UNIZAP vector system (Stratagene) or SUPERSCRIPT plasmid system (Life Technologies), using the recommended procedures or similar methods known in the art. (See, e.g., Ausubel, 1997, supra, units 5.1–6.6.) Reverse transcription was initiated using oligo d(T) or random primers. Synthetic oligonucleotide adapters were ligated to double stranded cDNA, and the cDNA was digested with the appropriate restriction enzyme or enzymes. For most libraries, the cDNA was size-selected (300–1000 bp) using SEPHACRYL S1000, SEPHAROSE CL2B, or SEPHAROSE CL4B column chromatography (Amersham Pharmacia Biotech) or preparative agarose gel electrophoresis. cDNAs were ligated into compatible restriction enzyme sites of the polylinker of a suitable plasmid, e.g., PBLUESCRIPT plasmid (Stratagene), PSPORT1 plasmid (Life Technologies), PCDNA2.1 plasmid (Invitrogen, Carlsbad Calif.), PBK-CMV plasmid (Stratagene), PCR2-TOPOTA (Invitrogen), PCMV-ICIS (Stratagene), or pINCY (Incyte Genomics, Palo Alto Calif.), or derivatives thereof. Recombinant plasmids were transformed into competent E. coli cells including XL1-Blue, XL1-BlueMRF, or SOLR from Stratagene or DH5α, DH10B, or ElectroMAX DH10B from Life Technologies.

II. Isolation of cDNA Clones

Plasmids obtained as described in Example I were recovered from host cells by in vivo excision using the UNIZAP vector system (Stratagene) or by cell lysis. Plasmids were purified using at least one of the following: a Magic or WIZARD Minipreps DNA purification system (Promega);

an AGTC Miniprep purification kit (Edge Biosystems, Gaithersburg Md.); and QIAWELL 8 Plasmid, QIAWELL 8 Plus Plasmid, QIAWELL 8 Ultra Plasmid purification systems or the R.E.A.L. PREP 96 plasmid purification kit from QIAGEN. Following precipitation, plasmids were resuspended in 0.1 ml of distilled water and stored, with or without lyophilization, at 4° C.

Alternatively, plasmid DNA was amplified from host cell lysates using direct link PCR in a high-throughput format (Rao, V. B. (1994) Anal. Biochem. 216:1–14). Host cell lysis and thermal cycling steps were carried out in a single reaction mixture. Samples were processed and stored in 384-well plates, and the concentration of amplified plasmid DNA was quantified fluorometrically using PICOGREEN dye (Molecular Probes, Eugene Oreg.) and a FLUOROSKAN II fluorescence scanner (Labsystems Oy, Helsinki, Finland).

III. Sequencing and Analysis

Incyte cDNA recovered in plasmids as described in Example II were sequenced as follows. Sequencing reactions were processed using standard methods or high-throughput instrumentation such as the ABI CATALYST 800 (Applied Biosystems) thermal cycler or the PTC-200 thermal cycler (MJ Research) in conjunction with the HYDRA microdispenser (Robbins Scientific) or the MICROLAB 2200 (Hamilton) liquid transfer system. cDNA sequencing reactions were prepared using reagents provided by Amersham Pharmacia Biotech or supplied in ABI sequencing kits such as the ABI PRISM BIGDYE Terminator cycle sequencing ready reaction kit (Applied Biosystems). Electrophoretic separation of cDNA sequencing reactions and detection of labeled polynucleotides were carried out using the MEGABACE 1000 DNA sequencing system (Molecular Dynamics); the ABI PRISM 373 or 377 sequencing system (Applied Biosystems) in conjunction with standard ABI protocols and base calling software; or other sequence analysis systems known in the art. Reading frames within the cDNA sequences were identified using standard methods (reviewed in Ausubel, 1997, supra, unit 7.7). Some of the cDNA sequences were selected for extension using the techniques disclosed in Example VIII.

The polynucleotide sequences derived from Incyte cDNAs were validated by removing vector, linker, and poly(A) sequences and by masking ambiguous bases, using algorithms and programs based on BLAST, dynamic programming, and dinucleotide nearest neighbor analysis. The Incyte cDNA sequences or translations thereof were then queried against a selection of public databases such as the GenBank primate, rodent, mammalian, vertebrate, and eukaryote databases, and BLOCKS, PRINTS, DOMO, PRODOM, and hidden Markov model (HMM)-based protein family databases such as PFAM. (HMM is a probabilistic approach which analyzes consensus primary structures of gene families. See, for example, Eddy, S. R. (1996) Curr. Opin. Struct. Biol. 6:361–365.) The queries were performed using programs based on BLAST, FASTA, BLIMPS, and HMMER. The Incyte cDNA sequences were assembled to produce full length polynucleotide sequences. Alternatively, GenBank cDNAs, GenBank ESTs, stitched sequences, stretched sequences, or Genscan-predicted coding sequences (see Examples IV and V) were used to extend Incyte cDNA assemblages to full length. Assembly was performed using programs based on Phred, Phrap, and Consed, and cDNA assemblages were screened for open reading frames using programs based on GeneMark, BLAST, and FASTA. The full length polynucleotide sequences were translated to derive the corresponding full length polypeptide sequences. Alternatively, a polypeptide of the invention may begin at any of the methionine residues of the full length translated polypeptide. Full length polypeptide sequences were subsequently analyzed by querying against databases such as the GenBank protein databases (genpept), SwissProt, BLOCKS, PRINTS, DOMO, PRODOM, Prosite, and hidden Markov model (HMM)-based protein family databases such as PFAM. Full length polynucleotide sequences are also analyzed using MACDNASIS PRO software (Hitachi Software Engineering, South San Francisco Calif.) and LASERGENE software (DNASTAR). Polynucleotide and polypeptide sequence alignments are generated using default parameters specified by the CLUSTAL algorithm as incorporated into the MEGALIGN multisequence alignment program (DNASTAR), which also calculates the percent identity between aligned sequences.

Table 7 summarizes the tools, programs, and algorithms used for the analysis and assembly of Incyte cDNA and full length sequences and provides applicable descriptions, references, and threshold parameters. The first column of Table 7 shows the tools, programs, and algorithms used, the second column provides brief descriptions thereof, the third column presents appropriate references, all of which are incorporated by reference herein in their entirety, and the fourth column presents, where applicable, the scores, probability values, and other parameters used to evaluate the strength of a match between two sequences (the higher the score or the lower the probability value, the greater the identity between two sequences).

The programs described above for the assembly and analysis of full length polynucleotide and polypeptide sequences were also used to identify polynucleotide sequence fragments from SEQ ID NO:25–48. Fragments from about 20 to about 4000 nucleotides which are useful in hybridization and amplification technologies are described in Table 4, column 4.

IV. Identification and Editing of Coding Sequences from Genomic DNA

Putative human kinases were initially identified by running the Genscan gene identification program against public genomic sequence databases (e.g., gbpri and gbhtg). Genscan is a general-purpose gene identification program which analyzes genomic DNA sequences from a variety of organisms (See Burge, C. and S. Karlin (1997) J. Mol. Biol. 268:78–94, and Burge, C. and S. Karlin (1998) Curr. Opin. Struct. Biol. 8:346–354). The program concatenates predicted exons to form an assembled cDNA sequence extending from a methionine to a stop codon. The output of Genscan is a FASTA database of polynucleotide and polypeptide sequences. The maximum range of sequence for Genscan to analyze at once was set to 30 kb. To determine which of these Genscan predicted cDNA sequences encode human kinases, the encoded polypeptides were analyzed by querying against PFAM models for human kinases. Potential human kinases were also identified by homology to Incyte cDNA sequences that had been annotated as human kinases. These selected Genscan-predicted sequences were then compared by BLAST analysis to the genpept and gbpri public databases. Where necessary, the Genscan-predicted sequences were then edited by comparison to the top BLAST hit from genpept to correct errors in the sequence predicted by Genscan, such as extra or omitted exons. BLAST analysis was also used to find any Incyte cDNA or public cDNA coverage of the Genscan-predicted sequences, thus providing evidence for transcription. When Incyte cDNA coverage was available, this information was used to correct or confirm the Genscan predicted sequence. Full length polynucleotide sequences were obtained by assembling Genscan-predicted coding sequences with Incyte cDNA sequences and/or public cDNA sequences using the assembly process described in Example III. Alternatively, full length polynucleotide sequences were derived entirely from edited or unedited Genscan-predicted coding sequences.

V. Assembly of Genomic Sequence Data with cDNA Sequence Data

"Stitched" Sequences

Partial cDNA sequences were extended with exons predicted by the Genscan gene identification program described in Example IV. Partial cDNAs assembled as described in Example III were mapped to genomic DNA and parsed into clusters containing related cDNAs and Genscan exon predictions from one or more genomic sequences. Each cluster was analyzed using an algorithm based on graph theory and dynamic programming to integrate cDNA and genomic information, generating possible splice variants that were subsequently confirmed, edited, or extended to create a full length sequence. Sequence intervals in which the entire length of the interval was present on more than one sequence in the cluster were identified, and intervals thus identified were considered to be equivalent by transitivity. For example, if an interval was present on a cDNA and two genomic sequences, then all three intervals were considered to be equivalent. This process allows unrelated but consecutive genomic sequences to be brought together, bridged by cDNA sequence. Intervals thus identified were then "stitched" together by the stitching algorithm in the order that they appear along their parent sequences to generate the longest possible sequence, as well as sequence variants. Linkages between intervals which proceed along one type of parent sequence (cDNA to cDNA or genomic sequence to genomic sequence) were given preference over linkages which change parent type (cDNA to genomic sequence). The resultant stitched sequences were translated and compared by BLAST analysis to the genpept and gbpri public databases. Incorrect exons predicted by Genscan were corrected by comparison to the top BLAST hit from genpept. Sequences were further extended with additional cDNA sequences, or by inspection of genomic DNA, when necessary.

"Stretched" Sequences

Partial DNA sequences were extended to full length with an algorithm based on BLAST analysis. First, partial cDNAs assembled as described in Example III were queried against public databases such as the GenBank primate, rodent, mammalian, vertebrate, and eukaryote databases using the BLAST program. The nearest GenBank protein homolog was then compared by BLAST analysis to either Incyte cDNA sequences or GenScan exon predicted sequences described in Example IV. A chimeric protein was generated by using the resultant high-scoring segment pairs (HSPs) to map the translated sequences onto the GenBank protein homolog. Insertions or deletions may occur in the chimeric protein with respect to the original GenBank protein homolog. The GenBank protein homolog, the chimeric protein, or both were used as probes to search for homologous genomic sequences from the public human genome databases. Partial DNA sequences were therefore "stretched" or extended by the addition of homologous genomic sequences. The resultant stretched sequences were examined to determine whether it contained a complete gene.

VI. Chromosomal Mapping of PKIN Encoding Polynucleotides

The sequences which were used to assemble SEQ ID NO:25–48 were compared with sequences from the Incyte LIFESEQ database and public domain databases using BLAST and other implementations of the Smith-Waterman algorithm. Sequences from these databases that matched SEQ ID NO:25–48 were assembled into clusters of contiguous and overlapping sequences using assembly algorithms such as Phrap (Table 7). Radiation hybrid and genetic mapping data available from public resources such as the Stanford Human Genome Center (SHGC), Whitehead Institute for Genome Research (WIGR), and Généthon were used to determine if any of the clustered sequences had been previously mapped. Inclusion of a mapped sequence in a cluster resulted in the assignment of all sequences of that cluster, including its particular SEQ ID NO:, to that map location.

Map locations are represented by ranges, or intervals, of human chromosomes. The map position of an interval, in centiMorgans, is measured relative to the terminus of the chromosome's p-arm. (The centiMorgan (cM) is a unit of measurement based on recombination frequencies between chromosomal markers. On average, 1 cM is roughly equivalent to 1 megabase (Mb) of DNA in humans, although this can vary widely due to hot and cold spots of recombination.) The cM distances are based on genetic markers mapped by Généthon which provide boundaries for radiation hybrid markers whose sequences were included in each of the clusters. Human genome maps and other resources available to the public, such as the NCBI "GeneMap '99" World Wide Web site (http://www.ncbi.nlm.nih.gov/genemap/), can be employed to determine if previously identified disease genes map within or in proximity to the intervals indicated above.

VII. Analysis of Polynucleotide Expression

Northern analysis is a laboratory technique used to detect the presence of a transcript of a gene and involves the hybridization of a labeled nucleotide sequence to a membrane on which RNAs from a particular cell type or tissue have been bound. (See, e.g., Sambrook, supra, ch. 7; Ausubel (1995) supra ch. 4 and 16.)

Analogous computer techniques applying BLAST were used to search for identical or related molecules in cDNA databases such as GenBank or LIFESEQ (Incyte Genomics). This analysis is much faster than multiple membrane-based hybridizations. In addition, the sensitivity of the computer search can be modified to determine whether any particular match is categorized as exact or similar. The basis of the search is the product score, which is defined as:

$$\frac{\text{BLAST Score} \times \text{Percent Identity}}{5 \times \text{minimum}\{\text{length(Seq. 1), length(Seq. 2)}\}}$$

The product score takes into account both the degree of similarity between two sequences and the length of the sequence match. The product score is a normalized value between 0 and 100, and is calculated as follows: the BLAST score is multiplied by the percent nucleotide identity and the product is divided by (5 times the length of the shorter of the two sequences). The BLAST score is calculated by assigning a score of +5 for every base that matches in a high-scoring segment pair (HSP), and −4 for every mismatch. Two sequences may share more than one HSP (separated by gaps). If there is more than one HSP, then the pair with the highest BLAST score is used to calculate the product score.

The product score represents a balance between fractional overlap and quality in a BLAST alignment. For example, a product score of 100 is produced only for 100% identity over the entire length of the shorter of the two sequences being compared. A product score of 70 is produced either by 100% identity and 70% overlap at one end, or by 88% identity and 100% overlap at the other. A product score of 50 is produced either by 100% identity and 50% overlap at one end, or 79% identity and 100% overlap.

Alternatively, polynucleotide sequences encoding PKIN are analyzed with respect to the tissue sources from which they were derived. For example, some full length sequences are assembled, at least in part, with overlapping Incyte cDNA sequences (see Example III). Each cDNA sequence is derived from a cDNA library constructed from a human tissue. Each human tissue is classified into one of the following organ/tissue categories: cardiovascular system; connective tissue; digestive system; embryonic structures; endocrine system; exocrine glands; genitalia, female; genitalia, male; germ cells; hemic and immune system; liver; musculoskeletal system; nervous system; pancreas; respiratory system; sense organs; skin; stomatognathic system; unclassified/mixed; or urinary tract. The number of libraries in each category is counted and divided by the total number of libraries across all categories. Similarly, each human tissue is classified into one of the following disease/condition categories: cancer, cell line, developmental, inflammation, neurological, trauma, cardiovascular, pooled, and other, and the number of libraries in each category is counted and divided by the total number of libraries across all categories. The resulting percentages reflect the tissue- and disease-specific expression of cDNA encoding PKIN. cDNA sequences and cDNA library/tissue information are found in the LIFESEQ GOLD database (Incyte Genomics, Palo Alto Calif.).

VIII. Extension of PKIN Encoding Polynucleotides

Full length polynucleotide sequences were also produced by extension of an appropriate fragment of the full length molecule using oligonucleotide primers designed from this fragment. One primer was synthesized to initiate 5' extension of the known fragment, and the other primer was synthesized to initiate 3' extension of the known fragment. The initial primers were designed using OLIGO 4.06 software (National Biosciences), or another appropriate program, to be about 22 to 30 nucleotides in length, to have a GC content of about 50% or more, and to anneal to the target sequence at temperatures of about 68° C. to about 72° C. Any stretch of nucleotides which would result in hairpin structures and primer-primer dimerizations was avoided.

Selected human cDNA libraries were used to extend the sequence. If more than one extension was necessary or desired, additional or nested sets of primers were designed.

High fidelity amplification was obtained by PCR using methods well known in the art. PCR was performed in 96-well plates using the PTC-200 thermal cycler (MJ Research, Inc.). The reaction mix contained DNA template, 200 nmol of each primer, reaction buffer containing $Mg^{2+}$, $(NH_4)_2SO_4$, and 2-mercaptoethanol, Taq DNA polymerase (Amersham Pharmacia Biotech), ELONGASE enzyme (Life Technologies), and Pfu DNA polymerase (Stratagene), with the following parameters for primer pair PCI A and PCI B: Step 1: 94° C., 3 min; Step 2: 94° C., 15 sec; Step 3: 60° C., 1 min; Step 4: 68° C., 2 min; Step 5: Steps 2, 3, and 4 repeated 20 times; Step 6: 68° C., 5 min; Step 7: storage at 4° C. In the alternative, the parameters for primer pair T7 and SK+ were as follows: Step 1: 94° C., 3 min; Step 2: 94° C., 15 sec; Step 3: 57° C., 1 min; Step 4: 68° C, 2 min; Step 5: Steps 2, 3, and 4 repeated 20 times; Step 6: 68° C., 5 min; Step 7: storage at 4° C.

The concentration of DNA in each well was determined by dispensing 100 µl PICOGREEN quantitation reagent (0.25% (v/v) PICOGREEN; Molecular Probes, Eugene Oreg.) dissolved in 1×TE and 0.5 µl of undiluted PCR product into each well of an opaque fluorimeter plate (Corning Costar, Acton Mass.), allowing the DNA to bind to the reagent. The plate was scanned in a Fluoroskan II (Labsystems Oy, Helsinki, Finland) to measure the fluorescence of the sample and to quantify the concentration of DNA. A 5 µl to 10 µl aliquot of the reaction mixture was analyzed by electrophoresis on a 1% agarose gel to determine which reactions were successful in extending the sequence.

The extended nucleotides were desalted and concentrated, transferred to 384-well plates, digested with CviJI cholera virus endonuclease (Molecular Biology Research, Madison Wis.), and sonicated or sheared prior to religation into pUC 18 vector (Amersham Pharmacia Biotech). For shotgun sequencing, the digested nucleotides were separated on low concentration (0.6 to 0.8%) agarose gels, fragments were excised, and agar digested with Agar ACE (Promega). Extended clones were religated using T4 ligase (New England Biolabs, Beverly Mass.) into pUC 18 vector (Amersham Pharmacia Biotech), treated with Pfu DNA polymerase (Stratagene) to fill-in restriction site overhangs, and transfected into competent E. coli cells. Transformed cells were selected on antibiotic-containing media, and individual colonies were picked and cultured overnight at 37° C. in 384-well plates in LB/2× carb liquid media.

The cells were lysed, and DNA was amplified by PCR using Taq DNA polymerase (Amersham Pharmacia Biotech) and Pfu DNA polymerase (Stratagene) with the following parameters: Step 1: 94° C., 3 min; Step 2: 94° C., 15 sec; Step 3: 60° C., 1 min; Step 4: 72° C., 2 min; Step 5: steps 2, 3, and 4 repeated 29 times; Step 6: 72° C., 5 min; Step 7: storage at 4° C. DNA was quantified by PICOGREEN reagent (Molecular Probes) as described above. Samples with low DNA recoveries were reamplified using the same conditions as described above. Samples were diluted with 20% dimethysulfoxide (1:2, v/v), and sequenced using DYENAMIC energy transfer sequencing primers and the DYENAMIC DIRECT kit (Amersham Pharmacia Biotech) or the ABI PRISM BIGDYE Terminator cycle sequencing ready reaction kit (Applied Biosystems).

In like manner, full length polynucleotide sequences are verified using the above procedure or are used to obtain 5' regulatory sequences using the above procedure along with oligonucleotides designed for such extension, and an appropriate genomic library.

IX. Labeling and Use of Individual Hybridization Probes

Hybridization probes derived from SEQ ID NO:25–48 are employed to screen cDNAs, genomic DNAs, or mRNAs. Although the labeling of oligonucleotides, consisting of about 20 base pairs, is specifically described, essentially the same procedure is used with larger nucleotide fragments. Oligonucleotides are designed using state-of-the-art software such as OLIGO 4.06 software (National Biosciences) and labeled by combining 50 pmol of each oligomer, 250 µCi of [$\gamma$-$^{32}$P] adenosine triphosphate (Amersham Pharmacia Biotech), and T4 polynucleotide kinase (DuPont NEN, Boston Mass.). The labeled oligonucleotides are substantially purified using a SEPHADEX G-25 superfine size exclusion dextran bead column (Amersham Pharmacia Biotech). An aliquot containing $10^7$ counts per minute of the labeled probe is used in a typical membrane-based hybridization analysis of human genomic DNA digested with one of the following endonucleases: Ase I, Bgl II, Eco RI, Pst I, Xba I, or Pvu II (DuPont NEN).

The DNA from each digest is fractionated on a 0.7% agarose gel and transferred to nylon membranes (Nytran Plus, Schleicher & Schuell, Durham N.H.). Hybridization is carried out for 16 hours at 40° C. To remove nonspecific signals, blots are sequentially washed at room temperature under conditions of up to, for example, 0.1× saline sodium citrate and 0.5% sodium dodecyl sulfate. Hybridization patterns are visualized using autoradiography or an alternative imaging means and compared.

X. Microarrays

The linkage or synthesis of array elements upon a microarray can be achieved utilizing photolithography, piezoelectric printing (ink-jet printing, See, e.g., Baldeschweiler, supra.), mechanical microspotting technologies, and derivatives thereof. The substrate in each of the aforementioned technologies should be uniform and solid with a non-porous surface (Schena (1999), supra). Suggested substrates include silicon, silica, glass slides, glass chips, and silicon wafers. Alternatively, a procedure analogous to a dot or slot blot may also be used to arrange and link elements to the surface of a substrate using thermal, UV, chemical, or mechanical bonding procedures. A typical array may be produced using available methods and machines well known to those of ordinary skill in the art and may contain any appropriate number of elements. (See, e.g., Schena, M. et al. (1995) Science 270:467–470; Shalon, D. et al. (1996) Genome Res. 6:639–645; Marshall, A. and J. Hodgson (1998) Nat. Biotechnol. 16:27–31.)

Full length cDNAs, Expressed Sequence Tags (ESTs), or fragments or oligomers thereof may comprise the elements of the microarray. Fragments or oligomers suitable for hybridization can be selected using software well known in the art such as LASERGENE software (DNASTAR). The array elements are hybridized with polynucleotides in a biological sample. The polynucleotides in the biological sample are conjugated to a fluorescent label or other molecular tag for ease of detection. After hybridization, nonhybridized nucleotides from the biological sample are removed, and a fluorescence scanner is used to detect hybridization at each array element. Alternatively, laser desorbtion and mass spectrometry may be used for detection of hybridization. The degree of complementarity and the relative abundance of each polynucleotide which hybridizes to an element on the microarray may be assessed. In one embodiment, microarray preparation and usage is described in detail below.

Tissue or Cell Sample Preparation

Total RNA is isolated from tissue samples using the guanidinium thiocyanate method and poly(A)$^+$ RNA is purified using the oligo-(dT) cellulose method. Each poly(A)$^+$ RNA sample is reverse transcribed using MMLV reverse-transcriptase, 0.05 pg/μl oligo-(dT) primer (21 mer), 1× first strand buffer, 0.03 units/μl RNase inhibitor, 500 μM dATP, 500 μM dGTP, 500 μM dTTP, 40 μM dCTP, 40 μM dCTP-Cy3 (BDS) or dCTP-Cy5 (Amersham Pharmacia Biotech). The reverse transcription reaction is performed in a 25 ml volume containing 200 ng poly(A)$^+$ RNA with GEM-BRIGHT kits (Incyte). Specific control poly(A)$^+$ RNAs are synthesized by in vitro transcription from non-coding yeast genomic DNA. After incubation at 37° C. for 2 hr, each reaction sample (one with Cy3 and another with Cy5 labeling) is treated with 2.5 ml of 0.5M sodium hydroxide and incubated for 20 minutes at 85° C. to the stop the reaction and degrade the RNA. Samples are purified using two successive CHROMA SPIN 30 gel filtration spin columns (CLONTECH Laboratories, Inc. (CLONTECH), Palo Alto Calif.) and after combining, both reaction samples are ethanol precipitated using 1 ml of glycogen (1 mg/ml), 60 ml sodium acetate, and 300 ml of 100% ethanol. The sample is then dried to completion using a SpeedVAC (Savant Instruments Inc., Holbrook N.Y.) and resuspended in 14 μl 5×SSC/0.2% SDS.

Microarray Preparation

Sequences of the present invention are used to generate array elements. Each array element is amplified from bacterial cells containing vectors with cloned cDNA inserts. PCR amplification uses primers complementary to the vector sequences flanking the cDNA insert. Array elements are amplified in thirty cycles of PCR from an initial quantity of 1–2 ng to a final quantity greater than 5 μg. Amplified array elements are then purified using SEPHACRYL-400 (Amersham Pharmacia Biotech).

Purified array elements are immobilized on polymer-coated glass slides. Glass microscope slides (Corning) are cleaned by ultrasound in 0.1% SDS and acetone, with extensive distilled water washes between and after treatments. Glass slides are etched in 4% hydrofluoric acid (VWR Scientific Products Corporation (VWR), West Chester Pa.), washed extensively in distilled water, and coated with 0.05% aminopropyl silane (Sigma) in 95% ethanol. Coated slides are cured in a 110° C. oven.

Array elements are applied to the coated glass substrate using a procedure described in U.S. Pat. No. 5,807,522, incorporated herein by reference. 1 μl of the array element DNA, at an average concentration of 100 ng/μl, is loaded into the open capillary printing element by a high-speed robotic apparatus. The apparatus then deposits about 5 nl of array element sample per slide.

Microarrays are UV-crosslinked using a STRATALINKER UV-crosslinker (Stratagene). Microarrays are washed at room temperature once in 0.2% SDS and three times in distilled water. Non-specific binding sites are blocked by incubation of microarrays in 0.2% casein in phosphate buffered saline (PBS) (Tropix, Inc., Bedford Mass.) for 30 minutes at 60° C. followed by washes in 0.2% SDS and distilled water as before.

Hybridization

Hybridization reactions contain 9 μl of sample mixture consisting of 0.2 μg each of Cy3 and Cy5 labeled cDNA synthesis products in 5×SSC, 0.2% SDS hybridization buffer. The sample mixture is heated to 65° C. for 5 minutes and is aliquoted onto the microarray surface and covered with an 1.8 cm$^2$ coverslip. The arrays are transferred to a waterproof chamber having a cavity just slightly larger than a microscope slide. The chamber is kept at 100% humidity internally by the addition of 140 μl of 5×SSC in a corner of the chamber. The chamber containing the arrays is incubated for about 6.5 hours at 60° C. The arrays are washed for 10 min at 45° C. in a first wash buffer (1×SSC, 0.1% SDS), three times for 10 minutes each at 45° C. in a second wash buffer (0.1×SSC), and dried.

Detection

Reporter-labeled hybridization complexes are detected with a microscope equipped with an Innova 70 mixed gas 10 W laser (Coherent, Inc., Santa Clara Calif.) capable of generating spectral lines at 488 nm for excitation of Cy3 and at 632 nm for excitation of Cy5. The excitation laser light is focused on the array using a 20× microscope objective (Nikon, Inc., Melville N.Y.). The slide containing the array is placed on a computer-controlled X-Y stage on the microscope and raster-scanned past the objective. The 1.8 cm×1.8 cm array used in the present example is scanned with a resolution of 20 micrometers.

In two separate scans, a mixed gas multiline laser excites the two fluorophores sequentially. Emitted light is split, based on wavelength, into two photomultiplier tube detectors (PMT R1477, Hamamatsu Photonics Systems, Bridgewater N.J.) corresponding to the two fluorophores. Appropriate filters positioned between the array and the photomultiplier tubes are used to filter the signals. The emission maxima of the fluorophores used are 565 nm for Cy3 and 650 nm for Cy5. Each array is typically scanned twice, one scan per fluorophore using the appropriate filters at the laser source, although the apparatus is capable of recording the spectra from both fluorophores simultaneously.

The sensitivity of the scans is typically calibrated using the signal intensity generated by a cDNA control species added to the sample mixture at a known concentration. A specific location on the array contains a complementary DNA sequence, allowing the intensity of the signal at that location to be correlated with a weight ratio of hybridizing species of 1:100,000. When two samples from different sources (e.g., representing test and control cells), each labeled with a different fluorophore, are hybridized to a single array for the purpose of identifying genes that are differentially expressed, the calibration is done by labeling samples of the calibrating cDNA with the two fluorophores and adding identical amounts of each to the hybridization mixture.

The output of the photomultiplier tube is digitized using a 12-bit RTI-835H analog-to-digital (A/D) conversion board (Analog Devices, Inc., Norwood Mass.) installed in an IBM-compatible PC computer. The digitized data are displayed as an image where the signal intensity is mapped using a linear 20-color transformation to a pseudocolor scale ranging from blue (low signal) to red (high signal). The data is also analyzed quantitatively. Where two different fluorophores are excited and measured simultaneously, the data are first corrected for optical crosstalk (due to overlapping emission spectra) between the fluorophores using each fluorophore's emission spectrum.

A grid is superimposed over the fluorescence signal image such that the signal from each spot is centered in each element of the grid. The fluorescence signal within each element is then integrated to obtain a numerical value corresponding to the average intensity of the signal. The software used for signal analysis is the GEMTOOLS gene expression analysis program (Incyte).

XI. Complementary Polynucleotides

Sequences complementary to the PKIN-encoding sequences, or any parts thereof, are used to detect, decrease, or inhibit expression of naturally occurring PKIN. Although use of oligonucleotides comprising from about 15 to 30 base pairs is described, essentially the same procedure is used with smaller or with larger sequence fragments. Appropriate oligonucleotides are designed using OLIGO 4.06 software (National Biosciences) and the coding sequence of PKIN. To inhibit transcription, a complementary oligonucleotide is designed from the most unique 5' sequence and used to prevent promoter binding to the coding sequence. To inhibit translation, a complementary oligonucleotide is designed to prevent ribosomal binding to the PKIN-encoding transcript.

XII. Expression of PKIN

Expression and purification of PKIN is achieved using bacterial or virus-based expression systems. For expression of PKIN in bacteria, cDNA is subcloned into an appropriate vector containing an antibiotic resistance gene and an inducible promoter that directs high levels of cDNA transcription. Examples of such promoters include, but are not limited to, the trp-lac (tac) hybrid promoter and the T5 or T7 bacteriophage promoter in conjunction with the lac operator regulatory element. Recombinant vectors are transformed into suitable bacterial hosts, e.g., BL21(DE3). Antibiotic resistant bacteria express PKIN upon induction with isopropyl beta-D-thiogalactopyranoside (IPTG). Expression of PKIN in eukaryotic cells is achieved by infecting insect or mammalian cell lines with recombinant *Autographica californica* nuclear polyhedrosis virus (AcMNPV), commonly known as baculovirus. The nonessential polyhedrin gene of baculovirus is replaced with cDNA encoding PKIN by either homologous recombination or bacterial-mediated transposition involving transfer plasmid intermediates. Viral infectivity is maintained and the strong polyhedrin promoter drives high levels of cDNA transcription. Recombinant baculovirus is used to infect *Spodoptera frugiperda* (Sf9) insect cells in most cases, or human hepatocytes, in some cases. Infection of the latter requires additional genetic modifications to baculovirus. (See Engelhard, E. K. et al. (1994) Proc. Natl. Acad. Sci. USA 91:3224–3227; Sandig, V. et al. (1996) Hum. Gene Ther. 7:1937–1945.)

In most expression systems, PKIN is synthesized as a fusion protein with, e.g., glutathione S-transferase (GST) or a peptide epitope tag, such as FLAG or 6-His, permitting rapid, single-step, affinity-based purification of recombinant fusion protein from crude cell lysates. GST, a 26-kilodalton enzyme from *Schistosoma japonicum,* enables the purification of fusion proteins on immobilized glutathione under conditions that maintain protein activity and antigenicity (Amersham Pharmacia Biotech). Following purification, the GST moiety can be proteolytically cleaved from PKIN at specifically engineered sites. FLAG, an 8-amino acid peptide, enables immunoaffinity purification using commercially available monoclonal and polyclonal anti-FLAG antibodies (Eastman Kodak). 6-His, a stretch of six consecutive histidine residues, enables purification on metal-chelate resins (QIAGEN). Methods for protein expression and purification are discussed in Ausubel (1995, supra, ch. 10 and 16). Purified PKIN obtained by these methods can be used directly in the assays shown in Examples XVI, XVII, XVIII, and XIX where applicable.

XIII. Functional Assays

PKIN function is assessed by expressing the sequences encoding PKIN at physiologically elevated levels in mammalian cell culture systems. cDNA is subcloned into a mammalian expression vector containing a strong promoter that drives high levels of cDNA expression. Vectors of choice include PCMV SPORT (Life Technologies) and PCR3.1 (Invitrogen, Carlsbad Calif.), both of which contain the cytomegalovirus promoter. 5–10 μg of recombinant vector are transiently transfected into a human cell line, for example, an endothelial or hematopoietic cell line, using either liposome formulations or electroporation. 1–2 μg of an additional plasmid containing sequences encoding a marker protein are co-transfected. Expression of a marker protein provides a means to distinguish transfected cells from nontransfected cells and is a reliable predictor of cDNA expression from the recombinant vector. Marker proteins of choice include, e.g., Green Fluorescent Protein (GFP; Clontech), CD64, or a CD64-GFP fusion protein. Flow cytometry (FCM), an automated, laser optics-based technique, is used to identify transfected cells expressing GFP or CD64-GFP and to evaluate the apoptotic state of the cells and other cellular properties. FCM detects and quantifies the uptake of fluorescent molecules that diagnose events preceding or coincident with cell death. These events include changes in nuclear DNA content as measured by staining of DNA with propidium iodide; changes in cell size and granularity as measured by forward light scatter and 90 degree side light scatter; down-regulation of DNA synthesis as measured by decrease in bromodeoxyuridine uptake; alterations in expression of cell surface and intracellular proteins as measured by reactivity with specific antibodies; and alterations in plasma membrane composition as measured by the binding of fluorescein-conjugated Annexin V protein to the cell surface. Methods in flow cytometry are discussed in Ormerod, M. G. (1994) *Flow Cytometry*, Oxford, New York N.Y.

The influence of PKIN on gene expression can be assessed using highly purified populations of cells transfected with sequences encoding PKIN and either CD64 or CD64-GFP. CD64 and CD64-GFP are expressed on the surface of transfected cells and bind to conserved regions of human immunoglobulin G (IgG). Transfected cells are efficiently separated from nontransfected cells using magnetic beads coated with either human IgG or antibody against CD64 (DYNAL, Lake Success N.Y.). mRNA can be purified from the cells using methods well known by those of skill in the art. Expression of mRNA encoding PKIN and other genes of interest can be analyzed by northern analysis or microarray techniques.

XIV. Production of PKIN Specific Antibodies

PKIN substantially purified using polyacrylamide gel electrophoresis (PAGE; see, e.g., Harrington, M. G. (1990) Methods Enzymol. 182:488–495), or other purification techniques, is used to immunize rabbits and to produce antibodies using standard protocols.

Alternatively, the PKIN amino acid sequence is analyzed using LASERGENE software (DNASTAR) to determine regions of high immunogenicity, and a corresponding oligopeptide is synthesized and used to raise antibodies by means known to those of skill in the art. Methods for selection of appropriate epitopes, such as those near the C-terminus or in hydrophilic regions are well described in the art. (See, e.g., Ausubel, 1995, supra, ch. 11.)

Typically, oligopeptides of about 15 residues in length are synthesized using an ABI 431A peptide synthesizer (Applied Biosystems) using FMOC chemistry and coupled to KLH (Sigma-Aldrich, St. Louis Mo.) by reaction with N-maleimidobenzoyl-N-hydroxysuccinimide ester (MBS) to increase immunogenicity. (See, e.g., Ausubel, 1995, supra.) Rabbits are immunized with the oligopeptide-KLH complex in complete Freund's adjuvant. Resulting antisera are tested for antipeptide and anti-PKIN activity by, for example, binding the peptide or PKIN to a substrate, blocking with 1% BSA, reacting with rabbit antisera, washing, and reacting with radio-iodinated goat anti-rabbit IgG.

XV. Purification of Naturally Occurring PKIN Using Specific Antibodies

Naturally occurring or recombinant PKIN is substantially purified by immunoaffinity chromatography using antibodies specific for PKIN. An immunoaffinity column is constructed by covalently coupling anti-PKIN antibody to an activated chromatographic resin, such as CNBr-activated SEPHAROSE (Amersham Pharmacia Biotech). After the coupling, the resin is blocked and washed according to the manufacturer's instructions.

Media containing PKIN are passed over the immunoaffinity column, and the column is washed under conditions that allow the preferential absorbance of PKIN (e.g., high ionic strength buffers in the presence of detergent). The column is eluted under conditions that disrupt antibody/PKIN binding (e.g., a buffer of pH 2 to pH 3, or a high concentration of a chaotrope, such as urea or thiocyanate ion), and PKIN is collected.

XVI. Identification of Molecules Which Interact with PKIN

PKIN, or biologically active fragments thereof, are labeled with $^{125}$I Bolton-Hunter reagent. (See, e.g., Bolton A. E. and W. M. Hunter (1973) Biochem. J. 133:529–539.) Candidate molecules previously arrayed in the wells of a multi-well plate are incubated with the labeled PKIN, washed, and any wells with labeled PKIN complex are assayed. Data obtained using different concentrations of PKIN are used to calculate values for the number, affinity, and association of PKIN with the candidate molecules.

Alternatively, molecules interacting with PKIN are analyzed using the yeast two-hybrid system as described in Fields, S. and O. Song (1989) Nature 340:245–246, or using commercially available kits based on the two-hybrid system, such as the MATCHMAKER system (Clontech).

PKIN may also be used in the PATHCALLING process (CuraGen Corp., New Haven Conn.) which employs the yeast two-hybrid system in a high-throughput manner to determine all interactions between the proteins encoded by two large libraries of genes (Nandabalan, K. et al. (2000) U.S. Pat. No. 6,057,101).

XVII. Demonstration of PKIN Activity

Generally, protein kinase activity is measured by quantifying the phosphorylation of a protein substrate by PKIN in the presence of [$\gamma$-$^{32}$P]ATP. PKIN is incubated with the protein substrate, $^{32}$P-ATP, and an appropriate kinase buffer. The $^{32}$P incorporated into the substrate is separated from free $^{32}$P-ATP by electrophoresis and the incorporated $^{32}$P is counted using a radioisotope counter. The amount of incorporated $^{32}$P is proportional to the activity of PKIN. A determination of the specific amino acid residue phosphorylated is made by phosphoamino acid analysis of the hydrolyzed protein.

In one alternative, protein kinase activity is measured by quantifying the transfer of gamma phosphate from adenosine triphosphate (ATP) to a serine, threonine or tyrosine residue in a protein substrate. The reaction occurs between a protein kinase sample with a biotinylated peptide substrate and gamma $^{32}$P-ATP. Following the reaction, free avidin in solution is added for binding to the biotinylated $^{32}$P-peptide product. The binding sample then undergoes a centrifugal ultrafiltration process with a membrane which will retain the product-avidin complex and allow passage of free gamma $^{32}$P-ATP. The reservoir of the centrifuged unit containing the $^{32}$P-peptide product as retentate is then counted in a scintillation counter. This procedure allows assay of any type of protein kinase sample, depending on the peptide substrate and kinase reaction buffer selected. This assay is provided in kit form (ASUA, Affinity Ultrafiltration Separation Assay, Transbio Corporation, Baltimore Md., U.S. Pat. No. 5,869, 275). Suggested substrates and their respective enzymes include but are not limited to: Histone H1 (Sigma) and p34$^{cdc2}$kinase, Annexin I, Angiotensin (Sigma) and EGF receptor kinase, Annexin II and src kinase, ERK1 & ERK2 substrates and MEK, and myelin basic protein and ERK (Pearson, J. D. et al. (1991) Methods Enzymol. 200:62–81).

In another alternative, protein kinase activity of PKIN is demonstrated in an assay containing PKIN, 50 μl of kinase buffer, 1 μg substrate, such as myelin basic protein (MBP) or synthetic peptide substrates, 1 mM DTT, 10 µg ATP, and 0.5 µCi [γ-$^{32}$P]ATP. The reaction is incubated at 30° C. for 30 minutes and stopped by pipetting onto P81 paper. The unincorporated [γ-$^{32}$P]ATP is removed by washing and the incorporated radioactivity is measured using a scintillation counter. Alternatively, the reaction is stopped by heating to 100° C. in the presence of SDS loading buffer and resolved on a 12% SDS polyacrylamide gel followed by autoradiography. The amount of incorporated $^{32}$P is proportional to the activity of PKIN.

In yet another alternative, adenylate kinase or guanylate kinase activity may be measured by the incorporation of $^{32}$P from [γ-$^{32}$P]ATP into ADP or GDP using a gamma radio-isotope counter. The enzyme, in a kinase buffer, is incubated together with the appropriate nucleotide mono-phosphate substrate (AMP or GMP) and $^{32}$P-labeled ATP as the phosphate donor. The reaction is incubated at 37° C. and terminated by addition of trichloroacetic acid. The acid extract is neutralized and subjected to gel electrophoresis to separate the mono-, di-, and triphosphonucleotide fractions. The diphosphonucleotide fraction is excised and counted. The radioactivity recovered is proportional to the enzyme activity.

In yet another alternative, other assays for PKIN include scintillation proximity assays (SPA), scintillation plate technology and filter binding assays. Useful substrates include recombinant proteins tagged with glutathione transferase, or synthetic peptide substrates tagged with biotin. Inhibitors of PKIN activity, such as small organic molecules, proteins or peptides, may be identified by such assays.

XVIII. Enhancement/Inhibition of Protein Kinase Activity

Agonists or antagonists of PKIN activation or inhibition may be tested using assays described in section XVII. Agonists cause an increase in PKIN activity and antagonists cause a decrease in PKIN activity.

XIX. Kinase Binding Assay

Binding of PKIN to a FLAG-CD44 cyt fusion protein can be determined by incubating PKIN to anti-PKIN-conjugated immunoaffinity beads followed by incubating portions of the beads (having 10–20 ng of protein) with 0.5 ml of a binding buffer (20 mM Tris-HCL (pH 7.4), 150 mM NaCl, 0.1% bovine serum albumin, and 0.05% Triton X-100) in the presence of $^{125}$I-labeled FLAG-CD44cyt fusion protein (5,000 cpm/ng protein) at 4 ° C. for 5 hours. Following binding, beads were washed thoroughly in the binding buffer and the bead-bound radioactivity measured in a scintillation counter (Bourguignon, L. Y. W. et al. (2001) J. Biol. Chem. 276:7327–7336). The amount of incorporated $^{32}$P is proportional to the amount of bound PKIN.

Various modifications and variations of the described methods and systems of the invention will be apparent to those skilled in the art without departing from the scope and spirit of the invention. Although the invention has been described in connection with certain embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

TABLE 1

| Incyte Project ID | Polypeptide SEQ ID NO: | Incyte Polypeptide ID | Polynucleotide SEQ ID NO: | Incyte Polynucleotide ID |
|---|---|---|---|---|
| 7312543 | 1 | 7312543CD1 | 25 | 7312543CB1 |
| 7477427 | 2 | 7477427CD1 | 26 | 7477427CB1 |
| 7481495 | 3 | 7481495CD1 | 27 | 7481495CB1 |
| 55053189 | 4 | 55053189CD1 | 28 | 55053189CB1 |
| 7474797 | 5 | 7474797CD1 | 29 | 7474797CB1 |
| 3296272 | 6 | 3296272CD1 | 30 | 3296272CB1 |
| 1989319 | 7 | 1989319CD1 | 31 | 1989319CB1 |
| 079284 | 8 | 079284CD1 | 32 | 079284CB1 |
| 5502218 | 9 | 5502218CD1 | 33 | 5502218CB1 |
| 55056054 | 10 | 55056054CD1 | 34 | 55056054CB1 |
| 7481989 | 11 | 7481989CD1 | 35 | 7481989CB1 |
| 55052990 | 12 | 55052990CD1 | 36 | 55052990CB1 |
| 7482377 | 13 | 7482377CD1 | 37 | 7482377CB1 |
| 7758364 | 14 | 7758364CD1 | 38 | 7758364CB1 |
| 5850001 | 15 | 5850001CD1 | 39 | 5850001CB1 |
| 7477062 | 16 | 7477062CD1 | 40 | 7477062CB1 |
| 7477207 | 17 | 7477207CD1 | 41 | 7477207CB1 |
| 4022651 | 18 | 4022651CD1 | 42 | 4022651CB1 |
| 7274927 | 19 | 7274927CD1 | 43 | 7274927CB1 |
| 7946584 | 20 | 7946584CD1 | 44 | 7946584CB1 |
| 8088078 | 21 | 8088078CD1 | 45 | 8088078CB1 |
| 2674269 | 22 | 2674269CD1 | 46 | 2674269CB1 |
| 7472409 | 23 | 7472409CD1 | 47 | 7472409CB1 |
| 7477484 | 24 | 7477484CD1 | 48 | 7477484CB1 |

TABLE 2

| Polypeptide SEQ ID NO: | Incyte Polypeptide ID | GenBank ID NO: or PROTEOME ID NO: | Probability Score | Annotation |
|---|---|---|---|---|
| 1 | 7312543CD1 | g4115429 | 9.0E–215 | [Rattus norvegicus] serin/threonine protein kinase (Amano, M. et al. (1996) Science 271: 648–650) |
| 2 | 7477427CD1 | g2736151 | 0.0 | [Rattus norvegicus] mytonic dystrophy kinase-related (Leung, T. et al. (1998) Mol. Cell. Biol. 18 (1), 130–140) |
| 3 | 7481495CD1 | g10945428 | 0.0 | [fl][Homo sapiens] membrane-associated guanylate kinase MAGI3 (Wu, Y. et al. (2000) J. Biol. Chem. 275 (28), 21477–21485) |
| 4 | 55053189CD1 | g1360110 | 5.8E–73 | [Plasmodium falciparum] mitogen-activated protein kinase 1, serine/threonine protein kinase (Doerig, C.M. et al. (1996) Gene 177 (1–2), 1–6) |
|  |  | g4220888 | 5.3E–171 | [Rattus norvegicus] extracellular signal-regulated kinase 7; ERK7 (Abe, M.K. et al. (1999) Mol. Cell. Biol. 19 (2), 1301–1312) |
|  |  | g2131000 | 4.2E–70 | [Leishmania mexicana] MAP-kinase homologue (Wiese, M. (1998) EMBO J. 17 (9), 2619–2628) |

TABLE 2-continued

| Polypeptide SEQ ID NO: | Incyte Polypeptide ID | GenBank ID NO: or PROTEOME ID NO: | Probability Score | Annotation |
|---|---|---|---|---|
| 5 | 7474797CD1 | g404634 | 2.6E−54 | [*Mus musculus*] serine/threonine kinase (Bielke, W. et al. (1994) Gene 139 (2), 235–239) |
| 6 | 3296272CD1 | g6690020 | 1.6E−157 | [*Mus musculus*] pantothenate kinase 1 beta (Rock, C.O. et al. (2000) J. Biol. Chem. 275 (2), 1377–1383) |
| 7 | 1989319CD1 | g6760436 | 9.2E−125 | [*Gallus gallus*] qin-induced kinase (Xia, Y. et al. (2000) Biochem. Biophys. Res. Commun. 276 (2), 564–570) |
| 8 | 79284CD1 | g5757703 | 0.0 | [*Mus musculus*] syntrophin-associated serine-threonine protein kinase (Lumeng, C. et al. (1999) Nat. Neurosci. 2 (7), 611–617) |
| 9 | 5502218CD1 | g8272557 | 0.0 | [*Rattus norvegicus*] protein kinase WNK1 (Xu, B. et al. (2000) J. Biol. Chem. 275 (22), 16795–16801) |
| 10 | 55056054CD1 | g162787 | 1.8E−213 | [*Bos taurus*] cAMP-dependent protein kinase II-beta catalytic (Wiemann, S. et al. (1991) J. Biol. Chem. 266, 5140–5145) |
| 11 | 7481989CD1 | g529073 | 8.2E−18 | [*Mus musculus*] tyrosine-specific protein kinase (Kohmura, N. et al. (1994) Mol. Cell. Biol. 14 (10), 6915–6925) |
| 12 | 55052990CD1 | g10177211 | 4.0E−21 | [fl][*Arabidopsis thaliana*] protein kinase |
| 13 | 7482377CD1 | g12005724 | 0.0 | [5' incom][*Homo sapiens*] mixed lineage kinase MLK1 |
|  |  | g3851202 | 0.0 | [*Homo sapiens*] MAGUK family member ZO-3 (Haskins, J. et al. (1998) J. Cell Biol. 141: 199–208) |
| 14 | 7758364CD1 | g6716518 | 4.4E−266 | [*Mus musculus*] doublecortin-like kinase (Burgess, H.A. et al. (1999) J. Neurosci. Res. 58 (4), 567–575) |
| 15 | 5850001CD1 | g6690020 | 9.9E−165 | [*Mus musculus*] pantothenate kinase 1 beta (Rock, C.O. et al. (2000) J. Biol. Chem. 275 (2), 1377–1383) |
| 16 | 7477062CD1 | g4115429 | 7.9E−53 | [*Rattus norvegicus*] serin/threonine protein kinase |
| 17 | 7477207CD1 | g12830335 | 1.0E−130 | [5' incom][*Homo sapiens*] bA550O8.2 (novel protein kinase) |
|  |  | g3136154 | 1.1E−17 | [*Mus musculus*] UNC-51-like kinase ULK1 (Kuroyanagi, H., et al. (1998) Genomics 51: 76–85) |
| 18 | 4022651CD1 | g3217028 | 0.0 | [*Homo sapiens*] putative serine/threonine protein kinase (Stanchi, F. et al. (2001) Yeast 18 (1), 69–80) |
| 19 | 7274927CD1 | g286232 | 3.1E−76 | [*Rattus norvegicus*] nucleoside diphosphate kinase beta isoform (Shimada, N. et al. (1993) J. Biol. Chem. 268 (4), 2583–2589) |
| 20 | 7946584CD1 | g7161864 | 7.3E−148 | [*Mus musculus*] serine/threonine protein kinase (Ruiz-Perez, V.L. et al. (2000) Nat. Genet. 24 (3), 283–286) |
| 21 | 8088078CD1 | g189992 | 1.2E−13 | [*Homo sapiens*] protein kinase C-gamma (Coussens, L. et al. (1986) Science 233 (4766), 859–866) |
| 22 | 2674269CD1 | g256855 | 5.6E−59 | [Mus sp.] serine/threonine- and tyrosine-specific protein kinase, Nek1 = NIMA cell cycle regulator homolog (Letwin, K. et al. (1992) EMBO J. 11 (10), 3521–3531) |
| 23 | 7472409CD1 | g256855 | 8.0E−64 | [Mus sp.] serine/threonine- and tyrosine-specific protein kinase, Nek1 = NIMA cell cycle regulator homolog (Letwin, K. et al. (1992) EMBO J. 11 (10), 3521–3531) |
| 24 | 7477484CD1 | g2459993 | 1.5E−153 | [*Mus musculus*] apoptosis associated tyrosine kinase (Gaozza, E. et al. (1997) Oncogene 15: 3127–35) |

TABLE 3

| SEQ ID NO: | Incyte Polypeptide ID | Amino Acid Residues | Potential Phosphorylation Sites | Potential Glycosylation Sites | Signature Sequences, Domains and Motifs | Analytical Methods and Databases |
|---|---|---|---|---|---|---|
| 1 | 7312543CD1 | 424 | S209 S257 S326 T150 T198 T215 T232 T285 T40 T418 | N85 | Eukaryotic protein kinase domain pkinase: Y53-V309 | HMMER_PFAM |
|  |  |  |  |  | PROTEIN KINASE DOMAIN DM00004\|JC1446\|20–261: E54-R303 DM00004\|P27448\|58–297: L55-G304 DM00004\|I48609\|55–294: L55-G304 DM00004\|Q05512\|55–294: L55-G304 | BLAST_DOMO |
|  |  |  |  |  | Tyrosine kinase catalytic site PR00109: Q128-P141, F164-L182, V234-A256 | BLIMPS_PRINTS |
|  |  |  |  |  | Protein kinase Ser/Thr active site domain Protein_Kinase_St: L170-L182 | MOTIFS |
|  |  |  |  |  | Protein kinase signatures and profile protein_kinase_tyr.prf: T150-G202 | PROFILESCAN |
|  |  |  |  |  | transmembrane domain: L228-T248 | HMMER |
| 2 | 7477427CD1 | 1719 | S167 S286 S344 S364 S369 S411 S459 S475 S507 S555 S616 S705 S750 S752 S781 S813 S877 S884 S917 S926 S940 S1532 T30 T423 | N560 N792 N854 N1629 N1688 N1691 | Eukaryotic protein kinase domain pkinase: F77-F343 | HMMER_PFAM |

TABLE 3-continued

| SEQ ID NO: | Incyte Polypeptide ID | Amino Acid Residues | Potential Phosphorylation Sites | Potential Glycosylation Sites | Signature Sequences, Domains and Motifs | Analytical Methods and Databases |
|---|---|---|---|---|---|---|
| | | | T591 T624 T64 T691 T746 T780 T788 T959 T981 T999 Y358 S1142 T1172 T1242 S1283 S1406 S1607 S1651 S1271 S1306 T1492 S1517 S1532 S1622 S1643 S1680 S1700 T1712 Y1201 T1070 | | Protein kinase C terminal domain pkinase_C: S344-D372 | HMMER_PFAM |
| | | | | | PROTEIN KINASE DOMAIN DM00004|Q09013|83–336: I79-Q331 DM00004|S42867|75–498: I79-L226, V238-Y404, P1602-D1677 DM00004|I38133|90–369: E78-L226, V238-G330 DM00004|P53894|353–658: L80-G221, D205-Q331 | BLAST_DOMO |
| | | | | | Tyrosine kinase catalytic site PR00109: M154-S167, S191-M209, C263-E285 | BLIMPS_PRINTS |
| | | | | | MYTONIC DYSTROPHY KINASE-RELATED CDC42-BINDING KINASE PHORBOLESTER BINDING PD143271: R1592-P1719 PD011252: D833-P994 PD075023: E630-N713 PD150840: W1467-S1591 | BLAST_PRODOM |
| | | | | | Phorbol ester/diacylglycerol binding domain DAG_PE-bind: H1000-C1049 | HMMER_PFAM |
| | | | | | Pleckstrin homology domain PH: T1070-K1188 | HMMER_PFAM |
| | | | | | Domain found in NIK1-like kinase, mouse citron CNH: K1215-K1499 | HMMER_PFAM |
| | | | | | Leucine_Zipper: L772-L793, L779-L800, L786-L807 | MOTIFS |
| | | | | | Protein kinase ATP binding domain Protein_Kinase_Atp: I83-K106 | MOTIFS |
| | | | | | Protein kinase Ser/Thr active site domain Protein_Kinase_St: Y197-M209 | MOTIFS |
| | | | | | Phorbol esters/DAG binding domain dag_pe_binding_domain.prf: C1013-A1071 | PROFILESCAN |
| 3 | 7481495CD1 | 1125 | S218 S227 S235 S278 S387 S388 S412 S572 S61 S66 S699 S785 S832 S889 S910 S949 S974 S987 S991 S1034 T102 T146 T190 T223 T224 T320 T365 T4 T417 T469 T520 T663 T668 T713 T805 T83 T868 Y303 Y353 | N249 N274 N277 N487 N629 | Guanylate kinase: T147-E243 | HMMER_PFAM |
| | | | | | Guanylate kinase protein BL00856: I143-I163 | BLIMPS_BLOCKS |
| | | | | | PROTEIN GUANYLATE KINASE MEMBRANE-ASSOCIATED ATROPHIN-1 INTERACTING INVERTED PUTATIVE BAI1-ASSOCIATED PD021703: M1-T146 | BLAST_PRODOM |
| | | | | | PROTEIN GUANYLATE KINASE MEMBRANE-ASSOCIATED ATROPHIN-1 INTERACTING INVERTED PAC PD029527: L326-Q379, E575-T663 | BLAST_PRODOM |
| | | | | | Guanylate_Kinase: T146-I163 | MOTIFS |
| | | | | | WW proline-rich motif binding domain WW: L295-P324 P324, L341-P370 | HMMER_PFAM |
| | | | | | WW/rsp5/WWP domain BL01159: Y310-P324 | BLIMPS_BLOCKS |
| | | | | | WW domain signature PR00403: L295-M308, Y310-P324 | BLIMPS_PRINTS |
| | | | | | Ww_Domain_1: W299-P324, W345-P370 | MOTIFS |
| | | | | | PDZ domain found in signaling proteins PDZ: R410-G493, L576-G655, D724-K809, D851-E937, P1021-G1102 | HMMER_PFAM |
| | | | | | PDZ domain PF00595: I1062-N1072 | BLIMPS_PFAM |
| | | | | | ATP/GTP binding site (P-loop) Atp_Gtp_A: G778-S785 | MOTIFS |
| 4 | 55053189CD1 | 500 | S161 S192 S238 S294 S359 S403 S75 T150 T273 T3 T308 T57 Y89 | N148 | KINASE PROTEIN TRANSFERASE ATP BINDING SERINE/THREONINE PROTEIN PHOSPHORYLATION RECEPTOR TYROSINE PROTEIN PRECURSOR TRANSMEMBRANE | BLAST_PRODOM |

TABLE 3-continued

| SEQ ID NO: | Incyte Polypeptide ID | Amino Acid Residues | Potential Phosphorylation Sites | Potential Glycosylation Sites | Signature Sequences, Domains and Motifs | Analytical Methods and Databases |
|---|---|---|---|---|---|---|
| | | | | | PD000001: Y183-E301 | |
| | | | | | Tyrosine kinase catalytic domain signature | BLIMPS_PRINTS |
| | | | | | PR00109: F127-L145, V199-T221, T273-A295 | |
| | | | | | Eukaryotic protein kinase domain pkinase: Y13-I299 | HMMER_PFAM |
| | | | | | Rgd R426-D428 | MOTIFS |
| | | | | | Protein_Kinase_Atp L19-K42 | MOTIFS |
| | | | | | Protein kinases signatures and profile | PROFILESCAN |
| | | | | | protein_kinase_tyr.prf: H113-D164 | |
| 5 | 7474797CD1 | 328 | S18 S184 S38 S57 S62 T251 T95 | N260 | PROTEIN KINASE DOMAIN DM00004|P25389|22–275: E26-K280 | BLAST_DOMO |
| | | | | | Tyrosine kinase catalytic domain signature | BLIMPS_PRINTS |
| | | | | | PR00109: L102-Q115, Y138-L156, S220-T242 | |
| | | | | | Eukaryotic protein kinase domain pkinase: Y25-G293 | HMMER_PFAM |
| | | | | | Protein_Kinase_Atp I31-K54 | MOTIFS |
| | | | | | Protein_Kinase_St I144-L156 | MOTIFS |
| | | | | | Protein kinases signatures and profile | PROFILESCAN |
| | | | | | protein_kinase_tyr.prf: L124-Q177 | |
| 6 | 3296272CD1 | 370 | S10 S167 S230 S239 S26 S283 S285 S330 S44 S47 T209 T226 T244 T34 | N103 N165, N368 | | |
| 7 | 1989319CD1 | 1369 | S1022 S1086 S1142 S1250 S1292 S1354 S146 S277 S307 S366 S464 S551 S592 S609 S674 S695 S877 T100 T1003 T1088 T134 T288 T391 T469 T585 T613 T653 T664 T84 | N1339 N422 N607 N692 N693 N832 | Protein kinases signatures and profile protein_kinase_tyr.prf: R136-G216 | PROFILESCAN |
| | | | | | PROTEIN KINASE DOMAIN DM00004|P27448|58–297: R70-R305 DM00004|I48609|55–294: R70-R305 DM00004|Q05512|55–294: R70-R305 DM00004|JC1446|20–261: E67-M308 | BLAST_DOMO |
| | | | | | Tyrosine kinase catalytic domain signature | BLIMPS_PRINTS |
| | | | | | PR00109: T142-V155, F178-L196, V244-S266 | |
| | | | | | Eukaryotic protein kinase domain: Y66-M317 | HMMER_PFAM |
| | | | | | Protein_Kinase_ATP-binding region signature: I72-K95 | MOTIFS |
| | | | | | Serine/Threonine protein kinases active-site signature: I184-L196 | MOTIFS |
| | | | | | Spscan Signal_cleavage: M1-G14 | SPSCAN |
| 8 | 079284CD1 | 2429 | S1038 S1048 S1057 S1060 S1065 S1071 S1098 S1112 S1119 S1122 S114 S1171 S1176 S1262 S1269 S1273 S1286 S1294 S1321 S1329 S1365 S1391 S1398 S1418 S1464 S1500 S1573 S1590 S1622 S1653 S1661 S1669 S1696 S1731 S1780 S1789 S1905 S1908 S1965 S1974 S1981 S1997 S2020 S2041 S2051 S2136 S2254 S2270 S2290 S2304 S2329 S2351 S2419 S31 S35 S364 S374 S63 S67 S670 S675 S681 S711 S719 S728 S768 S772 S840 S861 S886 S91 S927 S953 T1032 T1086 T127 T1277 T1450 T1470 T1568 T1575 T1712 T1718 T1786 T1798 | N1036 N1094 N1131 N14 N1657 N1673 N1864 N362 N766 N860 | Eukaryotic protein kinase domain pkinase: F376-F649 | HMMER_PFAM |
| | | | | | PDZ domain (Also known as DHR or GLGF) PDZ: Q946-F1034 | HMMER_PFAM |
| | | | | | Protein kinase signature protein_kinase_tyr.prf: F443-V523 | PROFILESCAN |

TABLE 3-continued

| SEQ ID NO: | Incyte Polypeptide ID | Amino Acid Residues | Potential Phosphorylation Sites | Potential Glycosylation Sites | Signature Sequences, Domains and Motifs | Analytical Methods and Databases |
|---|---|---|---|---|---|---|
| | | | T1811 T1827 T1945 T2083 T2144 T2160 T2171 T2181 T2235 T2322 T2362 T2397 T241 T378 T429 T445 T593 T679 T689 T695 T789 T880 T960 Y2185 | | | |
| | | | | | Tyrosine kinase catalytic domain PR00109: Y489-V507, V570-D592 | BLIMPS_PRINTS |
| | | | | | PROTEIN KINASE DOMAIN DM00004\|A54602\|455–712: T378-G636 DM00004\|S42867\|75–498: I379-K522 DM08046\|P05986\|1–397: S374-K522, V549-D697 DM08046\|P06244\|1–396: D375-K522 | BLAST_DOMO |
| | | | | | PROTEIN KINASE SERINE/THREONINE KIN4 MICROTUBULE ASSOCIATED TESTIS SPECIFIC TESTISSPECIFIC MAST205 PD041650: K183-D375 | BLAST_PRODOM |
| | | | | | MICROTUBULE ASSOCIATED TESTIS SPECIFIC SERINE/THREONINE PROTEIN KINASE 205KD MAST205 KINASE PD135564: M1-Y182 PD142315: H1151-A1412, P1969-P2107 PD182663: T725-N982 | BLAST_PRODOM |
| | | | | | Atp_Gtp_A: A1841-T1848 | MOTIFS |
| | | | | | Protein_Kinase_St: I495-V507 | MOTIFS |
| 9 | 5502218CD1 | 2135 | S1189 S1641 S1651 S1714 S174 S1765 S1790 S1814 S1818 S1874 S1888 S189 S1993 S1994 S2018 S2023 S2039 S231 S260 S29 S34 S363 S378 S469 S588 S679 S819 S843 S858 S863 S879 S929 S973 T1270 T1407 T160 T1682 T1723 T1881 T1998 T243 T258 T290 T308 T373 T436 T48 T60 T625 T73 T763 T850 T851 T868 T899 T91 Y1855 Y468 | N1046 N1078 N1628 N1798 N1808 N1816 N1904 N2016 N2116 N27 N877 N89 | Eukaryotic protein kinase domain pkinase: L221-F479 | HMMER_PFAM |
| | | | | | Protein kinase signature protein_kinase_tyr.prf: L324-S378 | PROFILESCAN |
| | | | | | Tyrosine kinase catalytic domain PR00109: T301-K314, H339-I357, V403-C425, A448-I470 | BLIMPS_PRINTS |
| | | | | | PROTEIN KINASE DOMAIN DM00004\|S49611\|39–259: I227-V447 DM00004\|P51957\|8–251: I227-I470 DM00004\|Q05609\|553–797: E226-C459 DM00004\|P41892\|11–249: I227-K471 | BLAST_DOMO |
| | | | | | Protein_Kinase_St: I345-I357 | MOTIFS |
| 10 | 55056054CD1 | 398 | S300 S373 S386 S62 T136 T326 T341 T37 T388 T43 T96 Y117 | N47 | Eukaryotic protein kinase domain pkinase: F91-F345 | HMMER_PFAM |
| | | | | | Protein kinase C terminal domain pkinase_C: A346-D377 | HMMER_PFAM |
| | | | | | Tyrosine kinase catalytic domain PR00109: M168-R181, Y204-I222, V267-D289 | BLIMPS_PRINTS |
| | | | | | PROTEIN KINASE DOMAIN DM00004\|P00517\|44–281: E92-G330 DM00004\|S19028\|46–283: R93-G330 DM00004\|B35755\|53–290: E92-G330 DM08046\|P06244\|1–396: T82-I387 | BLAST_DOMO |
| | | | | | CAMP-DEPENDENT SERINE/THREONINE PKA PROTEIN KINASE BETA2-CATALYTIC CBETA2 TRANSFERASE ATP-BINDING ALTERNATIVE SP PHOSPHORYLATION PD052800: M1-R61 | BLAST_PRODOM |
| | | | | | SERINE/THREONINE TYROSINE PROTEIN KINASE TRANSFERASE PHOSPHORYLATION | BLAST_PRODOM |

TABLE 3-continued

| SEQ ID NO: | Incyte Polypeptide ID | Amino Acid Residues | Potential Phosphorylation Sites | Potential Glycosylation Sites | Signature Sequences, Domains and Motifs | Analytical Methods and Databases |
|---|---|---|---|---|---|---|
| 11 | 7481989CD1 | 929 | S147 S258 S292 S298 S337 S482 S595 S603 S612 S642 S716 S845 S916 T139 T186 T293 T387 T394 T426 T436 T48 T822 Y312 Y402 | N594 N60 | TRANSMEMBRANE ATP-BINDING RECEPTOR PD000001: T243-F287, K94-V171, M166-V239, R104-G174, D289-F345 | |
| | | | | | Protein_Kinase_Atp: L97-K120 | MOTIFS |
| | | | | | Protein_Kinase_St: L210-I222 | MOTIFS |
| | | | | | Eukaryotic protein kinase domain pkinase: P652-P897 | HMMER_PFAM |
| | | | | | Protein kinases signatures protein_kinase_tyr.prf: T753-K800 | PROFILESCAN |
| | | | | | Tyrosine kinase catalytic site PR00109: F767-L785, V829-A851, F877-L899 | BLIMPS_PRINTS |
| | | | | | PROTEIN KINASE DOMAIN DM00004|A56040|233–476: G655-P897 DM00004|Q05609|553–797: Q656-P897 DM00004|P51813|419–658: Q656-P897 DM00004|S60612|419–658: Q656-P897 | BLAST_DOMO |
| | | | | | Protein_Kinase_Atp: L658-K681 | MOTIFS |
| | | | | | Protein_Kinase_St: L773-L785 | MOTIFS |
| 12 | 55052990CD1 | 1097 | S1017 S1023 S1034 S118 S233 S286 S541 S569 S611 S618 S648 S715 S778 S789 S816 S822 S829 S842 S888 S89 S974 T1035 T1056 T1059 T1083 T112 T145 T304 T373 T404 T405 T446 T565 T72 T785 T892 T964 T970 Y335 | N1015 N821 N870 | Eukaryotic protein kinase domain pkinase: L144-L403 | HMMER_PFAM |
| | | | | | SH3 domain SH3: P55-R114 | HMMER_PFAM |
| | | | | | Protein kinase signature protein_kinase_tyr.prf: L242-T305 | PROFILESCAN |
| | | | | | Receptor tyrosine kinase class II BL00239: E191-P238, L355-I399 | BLIMPS_BLOCKS |
| | | | | | Receptor tyrosine kinase class III BL00240: E300-V347, V347-I399 | BLIMPS_BLOCKS |
| | | | | | Tyrosine kinase catalytic domain PR00109: M220-S233, D258-I276, G311-I321, S330-I352, C374-F396 | BLIMPS_PRINTS |
| | | | | | SH3 domain signature PR00452: P55-A65, D69-K84, D91-N100, R102-R114 | BLIMPS_PRINTS |
| | | | | | PROTEIN KINASE DOMAIN DM00004|A53800|119–368: L146-F396 DM00004|I38044|100–349: L146-F396 DM00004|JC2363|126–356: W163-F396 | BLAST_DOMO |
| | | | | | ZIPPER MOTIF LEUCINE DM08113|I38044|392–721: R438-A749, P869-P893 | BLAST_DOMO |
| | | | | | KINASE DOMAIN SH3 MIXED LINEAGE SERINE/THREONINE WITH LEUCINE ZIPPER PD024997: I406-A749, F419-E833 PD034700: N855-R966, P934-P1022 | BLAST_PRODOM |
| | | | | | SERINE/THREONINEPROTEIN TYROSINE KINASE TRANSFERASE ATP-BINDING PHOSPHORYLATION RECEPTOR PRECURSOR TRANSMEMBRANE PD000001: L146-F222, W315-F349, L242-A317 | BLAST_PRODOM |
| | | | | | Protein_Kinase_Atp: I150-K171 | MOTIFS |
| | | | | | Protein_Kinase_St: I264-I276 | MOTIFS |
| | | | | | signal_cleavage: M1-A17 | SPSCAN |
| 13 | 7482377CD1 | 928 | S121 S147 S150 S155 S212 S258 S293 S298 S332 S336 S340 S347 S355 S368 S380 S422 S552 S600 | N256 N260 N445 N550 N755 N77 N95 | Guanylate kinase Guanylate_kin: R628-S729 | HMMER_PFAM |

TABLE 3-continued

| SEQ ID NO: | Incyte Polypeptide ID | Amino Acid Residues | Potential Phosphorylation Sites | Potential Glycosylation Sites | Signature Sequences, Domains and Motifs | Analytical Methods and Databases |
|---|---|---|---|---|---|---|
| | | | S625 S659 S690 S726 S729 S744 S787 S802 S814 S865 S893 S914 S915 T14 T262 T353 T447 T468 T491 T506 T597 T672 T730 T779 T818 T826 T832 T840 T97 Y488 | | | |
| | | | | | GUANYLATE KINASE DM00755\|Q07157\|628–788: E623-A780 DM00755\|I38757\|709–898: L670-W778 | BLAST_DOMO |
| | | | | | PDZ domain PDZ: T20-P101, S204-D280, R391-K471 | HMMER_PFAM |
| | | | | | GLGF DOMAIN DM00224\|Q07157\|1–94: M10-K99 DM00224\|Q07157\|402–488: P388-Q469 | BLAST_DOMO |
| | | | | | PDZ domain PF00595: I429-N439 | BLIMPS_PFAM |
| | | | | | Domain present in ZO-1 PF00791: I413-A451, L456-S498 | BLIMPS_PFAM |
| | | | | | TIGHT JUNCTION PROTEIN ZO2 ISOFORM ZO1 SH3 DOMAIN ALTERNATIVE SPLICING PD011344: R470-F626 PD021419: T730-D881 | BLAST_PRODOM |
| | | | | | ZO3 PD068424: P101-Q222 PD072431: F284-V392 | BLAST_PRODOM |
| | | | | | Leucine_Zipper: L733-L754 | MOTIFS |
| | | | | | Rgd: R507-D509 | MOTIFS |
| 14 | 7758364CD1 | 766 | S109 S129 S134 S182 S23 S3 S312 S334 S347 S484 S532 S623 S67 S710 S724 S93 T133 T173 T331 T389 T416 T461 T488 T542 T666 T693 T739 T760 | N164 N619 N681 | Eukaryotic protein kinase domain pkinase: Y394-V651 | HMMER_PFAM |
| | | | | | Protein kinase signature protein_Kinase_tyr.prf: D491-L548 | PROFILESCAN |
| | | | | | Tyrosine kinase catalytic domain PR00109: M469-T482, Y505-V523, V572-E594 | BLIMPS_PRINTS |
| | | | | | PROTEIN KINASE DOMAIN DM00004\|S57347\|21–266: V399-T641 DM00004\|JU0270\|16–262: I396-A642 DM00004\|A44412\|16–262: I396-A642 DM00004\|P11798\|15–261: I400-A642 | BLAST_DOMO |
| | | | | | LISSENCEPHALINX ISOFORM DOUBLECORTIN PD024506: I7-N322 | BLAST_PRODOM |
| | | | | | Protein_Kinase_Atp: I400-K423 | MOTIFS |
| | | | | | Protein_Kinase_St: I511-V523 | MOTIFS |
| 15 | 5850001CD1 | 447 | S121 S124 S23 S246 S316 S320 S362 S428 S45 S80 T111 T204 T286 T306 T307 T321 T59 | N180 | signal_cleavage: M1-A56 | SPSCAN |
| | | | | | PROTEIN T13D8.31 KINASE PANTOTHENATE TRANSFERASE D9719.34P CODED FOR BY C. ELEGANS PD018089: L93-L441 | BLAST_PRODOM |
| 16 | 7477062CD1 | 348 | S169 S19 S316 S99 T224 T28 T80 Y62 | | Tyrosine protein kinases specific active-site signature: A159-R208 | PROFILESCAN |
| | | | | | PROTEIN KINASE DOMAIN DM08046\|P06244\|1–396: G3-W263 DM00004\|B35755\|53–290: E63-L267 DM00004\|P22216\|200–456: L68-S316 DM00004\|P06245\|72–308: V65-W263 | BLAST_DOMO |
| | | | | | KINASE PROTEIN TRANSFERASE ATP-BINDING SERINE/THREONINE PROTEIN PHOSPHORYLATION RECEPTOR TYROSINE PROTEIN PRECURSOR TRANSMEMBRANE PD000001: A225-F273, Q166-V191, Y62-R97 | BLAST_PRODOM |
| | | | | | Tyrosine kinase catalytic domain PR00109: T137-Q150, Y173-V191, L244-P266 | BLIMPS_PRINTS |
| | | | | | Eukaryotic protein kinase domain: Y62-R315 | HMMER_PFAM |
| | | | | | Protein kinases ATP-binding region signature: L68-K91 | MOTIFS |
| | | | | | Serine/Threonine protein kinases active-site signature: L179-V191 | MOTIFS |
| 17 | 7477207CD1 | 341 | S100 S133 S180 S299 S31 S337 S59 | N141 N89 | Eukaryotic protein kinase domain: Y8-L325 | HMMER_PFAM |

TABLE 3-continued

| SEQ ID NO: | Incyte Polypeptide ID | Amino Acid Residues | Potential Phosphorylation Sites | Potential Glycosylation Sites | Signature Sequences, Domains and Motifs | Analytical Methods and Databases |
|---|---|---|---|---|---|---|
| | | | T175 T185 T235 T255 T261 | | | |
| | | | | | Tyrosine protein kinases specific active-site signature: T140-S200 | PROFILESCAN |
| | | | | | PROTEIN KINASE DOMAIN DM00004\|P39009\|202–470: R110-L251 DM00004\|Q02723\|16–259: E104-V196 DM00004\|P08414\|44–285: V118-V196 DM00004\|P23572\|6–277: L115-K195 | BLAST_DOMO |
| | | | | | KINASE PROTEIN TRANSFERASE ATP-BINDING SERINE/THREONINE PROTEIN PHOSPHORYLATION RECEPTOR TYROSINE PROTEIN PRECURSOR TRANSMEMBRANE PD000001: F144-A236 | BLAST_PRODOM |
| | | | | | Tyrosine kinase catalytic domain signature PR00109: M119-L132, F154-I172 | BLIMPS_PRINTS |
| | | | | | transmembrane domain: A238-D258 | HMMER |
| | | | | | Serine/Threonine protein kinases active-site signature: I160-I172 | MOTIFS |
| | | | | | Protein kinases ATP-binding region signature: V14-K37 | MOTIFS |
| 18 | 4022651CD1 | 664 | S123 S166 S290 S320 S342 S383 S423 S431 S477 S485 S508 S541 S565 S615 S631 S95 T110 T256 T439 T447 T497 T590 T652 Y591 | | Protein kinases signatures and profile: E113-S166 | PROFILESCAN |
| | | | | | PROTEIN KINASE DOMAIN DM00004\|P34244\|82–359: V36-T256 DM00004\|JC1446\|20–261: R16-L257 DM00004\|P54645\|17–258: L17-L257 DM00004\|A5362\|18–258: L17-L257 | BLAST_DOMO |
| | | | | | HRPOPK1 F15A2.6 PROTEIN, Protein Kinase PD039115: P278-N503, PD039117: W517-E623 | BLAST_PRODOM |
| | | | | | Tyrosine kinase catalytic domain signature PR00109: L91-V104, F127-L145, A193-D215 | BLIMPS_PRINTS |
| | | | | | Eukaryotic protein kinase domain: Y15-Y266 | HMMER_PFAM |
| | | | | | Protein kinases ATP-binding region signature: L21-K44 | MOTIFS |
| | | | | | Serine/Threonine protein kinases active-site signature: I133-L145 | MOTIFS |
| 19 | 7274927CD1 | 177 | S19 T111 T128 | | Nucleoside diphosphate kinases active site: N120-T168 | PROFILESCAN |
| | | | | | NUCLEOSIDE DIPHOSPHATE KINASES DM00773\|I39074\|19–168: E30-E177 DM00773\|P48817\|3–152: E30-E177 DM00773\|P50590\|1–150: E30-E177 DM00773\|Q07661\|1–148: E30-E177 | BLAST_DOMO |
| | | | | | KINASE DIPHOSPHATE NUCLEOSIDE TRANSFERASE NDK NDP ATP-BINDING PROTEIN I PRECURSOR PD001018: E30-E177 | BLAST_PRODOM |
| | | | | | Nucleoside diphosphate kinases proteins BL00469: W103-L157 | BLIMPS_BLOCKS |
| | | | | | Nucleoside diphosphate kinases ND: E30-E177 | HMMER_PFAM |
| | | | | | Nucleoside diphosphate kinases active site: N140-V148 | MOTIFS |
| | | | | | Spscan signal_cleavage: M1-G15 | SPSCAN |
| 20 | 7946584CD1 | 396 | S193 S194 S230 S6 S89 T122 T212 T45 T5 | N4 N43 | Protein kinases signatures and profile: T122-E174 | PROFILESCAN |
| | | | | | Eukaryotic protein kinase domain: F23-M281 | HMMER_PFAM |
| | | | | | PROTEIN KINASE DOMAIN DM00004\|P54644\|122–362: I25-S270 DM08046\|P05986\|1–397: D13-P300 DM00004\|P28178\|155–393: I25-R268 DM08046\|P06244\|1–396: F23-P300 | BLAST_DOMO |
| | | | | | Tyrosine kinase catalytic domain signature PR00109: V100-Q113, Y136-L154, V204-R226 | BLIMPS_PRINTS |
| | | | | | Protein kinases ATP-binding region signature: I29-K52 | MOTIFS |
| | | | | | Serine/Threonine protein kinases active-site signature: I142-L154 | MOTIFS |
| 21 | 8088078CD1 | 614 | S292 S295 S518 S525 S574 S578 T27 T389 T418 T499 T92 | N309 N595 N598 | C2 domain signature and profile: G39-V93 | PROFILESCAN |

TABLE 3-continued

| SEQ ID NO: | Incyte Polypeptide ID | Amino Acid Residues | Potential Phosphorylation Sites | Potential Glycosylation Sites | Signature Sequences, Domains and Motifs | Analytical Methods and Databases |
|---|---|---|---|---|---|---|
| | | | | | C2-DOMAIN DM00150\|P05129\|150–278: G39-L159 DM00150\|P13677\|186–313: G39-L159 | BLAST_DOMO |
| | | | | | PROTEIN KINASE C ALPHA DM04692\|P05130\|1–638: G39-G164 DM04692\|A37237\|1–676: G39-G164 | BLAST_DOMO |
| | | | | | C2 domain signature PR00360: Q66-L78, D95-P108 | BLIMPS_PRINTS |
| | | | | | C2 domain C2: L52-S139 | HMMER_PFAM |
| | | | | | PDZ domain (Also known as DHR or GLGF). PDZ: Q199-M275 | HMMER_PFAM |
| | | | | | ATP/GTP-binding site motif A (P-loop): G395-S402 | MOTIFS |
| 22 | 2674269CD1 | 484 | S122 S179 S222 S248 S295 S422 S445 T111 T27 T437 T65 | | Eukaryotic protein kinase domain: L44-C282 | HMMER_PFAM |
| | | | | | PROTEIN KINASE DOMAIN DM00004\|P51954\|6–248: D50-P271 DM00004\|P51957\|8–251: V42-P271 DM00004\|Q08942\|22–269: D50-P271 DM00004\|P51955\|10–261: R47-P271 | BLAST_DOMO |
| | | | | | Tyrosine kinase catalytic domain PR00109: M104-Q117 H142-L160 S208-A230 Y251-L273 | BLIMPS_PRINTS |
| | | | | | Protein kinases signatures and profile: I129-S182 | PROFILESCAN |
| | | | | | Serine/Threonine protein kinases active-site signature: I148-L160 | MOTIFS |
| 23 | 7472409CD1 | 460 | S155 S198 S224 S271 S398 S421 S98 T41 T413 T87 | | Eukaryotic protein kinase domain: Y4-C258 | HMMER_PFAM |
| | | | | | PROTEIN KINASE DOMAIN DM00004\|P51954\|6–248: R6-P247 DM00004\|P51957\|8–251: I7-P247 DM00004\|Q08942\|22–269: V9-P247 DM00004\|P11837\|13–285: I124-P247, V10-H120 | BLAST_DOMO |
| | | | | | Tyrosine kinase catalytic domain PR00109: M80-Q93 H118-L136 S184-A206 Y227-L249 | BLIMPS_PRINTS |
| | | | | | Protein kinases signatures and profile: I105-S158 | PROFILESCAN |
| | | | | | Protein kinases ATP-binding region signature: V10-K33 | MOTIFS |
| | | | | | Serine/Threonine protein kinases active-site signature: I124-L136 | MOTIFS |
| 24 | 7477484CD1 | 1413 | S1016 S1082 S118 S1269 S1285 S1295 S355 S400 S413 S471 S528 S547 S608 S649 S746 S818 S96 T1003 T1041 T1350 T279 T339 T467 T834 T880 T968 T995 Y185 Y748 | N1034 N1358 | Tyrosine protein kinases specific active-site signature: Y262-L274 | MOTIFS |
| | | | | | signal_cleavage: M1-A20 | SPSCAN |
| | | | | | PROTEIN KINASE DOMAIN DM00004\|S23008\|273–531: Q137-S400 DM00004\|P06213\|1024–1282: L136-S400 DM00004\|P15209\|538–798: Q137-R398 DM00004\|P08069\|1000–1258: Q137-S400 | BLAST_DOMO |
| | | | | | APOPTOSIS ASSOCIATED TYROSINE KINASE KIAA0641 PROTEIN PD148361: P1080-P1376 | BLAST_PRODOM |
| | | | | | APOPTOSIS ASSOCIATED TYROSINE KINASE PD059222: L56-Y135 | BLAST_PRODOM |
| | | | | | Kinase Protein Domain PD00584: I136-G145 | BLIMPS_BLOCKS |
| | | | | | Tyrosine kinase catalytic domain PR00109: H256-L274 I305-L315 S331-H353 Y380-S402 M210-R223 | BLIMPS_PRINTS |
| | | | | | Protein kinases signatures and profile: T242-E294 | PROFILESCAN |
| | | | | | Receptor tyrosine kinase class II signature: R270-E317 | PROFILESCAN |
| | | | | | signal peptide: M1-A20 | HMMER |
| | | | | | Eukaryotic protein kinase domain: L133-L404 | HMMER_PFAM |
| | | | | | Protein kinases ATP-binding region signature: I139-K164 | MOTIFS |

TABLE 4

| Polynucleotide SEQ ID NO: | Incyte Polynucleotide ID | Sequence Length | Selected Fragments | Sequence Fragments | 5' Position | 3' Position |
|---|---|---|---|---|---|---|
| 25 | 7312543CB1 | 2060 | 1–367, 1981–2060, 1721–1882, 1406–1638, 625–1129 | GBI.g9101216_8021815J1_8024094J1_edit | 961 | 1719 |
| | | | | 55067455J1 | 1 | 617 |
| | | | | FL7312543 | 1473 | 1716 |
| | | | | 71899371V1 | 448 | 986 |
| | | | | 6259135F8 (BMARTXT06) | 1891 | 2060 |
| | | | | 8024094J1 (BRABDIE02) | 920 | 1609 |
| 26 | 7477427CB1 | 5694 | 1807–4876, 1–869 | 7084221H1 (STOMTMR02) | 3331 | 3859 |
| | | | | 3081175H1 (BRAIUNT01) | 5209 | 5518 |
| | | | | 7341442H1 (COLNDIN02) | 2311 | 2964 |
| | | | | 6053208J1 (BRABDIR03) | 4727 | 5119 |
| | | | | 6051790H1 (BRABDIR03) | 3609 | 4274 |
| | | | | 452790T6 (TLYMNOT02) | 1146 | 1795 |
| | | | | 1340485F6 (COLNTUT03) | 1 | 601 |
| | | | | 6051790J1 (BRABDIR03) | 4347 | 4900 |
| | | | | 5048724H1 (BRSTNOT33) | 1016 | 1275 |
| | | | | 4954623H1 (ENDVUNT01) | 504 | 787 |
| | | | | 55099289J1 | 1599 | 2178 |
| | | | | g1441460 | 570 | 809 |
| | | | | 6355285H1 (LUNGDIS03) | 828 | 1103 |
| | | | | 2818149F6 (BRSTNOT14) | 5251 | 5694 |
| | | | | 6800667F6 (COLENOR03) | 2049 | 2603 |
| | | | | 6322587F7 (LUNGDIN02) | 3892 | 4570 |
| | | | | 5735737F6 (KIDCTMT01) | 4818 | 5470 |
| | | | | 6771396J1 (BRAUNOR01) | 3245 | 3857 |
| | | | | 6800667R6 (COLENOR03) | 2727 | 3335 |
| 27 | 7481495CB1 | 3520 | 1–40, 2862–3520, 1622–1689, 607–1074 | 71125065V1 | 2970 | 3520 |
| | | | | 71124933V1 | 2555 | 3203 |
| | | | | 71124726V1 | 1649 | 2196 |
| | | | | 55143095J1 | 1 | 476 |
| | | | | 6273371F8 (BRAIFEN03) | 2069 | 2812 |
| | | | | 7289965F8 (BRAIFER06) | 209 | 841 |
| | | | | GBI.g9755986_edit_1 | 1151 | 3394 |
| | | | | GBI.g9755986_edit_3 | 498 | 1231 |
| 28 | 55053189CB1 | 1988 | 1–1067 | 71911787V1 | 280 | 990 |
| | | | | 6959111H1 (SKINDIA01) | 1196 | 1852 |
| | | | | 71910755V1 | 1249 | 1959 |
| | | | | 2222335T6 (LUNGNOT18) | 1464 | 1988 |
| | | | | 55053117J1 | 1 | 491 |
| | | | | 71911607V1 | 547 | 1228 |
| 29 | 7474797CB1 | 1822 | 1–470, 963–1217 | GNN.g6850939_002 | 738 | 1734 |
| | | | | 55078203J1 | 135 | 920 |
| | | | | 55078259J1 | 1 | 917 |
| | | | | g3405101 | 1507 | 1822 |
| 30 | 3296272CB1 | 1814 | 1–34 | 8050406H1 (LUNGTUS02) | 724 | 1394 |
| | | | | 3296272F6 (TLYJINT01) | 52 | 723 |
| | | | | GNN.g7711609.edit1 | 124 | 1246 |
| | | | | 8010594H1 (NOSEDIC02) | 1 | 473 |
| | | | | 4550262T1 (HELAUNT01) | 1179 | 1814 |
| 31 | 1989319CB1 | 4381 | 1–606, 1171–2589, 3359–3731, 4352–4381, 3137–3182 | 6766365H1 (BRAUNOR01) | 3988 | 4381 |
| | | | | 6771934J1 (BRAUNOR01) | 1284 | 1867 |
| | | | | 7081255H1 (STOMTMR02) | 1899 | 2467 |
| | | | | 7074415H1 (BRAUTDR04) | 7 | 546 |
| | | | | 7233628H1 (BRAXTDR15) | 3192 | 3760 |
| | | | | 2972522F6 (HEAONOT02) | 3805 | 4374 |
| | | | | 3550738T6 (SYNONOT01) | 3467 | 4338 |
| | | | | 7689848H1 (PROSTME06) | 1200 | 1856 |
| | | | | 7643518H1 (SEMVTDE01) | 2454 | 3131 |
| | | | | 55056624J1 | 191 | 833 |
| | | | | GNN: g7139740_000020_002.edit | 1 | 273 |
| | | | | 6772392H1 (BRAUNOR01) | 670 | 1296 |
| | | | | 7641909J1 (SEMVTDE01) | 1390 | 2054 |
| | | | | 7039379H1 (UTRSTMR02) | 2393 | 2982 |
| | | | | 5965355H1 (BRATNOT05) | 2998 | 3635 |
| 32 | 079284CB1 | 7862 | 6343–7041, 1043–1581, 1–453, 2297–6211 | 6558834H1 (BRAFNON02) | 6806 | 7501 |

TABLE 4-continued

| Polynucleotide SEQ ID NO: | Incyte Polynucleotide ID | Sequence Length | Selected Fragments | Sequence Fragments | 5' Position | 3' Position |
|---|---|---|---|---|---|---|
| | | | | 6957453H1 (BLADNOR01) | 3532 | 4226 |
| | | | | 7030154F6 (BRAXTDR12) | 3084 | 3666 |
| | | | | 2696941F6 (UTRSNOT12) | 6628 | 7209 |
| | | | | 6993445H1 (BRAQTDR02) | 2679 | 3284 |
| | | | | 6315055H1 (NERDTDN03) | 5981 | 6672 |
| | | | | 7183303H1 (BONRFEC01) | 5329 | 5878 |
| | | | | 55032462H1 | 4893 | 5540 |
| | | | | 1005113H1 (BRSTNOT03) | 2531 | 2782 |
| | | | | 7034608H1 (SINTFER03) | 5826 | 6570 |
| | | | | 55032462J1 | 4430 | 5048 |
| | | | | g2224546_CD | 1221 | 7714 |
| | | | | 7740563H1 (THYMNOE01) | 4113 | 4788 |
| | | | | 6943723H1 (FTUBTUR01) | 1062 | 1416 |
| | | | | 7764524H1 (URETTUE01) | 545 | 1132 |
| | | | | 7030154R6 (BRAXTDR12) | 2885 | 3416 |
| | | | | 6493861H1 (MIXDUNB01) | 7457 | 7862 |
| | | | | 7764524J1 (URETTUE01) | 350 | 868 |
| | | | | 55111711H1 | 1 | 520 |
| 33 | 5502218CB1 | 7280 | 1–658, 1289–3582, 6450–7280, 4416–5337 | 71172233V1 | 5856 | 6502 |
| | | | | 7755001H1 (SPLNTUE01) | 4757 | 5331 |
| | | | | 71172416V1 | 5347 | 5905 |
| | | | | 7143606H1 (LIVRDIT07) | 2638 | 3173 |
| | | | | 8262215J1 (MIXDUNL12) | 4008 | 4571 |
| | | | | 71728206V1 | 6354 | 7056 |
| | | | | 1513828F6 (PANCTUT01) | 1481 | 2005 |
| | | | | 5504851F6 (BRADDIR01) | 2190 | 2722 |
| | | | | 71255229V1 | 2770 | 3388 |
| | | | | 7099033H2 (BRAWTDR02) | 3321 | 3964 |
| | | | | 7381635H1 (ENDMUNE01) | 4401 | 5070 |
| | | | | 6775620H1 (OVARDIR01) | 1 | 576 |
| | | | | 6773092H1 (BRAUNOR01) | 4072 | 4748 |
| | | | | 1852020T6 (LUNGFET03) | 6862 | 7280 |
| | | | | 71974333V1 | 823 | 1394 |
| | | | | 6246863H1 (TESTNOT17) | 1346 | 1961 |
| | | | | 71174478V1 | 5283 | 5874 |
| | | | | 7751827J1 (HEAONOE01) | 1888 | 2490 |
| | | | | 7733935J2 (COLDDIE01) | 5932 | 6548 |
| | | | | 6771926J1 (BRAUNOR01) | 629 | 1285 |
| | | | | 71088884V1 | 3416 | 4074 |
| | | | | 7437887H1 (ADRETUE02) | 128 | 705 |
| | | | | 7032601H1 (BRAXTDR12) | 6540 | 7193 |
| 34 | 55056054CB1 | 1260 | 817–1260 | 6391212H1 (LUNPTMC01) | 64 | 334 |
| | | | | GBI: g8516102_000009_000010_000008.edit | 1 | 1260 |
| | | | | 55076825J1 | 1 | 132 |
| 35 | 7481989CB1 | 3161 | 1–481, 1210–2220 | 70464274V1 | 2196 | 2774 |
| | | | | 70467406V1 | 2110 | 2701 |
| | | | | 7185326H1 (BONRFEC01) | 793 | 1415 |
| | | | | 7077190R8 (BRAUTDR04) | 1 | 674 |
| | | | | 70980877V1 | 1389 | 2032 |
| | | | | 55013474H1 (GPCRDNV60) | 1517 | 2149 |
| | | | | 70464964V1 | 2517 | 3161 |
| | | | | 71292191V1 | 518 | 1150 |
| 36 | 55052990CB1 | 3538 | 1–251, 1163–1869, 2604–3538, 695–858 | FL55052990_g4156209_g758593 | 1 | 3294 |
| | | | | 7580350H1 (BRAIFEC01) | 3068 | 3538 |
| 37 | 7482377CB1 | 3047 | 1–1419, 3022–3047 | 6931355H1 (SINITMR01) | 1317 | 1950 |
| | | | | 60203980U1 | 1971 | 2648 |
| | | | | 5871544H1 (COLTDIT04) | 2745 | 3043 |
| | | | | g2053163 | 2589 | 3047 |
| | | | | 6821548H1 (SINTNOR01) | 1691 | 2351 |
| | | | | 7171378H1 (BRSTTMC01) | 528 | 1120 |
| | | | | 1428568F6 (SINTBST01) | 2547 | 3019 |
| | | | | 1625022F6 (COLNPOT01) | 1053 | 1538 |
| | | | | 6822009J1 (SINTNOR01) | 1 | 666 |
| | | | | 8010427H1 (NOSEDIC02) | 693 | 1191 |
| 38 | 7758364CB1 | 2667 | 2375–2667, 702–1754, 1–178 | 7042389H1 (UTRSTMR02) | 1 | 445 |
| | | | | 6620147H1 (BRAUDIR01) | 1777 | 2400 |
| | | | | 55137902J1 | 89 | 943 |
| | | | | 72053219V1 | 1961 | 2667 |

TABLE 4-continued

| Polynucleotide SEQ ID NO: | Incyte Polynucleotide ID | Sequence Length | Selected Fragments | Sequence Fragments | 5' Position | 3' Position |
|---|---|---|---|---|---|---|
| | | | | 55053087J1 | 909 | 1802 |
| | | | | 7198790F8 (LUNGFER04) | 1091 | 1812 |
| 39 | 5850001CB1 | 1719 | 1108–1719 | 1773374R6 (MENTUNON3) | 1016 | 1417 |
| | | | | 2746336T6 (LUNGTUT11) | 1080 | 1719 |
| | | | | 8081565H1 (BMARTXN03) | 1 | 316 |
| | | | | 2746336F6 (LUNGTUT11) | 795 | 1320 |
| | | | | 6768690J1 (BRAUNOR01) | 324 | 914 |
| | | | | 4403478H1 (PROSDIT01) | 218 | 460 |
| 40 | 7477062CB1 | 1156 | 683–1156, 1–194, 472–644 | 8124387H1 (HEAONOC01) | 55 | 692 |
| | | | | 55149655J1 | 1 | 562 |
| | | | | GNN: g7191033_000008_002.edit | 108 | 1156 |
| | | | | 982271H1 (TONGTUT01) | 1044 | 1156 |
| 41 | 7477207CB1 | 1096 | 923–1096 | 6882293J1 (BRAHTDR03) | 1030 | 1096 |
| | | | | 55142304H1 | 1 | 782 |
| | | | | GNN: g10045521_000003_004 | 65 | 1090 |
| 42 | 4022651CB1 | 2647 | 1–29, 2556–2647, 2233–2392, 795–1365 | 6559541F8 (BRAFNON02) | 1619 | 2410 |
| | | | | GBI: g9739340_000017_000001_000005.edit | 1 | 178 |
| | | | | 6149427H1 (BRANDIT03) | 2099 | 2647 |
| | | | | 6559066F8 (BRAFNON02) | 1356 | 2049 |
| | | | | 6951446H1 (BRAITDR02) | 676 | 1375 |
| | | | | 7228092H1 (BRAXTDR15) | 621 | 1060 |
| | | | | 7947344H1 (BRABNOE02) | 79 | 645 |
| 43 | 7274927CB1 | 864 | 1–31, 822–864 | 70581831V1 | 1 | 700 |
| | | | | 70590694V1 | 186 | 864 |
| 44 | 7946584CB1 | 1594 | 1–199, 1369–1594 | 71928043V1 | 529 | 1231 |
| | | | | 55071303H1 | 1 | 353 |
| | | | | 7338592T6 (SINTNON02) | 884 | 1594 |
| | | | | 6885143F6 (BRAHTDR03) | 250 | 960 |
| 45 | 8088078CB1 | 1845 | 1–114, 1011–1845 | g1482596 | 537 | 981 |
| | | | | GBI: g10040007_14_edit2 | 1 | 160 |
| | | | | 71113779V1 | 754 | 1440 |
| | | | | FL8088078_g9801056_000005_g6707837_1_1-2 | 388 | 541 |
| | | | | 8088078F6 (BLADTUN02) | 110 | 527 |
| | | | | GBI: g10040007_1_edit | 461 | 1845 |
| 46 | 2674269CB1 | 1680 | 1–203, 991–1147 | 6248538F8 (LUNPTUT02) | 1288 | 1680 |
| | | | | 3156348F6 (TLYMTXT02) | 1125 | 1403 |
| | | | | GBI: g7321523_edit | 220 | 957 |
| | | | | 55074191J1 | 1 | 217 |
| | | | | 2674269H1 (KIDNNOT19) | 969 | 1213 |
| | | | | 7990470H2 (UTRCDIC01) | 209 | 851 |
| | | | | 3926891H1 (KIDNNOT19) | 19 | 291 |
| 47 | 7472409CB1 | 1528 | 1354–1528, 849–1005 | 6248538F8 (LUNPTUT02) | 1146 | 1528 |
| | | | | 3156348F6 (TLYMTXT02) | 983 | 1261 |
| | | | | GBI: g7321523_edit | 78 | 815 |
| | | | | 2674269H1 (KIDNNOT19) | 827 | 1071 |
| | | | | 7990470H2 (UTRCDIC01) | 1 | 709 |
| 48 | 7477484CB1 | 4988 | 4651–4742, 3382–4011, 1–491, 4429–4477, 1495–3210, 1074–1222, 4361–4388 | 7259537F6 (BRAWNOC01) | 2988 | 3998 |
| | | | | 4456665F8 (HEAADIR01) | 2819 | 3339 |
| | | | | 7087893H1 (BRAUTDR03) | 2095 | 2275 |
| | | | | FL7477484_g9690314_g3327096_1_1-2 | 800 | 1040 |
| | | | | 6763489J1 (BRAUNOR01) | 965 | 1524 |
| | | | | 7226615H1 (BRAXTDR15) | 206 | 721 |
| | | | | 6770515H1 (BRAUNOR01) | 1 | 510 |
| | | | | 6979719H1 (BRAHTDR04) | 4239 | 4801 |
| | | | | 6770515R8 (BRAUNOR01) | 1394 | 2240 |
| | | | | 3825546H1 (BRAIHCT02) | 4693 | 4988 |
| | | | | FL7477484_g9690314_g3327096_1_5-6 | 1248 | 1845 |
| | | | | 2570231T6 (HIPOAZT01) | 4505 | 4955 |
| | | | | FL7477484_g9690314_g3327096_1_15-16 | 3868 | 4333 |
| | | | | GNN: g9690314_008 | 247 | 4488 |

TABLE 5

| Polynucleotide SEQ ID NO: | Incyte Project ID: | Representative Library |
| --- | --- | --- |
| 25 | 7312543CB1 | BRABDIE02 |
| 26 | 7477427CB1 | THYMNOR02 |
| 27 | 7481495CB1 | BRAIFER06 |
| 28 | 55053189CB1 | LUNGNOT18 |
| 29 | 7474797CB1 | MIXDUNB01 |
| 30 | 3296272CB1 | CERVNOT01 |
| 31 | 1989319CB1 | BRAUNOR01 |
| 32 | 079284CB1 | UTRSNOT12 |
| 33 | 5502218CB1 | BRAUNOR01 |
| 34 | 55056054CB1 | LUNPTMC01 |
| 35 | 7481989CB1 | BLADNOT05 |

TABLE 5-continued

| Polynucleotide SEQ ID NO: | Incyte Project ID: | Representative Library |
| --- | --- | --- |
| 36 | 55052990CB1 | BMARUNR02 |
| 37 | 7482377CB1 | SINTNOR01 |
| 38 | 7758364CB1 | LUNGFER04 |
| 39 | 5850001CB1 | LUNGTUT11 |
| 40 | 7477062CB1 | TONGTUT01 |
| 41 | 7477207CB1 | SINTFEE02 |
| 42 | 4022651CB1 | BRANDIT03 |
| 43 | 7274927CB1 | MYEPTXT02 |
| 44 | 7946584CB1 | BRAHTDR03 |
| 45 | 8088078CB1 | ENDINOT02 |
| 46 | 2674269CB1 | TLYMTXT02 |
| 47 | 7472409CB1 | TLYMTXT02 |
| 48 | 7477484CB1 | BRAUNOR01 |

TABLE 6

| Library | Vector | Library Description |
| --- | --- | --- |
| BLADNOT05 | pINCY | Library was constructed using RNA isolated from bladder tissue removed from a 60-year-old Caucasian male during a radical cystectomy, prostatectomy, and vasectomy. Pathology for the associated tumor tissue indicated grade 3 transitional cell carcinoma. Carcinoma in-situ was identified in the dome and trigone. Patient history included tobacco use. |
| BMARUNR02 | PIGEN | This random primed library was constructed using RNA isolated from an untreated SH-SY5Y cell line derived from bone marrow neuroblastoma tumor cells removed from a 4-year-old Caucasian female. |
| BRABDIE02 | pINCY | This 5' biased random primed library was constructed using RNA isolated from diseased cerebellum tissue removed from the brain of a 57-year-old Caucasian male who died from a cerebrovascular accident. Serologies were negative. Patient history included Huntington's disease, emphysema, and tobacco abuse (3–4 packs per day, for 40 years). |
| BRAHTDR03 | PCDNA2.1 | This random primed library was constructed using RNA isolated from archaecortex, anterior hippocampus tissue removed from a 55-year-old Caucasian female who died from cholangiocarcinoma. Pathology indicated mild meningeal fibrosis predominately over the convexities, scattered axonal spheroids in the white matter of the cingulate cortex and the thalamus, and a few scattered neurofibrillary tangles in the entorhinal cortex and the periaqueductal gray region. Pathology for the associated tumor tissue indicated well-differentiated cholangiocarcinoma of the liver with residual or relapsed tumor. Patient history included cholangiocarcinoma, post-operative Budd-Chiari syndrome, biliary ascites, hydorthorax, dehydration, malnutrition, oliguria and acute renal failure. Previous surgeries included cholecystectomy and resection of 85% of the liver. |
| BRAIFER06 | PCDNA2.1 | This random primed library was constructed using RNA isolated from brain tissue removed from a Caucasian male fetus who was stillborn with a hypoplastic left heart at 23 weeks' gestation. Serologies were negative. |
| BRANDIT03 | pINCY | Library was constructed using RNA isolated from pineal gland tissue removed from a 79-year-old Caucasian female who died from pneumonia. Neuropathology indicated severe Alzheimer Disease, moderate to severe arteriolosclerosis of the intracranial blood vessels, moderate cerebral amyloid angiopathy and infarctions involving the parieto-occipital lobes. There was atrophy of all lobes, caudate, putamen, amygdala, hippocampus, vermis, optic nerve, and the cerebral cortical white matter. There was cystic cavitation in the left medial occipital lobe, the right posterior parietal region, the right side insular cortex, and the right occipital and inferior parietal lobes. The ventricular system was severely dilated. Stains show |

TABLE 6-continued

| Library | Vector | Library Description |
|---|---|---|
| | | numerous diffuse as well as neuritic amyloid plaques throughout all neocortical areas examined. There were numerous neurofibrillary tangles predominantly in the pyramidal cell neurons of layers 3 and 5, however, small interneurons in layers 3, 4, and 6 also contain tangles. The caudate and putamen contain large areas of mineralization and scattered neurofibrillary tangles. The amygdala was markedly gliotic containing numerous neurofibrillary, argyrophilic and ghost type tangles; and scattered cells with granulovacuolar degeneration and focal cells with Lewy-like body inclusions. The hippocampus contains marked gliosis with complete loss of pyramidal cell neurons in the CA1 region. Silver stained sections show numerous neuritic plaques and scattered neurofibrillary tangles within the dentate gyrus, CA2, and CA3 regions. The substantia nigra shows numerous neurofibrillary tangles in the periaqueductal grey region. Patient history included gastritis with bleeding, glaucoma, PVD, COPD, delayed onset tonic/clonic seizures, transient ischemic attacks, pseudophakia, and allergies to aspirin and clindamycin. Family history included Alzheimer disease. |
| BRAUNOR01 | pINCY | This random primed library was constructed using RNA isolated from striatum, globus pallidus and posterior putamen tissue removed from an 81-year-old Caucasian female who died from a hemorrhage and ruptured thoracic aorta due to atherosclerosis. Pathology indicated moderate atherosclerosis involving the internal carotids, bilaterally; microscopic infarcts of the frontal cortex and hippocampus; and scattered diffuse amyloid plaques and neurofibrillary tangles, consistent with age. Grossly, the leptomeninges showed only mild thickening and hyalinization along the superior sagittal sinus. The remainder of the leptomeninges was thin and contained some congested blood vessels. Mild atrophy was found mostly in the frontal poles and lobes, and temporal lobes, bilaterally. Microscopically, there were pairs of Alzheimer type II astrocytes within the deep layers of the neocortex. There was increased satellitosis around neurons in the deep gray matter in the middle frontal cortex. The amygdala contained rare diffuse plaques and neurofibrillary tangles. The posterior hippocampus contained a microscopic area of cystic cavitation with hemosiderinladen macrophages surrounded by reactive gliosis. Patient history included sepsis, cholangitis, post-operative atelectasis, pneumonia CAD, cardiomegaly due to left ventricular hypertrophy, splenomegaly, arteriolonephrosclerosis, nodular colloidal goiter, emphysema, CHF, hypothyroidism, and peripheral vascular disease. |
| CERVNOT01 | PSPORT1 | Library was constructed using RNA isolated from the uterine cervical tissue of a 35-year-old Caucasian female during a vaginal hysterectomy with dilation and curettage. Pathology indicated mild chronic cervicitis. Family history included atherosclerotic coronary artery disease and type II diabetes. |
| ENDINOT02 | pINCY | The library was constructed using RNA isolated from treated iliac artery endothelial cells removed from a Black female. The cells were treated with TNF alpha 10 ng/ml and IL-1 beta 10 ng/ml for 20 hours. |
| LUNGFER04 | PCDNA2.1 | This random primed library was constructed using RNA isolated from lung tissue removed from a Caucasian male fetus who died from fetal demise. |
| LUNGNOT18 | pINCY | Library was constructed using RNA isolated from left upper lobe lung tissue removed from a 66-year-old Caucasian female. Pathology for the associated tumor tissue indicated a grade 2 adenocarcinoma. Patient history included cerebrovascular disease, atherosclerotic coronary artery disease, and pulmonary insufficiency. Family history included a myocardial infarction and atherosclerotic coronary artery disease. |
| LUNGTUT11 | pINCY | Library was constructed using RNA isolated from lung tumor tissue removed from the right lower lobe a 57-year-old Caucasian male during a segmental lung resection. Pathology indicated an infiltrating grade 4 squamous cell carcinoma. Multiple intrapulmonary peribronchial lymph nodes showed metastatic squamous cell carcinoma. Patient history included a benign brain neoplasm and tobacco abuse. Family history included spinal cord cancer, type II diabetes, cerebrovascular disease, and malignant prostate neoplasm. |
| LUNPTMC01 | pINCY | This large size-fractionated library was constructed using RNA isolated from pleura tissue removed from a 58-year-old Caucasian female during segmental lung resection. Pathology for the matched tumor tissue indicated metastatic grade 4 |

TABLE 6-continued

| Library | Vector | Library Description |
|---|---|---|
| | | leiomyosarcoma, forming a mass in the left lower lobe lung, with extension into the lumen of the pulmonary vein. Patient history included a malignant retroperitoneum neoplasm with metastasis to lung, an unspecified respiratory abnormality, cough, hyperlipidemia, paralytic polio, benign bladder neoplasm, normal delivery, benign hypertension, and tobacco abuse in remission. Family history included benign hypertension, hyperlipidemia skin cancer, and cerebrovascular disease. |
| MIXDUNB01 | pINCY | Library was constructed using RNA isolated from myometrium removed from a 41-year-old Caucasian female during vaginal hysterectomy with a dilatation and curettage and untreated smooth muscle cells removed from the renal vein of a 57 year-old Caucasian male. Pathology indicated the myometrium and cervix were unremarkable. The endometrium was secretory and contained fragments of endometrial polyps. Benign endo- and ectocervical mucosa were identified in the endocervix. Pathology for the associated tumor tissue indicated uterine leiomyoma. Medical history included an unspecified menstrual disorder, ventral hernia, normal delivery, a benign ovarian neoplasm, and tobacco abuse. |
| MYEPTXT02 | pINCY | The library was constructed using RNA isolated from a treated K-562 cell line, derived from chronic myelogenous leukemia precursor cells removed from a 53-year-old female. The cells were treated with 1 micromolar PMA for 96 hours. |
| SINTFEE02 | PCDNA2.1 | This 5' biased random primed library was constructed using RNA isolated from small intestine tissue removed from a Caucasian male fetus who died from Patau's syndrome (trisomy 13) at 20-weeks' gestation. Serology was negative. |
| SINTNOR01 | PCDNA2.1 | This random primed library was constructed using RNA isolated from small intestine tissue removed from a 31-year-old Caucasian female during Roux-en-Y gastric bypass. Patient history included clinical obesity. |
| THYMNOR02 | pINCY | The library was constructed using RNA isolated from thymus tissue removed from a 2-year-old Caucasian female during a thymectomy and patch closure of left atrioventricular fistula. Pathology indicated there was no gross abnormality of the thymus. The patient presented with congenital heart abnormalities. Patient history included double inlet left ventricle and a rudimentary right ventricle, pulmonary hypertension, cyanosis, subaortic stenosis, seizures, and a fracture of the skull base. Family history included reflux neuropathy. |
| TLYMTXT02 | pINCY | Library was constructed using RNA isolated from CD4+ T cells obtained from a pool of donors. The cells were treated with CD3 antibodies. |
| TONGTUT01 | PSPORT1 | Library was constructed using RNA isolated from tongue tumor tissue obtained from a 36-year-old Caucasian male during a hemiglossectomy. Pathology indicated recurrent invasive grade 2 squamous-cell carcinoma. |
| UTRSNOT12 | pINCY | Library was constructed using RNA isolated from uterine myometrial tissue removed from a 41-year-old Caucasian female during a vaginal hysterectomy with dilation and curettage. The endometrium was secretory and contained fragments of endometrial polyps. Benign endo- and ectocervical mucosa were identified in the endocervix. Pathology for the associated tumor tissue indicated uterine leiomyoma. Patient history included ventral hernia and a benign ovarian neoplasm. |

TABLE 7

| Program | Description | Reference | Parameter Threshold |
|---|---|---|---|
| ABI FACTURA | A program that removes vector sequences and masks ambiguous bases in nucleic acid sequences. | Applied Biosystems, Foster City, CA. | |
| ABI/ PARACEL FDF | A Fast Data Finder useful in comparing and annotating amino acid or nucleic acid sequences. | Applied Biosystems, Foster City, CA; Paracel Inc., Pasadena, CA. | Mismatch <50% |
| ABI AutoAssembler | A program that assembles nucleic acid sequences. | Applied Biosystems, Foster City, CA. | |
| BLAST | A Basic Local Alignment Search Tool useful in sequence similarity search for amino acid and nucleic acid sequences. BLAST includes five functions: blastp, blastn, blastx, tblastn, and tblastx. | Altschul, S.F. et al. (1990) J. Mol. Biol. 215: 403–410; Altschul, S.F. et al. (1997) Nucleic Acids Res. 25: 3389–3402. | ESTs: Probability value = 1.0E−8 or less; Full Length sequences: Probability value = 1.0E−10 or less |

TABLE 7-continued

| Program | Description | Reference | Parameter Threshold |
|---|---|---|---|
| FASTA | A Pearson and Lipman algorithm that searches for similarity between a query sequence and a group of sequences of the same type. FASTA comprises as least five functions: fasta, tfasta, fastx, tfastx, and ssearch. | Pearson, W. R. and D. J. Lipman (1988) Proc. Natl. Acad Sci. USA 85: 2444–2448; Pearson, W. R. (1990) Methods Enzymol. 183: 63–98; and Smith, T. F. and M. S. Waterman (1981) Adv. Appl. Math. 2: 482–489. | ESTs: fasta E value = 1.06E-6; Assembled ESTs: fasta Identity = 95% or greater and Matchlength = 200 bases or greater; fastx E value = 1.0E-8 or less; Full Length sequences: fastx score = 100 or greater |
| BLIMPS | A BLocks IMProved Searcher that matches a sequence against those in BLOCKS, PRINTS, DOMO, PRODOM, and PFAM databases to search for gene families, sequence homology, and structural fingerprint regions. | Henikoff, S. and J. G. Henikoff (1991) Nucleic Acids Res. 19: 6565–6572; Henikoff, J. G. and S. Henikoff (1996) Methods Enzymol. 266: 88–105; and Attwood, T. K. et al. (1997) J. Chem. Inf. Comput. Sci. 37: 417–424. | Probability value = 1.0E-3 or less |
| HMMER | An algorithm for searching a query sequence against hidden Markov model (HMM)-based databases of protein family consensus sequences, such as PFAM, INCY, SMART and TIGRFAM. | Krogh, A. et al. (1994) J. Mol. Biol. 235: 1501–1531; Sonnhammer, E. L. L. et al. (1988) Nucleic Acids Res. 26: 320–322; Durbin, R. et al. (1998) Our World View, in a Nutshell, Cambridge Univ. Press, pp. 1–350. | PFAM, INCY, SMART or TIGRFAM hits: Probability value = 1.0E-3 or less; Signal peptide hits: Score = 0 or greater |
| ProfileScan | An algorithm that searches for structural and sequence motifs in protein sequences that match sequence patterns defined in Prosite. | Gribskov, M. et al. (1988) CABIOS 4: 61–66; Gribskov, M. et al. (1989) Methods Enzymol. 183: 146–159; Bairoch, A. et al. (1997) Nucleic Acids Res. 25: 217–221. | Normalized quality score $\geq$ GCG specified "HIGH" value for that particular Prosite motif. Generally, score = 1.4–2.1. |
| Phred | A base-calling algorithm that examines automated sequencer traces with high sensitivity and probability. | Ewing, B. et al. (1998) Genome Res. 8: 175–185; Ewing, B. and P. Green (1998) Genome Res. 8: 186–194. | |
| Phrap | A Phils Revised Assembly Program including SWAT and CrossMatch, programs based on efficient implementation of the Smith-Waterman algorithm, useful in searching sequence homology and assembling DNA sequences. | Smith, T. F. and M. S. Waterman (1981) Adv. Appl. Math. 2: 482–489; Smith, T. F. and M. S. Waterman (1981) J. Mol. Biol. 147: 195–197; and Green, P., University of Washington, Seattle, WA. | Score = 120 or greater; Match length = 56 or greater |
| Consed | A graphical tool for viewing and editing Phrap assemblies. | Gordon, D. et al. (1998) Genome Res. 8: 195–202. | |
| SPScan | A weight matrix analysis program that scans protein sequences for the presence of secretory signal peptides. | Nielson, H. et al. (1997) Protein Engineering 10: 1–6; Claverie, J. M. and S. Audic (1997) CABIOS 12: 431–439. | Score = 3.5 or greater |
| TMAP | A program that uses weight matrices to delineate transmembrane segments on protein sequences and determine orientation. | Persson, B. and P. Argos (1994) J. Mol. Biol. 237: 182–192; Persson, B. and P. Argos (1996) Protein Sci. 5: 363–371. | |
| TMHMMER | A program that uses a hidden Markov model (HMM) to delineate transmembrane segments on protein sequences and determine orientation. | Sonnhammer, E.L. et al. (1998) Proc. Sixth Intl. Conf. On Intelligent Systems for Mol. Biol., Glasgow et al., eds., The Am. Assoc. for Artificial Intelligence (AAAI) Press, Menlo Park, CA, and MIT Press, Cambridge, MA, pp. 175–182. | |
| Motifs | A program that searches amino acid sequences for patterns that matched those defined in Prosite. | Bairoch, A. et al. (1997) Nucleic Acids Res. 25: 217–221; Wisconsin Package Program Manual, version 9, page M51–59, Genetics Computer Group, Madison, WI. | |

What is claimed is:

1. An isolated polynucleotide encoding a human polypeptide selected from the group consisting of:
   a) a polypeptide comprising an amino acid sequence of SEQ ID NO:10; and
   b) a polypeptide comprising an amino acid sequence having at least 95% sequence identity to the amino acid sequence of SEQ ID NO:10, wherein the polypeptide has cAMP-dependent protein kinase beta-catalytic subunit activity.

2. An isolated polynucleotide encoding a polypeptide of SEQ ID NO:10.

3. An isolated polynucleotide of claim 2 comprising SEQ IID NO:34.

4. A recombinant polynucleotide comprising a promoter sequence operably linked to the polynucleotide of claim 1.

5. An isolated cell transformed with the recombinant polynucleotide of claim 4.

6. A method of producing a polypeptide encoded by the polynucleotide of claim 3, the method comprising:
   a) culturing a cell under conditions suitable for expression of the polypeptide, wherein said cell is transformed with a recombinant polynucleotide, and said recombinant polynucleotide comprises a promoter sequence operably linked to the polynucleotide of claim 1, and
   b) recovering the polypeptide so expressed.

7. The method of claim 6, wherein the polypeptide has the amino acid sequence of SEQ ID NO:10.

8. An isolated polynucleotide selected from the group consisting of:
   a) a polynucleotide comprising a polynucleotide sequence of SEQ ID NO:34,
   b) a polynucleotide comprising a polynucleotide sequence having at least 95% seciuence identity to the polynucleotide sequence of SEQ ID NO:34, wherein the polynucleotide encodes a polypeptide that has cAMP-dependent protein kinase beta-catalytic subunit activity,
   c) a polynucleotide completely complementary to the polynucleotide of a),
   d) a polynucleotide completely complementary to the polynucleotide of b), and
   e) an RNA equivalent of any one of a)–d).

9. The polynucleotide of claim 8, comprising the polynucleotide sequence of SEQ ID NO:34.

10. The polynucleotide of claim 1, encoding a polypeptide comprising an amino acid sequence having at least 96% sequence identity to the amino acid sequence of SEQ ID NO:10.

11. The polynucleotide of claim 1, encoding a polypeptide comprising an amino acid sequence having at least 97% sequence identity to the amino acid sequence of SEQ ID NO:10.

12. The polynucleotide of claim 1, encoding a polypeptide comprising an amino acid sequence having at least 98% sequence identity to the amino acid sequence of SEQ ID NO:10.

13. The polynucleotide of claim 1, encoding a polypeptide comprising an amino acid sequence having at least 99% sequence identity to the amino acid sequence of SEQ ID NO:10.

14. The polynucleotide of claim 8, comprising a polynucleotide sequence having at least 96% sequence identity to a polynucleotide sequence of SEQ ID NO:34.

15. The polynucleotide of claim 8, comprising a polynucleotide sequence having at least 97% sequence identity to a polynucleotide sequence of SEQ ID NO:34.

16. The polynucleotide of claim 8, comprising a polynucleotide sequence having at least 98% sequence identity to a polynucleotide sequence of SEQ ID NO:34.

17. The polynucleotide of claim 8, comprising a polynucleotide sequence having at least 99% sequence identity to a polynucleotide sequence of SEQ ID NO:34.

* * * * *

SEQUENCE LISTING

<160> NUMBER OF SEQ ID NOS: 48

<210> SEQ ID NO 1
<211> LENGTH: 424
<212> TYPE: PRT
<213> ORGANISM: Homo sapiens
<220> FEATURE:
<221> NAME/KEY: misc_feature
<223> OTHER INFORMATION: Incyte ID No: 7312543CD1

-continued

```
<400> SEQUENCE: 1

Met Ser Val Gly Cys Pro Glu Pro Glu Pro Arg Ser Leu Thr
 1               5                  10                  15

Cys Cys Gly Pro Gly Thr Ala Pro Gly Pro Gly Ala Gly Val Pro
                20                  25                  30

Leu Leu Thr Glu Asp Met Gln Ala Leu Thr Leu Arg Thr Leu Ala
                35                  40                  45

Ala Ser Asp Val Thr Lys His Tyr Glu Leu Val Arg Glu Leu Gly
                50                  55                  60

Lys Gly Thr Tyr Gly Lys Val Asp Leu Val Val Tyr Lys Gly Thr
                65                  70                  75

Gly Thr Lys Met Ala Leu Lys Phe Val Asn Lys Ser Lys Thr Lys
                80                  85                  90

Leu Lys Asn Phe Leu Arg Glu Val Ser Ile Thr Asn Ser Leu Ser
                95                 100                 105

Ser Ser Pro Phe Ile Ile Lys Val Phe Asp Val Val Phe Glu Thr
               110                 115                 120

Glu Asp Cys Tyr Val Phe Ala Gln Glu Tyr Ala Pro Ala Gly Asp
               125                 130                 135

Leu Phe Asp Ile Ile Pro Pro Gln Val Gly Leu Pro Glu Asp Thr
               140                 145                 150

Val Lys Arg Cys Val Gln Gln Leu Gly Leu Ala Leu Asp Phe Met
               155                 160                 165

His Gly Arg Gln Leu Val His Arg Asp Ile Lys Pro Glu Asn Val
               170                 175                 180

Leu Leu Phe Asp Arg Glu Cys Arg Arg Val Lys Leu Ala Asp Phe
               185                 190                 195

Gly Met Thr Arg Arg Val Gly Cys Arg Val Lys Arg Val Ser Gly
               200                 205                 210

Thr Ile Pro Tyr Thr Ala Pro Glu Val Cys Gln Ala Gly Arg Ala
               215                 220                 225

Asp Gly Leu Ala Val Asp Thr Gly Val Asp Val Trp Ala Phe Gly
               230                 235                 240

Val Leu Ile Phe Cys Val Leu Thr Gly Asn Phe Pro Trp Glu Ala
               245                 250                 255

Ala Ser Gly Ala Asp Ala Phe Phe Glu Glu Phe Val Arg Trp Gln
               260                 265                 270

Arg Gly Arg Leu Pro Gly Leu Pro Ser Gln Trp Arg Arg Phe Thr
               275                 280                 285

Glu Pro Ala Leu Arg Met Phe Gln Arg Leu Leu Ala Leu Glu Pro
               290                 295                 300

Glu Arg Arg Gly Pro Ala Lys Glu Val Phe Arg Phe Leu Lys His
               305                 310                 315

Glu Leu Thr Ser Glu Leu Arg Arg Arg Pro Ser His Arg Ala Arg
               320                 325                 330

Lys Pro Pro Gly Asp Arg Pro Ala Ala Gly Pro Leu Arg Leu
               335                 340                 345

Glu Ala Pro Gly Pro Leu Lys Arg Thr Val Leu Thr Glu Ser Gly
               350                 355                 360

Gly Gly Ser Arg Pro Ala Pro Ala Val Gly Ser Val Pro Leu
               365                 370                 375

Pro Val Pro Val Pro Val Pro Val Pro Val Pro Val Pro
               380                 385                 390
```

-continued

```
Glu Pro Gly Leu Ala Pro Gln Gly Pro Pro Gly Arg Thr Asp Gly
                395                 400                 405

Arg Ala Asp Lys Ser Lys Gly Gln Val Val Leu Ala Thr Ala Ile
                410                 415                 420

Glu Ile Cys Val

<210> SEQ ID NO 2
<211> LENGTH: 1719
<212> TYPE: PRT
<213> ORGANISM: Homo sapiens
<220> FEATURE:
<221> NAME/KEY: misc_feature
<223> OTHER INFORMATION: Incyte ID No: 7477427CD1

<400> SEQUENCE: 2

Met Ser Gly Glu Val Arg Leu Arg Gln Leu Glu Gln Phe Ile Leu
  1               5                  10                  15

Asp Gly Pro Ala Gln Thr Asn Gly Gln Cys Phe Ser Val Glu Thr
                 20                  25                  30

Leu Leu Asp Ile Leu Ile Cys Leu Tyr Asp Glu Cys Asn Asn Ser
                 35                  40                  45

Pro Leu Arg Arg Glu Lys Asn Ile Leu Glu Tyr Leu Glu Trp Ala
                 50                  55                  60

Lys Pro Phe Thr Ser Lys Val Lys Gln Met Arg Leu His Arg Glu
                 65                  70                  75

Asp Phe Glu Ile Leu Lys Val Ile Gly Arg Gly Ala Phe Gly Glu
                 80                  85                  90

Val Ala Val Val Lys Leu Lys Asn Ala Asp Lys Val Phe Ala Met
                 95                 100                 105

Lys Ile Leu Asn Lys Trp Glu Met Leu Lys Arg Ala Glu Thr Ala
                110                 115                 120

Cys Phe Arg Glu Glu Arg Asp Val Leu Val Asn Gly Asp Asn Lys
                125                 130                 135

Trp Ile Thr Thr Leu His Tyr Ala Phe Gln Asp Asp Asn Asn Leu
                140                 145                 150

Tyr Leu Val Met Asp Tyr Tyr Val Gly Gly Asp Leu Leu Thr Leu
                155                 160                 165

Leu Ser Lys Phe Glu Asp Arg Leu Pro Glu Asp Met Ala Arg Phe
                170                 175                 180

Tyr Leu Ala Glu Met Val Ile Ala Ile Asp Ser Val His Gln Leu
                185                 190                 195

His Tyr Val His Arg Asp Ile Lys Pro Asp Asn Ile Leu Met Asp
                200                 205                 210

Met Asn Gly His Ile Arg Leu Ala Asp Phe Gly Ser Cys Leu Lys
                215                 220                 225

Leu Met Glu Asp Gly Thr Val Gln Ser Ser Val Ala Val Gly Thr
                230                 235                 240

Pro Asp Tyr Ile Ser Pro Glu Ile Leu Gln Ala Met Glu Asp Gly
                245                 250                 255

Lys Gly Arg Tyr Gly Pro Glu Cys Asp Trp Trp Ser Leu Gly Val
                260                 265                 270

Cys Met Tyr Glu Met Leu Tyr Gly Glu Thr Pro Phe Tyr Ala Glu
                275                 280                 285

Ser Leu Val Glu Thr Tyr Gly Lys Ile Met Asn His Lys Glu Arg
                290                 295                 300
```

-continued

```
Phe Gln Phe Pro Ala Gln Val Thr Asp Val Ser Glu Asn Ala Lys
            305                 310                 315
Asp Leu Ile Arg Arg Leu Ile Cys Ser Arg Glu His Arg Leu Gly
            320                 325                 330
Gln Asn Gly Ile Glu Asp Phe Lys Lys His Pro Phe Phe Ser Gly
            335                 340                 345
Ile Asp Trp Asp Asn Ile Arg Asn Cys Glu Ala Pro Tyr Ile Pro
            350                 355                 360
Glu Val Ser Ser Pro Thr Asp Thr Ser Asn Phe Asp Val Asp Asp
            365                 370                 375
Asp Cys Leu Lys Asn Ser Glu Thr Met Pro Pro Thr His Thr
            380                 385                 390
Ala Phe Ser Gly His His Leu Pro Phe Val Gly Phe Thr Tyr Thr
            395                 400                 405
Ser Ser Cys Val Leu Ser Asp Arg Ser Cys Leu Arg Val Thr Ala
            410                 415                 420
Gly Pro Thr Ser Leu Asp Leu Asp Val Asn Val Gln Arg Thr Leu
            425                 430                 435
Asp Asn Asn Leu Ala Thr Glu Ala Tyr Glu Arg Arg Ile Lys Arg
            440                 445                 450
Leu Glu Gln Glu Lys Leu Glu Leu Ser Arg Lys Leu Gln Glu Ser
            455                 460                 465
Thr Gln Thr Val Gln Ala Leu Gln Tyr Ser Thr Val Asp Gly Pro
            470                 475                 480
Leu Thr Ala Ser Lys Asp Leu Glu Ile Lys Asn Leu Lys Glu Glu
            485                 490                 495
Ile Glu Lys Leu Arg Lys Gln Val Thr Glu Ser Ser His Leu Glu
            500                 505                 510
Gln Gln Leu Glu Glu Ala Asn Ala Val Arg Gln Glu Leu Asp Asp
            515                 520                 525
Ala Phe Arg Gln Ile Lys Ala Tyr Glu Lys Gln Ile Lys Thr Leu
            530                 535                 540
Gln Gln Glu Arg Glu Asp Leu Asn Lys Glu Leu Val Gln Ala Ser
            545                 550                 555
Glu Arg Leu Lys Asn Gln Ser Lys Glu Leu Lys Asp Ala His Cys
            560                 565                 570
Gln Arg Lys Leu Ala Met Gln Glu Phe Met Glu Ile Asn Glu Arg
            575                 580                 585
Leu Thr Glu Leu His Thr Gln Lys Gln Lys Leu Ala Arg His Val
            590                 595                 600
Arg Asp Lys Glu Glu Val Asp Leu Val Met Gln Lys Val Glu
            605                 610                 615
Ser Leu Arg Gln Glu Leu Arg Arg Thr Glu Arg Ala Lys Lys Glu
            620                 625                 630
Leu Glu Val His Thr Glu Ala Leu Ala Ala Glu Ala Ser Lys Asp
            635                 640                 645
Arg Lys Leu Arg Glu Gln Ser Glu His Tyr Ser Lys Gln Leu Glu
            650                 655                 660
Asn Glu Leu Glu Gly Leu Lys Gln Lys Gln Ile Ser Tyr Ser Pro
            665                 670                 675
Gly Val Cys Ser Ile Glu His Gln Gln Glu Ile Thr Lys Leu Lys
            680                 685                 690
```

-continued

```
Thr Asp Leu Glu Lys Lys Ser Ile Phe Tyr Glu Glu Leu Ser
            695                 700                 705

Lys Arg Glu Gly Ile His Ala Asn Glu Ile Lys Asn Leu Lys Lys
            710                 715                 720

Glu Leu His Asp Ser Glu Gly Gln Gln Leu Ala Leu Asn Lys Glu
            725                 730                 735

Ile Met Ile Leu Lys Asp Lys Leu Glu Lys Thr Arg Arg Glu Ser
            740                 745                 750

Gln Ser Glu Arg Glu Glu Phe Glu Ser Glu Phe Lys Gln Gln Tyr
            755                 760                 765

Glu Arg Glu Lys Val Leu Leu Thr Glu Glu Asn Lys Lys Leu Thr
            770                 775                 780

Ser Glu Leu Asp Lys Leu Thr Thr Leu Tyr Glu Asn Leu Ser Ile
            785                 790                 795

His Asn Gln Gln Leu Glu Glu Val Lys Asp Leu Ala Asp Lys
            800                 805                 810

Lys Glu Ser Val Ala His Trp Glu Ala Gln Ile Thr Glu Ile Ile
            815                 820                 825

Gln Trp Val Ser Asp Glu Lys Asp Ala Arg Gly Tyr Leu Gln Ala
            830                 835                 840

Leu Ala Ser Lys Met Thr Glu Glu Leu Glu Ala Leu Arg Asn Ser
            845                 850                 855

Ser Leu Gly Thr Arg Ala Thr Asp Met Pro Trp Lys Met Arg Arg
            860                 865                 870

Phe Ala Lys Leu Asp Met Ser Ala Arg Leu Glu Leu Gln Ser Ala
            875                 880                 885

Leu Asp Ala Glu Ile Arg Ala Lys Gln Ala Ile Gln Glu Glu Leu
            890                 895                 900

Asn Lys Val Lys Ala Ser Asn Ile Ile Thr Glu Cys Lys Leu Lys
            905                 910                 915

Asp Ser Glu Lys Lys Asn Leu Glu Leu Leu Ser Glu Ile Glu Gln
            920                 925                 930

Leu Ile Lys Asp Thr Glu Glu Leu Arg Ser Glu Lys Gly Ile Glu
            935                 940                 945

His Gln Asp Ser Gln His Ser Phe Leu Ala Phe Leu Asn Thr Pro
            950                 955                 960

Thr Asp Ala Leu Asp Gln Phe Glu Thr Val Asp Ser Thr Pro Leu
            965                 970                 975

Ser Val His Thr Pro Thr Leu Arg Lys Lys Gly Cys Pro Gly Ser
            980                 985                 990

Thr Gly Phe Pro Pro Lys Arg Lys Thr His Gln Phe Phe Val Lys
            995                1000                1005

Ser Phe Thr Thr Pro Thr Lys Cys His Gln Cys Thr Ser Leu Met
           1010                1015                1020

Val Gly Leu Ile Arg Gln Gly Cys Ser Cys Glu Val Cys Gly Phe
           1025                1030                1035

Ser Cys His Ile Thr Cys Val Asn Lys Ala Pro Thr Thr Cys Pro
           1040                1045                1050

Val Pro Pro Glu Gln Thr Lys Gly Pro Leu Gly Ile Asp Pro Gln
           1055                1060                1065

Lys Gly Ile Gly Thr Ala Tyr Glu Gly His Val Arg Ile Pro Lys
           1070                1075                1080

Pro Ala Gly Val Lys Lys Gly Trp Gln Arg Ala Leu Ala Ile Val
```

-continued

```
                1085                1090                1095
Cys Asp Phe Lys Leu Phe Leu Tyr Asp Ile Ala Glu Gly Lys Ala
                1100                1105                1110
Ser Gln Pro Ser Val Val Ile Ser Gln Val Ile Asp Met Arg Asp
                1115                1120                1125
Glu Glu Phe Ser Val Ser Ser Val Leu Ala Ser Asp Val Ile His
                1130                1135                1140
Ala Ser Arg Lys Asp Ile Pro Cys Ile Phe Arg Val Thr Ala Ser
                1145                1150                1155
Gln Leu Ser Ala Ser Asn Asn Lys Cys Ser Ile Leu Met Leu Ala
                1160                1165                1170
Asp Thr Glu Asn Glu Lys Asn Lys Trp Val Gly Val Leu Ser Glu
                1175                1180                1185
Leu His Lys Ile Leu Lys Lys Asn Lys Phe Arg Asp Arg Ser Val
                1190                1195                1200
Tyr Val Pro Lys Glu Ala Tyr Asp Ser Thr Leu Pro Leu Ile Lys
                1205                1210                1215
Thr Thr Gln Ala Ala Ala Ile Ile Asp His Glu Arg Ile Ala Leu
                1220                1225                1230
Gly Asn Glu Glu Gly Leu Phe Val Val His Val Thr Lys Asp Glu
                1235                1240                1245
Ile Ile Arg Val Gly Asp Asn Lys Lys Ile His Gln Ile Glu Leu
                1250                1255                1260
Ile Pro Asn Asp Gln Leu Val Ala Val Ile Ser Gly Arg Asn Arg
                1265                1270                1275
His Val Arg Leu Phe Pro Met Ser Ala Leu Asp Gly Arg Glu Thr
                1280                1285                1290
Asp Phe Tyr Lys Leu Ser Glu Thr Lys Gly Cys Gln Thr Val Thr
                1295                1300                1305
Ser Gly Lys Val Arg His Gly Ala Leu Thr Cys Leu Cys Val Ala
                1310                1315                1320
Met Lys Arg Gln Val Leu Cys Tyr Glu Leu Phe Gln Ser Lys Thr
                1325                1330                1335
Arg His Arg Lys Phe Lys Glu Ile Gln Val Pro Tyr Asn Val Gln
                1340                1345                1350
Trp Met Ala Ile Phe Ser Glu Gln Leu Cys Val Gly Phe Gln Ser
                1355                1360                1365
Gly Phe Leu Arg Tyr Pro Leu Asn Gly Glu Gly Asn Pro Tyr Ser
                1370                1375                1380
Met Leu His Ser Asn Asp His Thr Leu Ser Phe Ile Ala His Gln
                1385                1390                1395
Pro Met Asp Ala Ile Cys Ala Val Glu Ile Ser Ser Lys Glu Tyr
                1400                1405                1410
Leu Leu Cys Phe Asn Ser Ile Gly Ile Tyr Thr Asp Cys Gln Gly
                1415                1420                1425
Arg Arg Ser Arg Gln Gln Glu Leu Met Trp Pro Ala Asn Pro Ser
                1430                1435                1440
Ser Cys Cys Tyr Asn Ala Pro Tyr Leu Ser Val Tyr Ser Glu Asn
                1445                1450                1455
Ala Val Asp Ile Phe Asp Val Asn Ser Met Glu Trp Ile Gln Thr
                1460                1465                1470
Leu Pro Leu Lys Lys Val Arg Pro Leu Asn Asn Glu Gly Ser Leu
                1475                1480                1485
```

-continued

Asn Leu Leu Gly Leu Glu Thr Ile Arg Leu Ile Tyr Phe Lys Asn
                1490                1495                1500

Lys Met Ala Glu Gly Asp Glu Leu Val Val Pro Glu Thr Ser Asp
            1505                1510                1515

Asn Ser Arg Lys Gln Met Val Arg Asn Ile Asn Asn Lys Arg Arg
            1520                1525                1530

Tyr Ser Phe Arg Val Pro Glu Glu Arg Met Gln Gln Arg Arg
            1535                1540                1545

Glu Met Leu Arg Asp Pro Glu Met Arg Asn Lys Leu Ile Ser Asn
            1550                1555                1560

Pro Thr Asn Phe Asn His Ile Ala His Met Gly Pro Gly Asp Gly
            1565                1570                1575

Ile Gln Ile Leu Lys Asp Leu Pro Met Asn Pro Arg Pro Gln Glu
            1580                1585                1590

Ser Arg Thr Val Phe Ser Gly Ser Val Ser Ile Pro Ser Ile Thr
            1595                1600                1605

Lys Ser Arg Pro Glu Pro Gly Arg Ser Met Ser Ala Ser Ser Gly
            1610                1615                1620

Leu Ser Ala Arg Ser Ser Ala Gln Asn Gly Ser Ala Leu Lys Arg
            1625                1630                1635

Glu Phe Ser Gly Gly Ser Tyr Ser Ala Lys Arg Gln Pro Met Pro
            1640                1645                1650

Ser Pro Ser Glu Gly Ser Leu Ser Ser Gly Met Asp Gln Gly
            1655                1660                1665

Ser Asp Ala Pro Ala Arg Asp Phe Asp Gly Glu Asp Ser Asp Ser
            1670                1675                1680

Pro Arg His Ser Thr Ala Ser Asn Ser Ser Asn Leu Ser Ser Pro
            1685                1690                1695

Pro Ser Pro Val Ser Pro Arg Lys Thr Lys Ser Leu Ser Leu Glu
            1700                1705                1710

Ser Thr Asp Arg Gly Ser Trp Asp Pro
            1715

<210> SEQ ID NO 3
<211> LENGTH: 1125
<212> TYPE: PRT
<213> ORGANISM: Homo sapiens
<220> FEATURE:
<221> NAME/KEY: misc_feature
<223> OTHER INFORMATION: Incyte ID No: 7481495CD1

<400> SEQUENCE: 3

Met Ser Lys Thr Leu Lys Lys Lys His Trp Leu Ser Lys Val
 1               5                  10                  15

Gln Glu Cys Ala Val Ser Trp Ala Gly Pro Pro Gly Asp Phe Gly
                20                  25                  30

Ala Glu Ile Arg Gly Gly Ala Glu Arg Gly Glu Phe Pro Tyr Leu
            35                  40                  45

Gly Arg Leu Arg Glu Glu Pro Gly Gly Thr Cys Tyr Val Val
            50                  55                  60

Ser Gly Lys Ala Pro Ser Pro Gly Asp Val Leu Leu Glu Val Asn
            65                  70                  75

Gly Thr Pro Val Ser Gly Leu Thr Asn Arg Asp Thr Leu Ala Val
            80                  85                  90

Ile Arg His Phe Arg Glu Pro Ile Arg Leu Lys Thr Val Lys Pro

-continued

```
                95                 100                 105
Gly Lys Val Ile Asn Lys Asp Leu Arg His Tyr Leu Ser Leu Gln
            110                 115                 120
Phe Gln Lys Gly Ser Ile Asp His Lys Leu Gln Gln Val Ile Arg
            125                 130                 135
Asp Asn Leu Tyr Leu Arg Thr Ile Pro Cys Thr Thr Arg Ala Pro
            140                 145                 150
Arg Asp Gly Glu Val Pro Gly Val Asp Tyr Asn Phe Ile Ser Val
            155                 160                 165
Glu Gln Phe Lys Ala Leu Glu Glu Ser Gly Ala Leu Leu Glu Ser
            170                 175                 180
Gly Thr Tyr Asp Gly Asn Phe Tyr Gly Thr Pro Lys Pro Pro Ala
            185                 190                 195
Glu Pro Ser Pro Phe Gln Pro Asp Pro Val Asp Gln Val Leu Phe
            200                 205                 210
Asp Asn Glu Phe Asp Ala Glu Ser Gln Arg Lys Arg Thr Thr Ser
            215                 220                 225
Val Ser Lys Met Glu Arg Met Asp Ser Ser Leu Pro Glu Glu Glu
            230                 235                 240
Glu Asp Glu Asp Lys Glu Ala Ile Asn Gly Ser Gly Asn Ala Glu
            245                 250                 255
Asn Arg Glu Arg His Ser Glu Ser Ser Asp Trp Met Lys Thr Val
            260                 265                 270
Pro Ser Tyr Asn Gln Thr Asn Ser Ser Met Asp Phe Arg Asn Tyr
            275                 280                 285
Met Met Arg Asp Glu Thr Leu Glu Pro Leu Pro Lys Asn Trp Glu
            290                 295                 300
Met Ala Tyr Thr Asp Thr Gly Met Ile Tyr Phe Ile Asp His Asn
            305                 310                 315
Thr Lys Thr Thr Thr Trp Leu Asp Pro Arg Leu Cys Lys Lys Ala
            320                 325                 330
Lys Ala Pro Glu Asp Cys Glu Asp Gly Glu Leu Pro Tyr Gly Trp
            335                 340                 345
Glu Lys Ile Glu Asp Pro Gln Tyr Gly Thr Tyr Tyr Val Asp His
            350                 355                 360
Leu Asn Gln Lys Thr Gln Phe Glu Asn Pro Val Glu Glu Ala Lys
            365                 370                 375
Arg Lys Lys Gln Leu Gly Gln Val Glu Ile Gly Ser Ser Lys Pro
            380                 385                 390
Asp Met Glu Lys Ser His Phe Thr Arg Asp Pro Ser Gln Leu Lys
            395                 400                 405
Gly Val Leu Val Arg Ala Ser Leu Lys Lys Ser Thr Met Gly Phe
            410                 415                 420
Gly Phe Thr Ile Ile Gly Gly Asp Arg Pro Asp Glu Phe Leu Gln
            425                 430                 435
Val Lys Asn Val Leu Lys Asp Gly Pro Ala Ala Gln Asp Gly Lys
            440                 445                 450
Ile Ala Pro Gly Asp Val Ile Val Asp Ile Asn Gly Asn Cys Val
            455                 460                 465
Leu Gly His Thr His Ala Asp Val Val Gln Met Phe Gln Leu Val
            470                 475                 480
Pro Val Asn Gln Tyr Val Asn Leu Thr Leu Cys Arg Gly Tyr Pro
            485                 490                 495
```

-continued

```
Leu Pro Asp Asp Ser Glu Asp Pro Val Asp Ile Val Ala Ala
            500                 505                 510
Thr Pro Val Ile Asn Gly Gln Ser Leu Thr Lys Gly Glu Thr Cys
            515                 520                 525
Met Asn Pro Gln Asp Phe Lys Pro Gly Ala Met Val Leu Glu Gln
            530                 535                 540
Asn Gly Lys Ser Gly His Thr Leu Thr Gly Asp Gly Leu Asn Gly
            545                 550                 555
Pro Ser Asp Ala Ser Glu Gln Arg Val Ser Met Ala Ser Ser Gly
            560                 565                 570
Ser Ser Gln Pro Glu Leu Val Thr Ile Pro Leu Ile Lys Gly Pro
            575                 580                 585
Lys Gly Phe Gly Phe Ala Ile Ala Asp Ser Pro Thr Gly Gln Lys
            590                 595                 600
Val Lys Met Ile Leu Asp Ser Gln Trp Cys Gln Gly Leu Gln Lys
            605                 610                 615
Gly Asp Ile Ile Lys Glu Ile Tyr His Gln Asn Val Gln Asn Leu
            620                 625                 630
Thr His Leu Gln Val Val Glu Val Leu Lys Gln Phe Pro Val Gly
            635                 640                 645
Ala Asp Val Pro Leu Leu Ile Leu Arg Gly Gly Pro Pro Ser Pro
            650                 655                 660
Thr Lys Thr Ala Lys Met Lys Thr Asp Lys Lys Glu Asn Ala Gly
            665                 670                 675
Ser Leu Glu Ala Ile Asn Glu Pro Ile Pro Gln Pro Met Pro Phe
            680                 685                 690
Pro Pro Ser Ile Ile Arg Ser Gly Ser Pro Lys Leu Asp Pro Ser
            695                 700                 705
Glu Val Tyr Leu Lys Ser Lys Thr Leu Tyr Glu Asp Lys Pro Pro
            710                 715                 720
Asn Thr Lys Asp Leu Asp Val Phe Leu Arg Lys Gln Glu Ser Gly
            725                 730                 735
Phe Gly Phe Arg Val Leu Gly Gly Asp Gly Pro Asp Gln Ser Ile
            740                 745                 750
Tyr Ile Gly Ala Ile Ile Pro Leu Gly Ala Ala Glu Lys Asp Gly
            755                 760                 765
Arg Leu Arg Ala Ala Asp Glu Leu Met Cys Ile Asp Gly Ile Pro
            770                 775                 780
Val Lys Gly Lys Ser His Lys Gln Val Leu Asp Leu Met Thr Thr
            785                 790                 795
Ala Ala Arg Asn Gly His Val Leu Leu Thr Val Arg Arg Lys Ile
            800                 805                 810
Phe Tyr Gly Glu Lys Gln Pro Glu Asp Ser Ser Gln Ala Phe
            815                 820                 825
Ile Ser Thr Gln Asn Gly Ser Pro Arg Leu Asn Arg Ala Glu Val
            830                 835                 840
Pro Ala Arg Pro Ala Pro Gln Glu Pro Tyr Asp Val Val Leu Gln
            845                 850                 855
Arg Lys Glu Asn Glu Gly Phe Gly Phe Val Ile Leu Thr Ser Lys
            860                 865                 870
Asn Lys Pro Pro Pro Gly Val Ile Pro His Lys Ile Gly Arg Val
            875                 880                 885
```

-continued

```
Ile Glu Gly Ser Pro Ala Asp Arg Cys Gly Lys Leu Lys Val Gly
            890                 895                 900

Asp His Ile Ser Ala Val Asn Gly Gln Ser Ile Val Glu Leu Ser
            905                 910                 915

His Asp Asn Ile Val Gln Leu Ile Lys Asp Ala Gly Val Thr Val
            920                 925                 930

Thr Leu Thr Val Ile Ala Glu Glu His His Gly Pro Pro Ser
            935                 940                 945

Gly Thr Asn Ser Ala Arg Gln Ser Pro Ala Leu Gln His Arg Pro
            950                 955                 960

Met Gly Gln Ser Gln Ala Asn His Ile Pro Gly Asp Arg Ser Ala
            965                 970                 975

Leu Glu Gly Glu Ile Gly Lys Asp Val Ser Thr Ser Tyr Arg His
            980                 985                 990

Ser Trp Ser Asp His Lys His Leu Ala Gln Pro Asp Thr Ala Val
            995                1000                1005

Ile Ser Val Val Gly Ser Arg His Asn Gln Asn Leu Gly Cys Tyr
           1010                1015                1020

Pro Val Glu Leu Glu Arg Gly Pro Arg Gly Phe Gly Phe Ser Leu
           1025                1030                1035

Arg Gly Gly Lys Glu Tyr Asn Met Gly Leu Phe Ile Leu Arg Leu
           1040                1045                1050

Ala Glu Asp Gly Pro Ala Ile Lys Asp Gly Arg Ile His Val Gly
           1055                1060                1065

Asp Gln Ile Val Glu Ile Asn Gly Glu Pro Thr Gln Gly Ile Thr
           1070                1075                1080

His Thr Arg Ala Ile Glu Leu Ile Gln Ala Gly Gly Asn Lys Val
           1085                1090                1095

Leu Leu Leu Leu Arg Pro Gly Thr Gly Leu Ile Pro Asp His Gly
           1100                1105                1110

Leu Ala Pro Ser Gly Leu Cys Ser Tyr Val Lys Pro Glu Gln His
           1115                1120                1125

<210> SEQ ID NO 4
<211> LENGTH: 500
<212> TYPE: PRT
<213> ORGANISM: Homo sapiens
<220> FEATURE:
<221> NAME/KEY: misc_feature
<223> OTHER INFORMATION: Incyte ID No: 55053189CD1

<400> SEQUENCE: 4

Met Cys Thr Val Val Asp Pro Arg Ile Val Arg Arg Tyr Leu Leu
 1               5                  10                  15

Arg Arg Gln Leu Gly Gln Gly Ala Tyr Gly Ile Val Trp Lys Ala
            20                  25                  30

Val Asp Arg Arg Thr Gly Glu Val Val Ala Ile Lys Lys Ile Phe
            35                  40                  45

Asp Ala Phe Arg Asp Lys Thr Asp Ala Gln Arg Thr Phe Arg Glu
            50                  55                  60

Ile Thr Leu Leu Gln Glu Phe Gly Asp His Pro Asn Ile Ile Ser
            65                  70                  75

Leu Leu Asp Val Ile Arg Ala Glu Asn Asp Arg Asp Ile Tyr Leu
            80                  85                  90

Val Phe Glu Phe Met Asp Thr Asp Leu Asn Ala Val Ile Arg Lys
            95                 100                 105
```

```
Gly Gly Leu Leu Gln Asp Val His Val Arg Ser Ile Phe Tyr Gln
            110                 115                 120

Leu Leu Arg Ala Thr Arg Phe Leu His Ser Gly His Val His
            125                 130                 135

Arg Asp Gln Lys Pro Ser Asn Val Leu Leu Asp Ala Asn Cys Thr
            140                 145                 150

Val Lys Leu Cys Asp Phe Gly Leu Ala Arg Ser Leu Gly Asp Leu
            155                 160                 165

Pro Glu Gly Pro Glu Asp Gln Ala Val Thr Glu Tyr Val Ala Thr
            170                 175                 180

Arg Trp Tyr Arg Ala Pro Glu Val Leu Leu Ser Ser His Arg Tyr
            185                 190                 195

Thr Leu Gly Val Asp Met Trp Ser Leu Gly Cys Ile Leu Gly Glu
            200                 205                 210

Met Leu Arg Gly Arg Pro Leu Phe Pro Gly Thr Ser Thr Leu His
            215                 220                 225

Gln Leu Glu Leu Ile Leu Glu Thr Ile Pro Pro Pro Ser Glu Glu
            230                 235                 240

Asp Leu Leu Ala Leu Gly Ser Gly Cys Arg Ala Ser Val Leu His
            245                 250                 255

Gln Leu Gly Ser Arg Pro Arg Gln Thr Leu Asp Ala Leu Leu Pro
            260                 265                 270

Pro Asp Thr Ser Pro Glu Ala Leu Asp Leu Leu Arg Arg Leu Leu
            275                 280                 285

Val Phe Ala Pro Asp Lys Arg Leu Ser Ala Thr Gln Met Ile Leu
            290                 295                 300

Glu Cys Gly Gly Ser Ser Gly Thr Ser Arg Glu Lys Gly Pro Glu
            305                 310                 315

Gly Val Ser Pro Ser Gln Ala His Leu His Lys Pro Arg Ala Asp
            320                 325                 330

Pro Gln Leu Pro Ser Arg Thr Pro Val Gln Gly Pro Arg Pro Arg
            335                 340                 345

Pro Gln Ser Ser Pro Gly His Asp Pro Ala Glu His Glu Ser Pro
            350                 355                 360

Arg Ala Ala Lys Asn Val Pro Arg Gln Asn Ser Ala Pro Leu Leu
            365                 370                 375

Gln Thr Ala Leu Leu Gly Asn Gly Glu Arg Pro Pro Gly Ala Lys
            380                 385                 390

Glu Ala Pro Pro Leu Thr Leu Ser Leu Val Lys Pro Ser Gly Arg
            395                 400                 405

Gly Ala Ala Pro Ser Leu Thr Ser Gln Ala Ala Ala Gln Val Ala
            410                 415                 420

Asn Gln Ala Leu Ile Arg Gly Asp Trp Asn Arg Gly Gly Gly Val
            425                 430                 435

Arg Val Ala Ser Val Gln Gln Val Pro Pro Arg Leu Pro Pro Glu
            440                 445                 450

Ala Arg Pro Gly Arg Arg Met Phe Ser Thr Ser Ala Leu Gln Gly
            455                 460                 465

Ala Gln Gly Gly Ala Arg Ala Leu Leu Gly Gly Tyr Ser Gln Ala
            470                 475                 480

Tyr Gly Thr Val Cys His Ser Ala Leu Gly His Leu Pro Leu Leu
            485                 490                 495
```

```
Glu Gly His His Val
            500

<210> SEQ ID NO 5
<211> LENGTH: 328
<212> TYPE: PRT
<213> ORGANISM: Homo sapiens
<220> FEATURE:
<221> NAME/KEY: misc_feature
<223> OTHER INFORMATION: Incyte ID No: 7474797CD1

<400> SEQUENCE: 5

Met Gly Lys Gly Asp Val Leu Glu Ala Ala Pro Thr Thr Thr Ala
 1               5                  10                  15

Tyr His Ser Leu Met Asp Glu Tyr Gly Tyr Glu Val Gly Lys Ala
                20                  25                  30

Ile Gly His Gly Ser Tyr Gly Ser Val Tyr Glu Ala Phe Tyr Thr
                35                  40                  45

Lys Gln Lys Val Met Val Ala Val Lys Ile Ile Ser Lys Lys Lys
                50                  55                  60

Ala Ser Asp Asp Tyr Leu Asn Lys Phe Leu Pro Arg Glu Ile Gln
                65                  70                  75

Val Met Lys Val Leu Arg His Lys Tyr Leu Ile Asn Phe Tyr Arg
                80                  85                  90

Ala Ile Glu Ser Thr Ser Arg Val Tyr Ile Ile Leu Glu Leu Ala
                95                  100                 105

Gln Gly Gly Asp Val Leu Glu Trp Ile Gln Arg Tyr Gly Ala Cys
                110                 115                 120

Ser Glu Pro Leu Ala Gly Lys Trp Phe Ser Gln Leu Thr Leu Gly
                125                 130                 135

Ile Ala Tyr Leu His Ser Lys Ser Ile Val His Arg Asp Leu Lys
                140                 145                 150

Leu Glu Asn Leu Leu Leu Asp Lys Trp Glu Asn Val Lys Ile Ser
                155                 160                 165

Asp Phe Gly Phe Ala Lys Met Val Pro Ser Asn Gln Pro Val Gly
                170                 175                 180

Cys Ser Pro Ser Tyr Arg Gln Val Asn Cys Phe Ser His Leu Ser
                185                 190                 195

Gln Thr Tyr Cys Gly Ser Phe Ala Tyr Ala Cys Pro Glu Ile Leu
                200                 205                 210

Arg Gly Leu Pro Tyr Asn Pro Phe Leu Ser Asp Thr Trp Ser Met
                215                 220                 225

Gly Val Ile Leu Tyr Thr Leu Val Val Ala His Leu Pro Phe Asp
                230                 235                 240

Asp Thr Asn Leu Lys Lys Leu Arg Glu Thr Gln Lys Glu Val
                245                 250                 255

Thr Phe Pro Ala Asn His Thr Ile Ser Gln Glu Cys Lys Asn Leu
                260                 265                 270

Ile Leu Gln Met Val Arg Gln Ala Pro Lys Gly Ala Pro Leu Leu
                275                 280                 285

Asp Ile Ile Lys Asp Phe Trp Gly Val Lys Phe Gln Pro Glu Gln
                290                 295                 300

Pro Pro His Glu Ile Arg Leu Leu Glu Ala Met Cys Gln Leu Pro
                305                 310                 315

Asn Pro Pro Lys Gln Pro Gln Ser Leu Gln Ile Ser Pro
                320                 325
```

<210> SEQ ID NO 6
<211> LENGTH: 370
<212> TYPE: PRT
<213> ORGANISM: Homo sapiens
<220> FEATURE:
<221> NAME/KEY: misc_feature
<223> OTHER INFORMATION: Incyte ID No: 3296272CD1

<400> SEQUENCE: 6

```
Met Lys Ile Lys Asp Ala Lys Lys Pro Ser Phe Pro Trp Phe Gly
  1               5                  10                  15

Met Asp Ile Gly Gly Thr Leu Val Lys Leu Ser Tyr Phe Glu Pro
                 20                  25                  30

Ile Asp Ile Thr Ala Glu Glu Gln Glu Glu Val Glu Ser Leu
                 35                  40                  45

Lys Ser Ile Arg Lys Tyr Leu Thr Ser Asn Val Ala Tyr Gly Ser
                 50                  55                  60

Thr Gly Ile Arg Asp Val His Leu Glu Leu Lys Asp Leu Thr Leu
                 65                  70                  75

Phe Gly Arg Arg Gly Asn Leu His Phe Ile Arg Phe Pro Thr Gln
                 80                  85                  90

Asp Leu Pro Thr Phe Ile Gln Met Gly Arg Asp Lys Asn Phe Ser
                 95                 100                 105

Thr Leu Gln Thr Val Leu Cys Ala Thr Gly Gly Gly Ala Tyr Lys
                110                 115                 120

Phe Glu Lys Asp Phe Arg Thr Ile Gly Asn Leu His Leu His Lys
                125                 130                 135

Leu Asp Glu Leu Asp Cys Leu Val Lys Gly Leu Leu Tyr Ile Asp
                140                 145                 150

Ser Val Ser Phe Asn Gly Gln Ala Glu Cys Tyr Tyr Phe Ala Asn
                155                 160                 165

Ala Ser Glu Pro Glu Arg Cys Gln Lys Met Pro Phe Asn Leu Asp
                170                 175                 180

Asp Pro Tyr Pro Leu Leu Val Val Asn Ile Gly Ser Gly Val Ser
                185                 190                 195

Ile Leu Ala Val His Ser Lys Asp Asn Tyr Lys Arg Val Thr Gly
                200                 205                 210

Thr Ser Leu Gly Gly Gly Thr Tyr Thr Gly Phe Met Gln Leu Leu
                215                 220                 225

Thr Gly Cys Glu Ser Phe Glu Glu Ala Leu Glu Met Ala Ser Lys
                230                 235                 240

Gly Asp Ser Thr Gln Ala Asp Lys Leu Val Arg Asp Ile Tyr Gly
                245                 250                 255

Gly Asp Tyr Glu Arg Phe Gly Leu Pro Gly Trp Ala Val Ala Ser
                260                 265                 270

Ser Phe Gly Asn Met Ile Tyr Lys Glu Lys Arg Glu Ser Val Ser
                275                 280                 285

Lys Glu Asp Leu Ala Arg Ala Thr Leu Val Thr Ile Thr Asn Asn
                290                 295                 300

Ile Gly Ser Val Ala Arg Met Cys Ala Val Asn Glu Lys Ile Asn
                305                 310                 315

Arg Val Val Phe Val Gly Asn Phe Leu Arg Val Asn Thr Leu Ser
                320                 325                 330

Met Lys Leu Leu Ala Tyr Ala Leu Asp Tyr Trp Ser Lys Gly Gln
```

```
                      335                 340                 345
Leu Lys Ala Leu Phe Leu Glu His Glu Gly Tyr Phe Gly Ala Val
                350                 355                 360
Gly Ala Leu Leu Gly Leu Pro Asn Phe Ser
            365                 370

<210> SEQ ID NO 7
<211> LENGTH: 1369
<212> TYPE: PRT
<213> ORGANISM: Homo sapiens
<220> FEATURE:
<221> NAME/KEY: misc_feature
<223> OTHER INFORMATION: Incyte ID No: 1989319CD1

<400> SEQUENCE: 7

Met Ala Ala Ala Ala Ser Gly Ala Gly Ala Gly Ala
  1               5                  10              15

Gly Thr Gly Gly Ala Gly Pro Ala Gly Arg Leu Leu Pro Pro
              20                  25                  30

Ala Pro Gly Ser Pro Ala Ala Pro Ala Val Ser Pro Ala Ala
              35                  40                  45

Gly Gln Pro Arg Pro Ala Pro Ala Ser Arg Gly Pro Met Pro
              50                  55                  60

Ala Arg Ile Gly Tyr Tyr Glu Ile Asp Arg Thr Ile Gly Lys Gly
              65                  70                  75

Asn Phe Ala Val Val Lys Arg Ala Thr His Leu Val Thr Lys Ala
              80                  85                  90

Lys Val Ala Ile Lys Ile Ile Asp Lys Thr Gln Leu Asp Glu Glu
              95                 100                 105

Asn Leu Lys Lys Ile Phe Arg Glu Val Gln Ile Met Lys Met Leu
             110                 115                 120

Cys His Pro His Ile Ile Arg Leu Tyr Gln Val Met Glu Thr Glu
             125                 130                 135

Arg Met Ile Tyr Leu Val Thr Glu Tyr Ala Ser Gly Gly Glu Ile
             140                 145                 150

Phe Asp His Leu Val Ala His Gly Arg Met Ala Glu Lys Glu Ala
             155                 160                 165

Arg Arg Lys Phe Lys Gln Ile Val Thr Ala Val Tyr Phe Cys His
             170                 175                 180

Cys Arg Asn Ile Val His Arg Asp Leu Lys Ala Glu Asn Leu Leu
             185                 190                 195

Leu Asp Ala Asn Leu Asn Ile Lys Ile Ala Asp Phe Gly Phe Ser
             200                 205                 210

Asn Leu Phe Thr Pro Gly Gln Leu Leu Lys Thr Trp Cys Gly Ser
             215                 220                 225

Pro Pro Tyr Ala Ala Pro Glu Leu Phe Glu Gly Lys Glu Tyr Asp
             230                 235                 240

Gly Pro Lys Val Asp Ile Trp Ser Leu Gly Val Val Leu Tyr Val
             245                 250                 255

Leu Val Cys Gly Ala Leu Pro Phe Asp Gly Ser Thr Leu Gln Asn
             260                 265                 270

Leu Arg Ala Arg Val Leu Ser Gly Lys Phe Arg Ile Pro Phe Phe
             275                 280                 285

Met Ser Thr Glu Cys Glu His Leu Ile Arg His Met Leu Val Leu
             290                 295                 300
```

-continued

```
Asp Pro Asn Lys Arg Leu Ser Met Glu Gln Ile Cys Lys His Lys
            305                 310                 315
Trp Met Lys Leu Gly Asp Ala Asp Pro Asn Phe Asp Arg Leu Ile
            320                 325                 330
Ala Glu Cys Gln Gln Leu Lys Glu Glu Arg Gln Val Asp Pro Leu
            335                 340                 345
Asn Glu Asp Val Leu Leu Ala Met Glu Asp Met Gly Leu Asp Lys
            350                 355                 360
Glu Gln Thr Leu Gln Ser Leu Arg Ser Asp Ala Tyr Asp His Tyr
            365                 370                 375
Ser Ala Ile Tyr Ser Leu Leu Cys Asp Arg His Lys Arg His Lys
            380                 385                 390
Thr Leu Arg Leu Gly Ala Leu Pro Ser Met Pro Arg Ala Leu Ala
            395                 400                 405
Phe Gln Ala Pro Val Asn Ile Gln Ala Glu Gln Ala Gly Thr Ala
            410                 415                 420
Met Asn Ile Ser Val Pro Gln Val Gln Leu Ile Asn Pro Glu Asn
            425                 430                 435
Gln Ile Val Glu Pro Asp Gly Thr Leu Asn Leu Asp Ser Asp Glu
            440                 445                 450
Gly Glu Glu Pro Ser Pro Glu Ala Leu Val Arg Tyr Leu Ser Met
            455                 460                 465
Arg Arg His Thr Val Gly Val Ala Asp Pro Arg Thr Glu Val Met
            470                 475                 480
Glu Asp Leu Gln Lys Leu Leu Pro Gly Phe Pro Gly Val Asn Pro
            485                 490                 495
Gln Ala Pro Phe Leu Gln Val Ala Pro Asn Val Asn Phe Met His
            500                 505                 510
Asn Leu Leu Pro Met Gln Asn Leu Gln Pro Thr Gly Gln Leu Glu
            515                 520                 525
Tyr Lys Glu Gln Ser Leu Leu Gln Pro Pro Thr Leu Gln Leu Leu
            530                 535                 540
Asn Gly Met Gly Pro Leu Gly Arg Arg Ala Ser Asp Gly Gly Ala
            545                 550                 555
Asn Ile Gln Leu His Ala Gln Gln Leu Leu Lys Arg Pro Arg Gly
            560                 565                 570
Pro Ser Pro Leu Val Thr Met Thr Pro Ala Val Pro Ala Val Thr
            575                 580                 585
Pro Val Asp Glu Glu Ser Ser Asp Gly Glu Pro Asp Gln Glu Ala
            590                 595                 600
Val Gln Arg Tyr Leu Ala Asn Arg Ser Lys Arg His Thr Leu Ala
            605                 610                 615
Met Thr Asn Pro Thr Ala Glu Ile Pro Pro Asp Leu Gln Arg Gln
            620                 625                 630
Leu Gly Gln Gln Pro Phe Arg Ser Arg Val Trp Pro His Leu
            635                 640                 645
Val Pro Asp Gln His Arg Ser Thr Tyr Lys Asp Ser Asn Thr Leu
            650                 655                 660
His Leu Pro Thr Glu Arg Phe Ser Pro Val Arg Arg Phe Ser Asp
            665                 670                 675
Gly Ala Ala Ser Ile Gln Ala Phe Lys Ala His Leu Glu Lys Met
            680                 685                 690
Gly Asn Asn Ser Ser Ile Lys Gln Leu Gln Gln Glu Cys Glu Gln
```

```
                        695                 700                 705
Leu Gln Lys Met Tyr Gly Gly Gln Ile Asp Glu Arg Thr Leu Glu
            710                 715                 720
Lys Thr Gln Gln Gln His Met Leu Tyr Gln Gln Glu Gln His His
            725                 730                 735
Gln Ile Leu Gln Gln Gln Ile Gln Asp Ser Ile Cys Pro Pro Gln
            740                 745                 750
Pro Ser Pro Pro Leu Gln Ala Ala Cys Glu Asn Gln Pro Ala Leu
            755                 760                 765
Leu Thr His Gln Leu Gln Arg Leu Arg Ile Gln Pro Ser Ser Pro
            770                 775                 780
Pro Pro Asn His Pro Asn Asn His Leu Phe Arg Gln Pro Ser Asn
            785                 790                 795
Ser Pro Pro Pro Met Ser Ser Ala Met Ile Gln Pro His Gly Ala
            800                 805                 810
Ala Ser Ser Ser Gln Phe Gln Gly Leu Pro Ser Arg Ser Ala Ile
            815                 820                 825
Phe Gln Gln Gln Pro Glu Asn Cys Ser Ser Pro Pro Asn Val Ala
            830                 835                 840
Leu Thr Cys Leu Gly Met Gln Gln Pro Ala Gln Ser Gln Gln Val
            845                 850                 855
Thr Ile Gln Val Gln Glu Pro Val Asp Met Leu Ser Asn Met Pro
            860                 865                 870
Gly Thr Ala Ala Gly Ser Ser Gly Arg Gly Ile Ser Ile Ser Pro
            875                 880                 885
Ser Ala Gly Gln Met Gln Met Gln His Arg Thr Asn Leu Met Ala
            890                 895                 900
Thr Leu Ser Tyr Gly His Arg Pro Leu Ser Lys Gln Leu Ser Ala
            905                 910                 915
Asp Ser Ala Glu Ala His Ser Leu Asn Val Asn Arg Phe Ser Pro
            920                 925                 930
Ala Asn Tyr Asp Gln Ala His Leu His Pro His Leu Phe Ser Asp
            935                 940                 945
Gln Ser Arg Gly Ser Pro Ser Ser Tyr Ser Pro Ser Thr Gly Val
            950                 955                 960
Gly Phe Ser Pro Thr Gln Ala Leu Lys Val Pro Pro Leu Asp Gln
            965                 970                 975
Phe Pro Thr Phe Pro Pro Ser Ala His Gln Pro Pro His Tyr
            980                 985                 990
Thr Thr Ser Ala Leu Gln Gln Ala Leu Leu Ser Pro Thr Pro Pro
            995                 1000                1005
Asp Tyr Thr Arg His Gln Gln Val Pro His Ile Leu Gln Gly Leu
            1010                1015                1020
Leu Ser Pro Arg His Ser Leu Thr Gly His Ser Asp Ile Arg Leu
            1025                1030                1035
Pro Pro Thr Glu Phe Ala Gln Leu Ile Lys Arg Gln Gln Gln Gln
            1040                1045                1050
Arg Gln Gln Gln Gln Gln Gln Gln Gln Gln Glu Tyr Gln Glu
            1055                1060                1065
Leu Phe Arg His Met Asn Gln Gly Asp Ala Gly Ser Leu Ala Pro
            1070                1075                1080
Ser Leu Gly Gly Gln Ser Met Thr Glu Arg Gln Ala Leu Ser Tyr
            1085                1090                1095
```

```
Gln Asn Ala Asp Ser Tyr His His Thr Ser Pro Gln His Leu
              1100                1105                1110

Leu Gln Ile Arg Ala Gln Glu Cys Val Ser Gln Ala Ser Ser Pro
          1115                1120                1125

Thr Pro Pro His Gly Tyr Ala His Gln Pro Ala Leu Met His Ser
          1130                1135                1140

Glu Ser Met Glu Glu Asp Cys Ser Cys Glu Gly Ala Lys Asp Gly
          1145                1150                1155

Phe Gln Asp Ser Lys Ser Ser Ser Thr Leu Thr Lys Gly Cys His
          1160                1165                1170

Asp Ser Pro Leu Leu Leu Ser Thr Gly Gly Pro Gly Asp Pro Glu
          1175                1180                1185

Ser Leu Leu Gly Thr Val Ser His Ala Gln Glu Leu Gly Ile His
          1190                1195                1200

Pro Tyr Gly His Gln Pro Thr Ala Ala Phe Ser Lys Asn Lys Val
          1205                1210                1215

Pro Ser Arg Glu Pro Val Ile Gly Asn Cys Met Asp Arg Ser Ser
          1220                1225                1230

Pro Gly Gln Ala Val Glu Leu Pro Asp His Asn Gly Leu Gly Tyr
          1235                1240                1245

Pro Ala Arg Pro Ser Val His Glu His His Arg Pro Arg Ala Leu
          1250                1255                1260

Gln Arg His His Thr Ile Gln Asn Ser Asp Asp Ala Tyr Val Gln
          1265                1270                1275

Leu Asp Asn Leu Pro Gly Met Ser Leu Val Ala Gly Lys Ala Leu
          1280                1285                1290

Ser Ser Ala Arg Met Ser Asp Ala Val Leu Ser Gln Ser Ser Leu
          1295                1300                1305

Met Gly Ser Gln Gln Phe Gln Asp Gly Glu Asn Glu Glu Cys Gly
          1310                1315                1320

Ala Ser Leu Gly Gly His Glu His Pro Asp Leu Ser Asp Gly Ser
          1325                1330                1335

Gln His Leu Asn Ser Ser Cys Tyr Pro Ser Thr Cys Ile Thr Asp
          1340                1345                1350

Ile Leu Leu Ser Tyr Lys His Pro Glu Val Ser Phe Ser Met Glu
          1355                1360                1365

Gln Ala Gly Val

<210> SEQ ID NO 8
<211> LENGTH: 2429
<212> TYPE: PRT
<213> ORGANISM: Homo sapiens
<220> FEATURE:
<221> NAME/KEY: misc_feature
<223> OTHER INFORMATION: Incyte ID No: 079284CD1

<400> SEQUENCE: 8

Met Gly Met Ser Asp Pro Asn Phe Trp Thr Val Leu Ser Asn Phe
  1               5                  10                 15

Thr Leu Pro His Leu Arg Ser Gly Asn Arg Leu Arg Arg Thr Gln
              20                  25                  30

Ser Cys Arg Thr Ser Asn Arg Lys Ser Leu Ile Gly Asn Gly Gln
              35                  40                  45

Ser Pro Ala Leu Pro Arg Pro His Ser Pro Leu Ser Ala His Ala
              50                  55                  60
```

```
Gly Asn Ser Pro Gln Asp Ser Pro Arg Asn Phe Ser Pro Ser Ala
                 65                  70                  75

Ser Ala His Phe Ser Phe Ala Arg Arg Thr Asp Gly Arg Arg Trp
             80                  85                  90

Ser Leu Ala Ser Leu Pro Ser Ser Gly Tyr Gly Thr Asn Thr Pro
             95                 100                 105

Ser Ser Thr Val Ser Ser Cys Ser Ser Gln Glu Lys Leu His
            110                 115                 120

Gln Leu Pro Tyr Gln Pro Thr Pro Asp Glu Leu His Phe Leu Ser
            125                 130                 135

Lys His Phe Cys Thr Thr Glu Ser Ile Ala Thr Glu Asn Arg Cys
            140                 145                 150

Arg Asn Thr Pro Met Arg Pro Arg Ser Arg Ser Leu Ser Pro Gly
            155                 160                 165

Arg Ser Pro Ala Cys Cys Asp His Glu Ile Ile Met Met Asn His
            170                 175                 180

Val Tyr Lys Glu Arg Phe Pro Lys Ala Thr Ala Gln Met Glu Glu
            185                 190                 195

Arg Leu Lys Glu Ile Ile Thr Ser Tyr Ser Pro Asp Asn Val Leu
            200                 205                 210

Pro Leu Ala Asp Gly Val Leu Ser Phe Thr His His Gln Ile Ile
            215                 220                 225

Glu Leu Ala Arg Asp Cys Leu Asp Lys Ser His Gln Gly Leu Ile
            230                 235                 240

Thr Ser Arg Tyr Phe Leu Glu Leu Gln His Lys Leu Asp Lys Leu
            245                 250                 255

Leu Gln Glu Ala His Asp Arg Ser Glu Ser Gly Glu Leu Ala Phe
            260                 265                 270

Ile Lys Gln Leu Val Arg Lys Ile Leu Ile Val Ile Ala Arg Pro
            275                 280                 285

Ala Arg Leu Leu Glu Cys Leu Glu Phe Asp Pro Glu Glu Phe Tyr
            290                 295                 300

Tyr Leu Leu Glu Ala Ala Glu Gly His Ala Lys Glu Gly Gln Gly
            305                 310                 315

Ile Lys Thr Asp Ile Pro Arg Tyr Ile Ile Ser Gln Leu Gly Leu
            320                 325                 330

Asn Lys Asp Pro Leu Glu Glu Met Ala His Leu Gly Asn Tyr Asp
            335                 340                 345

Ser Gly Thr Ala Glu Thr Pro Glu Thr Asp Glu Ser Val Ser Ser
            350                 355                 360

Ser Asn Ala Ser Leu Lys Leu Arg Arg Lys Pro Arg Glu Ser Asp
            365                 370                 375

Phe Glu Thr Ile Lys Leu Ile Ser Asn Gly Ala Tyr Gly Ala Val
            380                 385                 390

Tyr Phe Val Arg His Lys Glu Ser Arg Gln Arg Phe Ala Met Lys
            395                 400                 405

Lys Ile Asn Lys Gln Asn Leu Ile Leu Arg Asn Gln Ile Gln Gln
            410                 415                 420

Ala Phe Val Glu Arg Asp Ile Leu Thr Phe Ala Glu Asn Pro Phe
            425                 430                 435

Val Val Ser Met Tyr Cys Ser Phe Glu Thr Arg Arg His Leu Cys
            440                 445                 450
```

-continued

```
Met Val Met Glu Tyr Val Gly Gly Asp Cys Ala Thr Leu Met
            455                 460                 465

Lys Asn Met Gly Pro Leu Pro Val Asp Met Ala Arg Met Tyr Phe
            470                 475                 480

Ala Glu Thr Val Leu Ala Leu Glu Tyr Leu His Asn Tyr Gly Ile
            485                 490                 495

Val His Arg Asp Leu Lys Pro Asp Asn Leu Leu Val Thr Ser Met
            500                 505                 510

Gly His Ile Lys Leu Thr Asp Phe Gly Leu Ser Lys Val Gly Leu
            515                 520                 525

Met Ser Met Thr Thr Asn Leu Tyr Glu Gly His Ile Glu Lys Asp
            530                 535                 540

Ala Arg Glu Phe Leu Asp Lys Gln Val Cys Gly Thr Pro Glu Tyr
            545                 550                 555

Ile Ala Pro Glu Val Ile Leu Arg Gln Gly Tyr Gly Lys Pro Val
            560                 565                 570

Asp Trp Trp Ala Met Gly Ile Ile Leu Tyr Glu Phe Leu Val Gly
            575                 580                 585

Cys Val Pro Phe Phe Gly Asp Thr Pro Glu Glu Leu Phe Gly Gln
            590                 595                 600

Val Ile Ser Asp Glu Ile Asn Trp Pro Glu Lys Asp Glu Ala Pro
            605                 610                 615

Pro Pro Asp Ala Gln Asp Leu Ile Thr Leu Leu Leu Arg Gln Asn
            620                 625                 630

Pro Leu Glu Arg Leu Gly Thr Gly Gly Ala Tyr Glu Val Lys Gln
            635                 640                 645

His Arg Phe Phe Arg Ser Leu Asp Trp Asn Ser Leu Leu Arg Gln
            650                 655                 660

Lys Ala Glu Phe Ile Pro Gln Leu Glu Ser Glu Asp Asp Thr Ser
            665                 670                 675

Tyr Phe Asp Thr Arg Ser Glu Lys Tyr His His Met Glu Thr Glu
            680                 685                 690

Glu Glu Asp Asp Thr Asn Asp Glu Asp Phe Asn Val Glu Ile Arg
            695                 700                 705

Gln Phe Ser Ser Cys Ser His Arg Phe Ser Lys Val Phe Ser Ser
            710                 715                 720

Ile Asp Arg Ile Thr Gln Asn Ser Ala Glu Glu Lys Glu Asp Ser
            725                 730                 735

Val Asp Lys Thr Lys Ser Thr Thr Leu Pro Ser Thr Glu Thr Leu
            740                 745                 750

Ser Trp Ser Ser Glu Tyr Ser Glu Met Gln Gln Leu Ser Thr Ser
            755                 760                 765

Asn Ser Ser Asp Thr Glu Ser Asn Arg His Lys Leu Ser Ser Gly
            770                 775                 780

Leu Leu Pro Lys Leu Ala Ile Ser Thr Glu Gly Glu Gln Asp Glu
            785                 790                 795

Ala Ala Ser Cys Pro Gly Asp Pro His Glu Glu Pro Gly Lys Pro
            800                 805                 810

Ala Leu Pro Pro Glu Glu Cys Ala Gln Glu Glu Pro Glu Val Thr
            815                 820                 825

Thr Pro Ala Ser Thr Ile Ser Ser Ser Thr Leu Ser Val Gly Ser
            830                 835                 840

Phe Ser Glu His Leu Asp Gln Ile Asn Gly Arg Ser Glu Cys Val
```

-continued

```
                845                 850                 855
Asp Ser Thr Asp Asn Ser Ser Lys Pro Ser Ser Glu Pro Ala Ser
            860                 865                 870
His Met Ala Arg Gln Arg Leu Glu Ser Thr Glu Lys Lys Lys Ile
            875                 880                 885
Ser Gly Lys Val Thr Lys Ser Leu Ser Ala Ser Ala Leu Ser Leu
            890                 895                 900
Met Ile Pro Gly Asp Met Phe Ala Val Ser Pro Leu Gly Ser Pro
            905                 910                 915
Met Ser Pro His Ser Leu Ser Ser Asp Pro Ser Ser Ser Arg Asp
            920                 925                 930
Ser Ser Pro Ser Arg Asp Ser Ser Ala Ala Ser Ala Ser Pro His
            935                 940                 945
Gln Pro Ile Val Ile His Ser Ser Gly Lys Asn Tyr Gly Phe Thr
            950                 955                 960
Ile Arg Ala Ile Arg Val Tyr Val Gly Asp Ser Asp Ile Tyr Thr
            965                 970                 975
Val His His Ile Val Trp Asn Val Glu Glu Gly Ser Pro Ala Cys
            980                 985                 990
Gln Ala Gly Leu Lys Ala Gly Asp Leu Ile Thr Pro Ile Asn Gly
            995                 1000                1005
Glu Pro Val His Gly Leu Val His Thr Glu Val Ile Glu Leu Leu
            1010                1015                1020
Leu Lys Ser Gly Asn Lys Val Ser Ile Thr Thr Thr Pro Phe Glu
            1025                1030                1035
Asn Thr Ser Ile Lys Thr Gly Pro Ala Arg Arg Asn Ser Tyr Lys
            1040                1045                1050
Ser Arg Met Val Arg Arg Ser Lys Lys Ser Lys Lys Lys Glu Ser
            1055                1060                1065
Leu Glu Arg Arg Arg Ser Leu Phe Lys Lys Leu Ala Lys Gln Pro
            1070                1075                1080
Ser Pro Leu Leu His Thr Ser Arg Ser Phe Ser Cys Leu Asn Arg
            1085                1090                1095
Ser Leu Ser Ser Gly Glu Ser Leu Pro Gly Ser Pro Thr His Ser
            1100                1105                1110
Leu Ser Pro Arg Ser Pro Thr Pro Ser Tyr Arg Ser Thr Pro Asp
            1115                1120                1125
Phe Pro Ser Gly Thr Asn Ser Ser Gln Ser Ser Ser Pro Ser Ser
            1130                1135                1140
Ser Ala Pro Asn Ser Pro Ala Gly Ser Gly His Ile Arg Pro Ser
            1145                1150                1155
Thr Leu His Gly Leu Ala Pro Lys Leu Gly Gly Gln Arg Tyr Arg
            1160                1165                1170
Ser Gly Arg Arg Lys Ser Ala Gly Asn Ile Pro Leu Ser Pro Leu
            1175                1180                1185
Ala Arg Thr Pro Ser Pro Thr Pro Gln Pro Thr Ser Pro Gln Arg
            1190                1195                1200
Ser Pro Ser Pro Leu Leu Gly His Ser Leu Gly Asn Ser Lys Ile
            1205                1210                1215
Ala Gln Ala Phe Pro Ser Lys Met His Ser Pro Pro Thr Ile Val
            1220                1225                1230
Arg His Ile Val Arg Pro Lys Ser Ala Glu Pro Pro Arg Ser Pro
            1235                1240                1245
```

-continued

```
Leu Leu Lys Arg Val Gln Ser Glu Glu Lys Leu Ser Pro Ser Tyr
            1250                1255                1260

Gly Ser Asp Lys Lys His Leu Cys Ser Arg Lys His Ser Leu Glu
        1265                1270                1275

Val Thr Gln Glu Glu Val Gln Arg Glu Gln Ser Gln Arg Glu Ala
            1280                1285                1290

Pro Leu Gln Ser Leu Asp Glu Asn Val Cys Asp Val Pro Pro Leu
        1295                1300                1305

Ser Arg Ala Arg Pro Val Glu Gln Gly Cys Leu Lys Arg Pro Val
        1310                1315                1320

Ser Arg Lys Val Gly Arg Gln Glu Ser Val Asp Asp Leu Asp Arg
        1325                1330                1335

Asp Lys Leu Lys Ala Lys Val Val Lys Lys Ala Asp Gly Phe
        1340                1345                1350

Pro Glu Lys Gln Glu Ser His Gln Lys Ser His Gly Pro Gly Ser
        1355                1360                1365

Asp Leu Glu Asn Phe Ala Leu Phe Lys Leu Glu Glu Arg Glu Lys
        1370                1375                1380

Lys Val Tyr Pro Lys Ala Val Glu Arg Ser Ser Thr Phe Glu Asn
        1385                1390                1395

Lys Ala Ser Met Gln Glu Ala Pro Pro Leu Gly Ser Leu Leu Lys
        1400                1405                1410

Asp Ala Leu His Lys Gln Ala Ser Val Arg Ala Ser Glu Gly Ala
        1415                1420                1425

Met Ser Asp Gly Pro Val Pro Ala Glu His Arg Gln Gly Gly Gly
        1430                1435                1440

Asp Phe Arg Arg Ala Pro Ala Pro Gly Thr Leu Gln Asp Gly Leu
        1445                1450                1455

Cys His Ser Leu Asp Arg Gly Ile Ser Gly Lys Gly Glu Gly Thr
        1460                1465                1470

Glu Lys Ser Ser Gln Ala Lys Glu Leu Leu Arg Cys Glu Lys Leu
        1475                1480                1485

Asp Ser Lys Leu Ala Asn Ile Asp Tyr Leu Arg Lys Lys Met Ser
        1490                1495                1500

Leu Glu Asp Lys Glu Asp Asn Leu Cys Pro Val Leu Lys Pro Lys
        1505                1510                1515

Met Thr Ala Gly Ser His Glu Cys Leu Pro Gly Asn Pro Val Arg
        1520                1525                1530

Pro Thr Gly Gly Gln Gln Glu Pro Pro Ala Ser Glu Ser Arg
        1535                1540                1545

Ala Phe Val Ser Ser Thr His Ala Ala Gln Met Ser Ala Val Ser
        1550                1555                1560

Phe Val Pro Leu Lys Ala Leu Thr Gly Arg Val Asp Ser Gly Thr
        1565                1570                1575

Glu Lys Pro Gly Leu Val Ala Pro Glu Ser Pro Val Arg Lys Ser
        1580                1585                1590

Pro Ser Glu Tyr Lys Leu Glu Gly Arg Ser Val Ser Cys Leu Lys
        1595                1600                1605

Pro Ile Glu Gly Thr Leu Asp Ile Ala Leu Leu Ser Gly Pro Gln
        1610                1615                1620

Ala Ser Lys Thr Glu Leu Pro Ser Pro Glu Ser Ala Gln Ser Pro
        1625                1630                1635
```

-continued

Ser Pro Ser Gly Asp Val Arg Ala Ser Val Pro Val Leu Pro
            1640                1645                1650

Ser Ser Ser Gly Lys Lys Asn Asp Thr Thr Ser Ala Arg Glu Leu
            1655                1660                1665

Ser Pro Ser Ser Leu Lys Met Asn Lys Ser Tyr Leu Leu Glu Pro
            1670                1675                1680

Trp Phe Leu Pro Pro Ser Arg Gly Leu Gln Asn Ser Pro Ala Val
            1685                1690                1695

Ser Leu Pro Asp Pro Glu Phe Lys Arg Asp Arg Lys Gly Pro His
            1700                1705                1710

Pro Thr Ala Arg Ser Pro Gly Thr Val Met Glu Ser Asn Pro Gln
            1715                1720                1725

Gln Arg Glu Gly Ser Ser Pro Lys His Gln Asp His Thr Thr Asp
            1730                1735                1740

Pro Lys Leu Leu Thr Cys Leu Gly Gln Asn Leu His Ser Pro Asp
            1745                1750                1755

Leu Ala Arg Pro Arg Cys Pro Leu Pro Pro Glu Ala Ser Pro Ser
            1760                1765                1770

Arg Glu Lys Pro Gly Leu Arg Glu Ser Ser Glu Arg Gly Pro Pro
            1775                1780                1785

Thr Ala Arg Ser Glu Arg Ser Ala Ala Arg Ala Asp Thr Cys Arg
            1790                1795                1800

Glu Pro Ser Met Glu Leu Cys Phe Pro Glu Thr Ala Lys Thr Ser
            1805                1810                1815

Asp Asn Ser Lys Asn Leu Leu Ser Val Gly Arg Thr His Pro Asp
            1820                1825                1830

Phe Tyr Thr Gln Thr Gln Ala Met Glu Lys Ala Trp Ala Pro Gly
            1835                1840                1845

Gly Lys Thr Asn His Lys Asp Gly Pro Gly Glu Ala Arg Pro Pro
            1850                1855                1860

Pro Arg Asp Asn Ser Ser Leu His Ser Ala Gly Ile Pro Cys Glu
            1865                1870                1875

Lys Glu Leu Gly Lys Val Arg Arg Gly Val Glu Pro Lys Pro Glu
            1880                1885                1890

Ala Leu Leu Ala Arg Arg Ser Leu Gln Pro Pro Gly Ile Glu Ser
            1895                1900                1905

Glu Lys Ser Glu Lys Leu Ser Ser Phe Pro Ser Leu Gln Lys Asp
            1910                1915                1920

Gly Ala Lys Glu Pro Glu Arg Lys Glu Gln Pro Leu Gln Arg His
            1925                1930                1935

Pro Ser Ser Ile Pro Pro Pro Leu Thr Ala Lys Asp Leu Ser
            1940                1945                1950

Ser Pro Ala Ala Arg Gln His Cys Ser Ser Pro Ser His Ala Ser
            1955                1960                1965

Gly Arg Glu Pro Gly Ala Lys Pro Ser Thr Ala Glu Pro Ser Ser
            1970                1975                1980

Ser Pro Gln Asp Pro Lys Pro Val Ala Ala His Ser Glu Ser
            1985                1990                1995

Ser Ser His Lys Pro Arg Pro Gly Pro Asp Pro Gly Pro Pro Lys
            2000                2005                2010

Thr Lys His Pro Asp Arg Ser Leu Ser Ser Gln Lys Pro Ser Val
            2015                2020                2025

Gly Ala Thr Lys Gly Lys Glu Pro Ala Thr Gln Ser Leu Gly Gly

-continued

```
                2030                2035                2040
Ser Ser Arg Glu Gly Lys Gly His Ser Lys Ser Gly Pro Asp Val
                2045                2050                2055
Phe Pro Ala Thr Pro Gly Ser Gln Asn Lys Ala Ser Asp Gly Ile
                2060                2065                2070
Gly Gln Gly Glu Gly Gly Pro Ser Val Pro Leu His Thr Asp Arg
                2075                2080                2085
Ala Pro Leu Asp Ala Lys Pro Gln Pro Thr Ser Gly Gly Arg Pro
                2090                2095                2100
Leu Glu Val Leu Glu Lys Pro Val His Leu Pro Arg Pro Gly His
                2105                2110                2115
Pro Gly Pro Ser Glu Pro Ala Asp Gln Lys Leu Ser Ala Val Gly
                2120                2125                2130
Glu Lys Gln Thr Leu Ser Pro Lys His Pro Lys Pro Ser Thr Val
                2135                2140                2145
Lys Asp Cys Pro Thr Leu Cys Lys Gln Thr Asp Asn Arg Gln Thr
                2150                2155                2160
Asp Lys Ser Pro Ser Gln Pro Ala Ala Asn Thr Asp Arg Arg Ala
                2165                2170                2175
Glu Gly Lys Lys Cys Thr Glu Ala Leu Tyr Ala Pro Ala Glu Gly
                2180                2185                2190
Asp Lys Leu Glu Ala Gly Leu Ser Phe Val His Ser Glu Asn Arg
                2195                2200                2205
Leu Lys Gly Ala Glu Arg Pro Ala Gly Val Gly Lys Gly Phe
                2210                2215                2220
Pro Glu Ala Arg Gly Lys Gly Pro Gly Pro Gln Lys Pro Pro Thr
                2225                2230                2235
Glu Ala Asp Lys Pro Asn Gly Met Lys Arg Ser Pro Ser Ala Thr
                2240                2245                2250
Gly Gln Ser Ser Phe Arg Ser Thr Ala Leu Pro Glu Lys Ser Leu
                2255                2260                2265
Ser Cys Ser Ser Ser Phe Pro Glu Thr Arg Ala Gly Val Arg Glu
                2270                2275                2280
Ala Ser Ala Ala Ser Ser Asp Thr Ser Ser Ala Lys Ala Ala Gly
                2285                2290                2295
Gly Met Leu Glu Leu Pro Ala Pro Ser Asn Arg Asp His Arg Lys
                2300                2305                2310
Ala Gln Pro Ala Gly Glu Gly Arg Thr His Met Thr Lys Ser Asp
                2315                2320                2325
Ser Leu Pro Ser Phe Arg Val Ser Thr Leu Pro Leu Glu Ser His
                2330                2335                2340
His Pro Asp Pro Asn Thr Met Gly Gly Ala Ser His Arg Asp Arg
                2345                2350                2355
Ala Leu Ser Val Thr Ala Thr Val Gly Glu Thr Lys Gly Lys Asp
                2360                2365                2370
Pro Ala Pro Ala Gln Pro Pro Ala Arg Lys Gln Asn Val Gly
                2375                2380                2385
Arg Asp Val Thr Lys Pro Ser Pro Ala Pro Asn Thr Asp Arg Pro
                2390                2395                2400
Ile Ser Leu Ser Asn Glu Lys Asp Phe Val Val Arg Gln Arg Arg
                2405                2410                2415
Gly Lys Glu Ser Leu Arg Ser Ser Pro His Lys Lys Ala Leu
                2420                2425
```

<210> SEQ ID NO 9
<211> LENGTH: 2135
<212> TYPE: PRT
<213> ORGANISM: Homo sapiens
<220> FEATURE:
<221> NAME/KEY: misc_feature
<223> OTHER INFORMATION: Incyte ID No: 5502218CD1

<400> SEQUENCE: 9

```
Met Ser Gly Gly Ala Ala Glu Lys Gln Ser Ser Thr Pro Gly Ser
 1               5                  10                  15

Leu Phe Leu Ser Pro Pro Ala Pro Ala Pro Lys Asn Gly Ser Ser
                20                  25                  30

Ser Asp Ser Ser Val Gly Glu Lys Leu Gly Ala Ala Ala Ala Asp
                35                  40                  45

Ala Val Thr Gly Arg Thr Glu Glu Tyr Arg Arg Arg His Thr
                50                  55                  60

Met Asp Lys Asp Ser Arg Gly Ala Ala Thr Thr Thr Thr Thr
                65                  70                  75

Glu His Arg Phe Phe Arg Arg Ser Val Ile Cys Asp Ser Asn Ala
                80                  85                  90

Thr Ala Leu Glu Leu Pro Gly Leu Pro Leu Ser Leu Pro Gln Pro
                95                 100                 105

Ser Ile Pro Ala Val Pro Gln Ser Ala Pro Pro Glu Pro His
               110                 115                 120

Arg Glu Glu Thr Val Thr Ala Thr Ala Thr Ser Gln Val Ala Gln
               125                 130                 135

Gln Pro Pro Ala Ala Ala Pro Gly Glu Gln Ala Val Ala Gly
               140                 145                 150

Pro Ala Pro Ser Thr Val Pro Ser Ser Thr Lys Asp Arg Pro
               155                 160                 165

Val Ser Gln Pro Ser Leu Val Gly Ser Lys Glu Pro Pro Pro
               170                 175                 180

Ala Arg Ser Gly Ser Gly Gly Ser Ala Lys Glu Pro Gln Glu
               185                 190                 195

Glu Arg Ser Gln Gln Gln Asp Asp Ile Glu Glu Leu Glu Thr Lys
               200                 205                 210

Ala Val Gly Met Ser Asn Asp Gly Arg Phe Leu Lys Phe Asp Ile
               215                 220                 225

Glu Ile Gly Arg Gly Ser Phe Lys Thr Val Tyr Lys Gly Leu Asp
               230                 235                 240

Thr Glu Thr Thr Val Glu Val Ala Trp Cys Glu Leu Gln Asp Arg
               245                 250                 255

Lys Leu Thr Lys Ser Glu Arg Gln Arg Phe Lys Glu Glu Ala Glu
               260                 265                 270

Met Leu Lys Gly Leu Gln His Pro Asn Ile Val Arg Phe Tyr Asp
               275                 280                 285

Ser Trp Glu Ser Thr Val Lys Gly Lys Lys Cys Ile Val Leu Val
               290                 295                 300

Thr Glu Leu Met Thr Ser Gly Thr Leu Lys Thr Tyr Leu Lys Arg
               305                 310                 315

Phe Lys Val Met Lys Ile Lys Val Leu Arg Ser Trp Cys Arg Gln
               320                 325                 330

Ile Leu Lys Gly Leu Gln Phe Leu His Thr Arg Thr Pro Pro Ile
```

-continued

```
                335                 340                 345
Ile His Arg Asp Leu Lys Cys Asp Asn Ile Phe Ile Thr Gly Pro
                350                 355                 360
Thr Gly Ser Val Lys Ile Gly Asp Leu Gly Leu Ala Thr Leu Lys
                365                 370                 375
Arg Ala Ser Phe Ala Lys Ser Val Ile Gly Thr Pro Glu Phe Met
                380                 385                 390
Ala Pro Glu Met Tyr Glu Glu Lys Tyr Asp Glu Ser Val Asp Val
                395                 400                 405
Tyr Ala Phe Gly Met Cys Met Leu Glu Met Ala Thr Ser Glu Tyr
                410                 415                 420
Pro Tyr Ser Glu Cys Gln Asn Ala Ala Gln Ile Tyr Arg Arg Val
                425                 430                 435
Thr Ser Gly Val Lys Pro Ala Ser Phe Asp Lys Val Ala Ile Pro
                440                 445                 450
Glu Val Lys Glu Ile Ile Glu Gly Cys Ile Arg Gln Asn Lys Asp
                455                 460                 465
Glu Arg Tyr Ser Ile Lys Asp Leu Leu Asn His Ala Phe Phe Gln
                470                 475                 480
Glu Glu Thr Gly Val Arg Val Glu Leu Ala Glu Glu Asp Asp Gly
                485                 490                 495
Glu Lys Ile Ala Ile Lys Leu Trp Leu Arg Ile Glu Asp Ile Lys
                500                 505                 510
Lys Leu Lys Gly Lys Tyr Lys Asp Asn Glu Ala Ile Glu Phe Ser
                515                 520                 525
Phe Asp Leu Glu Arg Asp Val Pro Glu Asp Val Ala Gln Glu Met
                530                 535                 540
Val Glu Ser Gly Tyr Val Cys Glu Gly Asp His Lys Thr Met Ala
                545                 550                 555
Lys Ala Ile Lys Asp Arg Val Ser Leu Ile Lys Arg Lys Arg Glu
                560                 565                 570
Gln Arg Gln Leu Val Arg Glu Glu Gln Glu Lys Lys Lys Gln Glu
                575                 580                 585
Glu Ser Ser Leu Lys Gln Gln Val Glu Gln Ser Ser Ala Ser Gln
                590                 595                 600
Thr Gly Ile Lys Gln Leu Pro Ser Ala Ser Thr Gly Ile Pro Thr
                605                 610                 615
Ala Ser Thr Thr Ser Ala Ser Val Ser Thr Gln Val Glu Pro Glu
                620                 625                 630
Glu Pro Glu Ala Asp Gln His Gln Gln Leu Gln Tyr Gln Gln Pro
                635                 640                 645
Ser Ile Ser Val Leu Ser Asp Gly Thr Val Asp Ser Gly Gln Gly
                650                 655                 660
Ser Ser Val Phe Thr Glu Ser Arg Val Ser Ser Gln Thr Val
                665                 670                 675
Ser Tyr Gly Ser Gln His Glu Gln Ala His Ser Thr Gly Thr Val
                680                 685                 690
Pro Gly His Ile Pro Ser Thr Val Gln Ala Gln Ser Gln Pro His
                695                 700                 705
Gly Val Tyr Pro Pro Ser Ser Val Ala Gln Gly Gln Ser Gln Gly
                710                 715                 720
Gln Pro Ser Ser Ser Ser Leu Thr Gly Val Ser Ser Ser Gln Pro
                725                 730                 735
```

-continued

Ile Gln His Pro Gln Gln Gln Gly Ile Gln Thr Ala Pro Pro
                740                 745                 750

Gln Gln Thr Val Gln Tyr Ser Leu Ser Gln Thr Ser Thr Ser Ser
            755                 760                 765

Glu Ala Thr Thr Ala Gln Pro Val Ser Gln Pro Gln Ala Pro Gln
            770                 775                 780

Val Leu Pro Gln Val Ser Ala Gly Lys Gln Ser Thr Gln Gly Val
            785                 790                 795

Ser Gln Val Ala Pro Ala Glu Pro Val Ala Val Ala Gln Pro Gln
            800                 805                 810

Ala Thr Gln Pro Thr Thr Leu Ala Ser Ser Val Asp Ser Ala His
            815                 820                 825

Ser Asp Val Ala Ser Gly Met Ser Asp Gly Asn Glu Asn Val Pro
            830                 835                 840

Ser Ser Ser Gly Arg His Glu Gly Arg Thr Thr Lys Arg His Tyr
            845                 850                 855

Arg Lys Ser Val Arg Ser Arg Ser Arg His Glu Lys Thr Ser Arg
            860                 865                 870

Pro Lys Leu Arg Ile Leu Asn Val Ser Asn Lys Gly Asp Arg Val
            875                 880                 885

Val Glu Cys Gln Leu Glu Thr His Asn Arg Lys Met Val Thr Phe
            890                 895                 900

Lys Phe Asp Leu Asp Gly Asp Asn Pro Glu Glu Ile Ala Thr Ile
            905                 910                 915

Met Val Asn Asn Asp Phe Ile Leu Ala Ile Glu Arg Glu Ser Phe
            920                 925                 930

Val Asp Gln Val Arg Glu Ile Ile Glu Lys Ala Asp Glu Met Leu
            935                 940                 945

Ser Glu Asp Val Ser Val Glu Pro Glu Gly Asp Gln Gly Leu Glu
            950                 955                 960

Ser Leu Gln Gly Lys Asp Asp Tyr Gly Phe Ser Gly Ser Gln Lys
            965                 970                 975

Leu Glu Gly Glu Phe Lys Gln Pro Ile Pro Ala Ser Ser Met Pro
            980                 985                 990

Gln Gln Ile Gly Ile Pro Thr Ser Ser Leu Thr Gln Val Val His
            995                 1000                1005

Ser Ala Gly Arg Arg Phe Ile Val Ser Pro Val Pro Glu Ser Arg
            1010                1015                1020

Leu Arg Glu Ser Lys Val Phe Pro Ser Glu Ile Thr Asp Thr Val
            1025                1030                1035

Ala Ala Ser Thr Ala Gln Ser Pro Gly Met Asn Leu Ser His Ser
            1040                1045                1050

Ala Ser Ser Leu Ser Leu Gln Gln Ala Phe Ser Glu Leu Arg Arg
            1055                1060                1065

Ala Gln Met Thr Glu Gly Pro Asn Thr Ala Pro Pro Asn Phe Ser
            1070                1075                1080

His Thr Gly Pro Thr Phe Pro Val Val Pro Pro Phe Leu Ser Ser
            1085                1090                1095

Ile Ala Gly Val Pro Thr Thr Ala Ala Ala Thr Ala Pro Val Pro
            1100                1105                1110

Ala Thr Ser Ser Pro Pro Asn Asp Ile Ser Thr Ser Val Ile Gln
            1115                1120                1125

```
Ser Glu Val Thr Val Pro Thr Glu Glu Gly Ile Ala Gly Val Ala
            1130                1135                1140

Thr Ser Thr Gly Val Val Thr Ser Gly Gly Leu Pro Ile Pro Pro
            1145                1150                1155

Val Ser Glu Ser Pro Val Leu Ser Ser Val Ser Ser Ile Thr
            1160                1165                1170

Ile Pro Ala Val Val Ser Ile Ser Thr Thr Ser Pro Ser Leu Gln
            1175                1180                1185

Val Pro Thr Ser Thr Ser Glu Ile Val Val Ser Ser Thr Ala Leu
            1190                1195                1200

Tyr Pro Ser Val Thr Val Ser Ala Thr Ser Ala Ser Ala Gly Gly
            1205                1210                1215

Ser Thr Ala Thr Pro Gly Pro Lys Pro Pro Ala Val Val Ser Gln
            1220                1225                1230

Gln Ala Ala Gly Ser Thr Thr Val Gly Ala Thr Leu Thr Ser Val
            1235                1240                1245

Ser Thr Thr Thr Ser Phe Pro Ser Thr Ala Ser Gln Leu Ser Ile
            1250                1255                1260

Gln Leu Ser Ser Ser Thr Ser Thr Pro Thr Leu Ala Glu Thr Val
            1265                1270                1275

Val Val Ser Ala His Ser Leu Asp Lys Thr Ser His Ser Ser Thr
            1280                1285                1290

Thr Gly Leu Ala Phe Ser Leu Ser Ala Pro Ser Ser Ser Ser Ser
            1295                1300                1305

Pro Gly Ala Gly Val Ser Ser Tyr Ile Ser Gln Pro Gly Gly Leu
            1310                1315                1320

His Pro Leu Val Ile Pro Ser Val Ile Ala Ser Thr Pro Ile Leu
            1325                1330                1335

Pro Gln Ala Ala Gly Pro Thr Ser Thr Pro Leu Leu Pro Gln Val
            1340                1345                1350

Pro Ser Ile Pro Pro Leu Val Gln Pro Val Ala Asn Val Pro Ala
            1355                1360                1365

Val Gln Gln Thr Leu Ile His Ser Gln Pro Gln Pro Ala Leu Leu
            1370                1375                1380

Pro Asn Gln Pro His Thr His Cys Pro Glu Val Asp Ser Asp Thr
            1385                1390                1395

Gln Pro Lys Ala Pro Gly Ile Asp Asp Ile Lys Thr Leu Glu Glu
            1400                1405                1410

Lys Leu Arg Ser Leu Phe Ser Glu His Ser Ser Ser Gly Ala Gln
            1415                1420                1425

His Ala Ser Val Ser Leu Glu Thr Ser Leu Val Ile Glu Ser Thr
            1430                1435                1440

Val Thr Pro Gly Ile Pro Thr Thr Ala Val Ala Pro Ser Lys Leu
            1445                1450                1455

Leu Thr Ser Thr Thr Ser Thr Cys Leu Pro Pro Thr Asn Leu Pro
            1460                1465                1470

Leu Gly Thr Val Ala Leu Pro Val Thr Pro Val Val Thr Pro Gly
            1475                1480                1485

Gln Val Ser Thr Pro Val Ser Thr Thr Ser Gly Val Lys Pro
            1490                1495                1500

Gly Thr Ala Pro Ser Lys Pro Pro Leu Thr Lys Ala Pro Val Leu
            1505                1510                1515

Pro Val Gly Thr Glu Leu Pro Ala Gly Thr Leu Pro Ser Glu Gln
```

-continued

```
                1520                1525                1530
Leu Pro Pro Phe Pro Gly Pro Ser Leu Thr Gln Ser Gln Gln Pro
                1535                1540                1545
Leu Glu Asp Leu Asp Ala Gln Leu Arg Arg Thr Leu Ser Pro Glu
                1550                1555                1560
Met Ile Thr Val Thr Ser Ala Val Gly Pro Val Ser Met Ala Ala
                1565                1570                1575
Pro Thr Ala Ile Thr Glu Ala Gly Thr Gln Pro Gln Lys Gly Val
                1580                1585                1590
Ser Gln Val Lys Glu Gly Pro Val Leu Ala Thr Ser Ser Gly Ala
                1595                1600                1605
Gly Val Phe Lys Met Gly Arg Phe Gln Val Ser Val Ala Ala Asp
                1610                1615                1620
Gly Ala Gln Lys Glu Gly Lys Asn Lys Ser Glu Asp Ala Lys Ser
                1625                1630                1635
Val His Phe Glu Ser Ser Thr Ser Glu Ser Ser Val Leu Ser Ser
                1640                1645                1650
Ser Ser Pro Glu Ser Thr Leu Val Lys Pro Glu Pro Asn Gly Ile
                1655                1660                1665
Thr Ile Pro Gly Ile Ser Ser Asp Val Pro Glu Ser Ala His Lys
                1670                1675                1680
Thr Thr Ala Ser Glu Ala Lys Ser Asp Thr Gly Gln Pro Thr Lys
                1685                1690                1695
Val Gly Arg Phe Gln Val Thr Thr Thr Ala Asn Lys Val Gly Arg
                1700                1705                1710
Phe Ser Val Ser Lys Thr Glu Asp Lys Ile Thr Asp Thr Lys Lys
                1715                1720                1725
Glu Gly Pro Val Ala Ser Pro Pro Phe Met Asp Leu Glu Gln Ala
                1730                1735                1740
Val Leu Pro Ala Val Ile Pro Lys Lys Glu Lys Pro Glu Leu Ser
                1745                1750                1755
Glu Pro Ser His Leu Asn Gly Pro Ser Ser Asp Pro Glu Ala Ala
                1760                1765                1770
Phe Leu Ser Arg Asp Val Asp Asp Gly Ser Gly Ser Pro His Ser
                1775                1780                1785
Pro His Gln Leu Ser Ser Lys Ser Leu Pro Ser Gln Asn Leu Ser
                1790                1795                1800
Gln Ser Leu Ser Asn Ser Phe Asn Ser Ser Tyr Met Ser Ser Asp
                1805                1810                1815
Asn Glu Ser Asp Ile Glu Asp Glu Asp Leu Lys Leu Glu Leu Arg
                1820                1825                1830
Arg Leu Arg Asp Lys His Leu Lys Glu Ile Gln Asp Leu Gln Ser
                1835                1840                1845
Arg Gln Lys His Glu Ile Glu Ser Leu Tyr Thr Lys Leu Gly Lys
                1850                1855                1860
Val Pro Pro Ala Val Ile Ile Pro Pro Ala Ala Pro Leu Ser Gly
                1865                1870                1875
Arg Arg Arg Arg Pro Thr Lys Ser Lys Gly Ser Lys Ser Ser Arg
                1880                1885                1890
Ser Ser Ser Leu Gly Asn Lys Ser Pro Gln Leu Ser Gly Asn Leu
                1895                1900                1905
Ser Gly Gln Ser Ala Ala Ser Val Leu His Pro Gln Gln Thr Leu
                1910                1915                1920
```

-continued

His Pro Pro Gly Asn Ile Pro Glu Ser Gly Gln Asn Gln Leu Leu
              1925                1930                1935

Gln Pro Leu Lys Pro Ser Pro Ser Ser Asp Asn Leu Tyr Ser Ala
              1940                1945                1950

Phe Thr Ser Asp Gly Ala Ile Ser Val Pro Ser Leu Ser Ala Pro
              1955                1960                1965

Gly Gln Gly Thr Ser Ser Thr Asn Thr Val Gly Ala Thr Val Asn
              1970                1975                1980

Ser Gln Ala Ala Gln Ala Gln Pro Pro Ala Met Thr Ser Ser Arg
              1985                1990                1995

Lys Gly Thr Phe Thr Asp Asp Leu His Lys Leu Val Asp Asn Trp
              2000                2005                2010

Ala Arg Asp Ala Met Asn Leu Ser Gly Arg Arg Gly Ser Lys Gly
              2015                2020                2025

His Met Asn Tyr Glu Gly Pro Gly Met Ala Arg Lys Phe Ser Ala
              2030                2035                2040

Pro Gly Gln Leu Cys Ile Ser Met Thr Ser Asn Leu Gly Gly Ser
              2045                2050                2055

Ala Pro Ile Ser Ala Ala Ser Ala Thr Ser Leu Gly His Phe Thr
              2060                2065                2070

Lys Ser Met Cys Pro Pro Gln Gln Tyr Gly Phe Pro Ala Thr Pro
              2075                2080                2085

Phe Gly Ala Gln Trp Ser Gly Thr Gly Gly Pro Ala Pro Gln Pro
              2090                2095                2100

Leu Gly Gln Phe Gln Pro Val Gly Thr Ala Ser Leu Gln Asn Phe
              2105                2110                2115

Asn Ile Ser Asn Leu Gln Lys Ser Ile Ser Asn Pro Pro Gly Ser
              2120                2125                2130

Asn Leu Arg Thr Thr
              2135

<210> SEQ ID NO 10
<211> LENGTH: 398
<212> TYPE: PRT
<213> ORGANISM: Homo sapiens
<220> FEATURE:
<221> NAME/KEY: misc_feature
<223> OTHER INFORMATION: Incyte ID No: 55056054CD1

<400> SEQUENCE: 10

Met Ala Ala Tyr Arg Glu Pro Pro Cys Asn Gln Tyr Thr Gly Thr
 1               5                  10                  15

Thr Thr Ala Leu Gln Lys Leu Glu Gly Phe Ala Ser Arg Leu Phe
                20                  25                  30

His Arg His Ser Lys Gly Thr Ala His Asp Gln Lys Thr Ala Leu
                35                  40                  45

Glu Asn Asp Ser Leu His Phe Ser Glu His Thr Ala Leu Trp Asp
                50                  55                  60

Arg Ser Met Lys Glu Phe Leu Ala Lys Ala Lys Glu Asp Phe Leu
 65                  70                  75

Lys Lys Trp Glu Asn Pro Thr Gln Asn Asn Ala Gly Leu Glu Asp
                80                  85                  90

Phe Glu Arg Lys Lys Thr Leu Gly Thr Gly Ser Phe Gly Arg Val
                95                  100                 105

Met Leu Val Lys His Lys Ala Thr Glu Gln Tyr Tyr Ala Met Lys

```
                        110                 115                 120

Ile Leu Asp Lys Gln Lys Val Val Lys Leu Lys Gln Ile Glu His
                125                 130                 135

Thr Leu Asn Glu Lys Arg Ile Leu Gln Ala Val Asn Phe Pro Phe
            140                 145                 150

Leu Val Arg Leu Glu Tyr Ala Phe Lys Asp Asn Ser Asn Leu Tyr
        155                 160                 165

Met Val Met Glu Tyr Val Pro Gly Gly Glu Met Phe Ser His Leu
    170                 175                 180

Arg Arg Ile Gly Arg Phe Ser Glu Pro His Ala Arg Phe Tyr Ala
185                 190                 195

Ala Gln Ile Val Leu Thr Phe Glu Tyr Leu His Ser Leu Asp Leu
                200                 205                 210

Ile Tyr Arg Asp Leu Lys Pro Glu Asn Leu Leu Ile Asp His Gln
            215                 220                 225

Gly Tyr Ile Gln Val Thr Asp Phe Gly Phe Ala Lys Arg Val Lys
        230                 235                 240

Gly Arg Thr Trp Thr Leu Cys Gly Thr Pro Glu Tyr Leu Ala Pro
    245                 250                 255

Glu Ile Ile Leu Ser Lys Gly Tyr Asn Lys Ala Val Asp Trp Trp
260                 265                 270

Ala Leu Gly Val Leu Ile Tyr Glu Met Ala Ala Gly Tyr Pro Pro
                275                 280                 285

Phe Phe Ala Asp Gln Pro Ile Gln Ile Tyr Glu Lys Ile Val Ser
            290                 295                 300

Gly Lys Val Arg Phe Pro Ser His Phe Ser Ser Asp Leu Lys Asp
        305                 310                 315

Leu Leu Arg Asn Leu Leu Gln Val Asp Leu Thr Lys Arg Phe Gly
    320                 325                 330

Asn Leu Lys Asn Gly Val Ser Asp Ile Lys Thr His Lys Trp Phe
335                 340                 345

Ala Thr Thr Asp Trp Ile Ala Ile Tyr Gln Arg Lys Val Glu Ala
                350                 355                 360

Pro Phe Ile Pro Lys Phe Arg Gly Ser Gly Asp Thr Ser Asn Phe
            365                 370                 375

Asp Asp Tyr Glu Glu Glu Asp Ile Arg Val Ser Ile Thr Glu Lys
        380                 385                 390

Cys Ala Lys Glu Phe Gly Glu Phe
    395

<210> SEQ ID NO 11
<211> LENGTH: 929
<212> TYPE: PRT
<213> ORGANISM: Homo sapiens
<220> FEATURE:
<221> NAME/KEY: misc_feature
<223> OTHER INFORMATION: Incyte ID No: 7481989CD1

<400> SEQUENCE: 11

Met Glu Gly Asp Gly Val Pro Trp Gly Ser Glu Pro Val Ser Gly
1               5                   10                  15

Pro Gly Pro Gly Gly Gly Met Ile Arg Glu Leu Cys Arg Gly
            20                  25                  30

Phe Gly Arg Tyr Arg Arg Tyr Leu Gly Arg Leu Arg Gln Asn Leu
        35                  40                  45
```

-continued

```
Arg Glu Thr Gln Lys Phe Phe Arg Asp Ile Lys Cys Ser His Asn
                 50                  55                  60

His Thr Cys Leu Ser Ser Leu Thr Gly Gly Gly Ala Glu Arg
             65                  70                  75

Gly Pro Ala Gly Asp Val Ala Glu Thr Gly Leu Gln Ala Gly Gln
             80                  85                  90

Leu Ser Cys Ile Ser Phe Pro Pro Lys Glu Glu Lys Tyr Leu Gln
             95                 100                 105

Gln Ile Val Asp Cys Leu Pro Cys Ile Leu Ile Leu Gly Gln Asp
            110                 115                 120

Cys Asn Val Lys Cys Gln Leu Leu Asn Leu Leu Leu Gly Val Gln
            125                 130                 135

Val Leu Pro Thr Thr Lys Leu Gly Ser Glu Glu Ser Cys Lys Leu
            140                 145                 150

Arg Arg Leu Arg Phe Thr Tyr Gly Thr Gln Thr Arg Val Ser Leu
            155                 160                 165

Ala Leu Pro Gly Gln Tyr Glu Leu Val His Thr Leu Val Ala His
            170                 175                 180

Gln Gly Asn Trp Glu Thr Ile Pro Glu Glu Asp Leu Glu Val Gln
            185                 190                 195

Glu Asn Asn Glu Asp Ala Ala His Val Leu Ala Glu Leu Glu Val
            200                 205                 210

Thr Met His His Ala Leu Leu Gln Glu Val Asp Val Val Ala
            215                 220                 225

Pro Cys Gln Gly Leu Arg Pro Thr Val Asp Val Leu Gly Asp Leu
            230                 235                 240

Val Asn Asp Phe Leu Pro Val Ile Thr Tyr Ala Leu His Lys Asp
            245                 250                 255

Glu Leu Ser Glu Arg Asp Glu Gln Glu Leu Gln Glu Ile Arg Lys
            260                 265                 270

Tyr Phe Ser Phe Pro Val Phe Phe Lys Val Pro Lys Leu Gly
            275                 280                 285

Ser Glu Ile Ile Asp Ser Ser Thr Arg Arg Met Glu Ser Glu Arg
            290                 295                 300

Ser Pro Leu Tyr Arg Gln Leu Ile Asp Leu Gly Tyr Leu Ser Ser
            305                 310                 315

Ser His Trp Asn Cys Gly Ala Pro Gly Gln Asp Thr Lys Ala Gln
            320                 325                 330

Ser Met Leu Val Glu Gln Ser Glu Lys Leu Arg His Leu Ser Thr
            335                 340                 345

Phe Ser His Gln Val Leu Gln Thr Arg Leu Val Asp Ala Ala Lys
            350                 355                 360

Ala Leu Asn Leu Val His Cys His Cys Leu Asp Ile Phe Ile Asn
            365                 370                 375

Gln Ala Phe Asp Met Gln Arg Asp Leu Gln Ile Thr Pro Lys Arg
            380                 385                 390

Leu Glu Tyr Thr Arg Lys Lys Glu Asn Glu Leu Tyr Glu Ser Leu
            395                 400                 405

Met Asn Ile Ala Asn Arg Lys Gln Glu Glu Met Lys Asp Met Ile
            410                 415                 420

Val Glu Thr Leu Asn Thr Met Lys Glu Glu Leu Leu Asp Asp Ala
            425                 430                 435

Thr Asn Met Glu Phe Lys Asp Val Ile Val Pro Glu Asn Gly Glu
```

-continued

```
                   440                 445                 450
Pro Val Gly Thr Arg Glu Ile Lys Cys Cys Ile Arg Gln Ile Gln
               455                 460                 465
Glu Leu Ile Ile Ser Arg Leu Asn Gln Ala Val Ala Asn Lys Leu
               470                 475                 480
Ile Ser Ser Val Asp Tyr Leu Arg Glu Ser Phe Val Gly Thr Leu
               485                 490                 495
Glu Arg Cys Leu Gln Ser Leu Glu Lys Ser Gln Asp Val Ser Val
               500                 505                 510
His Ile Thr Ser Asn Tyr Leu Lys Gln Ile Leu Asn Ala Ala Tyr
               515                 520                 525
His Val Glu Val Thr Phe His Ser Gly Ser Ser Val Thr Arg Met
               530                 535                 540
Leu Trp Glu Gln Ile Lys Gln Ile Ile Gln Arg Ile Thr Trp Val
               545                 550                 555
Ser Pro Pro Ala Ile Thr Leu Glu Trp Lys Arg Lys Val Ala Gln
               560                 565                 570
Glu Ala Ile Glu Ser Leu Ser Ala Ser Lys Leu Ala Lys Ser Ile
               575                 580                 585
Cys Ser Gln Phe Arg Thr Arg Leu Asn Ser Ser His Glu Ala Phe
               590                 595                 600
Ala Ala Ser Leu Arg Gln Leu Glu Ala Gly His Ser Gly Arg Leu
               605                 610                 615
Glu Lys Thr Glu Asp Leu Trp Leu Arg Val Arg Lys Asp His Ala
               620                 625                 630
Pro Arg Leu Ala Arg Leu Ser Leu Glu Ser Arg Ser Leu Gln Asp
               635                 640                 645
Val Leu Leu His Arg Lys Pro Lys Leu Gly Gln Glu Leu Gly Arg
               650                 655                 660
Gly Gln Tyr Gly Val Val Tyr Leu Cys Asp Asn Trp Gly Gly His
               665                 670                 675
Phe Pro Cys Ala Leu Lys Ser Val Val Pro Pro Asp Glu Lys His
               680                 685                 690
Trp Asn Asp Leu Ala Leu Glu Phe His Tyr Met Arg Ser Leu Pro
               695                 700                 705
Lys His Glu Arg Leu Val Asp Leu His Gly Ser Val Ile Asp Tyr
               710                 715                 720
Asn Tyr Gly Gly Gly Ser Ser Ile Ala Val Leu Leu Ile Met Glu
               725                 730                 735
Arg Leu His Arg Asp Leu Tyr Thr Gly Leu Lys Ala Gly Leu Thr
               740                 745                 750
Leu Glu Thr Arg Leu Gln Ile Ala Leu Asp Val Val Glu Gly Ile
               755                 760                 765
Arg Phe Leu His Ser Gln Gly Leu Val His Arg Asp Ile Lys Leu
               770                 775                 780
Lys Asn Val Leu Leu Asp Lys Gln Asn Arg Ala Lys Ile Thr Asp
               785                 790                 795
Leu Gly Phe Cys Lys Pro Glu Ala Met Met Ser Gly Ser Ile Val
               800                 805                 810
Gly Thr Pro Ile His Met Ala Pro Glu Leu Phe Thr Gly Lys Tyr
               815                 820                 825
Asp Asn Ser Val Asp Val Tyr Ala Phe Gly Ile Leu Phe Trp Tyr
               830                 835                 840
```

```
Ile Cys Ser Gly Ser Val Lys Leu Pro Glu Ala Phe Glu Arg Cys
            845                 850                 855

Ala Ser Lys Asp His Leu Trp Asn Asn Val Arg Arg Gly Ala Arg
            860                 865                 870

Pro Glu Arg Leu Pro Val Phe Asp Glu Glu Cys Trp Gln Leu Met
            875                 880                 885

Glu Ala Cys Trp Asp Gly Asp Pro Leu Lys Arg Pro Leu Leu Gly
            890                 895                 900

Ile Val Gln Pro Met Leu Gln Gly Ile Met Asn Arg Leu Cys Lys
            905                 910                 915

Ser Asn Ser Glu Gln Pro Asn Arg Gly Leu Asp Asp Ser Thr
            920                 925

<210> SEQ ID NO 12
<211> LENGTH: 1097
<212> TYPE: PRT
<213> ORGANISM: Homo sapiens
<220> FEATURE:
<221> NAME/KEY: misc_feature
<223> OTHER INFORMATION: Incyte ID No: 55052990CD1

<400> SEQUENCE: 12

Met Glu Pro Ser Arg Ala Leu Leu Gly Cys Leu Ala Ser Ala Ala
  1               5                  10                  15

Ala Ala Ala Pro Pro Gly Glu Asp Gly Ala Gly Ala Gly Ala Glu
            20                  25                  30

Glu Glu Glu Glu Glu Glu Glu Glu Ala Ala Ala Val Gly Pro
            35                  40                  45

Gly Glu Leu Gly Cys Asp Ala Pro Leu Pro Tyr Trp Thr Ala Val
            50                  55                  60

Phe Glu Tyr Glu Ala Ala Gly Glu Asp Glu Leu Thr Leu Arg Leu
            65                  70                  75

Gly Asp Val Val Glu Val Leu Ser Lys Asp Ser Gln Val Ser Gly
            80                  85                  90

Asp Glu Gly Trp Trp Thr Gly Gln Leu Asn Gln Arg Val Gly Ile
            95                 100                 105

Phe Pro Ser Asn Tyr Val Thr Pro Arg Ser Ala Phe Ser Ser Arg
           110                 115                 120

Cys Gln Pro Gly Gly Glu Asp Pro Ser Cys Tyr Pro Pro Ile Gln
           125                 130                 135

Leu Leu Glu Ile Asp Phe Ala Glu Leu Thr Leu Glu Glu Ile Ile
           140                 145                 150

Gly Ile Gly Gly Phe Gly Lys Val Tyr Arg Ala Phe Trp Ile Gly
           155                 160                 165

Asp Glu Val Ala Val Lys Ala Ala Arg His Asp Pro Asp Glu Asp
           170                 175                 180

Ile Ser Gln Thr Ile Glu Asn Val Arg Gln Glu Ala Lys Leu Phe
           185                 190                 195

Ala Met Leu Lys His Pro Asn Ile Ile Ala Leu Arg Gly Val Cys
           200                 205                 210

Leu Lys Glu Pro Asn Leu Cys Leu Val Met Glu Phe Ala Arg Gly
           215                 220                 225

Gly Pro Leu Asn Arg Val Leu Ser Gly Lys Arg Ile Pro Pro Asp
           230                 235                 240

Ile Leu Val Asn Trp Ala Val Gln Ile Ala Arg Gly Met Asn Tyr
```

```
                    245                 250                 255
Leu Leu Asp Glu Ala Ile Val Pro Ile Ile His Arg Asp Leu Lys
            260                 265                 270
Ser Ser Asn Ile Leu Ile Leu Gln Lys Val Glu Asn Gly Asp Leu
            275                 280                 285
Ser Asn Lys Ile Leu Lys Ile Thr Asp Phe Gly Leu Ala Arg Glu
            290                 295                 300
Trp His Arg Thr Thr Lys Met Ser Ala Ala Gly Thr Tyr Ala Trp
            305                 310                 315
Met Ala Pro Glu Val Ile Arg Ala Ser Met Phe Ser Lys Gly Ser
            320                 325                 330
Asp Val Trp Ser Tyr Gly Val Leu Leu Trp Glu Leu Leu Thr Gly
            335                 340                 345
Glu Val Pro Phe Arg Gly Ile Asp Gly Leu Ala Val Ala Tyr Gly
            350                 355                 360
Val Ala Met Asn Lys Leu Ala Leu Pro Ile Pro Ser Thr Cys Pro
            365                 370                 375
Glu Pro Phe Ala Lys Leu Met Glu Asp Cys Trp Asn Pro Asp Pro
            380                 385                 390
His Ser Arg Pro Ser Phe Thr Asn Ile Leu Asp Gln Leu Thr Thr
            395                 400                 405
Ile Glu Glu Ser Gly Phe Phe Glu Met Pro Lys Asp Ser Phe His
            410                 415                 420
Cys Leu Gln Asp Asn Trp Lys His Glu Ile Gln Glu Met Phe Asp
            425                 430                 435
Gln Leu Arg Ala Lys Glu Lys Glu Leu Arg Thr Trp Glu Glu Glu
            440                 445                 450
Leu Thr Arg Ala Ala Leu Gln Gln Lys Asn Gln Glu Glu Leu Leu
            455                 460                 465
Arg Arg Arg Glu Gln Glu Leu Ala Glu Arg Glu Ile Asp Ile Leu
            470                 475                 480
Glu Arg Glu Leu Asn Ile Ile Ile His Gln Leu Cys Gln Glu Lys
            485                 490                 495
Pro Arg Val Lys Lys Arg Lys Gly Lys Phe Arg Lys Ser Arg Leu
            500                 505                 510
Lys Leu Lys Asp Gly Asn Arg Ile Ser Leu Pro Ser Asp Phe Gln
            515                 520                 525
His Lys Phe Thr Val Gln Ala Ser Pro Thr Met Asp Lys Arg Lys
            530                 535                 540
Ser Leu Ile Asn Ser Arg Ser Ser Pro Ala Ser Pro Thr Ile
            545                 550                 555
Ile Pro Arg Leu Arg Ala Ile Gln Leu Thr Pro Gly Glu Ser Ser
            560                 565                 570
Lys Thr Trp Gly Arg Ser Ser Val Val Pro Lys Glu Glu Gly Glu
            575                 580                 585
Glu Glu Glu Lys Arg Ala Pro Lys Lys Lys Gly Arg Thr Trp Gly
            590                 595                 600
Pro Gly Thr Leu Gly Gln Lys Glu Leu Ala Ser Gly Asp Glu Gly
            605                 610                 615
Leu Lys Ser Leu Val Asp Gly Tyr Lys Gln Trp Ser Ser Ala
            620                 625                 630
Pro Asn Leu Val Lys Gly Pro Arg Ser Ser Pro Ala Leu Pro Gly
            635                 640                 645
```

```
Phe Thr Ser Leu Met Glu Met Glu Asp Glu Asp Ser Glu Gly Pro
            650                 655                 660

Gly Ser Gly Glu Ser Arg Leu Gln His Ser Pro Ser Gln Ser Tyr
            665                 670                 675

Leu Cys Ile Pro Phe Pro Arg Gly Glu Asp Gly Asp Gly Pro Ser
            680                 685                 690

Ser Asp Gly Ile His Glu Glu Pro Thr Pro Val Asn Ser Ala Thr
            695                 700                 705

Ser Thr Pro Gln Leu Thr Pro Thr Asn Ser Leu Lys Arg Gly Gly
            710                 715                 720

Ala His His Arg Arg Cys Glu Val Ala Leu Leu Gly Cys Gly Ala
            725                 730                 735

Val Leu Ala Ala Thr Gly Leu Gly Phe Asp Leu Leu Glu Ala Gly
            740                 745                 750

Lys Cys Gln Leu Leu Pro Leu Glu Glu Pro Glu Pro Pro Ala Arg
            755                 760                 765

Glu Glu Lys Lys Arg Arg Glu Gly Leu Phe Gln Arg Ser Ser Arg
            770                 775                 780

Pro Arg Arg Ser Thr Ser Pro Pro Ser Arg Lys Leu Phe Lys Lys
            785                 790                 795

Glu Glu Pro Met Leu Leu Leu Gly Asp Pro Ser Ala Ser Leu Thr
            800                 805                 810

Leu Leu Ser Leu Ser Ser Ile Ser Glu Cys Asn Ser Thr Arg Ser
            815                 820                 825

Leu Leu Arg Ser Asp Ser Asp Glu Ile Val Val Tyr Glu Met Pro
            830                 835                 840

Val Ser Pro Val Glu Ala Pro Pro Leu Ser Pro Cys Thr His Asn
            845                 850                 855

Pro Leu Val Asn Val Arg Val Glu Arg Phe Lys Arg Asp Pro Asn
            860                 865                 870

Gln Ser Leu Thr Pro Thr His Val Thr Leu Thr Thr Pro Ser Gln
            875                 880                 885

Pro Ser Ser His Arg Arg Thr Pro Ser Asp Gly Ala Leu Lys Pro
            890                 895                 900

Glu Thr Leu Leu Ala Ser Arg Ser Pro Ser Asn Gly Leu Ser
            905                 910                 915

Pro Ser Pro Gly Ala Gly Glu Ser Ser Ser Phe Leu Phe Pro
            920                 925                 930

Phe Phe Val Pro Pro Gln Gly Met Leu Lys Thr Pro Ser Pro Ser
            935                 940                 945

Arg Asp Pro Gly Glu Phe Pro Arg Leu Pro Asp Pro Asn Val Val
            950                 955                 960

Phe Pro Pro Thr Pro Arg Arg Trp Asn Thr Gln Gln Asp Ser Thr
            965                 970                 975

Leu Glu Arg Pro Lys Thr Leu Glu Phe Leu Pro Arg Pro Arg Pro
            980                 985                 990

Ser Ala Asn Arg Gln Arg Leu Asp Pro Trp Trp Phe Val Ser Pro
            995                 1000                1005

Ser His Ala Arg Ser Thr Ser Pro Ala Asn Ser Ser Ser Thr Glu
            1010                1015                1020

Thr Pro Ser Asn Leu Asp Ser Cys Phe Ala Ser Ser Ser Ser Thr
            1025                1030                1035
```

-continued

Val Glu Glu Arg Pro Gly Leu Pro Ala Leu Leu Pro Phe Gln Ala
               1040                1045                1050

Gly Pro Leu Pro Pro Thr Glu Arg Thr Leu Leu Asp Leu Asp Ala
               1055                1060                1065

Glu Gly Gln Ser Gln Asp Ser Thr Val Pro Leu Cys Arg Ala Glu
               1070                1075                1080

Leu Asn Thr His Arg Pro Ala Pro Tyr Glu Ile Gln Gln Glu Phe
               1085                1090                1095

Trp Ser

<210> SEQ ID NO 13
<211> LENGTH: 928
<212> TYPE: PRT
<213> ORGANISM: Homo sapiens
<220> FEATURE:
<221> NAME/KEY: misc_feature
<223> OTHER INFORMATION: Incyte ID No: 7482377CD1

<400> SEQUENCE: 13

Met Ala Val Arg Phe Gln Val Ala Asp Met Glu Glu Leu Thr Ile
 1               5                  10                  15

Trp Glu Gln His Thr Ala Thr Leu Ser Lys Asp Pro Arg Arg Gly
                20                  25                  30

Phe Gly Ile Ala Ile Ser Gly Gly Arg Asp Arg Pro Gly Gly Ser
                35                  40                  45

Met Val Val Ser Asp Val Val Pro Gly Gly Pro Ala Glu Gly Arg
                50                  55                  60

Leu Gln Thr Gly Asp His Ile Val Met Val Asn Gly Val Ser Met
                65                  70                  75

Glu Asn Ala Thr Ser Ala Phe Ala Ile Gln Ile Leu Lys Thr Cys
                80                  85                  90

Thr Lys Met Ala Asn Ile Thr Val Lys Arg Pro Arg Arg Ile His
                95                 100                 105

Leu Pro Ala Thr Lys Ala Ser Pro Ser Ser Pro Gly Arg Gln Asp
               110                 115                 120

Ser Asp Glu Asp Asp Gly Pro Gln Arg Val Glu Glu Val Asp Gln
               125                 130                 135

Gly Arg Gly Tyr Asp Gly Asp Ser Ser Gly Ser Gly Arg Ser
               140                 145                 150

Trp Asp Glu Arg Ser Arg Arg Pro Arg Pro Gly Arg Arg Gly Arg
               155                 160                 165

Ala Gly Ser His Gly Arg Arg Ser Pro Gly Gly Gly Ser Glu Ala
               170                 175                 180

Asn Gly Leu Ala Leu Val Ser Gly Phe Lys Arg Leu Pro Arg Gln
               185                 190                 195

Asp Val Gln Met Lys Pro Val Lys Ser Val Leu Val Lys Arg Arg
               200                 205                 210

Asp Ser Glu Glu Phe Gly Val Lys Leu Gly Ser Gln Ile Phe Ile
               215                 220                 225

Lys His Ile Thr Asp Ser Gly Leu Ala Ala Arg His Arg Gly Leu
               230                 235                 240

Gln Glu Gly Asp Leu Ile Leu Gln Ile Asn Gly Val Ser Ser Gln
               245                 250                 255

Asn Leu Ser Leu Asn Asp Thr Arg Arg Leu Ile Glu Lys Ser Glu
               260                 265                 270

-continued

```
Gly Lys Leu Ser Leu Leu Val Leu Arg Asp Arg Gly Gln Phe Leu
            275                 280                 285

Val Asn Ile Pro Pro Ala Val Ser Asp Ser Asp Ser Pro Leu
            290                 295                 300

Glu Asp Ile Ser Asp Leu Ala Ser Glu Leu Ser Gln Ala Pro Pro
            305                 310                 315

Ser His Ile Pro Pro Pro Arg His Ala Gln Arg Ser Pro Glu
            320                 325                 330

Ala Ser Gln Thr Asp Ser Pro Val Glu Ser Pro Arg Leu Arg Arg
            335                 340                 345

Glu Ser Ser Val Asp Ser Arg Thr Ile Ser Glu Pro Asp Glu Gln
            350                 355                 360

Arg Ser Glu Leu Pro Arg Glu Ser Ser Tyr Asp Ile Tyr Arg Val
            365                 370                 375

Pro Ser Ser Gln Ser Met Glu Asp Arg Gly Tyr Ser Pro Asp Thr
            380                 385                 390

Arg Val Val Arg Phe Leu Lys Gly Lys Ser Ile Gly Leu Arg Leu
            395                 400                 405

Ala Gly Gly Asn Asp Val Gly Ile Phe Val Ser Gly Val Gln Ala
            410                 415                 420

Gly Ser Pro Ala Asp Gly Gln Gly Ile Gln Glu Gly Asp Gln Ile
            425                 430                 435

Leu Gln Val Asn Asp Val Pro Phe Gln Asn Leu Thr Arg Glu Glu
            440                 445                 450

Ala Val Gln Phe Leu Leu Gly Leu Pro Pro Gly Glu Glu Met Glu
            455                 460                 465

Leu Val Thr Gln Arg Lys Gln Asp Ile Phe Trp Lys Met Val Gln
            470                 475                 480

Ser Arg Val Gly Asp Ser Phe Tyr Ile Arg Thr His Phe Glu Leu
            485                 490                 495

Glu Pro Ser Pro Pro Ser Gly Leu Gly Phe Thr Arg Gly Asp Val
            500                 505                 510

Phe His Val Leu Asp Thr Leu His Pro Gly Pro Gly Gln Ser His
            515                 520                 525

Ala Arg Gly Gly His Trp Leu Ala Val Arg Met Gly Arg Asp Leu
            530                 535                 540

Arg Glu Gln Glu Arg Gly Ile Ile Pro Asn Gln Ser Arg Ala Glu
            545                 550                 555

Gln Leu Ala Ser Leu Glu Ala Ala Gln Arg Ala Val Gly Val Gly
            560                 565                 570

Pro Gly Ser Ser Ala Gly Ser Asn Ala Arg Ala Glu Phe Trp Arg
            575                 580                 585

Leu Arg Gly Leu Arg Arg Gly Ala Lys Lys Thr Thr Gln Arg Ser
            590                 595                 600

Arg Glu Asp Leu Ser Ala Leu Thr Arg Gln Gly Arg Tyr Pro Pro
            605                 610                 615

Tyr Glu Arg Val Val Leu Arg Glu Ala Ser Phe Lys Arg Pro Val
            620                 625                 630

Val Ile Leu Gly Pro Val Ala Asp Ile Ala Met Gln Lys Leu Thr
            635                 640                 645

Ala Glu Met Pro Asp Gln Phe Glu Ile Ala Glu Thr Val Ser Arg
            650                 655                 660

Thr Asp Ser Pro Ser Lys Ile Ile Lys Leu Asp Thr Val Arg Val
```

-continued

```
                665                 670                 675

Ile Ala Glu Lys Asp Lys His Ala Leu Leu Asp Val Thr Pro Ser
            680                 685                 690

Ala Ile Glu Arg Leu Asn Tyr Val Gln Tyr Tyr Pro Ile Val Val
        695                 700                 705

Phe Phe Ile Pro Glu Ser Arg Pro Ala Leu Lys Ala Leu Arg Gln
    710                 715                 720

Trp Leu Ala Pro Ala Ser Arg Arg Ser Thr Arg Arg Leu Tyr Ala
725                 730                 735

Gln Ala Gln Lys Leu Arg Lys His Ser Ser His Leu Phe Thr Ala
            740                 745                 750

Thr Ile Pro Leu Asn Gly Thr Ser Asp Thr Trp Tyr Gln Glu Leu
        755                 760                 765

Lys Ala Ile Ile Arg Glu Gln Gln Thr Arg Pro Ile Trp Thr Ala
    770                 775                 780

Glu Asp Gln Leu Asp Gly Ser Leu Glu Asp Asn Leu Asp Leu Pro
785                 790                 795

His His Gly Leu Ala Asp Ser Ser Ala Asp Leu Ser Cys Asp Ser
            800                 805                 810

Arg Val Asn Ser Asp Tyr Glu Thr Asp Gly Glu Gly Gly Ala Tyr
        815                 820                 825

Thr Asp Gly Glu Gly Tyr Thr Asp Gly Glu Gly Pro Tyr Thr
    830                 835                 840

Asp Val Asp Asp Glu Pro Pro Ala Pro Ala Leu Ala Arg Ser Ser
845                 850                 855

Glu Pro Val Gln Ala Asp Glu Ser Gln Ser Pro Arg Asp Arg Gly
            860                 865                 870

Arg Ile Ser Ala His Gln Gly Ala Gln Val Asp Ser Arg His Pro
        875                 880                 885

Gln Gly Gln Trp Arg Gln Asp Ser Met Arg Thr Tyr Glu Arg Glu
    890                 895                 900

Ala Leu Lys Lys Lys Phe Met Arg Val His Asp Ala Glu Ser Ser
905                 910                 915

Asp Glu Asp Gly Tyr Asp Trp Gly Pro Ala Thr Asp Leu
            920                 925

<210> SEQ ID NO 14
<211> LENGTH: 766
<212> TYPE: PRT
<213> ORGANISM: Homo sapiens
<220> FEATURE:
<221> NAME/KEY: misc_feature
<223> OTHER INFORMATION: Incyte ID No: 7758364CD1

<400> SEQUENCE: 14

Met Ala Ser Thr Arg Ser Ile Glu Leu Glu His Phe Glu Glu Arg
 1               5                  10                  15

Asp Lys Arg Pro Arg Pro Gly Ser Arg Gly Ala Pro Ser Ser
            20                  25                  30

Ser Gly Gly Ser Ser Ser Ser Gly Pro Lys Gly Asn Gly Leu Ile
        35                  40                  45

Pro Ser Pro Ala His Ser Ala His Cys Ser Phe Tyr Arg Thr Arg
    50                  55                  60

Thr Leu Gln Ala Leu Ser Ser Glu Lys Lys Ala Lys Lys Ala Arg
65                  70                  75
```

-continued

```
Phe Tyr Arg Asn Gly Asp Arg Tyr Phe Lys Gly Leu Val Phe Ala
             80                  85                  90

Ile Ser Ser Asp Arg Phe Arg Ser Phe Asp Ala Leu Leu Ile Glu
             95                 100                 105

Leu Thr Arg Ser Leu Ser Asp Asn Val Asn Leu Pro Gln Gly Val
            110                 115                 120

Arg Thr Ile Tyr Thr Ile Asp Gly Ser Arg Lys Val Thr Ser Leu
            125                 130                 135

Asp Glu Leu Leu Glu Gly Ser Tyr Val Cys Ala Ser Asn Glu
            140                 145                 150

Pro Phe Arg Lys Val Asp Tyr Thr Lys Asn Ile Asn Pro Asn Trp
            155                 160                 165

Ser Val Asn Ile Lys Gly Gly Thr Ser Arg Ala Leu Ala Ala Ala
            170                 175                 180

Ser Ser Val Lys Ser Glu Val Lys Glu Ser Lys Asp Phe Ile Lys
            185                 190                 195

Pro Lys Leu Val Thr Val Ile Arg Ser Gly Val Lys Pro Arg Lys
            200                 205                 210

Ala Val Arg Ile Leu Leu Asn Lys Lys Thr Ala His Ser Phe Glu
            215                 220                 225

Gln Val Leu Thr Asp Ile Thr Glu Ala Ile Lys Leu Asp Ser Gly
            230                 235                 240

Val Val Lys Arg Leu Cys Thr Leu Asp Gly Lys Gln Val Thr Cys
            245                 250                 255

Leu Gln Asp Phe Phe Gly Asp Asp Val Phe Ile Ala Cys Gly
            260                 265                 270

Pro Glu Lys Phe Arg Tyr Ala Gln Asp Phe Val Leu Asp His
            275                 280                 285

Ser Glu Cys Arg Val Leu Lys Ser Ser Tyr Ser Arg Ser Ser Ala
            290                 295                 300

Val Lys Tyr Ser Gly Ser Lys Ser Pro Gly Pro Ser Arg Arg Ser
            305                 310                 315

Lys Ser Pro Ala Ser Val Asn Gly Thr Pro Ser Ser Gln Leu Ser
            320                 325                 330

Thr Pro Lys Ser Thr Lys Ser Ser Ser Ser Pro Thr Ser Pro
            335                 340                 345

Gly Ser Phe Arg Gly Leu Lys Gln Ile Ser Ala His Gly Arg Ser
            350                 355                 360

Ser Ser Asn Val Asn Gly Gly Pro Glu Leu Asp Arg Cys Ile Ser
            365                 370                 375

Pro Glu Gly Val Asn Gly Asn Arg Cys Ser Glu Ser Ser Thr Leu
            380                 385                 390

Leu Glu Lys Tyr Lys Ile Gly Lys Val Ile Gly Asp Gly Asn Phe
            395                 400                 405

Ala Val Val Lys Glu Cys Ile Asp Arg Ser Thr Gly Lys Glu Phe
            410                 415                 420

Ala Leu Lys Ile Ile Asp Lys Ala Lys Cys Cys Gly Lys Glu His
            425                 430                 435

Leu Ile Glu Asn Glu Val Ser Ile Leu Arg Arg Val Lys His Pro
            440                 445                 450

Asn Ile Ile Met Leu Val Glu Glu Met Glu Thr Ala Thr Glu Leu
            455                 460                 465

Phe Leu Val Met Glu Leu Val Lys Gly Gly Asp Leu Phe Asp Ala
```

-continued

```
            470                 475                 480
Ile Thr Ser Ser Thr Lys Tyr Thr Glu Arg Asp Gly Ser Ala Met
        485                 490                 495
Val Tyr Asn Leu Ala Asn Ala Leu Arg Tyr Leu His Gly Leu Ser
    500                 505                 510
Ile Val His Arg Asp Ile Lys Pro Glu Asn Leu Leu Val Cys Glu
515                 520                 525
Tyr Pro Asp Gly Thr Lys Ser Leu Lys Leu Gly Asp Phe Gly Leu
            530                 535                 540
Ala Thr Val Val Glu Gly Pro Leu Tyr Thr Val Cys Gly Thr Pro
        545                 550                 555
Thr Tyr Val Ala Pro Glu Ile Ile Ala Glu Thr Gly Tyr Gly Leu
    560                 565                 570
Lys Val Asp Ile Trp Ala Ala Gly Val Ile Thr Tyr Ile Leu Leu
575                 580                 585
Cys Gly Phe Pro Pro Phe Arg Ser Glu Asn Asn Leu Gln Glu Asp
            590                 595                 600
Leu Phe Asp Gln Ile Leu Ala Gly Lys Leu Glu Phe Pro Ala Pro
        605                 610                 615
Tyr Trp Asp Asn Ile Thr Asp Ser Ala Lys Glu Leu Ile Ser Gln
    620                 625                 630
Met Leu Gln Val Asn Val Glu Ala Arg Cys Thr Ala Gly Gln Ile
635                 640                 645
Leu Ser His Pro Trp Val Ser Asp Asp Ala Ser Gln Glu Asn Asn
            650                 655                 660
Met Gln Ala Glu Val Thr Gly Lys Leu Lys Gln His Phe Asn Asn
        665                 670                 675
Ala Leu Pro Lys Gln Asn Ser Thr Thr Thr Gly Val Ser Val Ile
    680                 685                 690
Met Asn Thr Ala Leu Asp Lys Glu Gly Gln Ile Phe Cys Ser Lys
695                 700                 705
His Cys Gln Asp Ser Gly Arg Pro Gly Met Glu Pro Ile Ser Pro
            710                 715                 720
Val Pro Pro Ser Val Glu Glu Ile Pro Val Pro Gly Glu Ala Val
        725                 730                 735
Pro Ala Pro Thr Pro Pro Glu Ser Pro Thr Pro His Cys Pro Pro
    740                 745                 750
Ala Ala Pro Gly Gly Glu Arg Ala Gly Thr Trp Arg Arg His Arg
755                 760                 765
Asp

<210> SEQ ID NO 15
<211> LENGTH: 447
<212> TYPE: PRT
<213> ORGANISM: Homo sapiens
<220> FEATURE:
<221> NAME/KEY: misc_feature
<223> OTHER INFORMATION: Incyte ID No: 5850001CD1

<400> SEQUENCE: 15

Met Gly Ala Gly Arg Leu Gly Ala Pro Met Glu Arg His Gly Arg
 1               5                  10                  15
Ala Ser Ala Thr Ser Val Ser Ser Ala Gly Glu Gln Ala Ala Gly
                20                  25                  30
Asp Pro Glu Gly Arg Arg Gln Glu Pro Leu Arg Arg Arg Ala Ser
```

```
                    35                  40                  45
Ser Ala Ser Val Pro Ala Val Gly Ala Ser Ala Glu Gly Thr Arg
                50                  55                  60
Arg Asp Arg Leu Gly Ser Tyr Ser Gly Pro Thr Ser Val Ser Arg
                65                  70                  75
Gln Arg Val Glu Ser Leu Arg Lys Lys Arg Pro Leu Phe Pro Trp
                80                  85                  90
Phe Gly Leu Asp Ile Gly Gly Thr Leu Val Lys Leu Val Tyr Phe
                95                 100                 105
Glu Pro Lys Asp Ile Thr Ala Glu Glu Glu Glu Val Glu
               110                 115                 120
Ser Leu Lys Ser Ile Arg Lys Tyr Leu Thr Ser Asn Val Ala Tyr
               125                 130                 135
Gly Ser Thr Gly Ile Arg Asp Val His Leu Glu Leu Lys Asp Leu
               140                 145                 150
Thr Leu Cys Gly Arg Lys Gly Asn Leu His Phe Ile Arg Phe Pro
               155                 160                 165
Thr His Asp Met Pro Ala Phe Ile Gln Met Gly Arg Asp Lys Asn
               170                 175                 180
Phe Ser Ser Leu His Thr Val Phe Cys Ala Thr Gly Gly Gly Ala
               185                 190                 195
Tyr Lys Phe Glu Gln Asp Phe Leu Thr Ile Gly Asp Leu Gln Leu
               200                 205                 210
Cys Lys Leu Asp Glu Leu Asp Cys Leu Ile Lys Gly Ile Leu Tyr
               215                 220                 225
Ile Asp Ser Val Gly Phe Asn Gly Arg Ser Gln Cys Tyr Tyr Phe
               230                 235                 240
Glu Asn Pro Ala Asp Ser Glu Lys Cys Gln Lys Leu Pro Phe Asp
               245                 250                 255
Leu Lys Asn Pro Tyr Pro Leu Leu Leu Val Asn Ile Gly Ser Gly
               260                 265                 270
Val Ser Ile Leu Ala Val Tyr Ser Lys Asp Asn Tyr Lys Arg Val
               275                 280                 285
Thr Gly Thr Ser Leu Gly Gly Thr Phe Phe Gly Leu Cys Cys
               290                 295                 300
Leu Leu Thr Gly Cys Thr Thr Phe Glu Glu Ala Leu Glu Met Ala
               305                 310                 315
Ser Arg Gly Asp Ser Thr Lys Val Asp Lys Leu Val Arg Asp Ile
               320                 325                 330
Tyr Gly Gly Asp Tyr Glu Arg Phe Gly Leu Pro Gly Trp Ala Val
               335                 340                 345
Ala Ser Ser Phe Gly Asn Met Met Ser Lys Glu Lys Arg Glu Ala
               350                 355                 360
Val Ser Lys Glu Asp Leu Ala Arg Ala Thr Leu Ile Thr Ile Thr
               365                 370                 375
Asn Asn Ile Gly Ser Ile Ala Arg Met Cys Ala Leu Asn Glu Asn
               380                 385                 390
Ile Asn Gln Val Val Phe Val Gly Asn Phe Leu Arg Ile Asn Thr
               395                 400                 405
Ile Ala Met Arg Leu Leu Ala Tyr Ala Leu Asp Tyr Trp Ser Lys
               410                 415                 420
Gly Gln Leu Lys Ala Leu Phe Ser Glu His Glu Gly Tyr Phe Gly
               425                 430                 435
```

```
Ala Val Gly Ala Leu Leu Glu Leu Leu Lys Ile Pro
                440                 445
```

<210> SEQ ID NO 16
<211> LENGTH: 348
<212> TYPE: PRT
<213> ORGANISM: Homo sapiens
<220> FEATURE:
<221> NAME/KEY: misc_feature
<223> OTHER INFORMATION: Incyte ID No: 7477062CD1

<400> SEQUENCE: 16

```
Met Pro Gly Lys Gln Ser Glu Glu Gly Pro Ala Glu Ala Gly Ala
 1               5                  10                  15

Ser Glu Asp Ser Glu Glu Gly Leu Gly Gly Leu Thr Leu Glu
                20                  25                  30

Glu Leu Gln Gln Gly Gln Glu Ala Ala Arg Ala Leu Glu Asp Met
                35                  40                  45

Met Thr Leu Ser Ala Gln Thr Leu Val Arg Ala Glu Val Asp Glu
                50                  55                  60

Leu Tyr Glu Glu Val Arg Pro Leu Gly Gln Gly Arg Tyr Gly Arg
                65                  70                  75

Val Leu Leu Val Thr His Arg Gln Lys Gly Thr Pro Leu Ala Leu
                80                  85                  90

Lys Gln Leu Pro Lys Pro Arg Thr Ser Leu Arg Gly Phe Leu Tyr
                95                  100                 105

Glu Phe Cys Val Gly Leu Ser Leu Gly Ala His Ser Ala Ile Val
                110                 115                 120

Thr Ala Tyr Gly Ile Gly Ile Glu Ser Ala His Ser Tyr Ser Phe
                125                 130                 135

Leu Thr Glu Pro Val Leu His Gly Asp Leu Met Ala Phe Ile Gln
                140                 145                 150

Pro Lys Val Gly Leu Pro Gln Pro Ala Val His Arg Cys Ala Ala
                155                 160                 165

Gln Leu Ala Ser Ala Leu Glu Tyr Ile His Ala Arg Gly Leu Val
                170                 175                 180

Tyr Arg Asp Leu Lys Pro Glu Asn Val Leu Val Cys Asp Pro Ala
                185                 190                 195

Cys Arg Arg Phe Lys Leu Thr Asp Phe Gly His Thr Arg Pro Arg
                200                 205                 210

Gly Thr Leu Leu Arg Leu Ala Gly Pro Pro Ile Pro Tyr Thr Ala
                215                 220                 225

Pro Glu Leu Cys Ala Pro Pro Leu Pro Glu Gly Leu Pro Ile
                230                 235                 240

Gln Pro Ala Leu Asp Ala Trp Ala Leu Gly Val Leu Leu Phe Cys
                245                 250                 255

Leu Leu Thr Gly Tyr Phe Pro Trp Asp Arg Pro Leu Ala Glu Ala
                260                 265                 270

Asp Pro Phe Tyr Glu Asp Phe Leu Ile Trp Gln Ala Ser Gly Gln
                275                 280                 285

Pro Arg Asp Arg Pro Gln Pro Trp Phe Gly Leu Ala Ala Ala Ala
                290                 295                 300

Asp Ala Leu Leu Arg Gly Leu Leu Asp Pro His Pro Arg Arg Arg
                305                 310                 315

Ser Ala Val Ile Ala Ile Arg Glu His Leu Gly Arg Pro Trp Arg
```

-continued

```
                320                 325                 330
Gln Arg Glu Gly Glu Ala Glu Ala Val Gly Ala Val Glu Glu Glu
                335                 340                 345

Ala Gly Gln

<210> SEQ ID NO 17
<211> LENGTH: 341
<212> TYPE: PRT
<213> ORGANISM: Homo sapiens
<220> FEATURE:
<221> NAME/KEY: misc_feature
<223> OTHER INFORMATION: Incyte ID No: 7477207CD1

<400> SEQUENCE: 17

Met Val Ser Ser Gln Pro Lys Tyr Asp Leu Ile Arg Glu Val Gly
  1               5                  10                  15

Arg Gly Ser Tyr Gly Val Val Tyr Glu Ala Val Ile Arg Lys Thr
                 20                  25                  30

Ser Ala Arg Val Ala Val Lys Lys Ile Arg Cys His Ala Pro Glu
                 35                  40                  45

Asn Val Glu Leu Ala Leu Arg Glu Phe Trp Ala Leu Ser Ser Ile
                 50                  55                  60

Lys Ser Gln His Pro Asn Val Ile His Leu Glu Glu Cys Ile Leu
 65                  70                                  75

Gln Lys Asp Gly Met Val Gln Lys Met Ser His Gly Ser Asn Ser
                 80                  85                  90

Ser Leu Tyr Leu Gln Leu Val Glu Thr Ser Leu Lys Gly Glu Ile
                 95                 100                 105

Ala Phe Asp Pro Arg Ser Ala Tyr Tyr Leu Trp Phe Val Met Asp
                110                 115                 120

Phe Cys Asp Gly Gly Asp Met Asn Glu Tyr Leu Leu Ser Arg Lys
                125                 130                 135

Pro Asn Arg Lys Thr Asn Thr Ser Phe Met Leu Gln Leu Ser Ser
                140                 145                 150

Ala Leu Ala Phe Leu His Lys Asn Gln Ile Ile His Arg Asp Leu
                155                 160                 165

Lys Pro Asp Asn Ile Leu Ile Ser Gln Thr Arg Leu Asp Thr Ser
                170                 175                 180

Asp Leu Glu Pro Thr Leu Lys Val Ala Asp Phe Gly Leu Ser Lys
                185                 190                 195

Val Cys Ser Ala Ser Gly Gln Asn Pro Glu Glu Pro Val Ser Val
                200                 205                 210

Asn Lys Cys Phe Leu Ser Thr Ala Cys Gly Thr Asp Phe Tyr Met
                215                 220                 225

Ala Pro Glu Val Trp Glu Gly His Tyr Thr Ala Lys Ala Asp Ile
                230                 235                 240

Phe Ala Leu Gly Ile Ile Ile Trp Ala Met Leu Glu Arg Ile Thr
                245                 250                 255

Phe Ile Asp Thr Glu Thr Lys Lys Glu Leu Leu Gly Ser Tyr Val
                260                 265                 270

Lys Gln Gly Thr Glu Ile Val Pro Val Gly Glu Ala Leu Leu Glu
                275                 280                 285

Asn Pro Lys Met Glu Leu Leu Ile Pro Val Lys Lys Ser Met
                290                 295                 300

Asn Gly Arg Met Lys Gln Leu Ile Lys Glu Met Leu Ala Ala Asn
```

```
                    305                 310                 315
Pro Gln Asp Arg Pro Asp Ala Phe Glu Leu Glu Leu Arg Leu Val
                320                 325                 330
Gln Ile Ala Phe Lys Asp Ser Ser Trp Glu Thr
                335                 340

<210> SEQ ID NO 18
<211> LENGTH: 664
<212> TYPE: PRT
<213> ORGANISM: Homo sapiens
<220> FEATURE:
<221> NAME/KEY: misc_feature
<223> OTHER INFORMATION: Incyte ID No: 4022651CD1

<400> SEQUENCE: 18

Met Ala Ser Ala Glu Thr Pro Gly Gln Trp Tyr Val Gly Pro Tyr
  1               5                  10                  15
Arg Leu Glu Lys Thr Leu Gly Lys Gly Gln Thr Gly Leu Val Lys
                 20                  25                  30
Leu Gly Val His Cys Val Thr Cys Gln Lys Val Ala Ile Lys Ile
                 35                  40                  45
Val Asn Arg Glu Lys Leu Ser Glu Ser Val Leu Met Lys Val Glu
                 50                  55                  60
Arg Glu Ile Ala Ile Leu Lys Leu Ile Glu His Pro His Val Leu
 65                  70                  75
Lys Leu His Asp Val Tyr Glu Asn Lys Lys Tyr Leu Tyr Leu Val
                 80                  85                  90
Leu Glu His Val Ser Gly Gly Glu Leu Phe Asp Tyr Leu Val Lys
                 95                 100                 105
Lys Gly Arg Leu Thr Pro Lys Glu Ala Arg Lys Phe Phe Arg Gln
                110                 115                 120
Ile Ile Ser Ala Leu Asp Phe Cys His Ser His Ser Ile Cys His
                125                 130                 135
Arg Asp Leu Lys Pro Glu Asn Leu Leu Leu Asp Glu Lys Asn Asn
                140                 145                 150
Ile Arg Ile Ala Asp Phe Gly Met Ala Ser Leu Gln Val Gly Asp
                155                 160                 165
Ser Leu Leu Glu Thr Ser Cys Gly Ser Pro His Tyr Ala Cys Pro
                170                 175                 180
Glu Val Ile Arg Gly Glu Lys Tyr Asp Gly Arg Lys Ala Asp Val
                185                 190                 195
Trp Ser Cys Gly Val Ile Leu Phe Ala Leu Leu Val Gly Ala Leu
                200                 205                 210
Pro Phe Asp Asp Asp Asn Leu Arg Gln Leu Leu Glu Lys Val Lys
                215                 220                 225
Arg Gly Val Phe His Met Pro His Phe Ile Pro Pro Asp Cys Gln
                230                 235                 240
Ser Leu Leu Arg Gly Met Ile Glu Val Asp Ala Ala Arg Arg Leu
                245                 250                 255
Thr Leu Glu His Ile Gln Lys His Ile Trp Tyr Ile Gly Gly Lys
                260                 265                 270
Asn Glu Pro Glu Pro Glu Gln Pro Ile Pro Arg Lys Val Gln Ile
                275                 280                 285
Arg Ser Leu Pro Ser Leu Glu Asp Ile Asp Pro Asp Val Leu Asp
                290                 295                 300
```

-continued

```
Ser Met His Ser Leu Gly Cys Phe Arg Asp Arg Asn Lys Leu Leu
            305                 310                 315

Gln Asp Leu Leu Ser Glu Glu Asn Gln Glu Lys Met Ile Tyr
            320                 325                 330

Phe Leu Leu Leu Asp Arg Lys Glu Arg Tyr Pro Ser Gln Glu Asp
            335                 340                 345

Glu Asp Leu Pro Pro Arg Asn Glu Ile Asp Pro Pro Arg Lys Arg
            350                 355                 360

Val Asp Ser Pro Met Leu Asn Arg His Gly Lys Arg Pro Glu
            365                 370                 375

Arg Lys Ser Met Glu Val Leu Ser Val Thr Asp Gly Gly Ser Pro
            380                 385                 390

Val Pro Ala Arg Arg Ala Ile Glu Met Ala Gln His Gly Gln Arg
            395                 400                 405

Ser Arg Ser Ile Ser Gly Ala Ser Ser Gly Leu Ser Thr Ser Pro
            410                 415                 420

Leu Ser Ser Pro Arg Val Thr Pro His Pro Ser Pro Arg Gly Ser
            425                 430                 435

Pro Leu Pro Thr Pro Lys Gly Thr Pro Val His Thr Pro Lys Glu
            440                 445                 450

Ser Pro Ala Gly Thr Pro Asn Pro Thr Pro Pro Ser Ser Pro Ser
            455                 460                 465

Val Gly Gly Val Pro Trp Arg Ala Arg Leu Asn Ser Ile Lys Asn
            470                 475                 480

Ser Phe Leu Gly Ser Pro Arg Phe His Arg Arg Lys Leu Gln Val
            485                 490                 495

Pro Thr Pro Glu Glu Met Ser Asn Leu Thr Pro Glu Ser Ser Pro
            500                 505                 510

Glu Leu Ala Lys Lys Ser Trp Phe Gly Asn Phe Ile Ser Leu Glu
            515                 520                 525

Lys Glu Glu Gln Ile Phe Val Val Ile Lys Asp Lys Pro Leu Ser
            530                 535                 540

Ser Ile Lys Ala Asp Ile Val His Ala Phe Leu Ser Ile Pro Ser
            545                 550                 555

Leu Ser His Ser Val Ile Ser Gln Thr Ser Phe Arg Ala Glu Tyr
            560                 565                 570

Lys Ala Thr Gly Gly Pro Ala Val Phe Gln Lys Pro Val Lys Phe
            575                 580                 585

Gln Val Asp Ile Thr Tyr Thr Glu Gly Gly Glu Ala Gln Lys Glu
            590                 595                 600

Asn Gly Ile Tyr Ser Val Thr Phe Thr Leu Leu Ser Gly Pro Ser
            605                 610                 615

Arg Arg Phe Lys Arg Val Val Glu Thr Ile Gln Ala Gln Leu Leu
            620                 625                 630

Ser Thr His Asp Pro Pro Ala Ala Gln His Leu Ser Asp Thr Thr
            635                 640                 645

Asn Cys Met Glu Met Met Thr Gly Arg Leu Ser Lys Cys Gly Ile
            650                 655                 660

Ile Pro Lys Ser

<210> SEQ ID NO 19
<211> LENGTH: 177
<212> TYPE: PRT
<213> ORGANISM: Homo sapiens
```

-continued

```
<220> FEATURE:
<221> NAME/KEY: misc_feature
<223> OTHER INFORMATION: Incyte ID No: 7274927CD1

<400> SEQUENCE: 19

Met Val Leu Leu Ser Thr Leu Gly Ile Val Phe Gln Gly Glu Gly
  1               5                  10                  15

Pro Pro Ile Ser Ser Cys Asp Thr Gly Thr Met Ala Asn Cys Glu
                 20                  25                  30

Arg Thr Phe Ile Ala Ile Lys Pro Asp Gly Val Gln Arg Gly Leu
                 35                  40                  45

Val Gly Glu Ile Ile Lys Arg Phe Glu Gln Lys Gly Phe Arg Leu
             50                  55                  60

Val Gly Leu Lys Phe Met Gln Ala Ser Glu Asp Leu Leu Lys Glu
         65                  70                  75

His Tyr Val Asp Leu Lys Asp Arg Pro Phe Phe Ala Gly Leu Val
             80                  85                  90

Lys Tyr Met His Ser Gly Pro Val Val Ala Met Val Trp Glu Gly
                 95                 100                 105

Leu Asn Val Val Lys Thr Gly Arg Val Met Leu Gly Glu Thr Asn
                110                 115                 120

Pro Ala Asp Ser Lys Pro Gly Thr Ile Arg Gly Asp Phe Cys Ile
                125                 130                 135

Gln Val Gly Arg Asn Ile Ile His Gly Ser Asp Ser Val Glu Ser
                140                 145                 150

Ala Glu Lys Glu Ile Gly Leu Trp Phe His Pro Glu Glu Leu Val
                155                 160                 165

Asp Tyr Thr Ser Cys Ala Gln Asn Trp Ile Tyr Glu
                170                 175

<210> SEQ ID NO 20
<211> LENGTH: 396
<212> TYPE: PRT
<213> ORGANISM: Homo sapiens
<220> FEATURE:
<221> NAME/KEY: misc_feature
<223> OTHER INFORMATION: Incyte ID No: 7946584CD1

<400> SEQUENCE: 20

Met Gly Ala Asn Thr Ser Arg Lys Pro Pro Val Phe Asp Glu Asn
  1               5                  10                  15

Glu Asp Val Asn Phe Asp His Phe Glu Ile Leu Arg Ala Ile Gly
                 20                  25                  30

Lys Gly Ser Phe Gly Lys Val Cys Ile Val Gln Lys Asn Asp Thr
                 35                  40                  45

Lys Lys Met Tyr Ala Met Lys Tyr Met Asn Lys Gln Lys Cys Val
             50                  55                  60

Glu Arg Asn Glu Val Arg Asn Val Phe Lys Glu Leu Gln Ile Met
             65                  70                  75

Gln Gly Leu Glu His Pro Phe Leu Val Asn Leu Trp Tyr Ser Phe
             80                  85                  90

Gln Asp Glu Glu Asp Met Phe Met Val Val Asp Leu Leu Leu Gly
                 95                 100                 105

Gly Asp Leu Arg Tyr His Leu Gln Gln Asn Val His Phe Lys Glu
                110                 115                 120

Glu Thr Val Lys Leu Phe Ile Cys Glu Leu Val Met Ala Leu Asp
                125                 130                 135
```

-continued

```
Tyr Leu Gln Asn Gln Arg Ile Ile His Arg Asp Met Lys Pro Asp
            140                 145                 150

Asn Ile Leu Leu Asp Glu His Gly His Val His Ile Thr Asp Phe
            155                 160                 165

Asn Ile Ala Ala Met Leu Pro Arg Glu Thr Gln Ile Thr Thr Met
            170                 175                 180

Ala Gly Thr Lys Pro Tyr Met Ala Pro Glu Met Phe Ser Ser Arg
            185                 190                 195

Lys Gly Ala Gly Tyr Ser Phe Ala Val Asp Trp Trp Ser Leu Gly
            200                 205                 210

Val Thr Ala Tyr Glu Leu Leu Arg Gly Arg Arg Pro Tyr His Ile
            215                 220                 225

Arg Ser Ser Thr Ser Ser Lys Glu Ile Val His Thr Phe Glu Thr
            230                 235                 240

Thr Val Val Thr Tyr Pro Ser Ala Trp Ser Gln Glu Met Val Ser
            245                 250                 255

Leu Leu Lys Lys Leu Leu Glu Pro Asn Pro Asp Gln Arg Phe Ser
            260                 265                 270

Gln Leu Ser Asp Val Gln Asn Phe Pro Tyr Met Asn Asp Ile Asn
            275                 280                 285

Trp Asp Ala Val Phe Gln Lys Arg Leu Ile Pro Gly Phe Ile Pro
            290                 295                 300

Asn Lys Gly Arg Leu Asn Cys Asp Pro Thr Phe Glu Leu Glu Glu
            305                 310                 315

Met Ile Leu Glu Ser Lys Pro Leu His Lys Lys Lys Arg Leu
            320                 325                 330

Ala Lys Lys Glu Lys Asp Met Arg Lys Cys Asp Ser Ser Gln Thr
            335                 340                 345

Cys Leu Leu Gln Glu His Leu Asp Ser Val Gln Lys Glu Phe Ile
            350                 355                 360

Ile Phe Asn Arg Glu Lys Val Asn Arg Asp Phe Asn Lys Arg Gln
            365                 370                 375

Pro Asn Leu Ala Leu Glu Gln Thr Lys Asp Pro Gln Gly Glu Asp
            380                 385                 390

Gly Gln Asn Asn Asn Leu
            395

<210> SEQ ID NO 21
<211> LENGTH: 614
<212> TYPE: PRT
<213> ORGANISM: Homo sapiens
<220> FEATURE:
<221> NAME/KEY: misc_feature
<223> OTHER INFORMATION: Incyte ID No: 8088078CD1

<400> SEQUENCE: 21

Met Glu Trp Leu Ser Pro Asp Ile Ala Leu Pro Arg Arg Asp Glu
  1               5                  10                  15

Trp Thr Gln Thr Ser Pro Ala Arg Lys Arg Ile Thr His Ala Lys
             20                  25                  30

Val Gln Gly Ala Gly Lys Ser Ile Gly Gln Leu Arg Leu Ser Ile
             35                  40                  45

Asp Ala Gln Asp Arg Val Leu Leu His Ile Ile Glu Gly Lys
             50                  55                  60

Gly Leu Ile Ser Lys Gln Pro Gly Thr Cys Asp Pro Tyr Val Lys
```

-continued

```
                65                  70                  75
Ile Ser Leu Ile Pro Glu Asp Ser Arg Leu Arg His Gln Lys Thr
                80                  85                  90
Gln Thr Val Pro Asp Cys Arg Asp Pro Ala Phe His Glu His Phe
                95                 100                 105
Phe Phe Pro Val Gln Glu Asp Asp Gln Lys Arg Leu Leu Val
               110                 115                 120
Thr Val Trp Asn Arg Ala Ser Gln Ser Arg Gln Ser Gly Leu Ile
               125                 130                 135
Gly Cys Met Ser Phe Gly Val Lys Ser Leu Leu Thr Pro Asp Lys
               140                 145                 150
Glu Ile Ser Gly Trp Tyr Tyr Leu Leu Gly Glu His Leu Gly Arg
               155                 160                 165
Thr Lys His Leu Lys Val Ala Arg Arg Leu Arg Pro Leu Arg
               170                 175                 180
Asp Pro Leu Leu Arg Met Pro Gly Gly Asp Thr Glu Asn Gly
               185                 190                 195
Lys Lys Leu Gln Ile Thr Ile Pro Arg Gly Lys Asp Gly Phe Gly
               200                 205                 210
Phe Thr Ile Cys Cys Asp Ser Pro Val Arg Val Gln Ala Val Asp
               215                 220                 225
Ser Gly Gly Pro Ala Glu Arg Ala Gly Leu Gln Gln Leu Asp Thr
               230                 235                 240
Val Leu Gln Leu Asn Glu Arg Pro Val Glu His Trp Lys Cys Val
               245                 250                 255
Glu Leu Ala His Glu Ile Arg Ser Cys Pro Ser Glu Ile Ile Leu
               260                 265                 270
Leu Val Trp Arg Met Val Pro Gln Val Lys Pro Gly Pro Asp Gly
               275                 280                 285
Gly Val Leu Arg Arg Ala Ser Cys Lys Ser Thr His Asp Leu Gln
               290                 295                 300
Ser Pro Pro Asn Lys Arg Glu Lys Asn Cys Thr His Gly Val Gln
               305                 310                 315
Ala Arg Pro Glu Gln Arg His Ser Cys His Leu Val Cys Asp Ser
               320                 325                 330
Ser Asp Gly Leu Leu Leu Gly Gly Trp Glu Arg Tyr Thr Glu Val
               335                 340                 345
Ala Lys Arg Gly Gly Gln His Thr Leu Pro Ala Leu Ser Arg Ala
               350                 355                 360
Thr Ala Pro Thr Asp Pro Asn Tyr Ile Ile Leu Ala Pro Leu Asn
               365                 370                 375
Pro Gly Ser Gln Leu Leu Arg Pro Val Tyr Gln Glu Asp Thr Ile
               380                 385                 390
Pro Glu Glu Ser Gly Ser Pro Ser Lys Gly Lys Ser Tyr Thr Gly
               395                 400                 405
Leu Gly Lys Lys Ser Arg Leu Met Lys Thr Val Gln Thr Met Lys
               410                 415                 420
Gly His Gly Asn Tyr Gln Asn Cys Pro Val Val Arg Pro His Ala
               425                 430                 435
Thr His Ser Ser Tyr Gly Thr Tyr Val Thr Leu Ala Pro Lys Val
               440                 445                 450
Leu Val Phe Pro Val Phe Val Gln Pro Leu Asp Leu Cys Asn Pro
               455                 460                 465
```

-continued

```
Ala Arg Thr Leu Leu Leu Ser Glu Glu Leu Leu Tyr Glu Gly
                470                 475                 480

Arg Asn Lys Ala Ala Glu Val Thr Leu Phe Ala Tyr Ser Asp Leu
            485                 490                 495

Leu Leu Phe Thr Lys Glu Asp Glu Pro Gly Arg Cys Asp Val Leu
        500                 505                 510

Arg Asn Pro Leu Tyr Leu Gln Ser Val Lys Leu Gln Glu Gly Ser
    515                 520                 525

Ser Glu Asp Leu Lys Phe Cys Val Leu Tyr Leu Ala Glu Lys Ala
530                 535                 540

Glu Cys Leu Phe Thr Leu Glu Ala His Ser Gln Glu Gln Lys Lys
            545                 550                 555

Arg Val Cys Trp Cys Leu Ser Glu Asn Ile Ala Lys Gln Gln Gln
        560                 565                 570

Leu Ala Ala Ser Pro Pro Asp Ser Lys Lys Leu His Pro Phe Gly
    575                 580                 585

Ser Leu Gln Gln Glu Met Gly Pro Val Asn Ser Thr Asn Ala Thr
590                 595                 600

Gln Asp Arg Ser Phe Thr Ser Pro Gly Gln Thr Leu Ile Gly
            605                 610

<210> SEQ ID NO 22
<211> LENGTH: 484
<212> TYPE: PRT
<213> ORGANISM: Homo sapiens
<220> FEATURE:
<221> NAME/KEY: misc_feature
<223> OTHER INFORMATION: Incyte ID No: 2674269CD1

<400> SEQUENCE: 22

Met Ser Thr Glu Gly Arg Leu Pro Ser Cys Ser Ala Cys Val Lys
  1               5                  10                  15

Gly Glu Leu Arg Val Leu Thr Ser Ala Ala Leu Thr Ser Arg Asp
                 20                  25                  30

Gly Pro Arg Pro Cys His Val Leu Phe Arg Ile Val His Leu Cys
             35                  40                  45

Leu Arg Lys Ala Asp Gln Lys Leu Val Ile Ile Lys Gln Ile Pro
         50                  55                  60

Val Glu Gln Met Thr Lys Glu Glu Arg Gln Ala Ala Gln Asn Glu
     65                  70                  75

Cys Gln Val Leu Lys Leu Leu Asn His Pro Asn Val Ile Glu Tyr
 80                  85                  90

Tyr Glu Asn Phe Leu Glu Asp Lys Ala Leu Met Ile Ala Met Glu
                 95                 100                 105

Tyr Ala Pro Gly Gly Thr Leu Ala Glu Phe Ile Gln Lys Arg Cys
            110                 115                 120

Asn Ser Leu Leu Glu Glu Glu Thr Ile Leu His Phe Val Gln
         125                 130                 135

Ile Leu Leu Ala Leu His His Val His Thr His Leu Ile Leu His
     140                 145                 150

Arg Asp Leu Lys Thr Gln Asn Ile Leu Leu Asp Lys His Arg Met
 155                 160                 165

Val Val Lys Ile Gly Asp Phe Gly Ile Ser Lys Ile Leu Ser Ser
                 170                 175                 180

Lys Ser Lys Ala Tyr Thr Val Val Gly Thr Pro Cys Tyr Ile Ser
```

-continued

```
                185                 190                 195
Pro Glu Leu Cys Glu Gly Lys Pro Tyr Asn Gln Lys Ser Asp Ile
            200                 205                 210
Trp Ala Leu Gly Cys Val Leu Tyr Glu Leu Ala Ser Leu Lys Arg
        215                 220                 225
Ala Phe Glu Ala Ala Asn Leu Pro Ala Leu Val Leu Lys Ile Met
    230                 235                 240
Ser Gly Thr Phe Ala Pro Ile Ser Asp Arg Tyr Ser Pro Glu Leu
                245                 250                 255
Arg Gln Leu Val Leu Ser Leu Leu Ser Leu Glu Pro Ala Gln Arg
            260                 265                 270
Pro Pro Leu Ser His Ile Met Ala Gln Pro Leu Cys Ile Arg Ala
        275                 280                 285
Leu Leu Asn Leu His Thr Asp Val Gly Ser Val Arg Met Arg Arg
    290                 295                 300
Pro Val Gln Gly Gln Arg Ala Val Leu Gly Arg Val Trp Ala
                305                 310                 315
Pro Ser Gly Ser Thr Gly Gly Leu Arg Gln Arg Glu Thr Trp Gly
            320                 325                 330
Lys Ser Ser Leu Pro Ala Cys Arg Asn Val Arg Arg Val Phe Val
        335                 340                 345
Leu Arg Pro Pro Ser Val Leu Gln Gly Arg Glu Val Arg Gly Pro
    350                 355                 360
Gln Gln His Arg Glu Gln Asp His Gln Cys Pro Leu Gln Arg Tyr
                365                 370                 375
Pro Pro Gly Thr Cys Glu Ala Ser His Pro Thr Thr Val Val
            380                 385                 390
Ser Val Cys Leu Gly Trp Trp Ala Gly His Pro Ala Ala Ala
        395                 400                 405
Asn Ala Gln His Arg Gly Gly Pro Gly Gly Ser Trp Ala His Ala
    410                 415                 420
Glu Ser Arg Arg His Ala Leu Trp Ala Ser His Pro Val Gly Gly
                425                 430                 435
Pro Thr Pro Arg Cys Arg Arg Arg Gln Ser Pro Ser Trp Gly Ser
            440                 445                 450
Gly Ala Ala Thr Ala Pro Val His Leu Ala Phe Pro Gly Gly Pro
        455                 460                 465
Val Gly Cys Asp His Gln Ala Arg Gly Leu Trp Gly Leu Leu His
    470                 475                 480
Cys Leu Pro Asp

<210> SEQ ID NO 23
<211> LENGTH: 460
<212> TYPE: PRT
<213> ORGANISM: Homo sapiens
<220> FEATURE:
<221> NAME/KEY: misc_feature
<223> OTHER INFORMATION: Incyte ID No: 7472409CD1

<400> SEQUENCE: 23

Met Glu Lys Tyr Glu Arg Ile Arg Val Val Gly Arg Gly Ala Phe
 1               5                  10                  15
Gly Ile Val His Leu Cys Leu Arg Lys Ala Asp Gln Lys Leu Val
                20                  25                  30
Ile Ile Lys Gln Ile Pro Val Glu Gln Met Thr Lys Glu Glu Arg
```

-continued

```
                  35                  40                  45
Gln Ala Ala Gln Asn Glu Cys Gln Val Leu Lys Leu Leu Asn His
                  50                  55                  60
Pro Asn Val Ile Glu Tyr Tyr Glu Asn Phe Leu Glu Asp Lys Ala
                  65                  70                  75
Leu Met Ile Ala Met Glu Tyr Ala Pro Gly Gly Thr Leu Ala Glu
                  80                  85                  90
Phe Ile Gln Lys Arg Cys Asn Ser Leu Leu Glu Glu Thr Ile
                  95                 100                 105
Leu His Phe Phe Val Gln Ile Leu Leu Ala Leu His His Val His
                 110                 115                 120
Thr His Leu Ile Leu His Arg Asp Leu Lys Thr Gln Asn Ile Leu
                 125                 130                 135
Leu Asp Lys His Arg Met Val Val Lys Ile Gly Asp Phe Gly Ile
                 140                 145                 150
Ser Lys Ile Leu Ser Ser Lys Ser Lys Ala Tyr Thr Val Val Gly
                 155                 160                 165
Thr Pro Cys Tyr Ile Ser Pro Glu Leu Cys Glu Gly Lys Pro Tyr
                 170                 175                 180
Asn Gln Lys Ser Asp Ile Trp Ala Leu Gly Cys Val Leu Tyr Glu
                 185                 190                 195
Leu Ala Ser Leu Lys Arg Ala Phe Glu Ala Ala Asn Leu Pro Ala
                 200                 205                 210
Leu Val Leu Lys Ile Met Ser Gly Thr Phe Ala Pro Ile Ser Asp
                 215                 220                 225
Arg Tyr Ser Pro Glu Leu Arg Gln Leu Val Leu Ser Leu Leu Ser
                 230                 235                 240
Leu Glu Pro Ala Gln Arg Pro Pro Leu Ser His Ile Met Ala Gln
                 245                 250                 255
Pro Leu Cys Ile Arg Ala Leu Leu Asn Leu His Thr Asp Val Gly
                 260                 265                 270
Ser Val Arg Met Arg Arg Pro Val Gln Gly Gln Arg Ala Val Leu
                 275                 280                 285
Gly Gly Arg Val Trp Ala Pro Ser Gly Ser Thr Gly Gly Leu Arg
                 290                 295                 300
Gln Arg Glu Thr Trp Gly Lys Ser Ser Leu Pro Ala Cys Arg Asn
                 305                 310                 315
Val Arg Arg Val Phe Val Leu Arg Pro Pro Ser Val Leu Gln Gly
                 320                 325                 330
Arg Glu Val Arg Gly Pro Gln Gln His Arg Glu Gln Asp His Gln
                 335                 340                 345
Cys Pro Leu Gln Arg Tyr Pro Pro Gly Thr Cys Glu Ala Ser His
                 350                 355                 360
Pro Thr Thr Thr Val Val Ser Val Cys Leu Gly Trp Trp Ala Gly
                 365                 370                 375
His Pro Pro Ala Ala Asn Ala Gln His Arg Gly Gly Pro Gly
                 380                 385                 390
Gly Ser Trp Ala His Ala Glu Ser Arg Arg His Ala Leu Trp Ala
                 395                 400                 405
Ser His Pro Val Gly Pro Thr Pro Arg Cys Arg Arg Gln
                 410                 415                 420
Ser Pro Ser Trp Gly Ser Gly Ala Ala Thr Ala Pro Val His Leu
                 425                 430                 435
```

```
Ala Phe Pro Gly Gly Pro Val Gly Cys Asp His Gln Ala Arg Gly
            440                 445                 450

Leu Trp Gly Leu Leu His Cys Leu Pro Asp
            455                 460

<210> SEQ ID NO 24
<211> LENGTH: 1413
<212> TYPE: PRT
<213> ORGANISM: Homo sapiens
<220> FEATURE:
<221> NAME/KEY: misc_feature
<223> OTHER INFORMATION: Incyte ID No: 7477484CD1

<400> SEQUENCE: 24

Met Pro Ala Pro Gly Ala Leu Ile Leu Leu Ala Ala Val Ser Ala
  1               5                  10                  15

Ser Gly Cys Leu Ala Ser Pro Ala His Pro Asp Gly Phe Ala Leu
                 20                  25                  30

Gly Arg Ala Pro Leu Ala Pro Pro Tyr Ala Val Val Leu Ile Ser
                 35                  40                  45

Cys Ser Gly Leu Leu Ala Phe Ile Phe Leu Leu Leu Thr Cys Leu
                 50                  55                  60

Cys Cys Lys Arg Gly Asp Val Gly Phe Lys Glu Phe Glu Asn Pro
              65                  70                  75

Glu Gly Glu Asp Cys Ser Gly Glu Tyr Thr Pro Pro Ala Glu Glu
                 80                  85                  90

Thr Ser Ser Ser Gln Ser Leu Pro Asp Val Tyr Ile Leu Pro Leu
                 95                 100                 105

Ala Glu Val Ser Leu Pro Met Pro Ala Pro Gln Pro Ser His Ser
                110                 115                 120

Asp Met Thr Thr Pro Leu Gly Leu Ser Arg Gln His Leu Ser Tyr
                125                 130                 135

Leu Gln Glu Ile Gly Ser Gly Trp Phe Gly Lys Val Ile Leu Gly
                140                 145                 150

Glu Ile Phe Ser Asp Tyr Thr Pro Ala Gln Val Val Val Lys Glu
                155                 160                 165

Leu Arg Ala Ser Ala Gly Pro Leu Glu Gln Arg Lys Phe Ile Ser
                170                 175                 180

Glu Ala Gln Pro Tyr Arg Ser Leu Gln His Pro Asn Val Leu Gln
                185                 190                 195

Cys Leu Gly Leu Cys Val Glu Thr Leu Pro Phe Leu Leu Ile Met
                200                 205                 210

Glu Phe Cys Gln Leu Gly Asp Leu Lys Arg Tyr Leu Arg Ala Gln
                215                 220                 225

Arg Pro Pro Glu Gly Leu Ser Pro Glu Leu Pro Pro Arg Asp Leu
                230                 235                 240

Arg Thr Leu Gln Arg Met Gly Leu Glu Ile Ala Arg Gly Leu Ala
                245                 250                 255

His Leu His Ser His Asn Tyr Val His Ser Asp Leu Ala Leu Arg
                260                 265                 270

Asn Cys Leu Leu Thr Ser Asp Leu Thr Val Arg Ile Gly Asp Tyr
                275                 280                 285

Gly Leu Ala His Ser Asn Tyr Lys Glu Asp Tyr Tyr Leu Thr Pro
                290                 295                 300

Glu Arg Leu Trp Ile Pro Leu Arg Trp Ala Ala Pro Glu Leu Leu
```

-continued

```
                305                 310                 315

Gly Glu Leu His Gly Thr Phe Met Val Val Asp Gln Ser Arg Glu
                320                 325                 330

Ser Asn Ile Trp Ser Leu Gly Val Thr Leu Trp Glu Leu Phe Glu
                335                 340                 345

Phe Gly Ala Gln Pro Tyr Arg His Leu Ser Asp Glu Glu Val Leu
                350                 355                 360

Ala Phe Val Val Arg Gln Gln His Val Lys Leu Ala Arg Pro Arg
                365                 370                 375

Leu Lys Leu Pro Tyr Ala Asp Tyr Trp Tyr Asp Ile Leu Gln Ser
                380                 385                 390

Cys Trp Arg Pro Pro Ala Gln Arg Pro Ser Ala Ser Asp Leu Gln
                395                 400                 405

Leu Gln Leu Thr Tyr Leu Leu Ser Glu Arg Pro Pro Arg Pro Pro
                410                 415                 420

Pro Pro Pro Pro Pro Arg Asp Gly Pro Phe Pro Trp Pro Trp
                425                 430                 435

Pro Pro Ala His Ser Ala Pro Arg Pro Gly Thr Leu Ser Ser Pro
                440                 445                 450

Phe Pro Leu Leu Asp Gly Phe Pro Gly Ala Asp Pro Asp Asp Val
                455                 460                 465

Leu Thr Val Thr Glu Ser Ser Arg Gly Leu Asn Leu Glu Cys Leu
                470                 475                 480

Trp Glu Lys Ala Arg Arg Gly Ala Gly Arg Gly Gly Ala Pro
                485                 490                 495

Ala Trp Gln Pro Ala Ser Ala Pro Pro Ala Pro His Ala Asn Pro
                500                 505                 510

Ser Asn Pro Phe Tyr Glu Ala Leu Ser Thr Pro Ser Val Leu Pro
                515                 520                 525

Val Ile Ser Ala Arg Ser Pro Ser Val Ser Ser Glu Tyr Tyr Ile
                530                 535                 540

Arg Leu Glu Glu His Gly Ser Pro Pro Glu Pro Leu Phe Pro Asn
                545                 550                 555

Asp Trp Asp Pro Leu Asp Pro Gly Val Pro Ala Pro Gln Ala Pro
                560                 565                 570

Gln Ala Pro Ser Glu Val Pro Gln Leu Val Ser Glu Thr Trp Ala
                575                 580                 585

Ser Pro Leu Phe Pro Ala Pro Arg Pro Phe Pro Ala Gln Ser Ser
                590                 595                 600

Ala Ser Gly Ser Phe Leu Leu Ser Gly Trp Asp Pro Glu Gly Arg
                605                 610                 615

Gly Ala Gly Glu Thr Leu Ala Gly Asp Pro Ala Glu Val Leu Gly
                620                 625                 630

Glu Arg Gly Thr Ala Pro Trp Val Glu Glu Glu Glu Glu
                635                 640                 645

Glu Gly Ser Ser Pro Gly Glu Asp Ser Ser Leu Gly Gly Arg
                650                 655                 660

Leu Leu Ala Ala Gly Arg Ala Gly Leu Pro Gly Arg Leu Ala His
                665                 670                 675

Gly Pro Pro Ala Ser Ala Pro Pro Glu Phe Leu Asp Pro Leu Met
                680                 685                 690

Gly Ala Ala Ala Pro Gln Tyr Pro Gly Arg Gly Pro Pro Ala
                695                 700                 705
```

```
Pro Pro Pro Pro Pro Pro Pro Arg Ala Pro Asp Pro Ala
            710                 715                 720

Ala Ser Pro Asp Pro Ser Ala Val Ala Ser Pro Gly Ser Gly
            725                 730                 735

Leu Ser Ser Pro Gly Pro Lys Pro Gly Asp Ser Gly Tyr Glu Thr
            740                 745                 750

Glu Thr Pro Phe Ser Pro Glu Gly Ala Phe Pro Gly Gly Gly Ala
            755                 760                 765

Ala Glu Glu Glu Gly Val Pro Arg Pro Ala Pro Pro Glu Pro
            770                 775                 780

Pro Asp Pro Gly Ala Pro Arg Pro Pro Asp Pro Gly Pro Leu
            785                 790                 795

Pro Leu Pro Gly Pro Arg Glu Lys Pro Thr Phe Val Val Gln Val
            800                 805                 810

Ser Thr Glu Gln Leu Leu Met Ser Leu Arg Glu Asp Val Thr Arg
            815                 820                 825

Asn Leu Leu Gly Glu Lys Gly Ala Thr Ala Arg Glu Thr Gly Pro
            830                 835                 840

Arg Lys Ala Gly Arg Gly Pro Gly Asn Arg Glu Lys Val Pro Gly
            845                 850                 855

Leu Asn Arg Asp Pro Thr Val Leu Gly Asn Gly Lys Gln Ala Pro
            860                 865                 870

Ser Leu Ser Leu Pro Val Asn Gly Val Thr Val Leu Glu Asn Gly
            875                 880                 885

Asp Gln Arg Ala Pro Gly Ile Glu Glu Lys Ala Ala Glu Asn Gly
            890                 895                 900

Ala Leu Gly Ser Pro Glu Arg Glu Lys Val Leu Glu Asn Gly
            905                 910                 915

Glu Leu Thr Pro Arg Arg Glu Glu Lys Ala Leu Glu Asn Gly
            920                 925                 930

Glu Leu Arg Ser Pro Glu Ala Gly Glu Lys Val Leu Val Asn Gly
            935                 940                 945

Gly Leu Thr Pro Pro Lys Ser Glu Asp Lys Val Ser Glu Asn Gly
            950                 955                 960

Gly Leu Arg Phe Pro Arg Asn Thr Glu Arg Pro Pro Glu Thr Gly
            965                 970                 975

Pro Trp Arg Ala Pro Gly Pro Trp Glu Lys Thr Pro Glu Ser Trp
            980                 985                 990

Gly Pro Ala Pro Thr Ile Gly Glu Pro Ala Pro Glu Thr Ser Leu
            995                1000                1005

Glu Arg Ala Pro Ala Pro Ser Ala Val Val Ser Ser Arg Asn Gly
           1010                1015                1020

Gly Glu Thr Ala Pro Gly Pro Leu Gly Pro Ala Pro Lys Asn Gly
           1025                1030                1035

Thr Leu Glu Pro Gly Thr Glu Arg Arg Ala Pro Glu Thr Gly Gly
           1040                1045                1050

Ala Pro Arg Ala Pro Gly Ala Gly Arg Leu Asp Leu Gly Ser Gly
           1055                1060                1065

Gly Arg Ala Pro Val Gly Thr Gly Thr Ala Pro Gly Gly Gly Pro
           1070                1075                1080

Gly Ser Gly Val Asp Ala Lys Ala Gly Trp Val Asp Asn Thr Arg
           1085                1090                1095
```

```
Pro Gln Pro Pro Pro Pro Leu Pro Pro Pro Glu Ala Gln
            1100                1105            1110

Pro Arg Arg Leu Glu Pro Ala Pro Pro Arg Ala Arg Pro Glu Val
            1115                1120            1125

Ala Pro Glu Gly Glu Pro Gly Ala Pro Asp Ser Arg Ala Gly Gly
            1130                1135            1140

Asp Thr Ala Leu Ser Gly Asp Gly Asp Pro Pro Lys Pro Glu Arg
            1145                1150            1155

Lys Gly Pro Glu Met Pro Arg Leu Phe Leu Asp Leu Gly Pro Pro
            1160                1165            1170

Gln Gly Asn Ser Glu Gln Ile Lys Ala Arg Leu Ser Arg Leu Ser
            1175                1180            1185

Leu Ala Leu Pro Pro Leu Thr Leu Thr Pro Phe Pro Gly Pro Gly
            1190                1195            1200

Pro Arg Arg Pro Pro Trp Glu Gly Ala Asp Ala Gly Ala Ala Gly
            1205                1210            1215

Gly Glu Ala Gly Gly Ala Gly Ala Pro Gly Pro Ala Glu Glu Asp
            1220                1225            1230

Gly Glu Asp Glu Asp Glu Asp Glu Glu Glu Asp Glu Glu Ala Ala
            1235                1240            1245

Ala Pro Gly Ala Ala Ala Gly Pro Arg Gly Pro Gly Arg Ala Arg
            1250                1255            1260

Ala Ala Pro Val Pro Val Val Ser Ser Ala Asp Ala Asp Ala
            1265                1270            1275

Ala Arg Pro Leu Arg Gly Leu Leu Lys Ser Pro Arg Gly Ala Asp
            1280                1285            1290

Glu Pro Glu Asp Ser Glu Leu Glu Arg Lys Arg Lys Met Val Ser
            1295                1300            1305

Phe His Gly Asp Val Thr Val Tyr Leu Phe Asp Gln Glu Thr Pro
            1310                1315            1320

Thr Asn Glu Leu Ser Val Gln Ala Pro Pro Glu Gly Asp Thr Asp
            1325                1330            1335

Pro Ser Thr Pro Pro Ala Pro Pro Thr Pro Pro His Pro Ala Thr
            1340                1345            1350

Pro Gly Asp Gly Phe Pro Ser Asn Asp Ser Gly Phe Gly Ser
            1355                1360            1365

Phe Glu Trp Ala Glu Asp Phe Pro Leu Leu Pro Pro Pro Gly Pro
            1370                1375            1380

Pro Leu Cys Phe Ser Arg Phe Ser Val Ser Pro Ala Leu Glu Thr
            1385                1390            1395

Pro Gly Pro Pro Ala Arg Ala Pro Asp Ala Arg Pro Ala Gly Pro
            1400                1405            1410

Val Glu Asn

<210> SEQ ID NO 25
<211> LENGTH: 2060
<212> TYPE: DNA
<213> ORGANISM: Homo sapiens
<220> FEATURE:
<221> NAME/KEY: misc_feature
<223> OTHER INFORMATION: Incyte ID No: 7312543CB1

<400> SEQUENCE: 25
aagacagcaa gccccctacg gcaccgcaag gactcccccct cctcagtctg ggccccccgcc      60 ccaagaccta gaacgcagtg ccccccaggcc gggattgcga gaaccccctc ccaagatccg     120
```

```
gtcattacaa ctccacacct caagacaaga agacccagct cagaacgccc ctagatcagg        180
ggatcccaat tccccccaac tccggtacat agaaatccca aatctaggca gccggggaca        240
gcaagagaca ctctcaccag caagaagcct cggggatccc ccccctaaag ctccaggact        300
tgggcgactg agccctggcc ggcaccgctt gcaccccggt ccatggtcgt ggcgccctga        360 gccccccgggg ccgggcagac gaagaccgcg acggcgccca ggcccctgcc gcggcgtcc        420 ccgcggcccc agcccaggga aagatgagcg tgggctgcc cagagcctga gccgccccgc        480
tccctgacct gctgtgggcc ggggactgcc cctgggcctg gtgccggtgt gccccttctc        540
actgaagaca tgcaggccct gactctccgc acactggccg ccagcgacgt caccaagcac        600
tacgaactag tccgggagct gggcaaaggc acctatggga aggttgacct ggtggtctac        660
aagggcacag gcacaaaaat ggcactgaag tttgtgaaca agagcaaaac caagctgaag        720
aacttcctac gggaggtgag catcaccaac agcctctcct ccagcccctt catcatcaag        780
gtctttgacg tggtctttga gacagaggac tgctacgtct tgcccaggaa gtacgcacct        840 gctgggacc tgtttgacat catccctccc caggtggggc tccctgagga cacggtgaag        900
cgctgtgtgc agcagctggg cctggcgctg gacttcatgc acgggcggca gctggtgcac        960
cgcgacatca gcccgagaa cgtgctgctg ttcgaccgcg agtgccgccg cgtaaagctg       1020
gccgacttcg gcatgacgcg ccgcgtgggc tgccgcgtca agcgcgtgag cggcaccatc       1080
ccttacacgg cgcctgaggt gtgccaggcg ggccgcgccg acgggctggc ggtggacacg       1140
ggcgtggacg tgtgggcctt cggcgtgctc atcttctgcg tgctcaccgg caacttcccg       1200
tgggaggcgg cgtcgggcgc cgacgccttc ttcgaggagt tcgtgcgctg gcagcggggc       1260
cgcctgccgg ggctgccttc gcagtggcgc cgcttcaccg agcccgcgct gcgcatgttc       1320
cagcgcttac tggccctgga gccgagcgc gcgcggccca gccaaggaggt gttccgcttc       1380 ctcaagcacg agctcacgtc cgagctgcgc gccggccct cgcaccgcgc gcgcaagccc       1440
cccggggacc gccgccccgc cgccgggcca ctgcgcctcg aggcgcctgg gccgctcaag       1500
cggacggtgc tgaccgagag cggcggcggc tccggcccg cgcccccgc cgtcgggtcg       1560 gtgcccttgc ccgtgccggt gccggtgcca gtgcccgtgc cggtgcctgt gcccgagccc       1620
ggcctagctc cccaggggcc cccggccgg accgacggcc gcgcggacaa gagcaaaggg       1680
caggtggtgc tggccacggc catcgagatc tgcgtctgag tctgcctcct ccgcgcctcg       1740
gacccgggag cagcccggc ccgccccgag ccggtgcccg tgacgacgg tagggaatgg       1800 agccacctcg ccgcggggca ggggcgcag cggtagatct aggcagatcg cggcccggca       1860
cctggtccgt ccccggcggg cttggtgagg gggccacaca aagaccccta gcgcggcctg       1920
gtgagcgggg gcttggccca gaggagccaa gccgcacaga cccgagaatt cggaggccac       1980
cacacaacac acacacacac acacacacac acacacacac acacacgcca              2040
gagagcaagg gagctcttcg                                                  2060
```

<210> SEQ ID NO 26
<211> LENGTH: 5694
<212> TYPE: DNA
<213> ORGANISM: Homo sapiens
<220> FEATURE:
<221> NAME/KEY: misc_feature
<223> OTHER INFORMATION: Incyte ID No: 7477427CB1

<400> SEQUENCE: 26

```
ttttttttgtt tttttaaaga agtgttgact ctctagttcg ttgtactttt aagtatgagt         60
```

```
tttatttaaa tatacgactt aattgtattc ttttaaaaat gcattaagta tatattttat      120
ggtaatttta ccctcaaaat agatgtatat gggtgaaatt gaagacgctt cagttaagtg      180
aggttactgg tgtgttggat gtttaattca gcaccagcat tgcatgacag ttgtttgaat      240
aacaagtggt ttatttttaa aaccatacct tttaaaattt aggttcagat aatagtaaaa      300
gtcatcataa taatttaaag gaaaaccagc agaaatcgaa gcaaacatgt ctggagaagt      360
gcgtttgagg cagttggagc agtttatttt ggacgggccc gctcagacca atgggcagtg      420
cttcagtgtg gagacattac tggatatact catctgcctt tatgatgaat gcaataattc      480
tccattgaga agagagaaga acattctcga atacctagaa tgggctaaac catttacttc      540
taaagtgaaa caaatgcgat tacatagaga agactttgaa atattaaagg tgattggtcg      600
aggagctttt ggggaggttg ctgtagtaaa actaaaaaat gcagataaag tgtttgccat      660
gaaaatattg aataaatggg aaatgctgaa agagctgag acagcatgtt tcgtgaaga       720 aagggatgta ttagtgaatg gagacaataa atggattaca accttgcact atgctttcca      780
ggatgacaat aacttatacc tggttatgga ttattatgtt ggtggggatt tgcttactct      840
actcagcaaa tttgaagata gattgcctga agatatggct agattttact tggctgagat      900
ggtgatagca attgactcag ttcatcagct acattatgta cacagagaca ttaaacctga      960
caatatactg atggatatga atggacatat tcggttagca gattttggtt cttgtctgaa     1020
gctgatggaa gatggaacgg ttcagtcctc agtggctgta ggaactccag attatatctc     1080
tcctgaaatc cttcaagcca tggaagatgg aaaagggaga tatggacctg aatgtgactg     1140
gtggtctttg ggggtctgta tgtatgaaat gctttacgga gaaacaccat tttatgcaga     1200
atcgctggtg gagacatacg gaaaaatcat gaaccacaaa gagaggtttc agtttccagc     1260
ccaagtgact gatgtgtctg aaaatgctaa ggatcttatt cgaaggctca tttgtagcag     1320
agaacatcga cttggtcaaa atggaataga agactttaag aaacacccat ttttcagtgg     1380
aattgattgg gataatattc ggaactgtga agcaccttat attccagaag ttagtagccc     1440
aacagataca tcgaattttg atgtagatga tgattgttta aaaaattctg aaacgatgcc     1500
cccaccaaca catactgcat tttctggcca ccatctgcca tttgttggtt ttacatatac     1560
tagtagctgt gtactttctg atcggagctg tttaagagtt acggctggtc ccacctcact     1620
ggatcttgat gttaatgttc agaggactct agacaacaac ttagcaactg aagcttatga     1680
aagaagaatt aagcgccttg agcaagaaaa acttgaactc agtagaaaac ttcaagagtc     1740
aacacagact gtccaagctc tgcagtattc aactgttgat ggtccactaa cagcaagcaa     1800
agatttagaa ataaaaaact taaagaaga aattgaaaaa ctaagaaaac aagtaacaga     1860
atcaagtcat ttggaacagc aacttgaaga agctaatgct gtgaggcaag aactagatga     1920
tgcttttaga caaatcaagg cttatgaaaa acaaatcaaa acgttacaac aagaaagaga     1980
agatctaaat aaggaactag tccaggctag tgagcgatta aaaaaccaat ccaaagagct     2040
gaaagacgca cactgtcaga ggaaactggc catgcaggaa ttcatggaga tcaatgagcg     2100
gctaacagaa ttgcacaccc aaaaacagaa acttgctcgc catgtccgag ataaggaaga     2160
agaggtggac ctggtgatgc aaaaagttga agcttaagg caagaactgc gcagaacaga      2220
aagagccaaa aaagagctgg aagttcatac agaagctcta gctgctgaag catctaaaga     2280
caggaagcta cgtgaacaga gtgagcacta ttctaagcaa ctggaaaatg aattggaggg     2340
actgaagcaa aaacaaatta gttactcacc aggagtatgc agcatagaac atcagcaaga     2400
```

```
gataaccaaa ctaaagactg atttggaaaa gaaaagtatc ttttatgaag aagaattatc  2460
taaaagagaa ggaatacatg caaatgaaat aaaaaatctt aagaaagaac tgcatgattc  2520
agaaggtcag caacttgctc tcaacaaaga aattatgatt ttaaaagaca aattggaaaa  2580
aaccagaaga gaaagtcaaa gtgaaaggga ggaatttgaa agtgagttca acaacaata  2640 tgaacgagaa aaagtgttgt taactgaaga aaataaaaag ctgacgagtg aacttgataa  2700
gcttactact ttgtatgaga acttaagtat acacaaccag cagttagaag aagaggttaa  2760
agatctagca gacaagaaag aatcagttgc acattgggaa gcccaaatca cagaaataat  2820
tcagtgggtc agcgatgaaa aggatgcacg agggtatctt caggccttag cttctaaaat  2880
gactgaagaa ttggaggcat taagaaattc cagcttgggt acacgagcaa cagatatgcc  2940
ctggaaaatg cgtcgttttg cgaaactgga tatgtcagct agactggagt tgcagtcggc  3000
tctggatgca gaaataagag ccaaacaggc catccaagaa gagttgaata agttaaagc  3060 atctaatatc ataacagaat gtaaactaaa agattcagag aagaagaact tggaactact  3120
ctcagaaatc gaacagctga taaaggacac tgaagagctt agatctgaaa agggtataga  3180
gcaccaagac tcacagcatt cttttcttggc atttttgaat acgcctaccg atgctctgga  3240
tcaatttgaa actgtagact ccactccact ttcagttcac acaccaacct taaggaaaaa  3300
aggatgtcct ggttcaactg gcttttccacc taagcgcaag actcaccagt tttttgtaaa  3360
atcttttact actcctacca gtgtcatca gtgtacctcc ttgatggtgg gtttaataag  3420
acagggctgt tcatgtgaag tgtgtggatt ctcatgccat ataacttgtg taaacaaagc  3480
tccaaccact tgtccagttc ctcctgaaca gacaaaaggt cccctgggta tagatcctca  3540
gaaaggaata ggaacagcat atgaaggtca tgtcaggatt cctaagccag ctggagtgaa  3600
gaaagggtgg cagagagcac tggctatagt gtgtgacttc aaactctttc tgtacgatat  3660
tgctgaagga aaagcatctc agcccagtgt tgtcattagt caagtgattg acatgaggga  3720
tgaagaattt tctgtgagtt cagtcttggc ttctgatgtt atccatgcaa gtcggaaaga  3780 tatccctgt atatttaggg tcacagcttc ccagctctca gcatctaata caaatgttc  3840 aatcctgatg ctagcagaca ctgagaatga gaagaataag tgggtgggag tgctgagtga  3900
attgcacaag attttgaaga aaacaaatt cagagaccgc tcagtctatg ttcccaaaga  3960
ggcttatgac agcactctac ccctcattaa acaacccag gcagccgcaa tcatagatca  4020
tgaaagaatt gctttgggaa acgaagaagg gttatttgtt gtacatgtca ccaaagatga  4080
aattattaga gttggtgaca ataagaagat tcatcagatt gaactcattc caatgatca  4140 gcttgttgct gtgatctcag gacgaaatcg tcatgtacga cttttttccta tgtcagcatt  4200 ggatgggcga gagaccgatt tttacaagct gtcagaaact aaagggtgtc aaaccgtaac  4260
ttctggaaag gtgcgccatg gagctctcac atgcctgtgt gtggctatga aaggcaggt  4320 cctctgttat gaactatttc agagcaagac ccgtcacaga aaatttaaag aaattcaagt  4380
cccatataat gtccagtgga tggcaatctt cagtgaacaa ctctgtgtgg gattccagtc  4440
aggatttcta agatacccct tgaatggaga aggaaatcca tacagtatgc tccattcaaa  4500
tgaccataca ctatcatta tgcacatca accaatggat gctatctgcg cagttgagat  4560
ctccagtaaa gaatatctgc tgtgtttaa cagcattggg atatacactg actgccaggg  4620
ccgaagatct agacaacagg aattgatgtg gccagcaaat ccttcctctt gttgttacaa  4680
tgcaccatat ctctcggtgt acagtgaaaa tgcagttgat atctttgatg tgaactccat  4740
ggaatggatt cagactcttc ctctcaaaaa ggttcgaccc ttaaacaatg aaggatcatt  4800
```

| | |
|---|---|
| aaatctttta gggttggaga ccattagatt aatatatttc aaaaataaga tggcagaagg | 4860 |
| ggacgaactg gtagtacctg aaacatcaga taatagtcgg aaacaaatgg ttagaaacat | 4920 |
| taacaataag cggcgttatt ccttcagagt cccagaagag gaaaggatgc agcagaggag | 4980 |
| ggaaatgcta cgagatccag aaatgagaaa taaattaatt tctaatccaa ctaattttaa | 5040 |
| tcacatagca cacatgggtc ctggagatgg aatacagatc ctgaaagatc tgcccatgaa | 5100 |
| ccctcggcct caggaaagtc ggacagtatt cagtggctca gtcagtattc catctatcac | 5160 |
| caaatcccgc cctgagccag gccgctccat gagtgctagc agtggcttgt cagcaaggtc | 5220 |
| atccgcacag aatggcagcg cattaaagag ggaattctct ggaggaagct acagtgccaa | 5280 |
| gcggcagccc atgccctccc cgtcagaggg ctctttgtcc tctggaggca tggaccaagg | 5340 |
| aagtgatgcc ccagcgaggg actttgacgg agaggactct gactctccga ggcattccac | 5400 |
| agcttccaac agttccaacc taagcagccc cccaagccca gtttcacccc gaaaaaccaa | 5460 |
| gagcctctcc ctggagagca ctgaccgcgg gagctgggac ccgtgagctg cctcagcact | 5520 |
| gggacctctc gctctccgct ccctgccact cgcctcctct cactttcatc tcttccctcc | 5580 |
| acctcgcctg ctcggcctga aagccaccag gggctggcag cagtagcagg acagggattc | 5640 |
| aggagttctg acgacacgac tctcagatcc acgccccagc taacagcaaa acaa | 5694 |

<210> SEQ ID NO 27
<211> LENGTH: 3520
<212> TYPE: DNA
<213> ORGANISM: Homo sapiens
<220> FEATURE:
<221> NAME/KEY: misc_feature
<223> OTHER INFORMATION: Incyte ID No: 7481495CB1

<400> SEQUENCE: 27

| | |
|---|---|
| cggggccgga gcggcgcccc ggccgcccgc gcggggtctc ccccatggtg cagcggggtt | 60 |
| cgggatgtcg aagacgctga agaagaagaa gcactggctc agcaaggtgc aggagtgcgc | 120 |
| cgtgtcctgg gccgggcccc cggcgactt cggcgcggag atccgcgtg gcgcggagcg | 180 |
| tggcgagttc ccctacctgg ggcggctccg cgaggagccc ggcgggggca cctgctacgt | 240 |
| cgtctcgggc aaggcgccca gcccaggcga tgtgctgctg gaggtaaacg ggacgcctgt | 300 |
| cagcgggctc accaaccggg acaccctggc tgtcatccgc cacttccgcg agcccatccg | 360 |
| tctcaagact gtgaaaccag gcaaagtcat taataaagat ttgcggcatt acctaagtct | 420 |
| tcagtttcaa aaaggatcaa ttgaccacaa actgcagcaa gtgatcagag ataatctcta | 480 |
| cttgagaacc attccatgca ctacaagggc ccccagggat ggagaagtac caggagtgga | 540 |
| ttataatttc atttccgttg aacagttcaa agcactggaa gagagtggag cattgttaga | 600 |
| aagtgggaca tatgatggaa acttctatgg aactcccaag cctccagcag aacccagccc | 660 |
| tttttcagcca gatccagttg atcaagtcct ctttgataat gagtttgatg cagaatctca | 720 |
| aagaaaacga acgacatctg tcagcaagat ggaaagaatg gatagctctc ttcctgaaga | 780 |
| ggaagaagat gaggacaagg aagctattaa tggcagtgga aacgcagaaa acagagagag | 840 |
| gcattctgag tcatctgact ggatgaagac tgttccaagt acaaccaaa caaatagctc | 900 |
| catggacttt agaaattata tgatgagaga tgagactctg gaaccactgc ccaaaaactg | 960 |
| ggaaatggcc tacactgaca cagggatgat ctacttcatt gaccacaata ccaagacaac | 1020 |
| cacctggttg gatcctcgtc tttgtaagaa agccaaagcc cctgaagact gtgaagatgg | 1080 |
| agagcttcct tatggctggg agaaaataga ggaccctcag tatgggacat actatgttga | 1140 |

```
tcaccttaac cagaaaaccc agtttgaaaa tccagtggag gaagccaaaa ggaaaaagca   1200
gttaggacag gttgaaattg ggtcttcaaa accagatatg gaaaaatcac acttcacaag   1260
agatccatcc cagcttaaag gtgtccttgt tcgagcatca ctgaaaaaaa gcacaatggg   1320
atttggtttt actattattg gtggagatag acctgatgag ttcctacaag tgaaaaatgt   1380
gctgaaagat ggtcccgcag ctcaggatgg gaaaattgca ccaggcgatg ttattgtaga   1440
catcaatggc aactgtgtcc tcggtcacac tcatgcagat gttgtccaga tgtttcaatt   1500
ggtacctgtc aatcagtatg taaacctcac tttatgtcgt ggttatccac ttcctgatga   1560
cagtgaagat cctgttgtgg acattgttgc tgctaccccct gtcatcaatg gacagtcatt   1620
aaccaaggga gagacttgca tgaatcctca ggattttaag ccaggagcaa tggttctgga   1680
gcagaatgga aaatcgggac acactttgac tggtgatggt ctcaatggac catcagatgc   1740
aagtgagcag agagtatcca tggcatcgtc aggcagctcc cagcctgaac tagtgactat   1800 cccctttgatt aagggcccta aagggtttgg gtttgcaatt gctgacagcc ctactggaca   1860
gaaggtgaaa atgatactgg atagtcagtg gtgtcaaggc cttcagaaag gagatataat   1920
taaggaaata taccatcaaa atgtgcagaa tttaacacat ctccaagtgg tagaggtgct   1980
aaagcagttt ccagtaggtg ctgatgtacc attgcttatc ttaagaggag gtcctccttc   2040
accaaccaaa actgccaaaa tgaaaacaga taaaaaggaa aatgcaggaa gtttggaggc   2100
cataaatgag cctattcctc agcctatgcc ttttccaccg agcattatca ggtcaggatc   2160
cccaaaattg gatccttctg aggtctacct gaaatctaag actttatatg aagataaacc   2220
accaaacacc aaagatttgg atgttttttct tcgaaaacaa gagtcagggt ttggcttcag   2280
ggtgctagga ggagatggac ctgaccagtc tatatatatt ggggctatta ttccctgggg   2340
agcagctgag aaagatggtc ggctccgcgc agctgatgaa ctaatgtgca ttgatggaat   2400
tcctgttaaa gggaaatcac acaaacaagt cttggacctc atgacaactg ctgctcgaaa   2460
tggccatgtg ttactaactg tcagacggaa gatcttctat ggagaaaaac aacccgagga   2520
cgacagctct caggccttca tttcaacgca gaatggatct ccccgcctga accgggcaga   2580
ggtcccagcc aggcctgcac cccaggagcc ctatgatgtt gtcttgcaac gaaaagaaaa   2640
tgaaggattt ggctttgtca tcctcacctc caaaaacaaa ccacctccag gagttattcc   2700
tcataaaatt ggccgagtca tagaaggaag tccggctgac cgctgtggaa aactgaaagt   2760
tggagatcat atctctgcag tgaatgggca gtccattgtt gaactgtctc atgataacat   2820
tgttcagctg atcaaagatg ctggtgtcac cgtcacacta acggtcattg ctgaagaaga   2880
gcatcatggt ccaccatcag gaacaaactc agccaggcaa agcccagccc tgcagcacag   2940
gcccatggga cagtcacagg ccaaccacat acctgggggac agaagtgccc tagaaggtga   3000
aattggaaaa gatgtctcca cttcttacag acattcttgg tcagaccaca agcaccttgc   3060
acagcctgac accgcagtaa tttcagttgt aggcagtcgg cacaatcaga accttggttg   3120
ttatccagta gagctggaga gaggcccccg gggctttgga ttcagcctcc gaggggggaa   3180
ggagtacaac atggggctgt tcatccttcg tcttgctgaa gatggtcctg ccatcaaaga   3240
tggcagaatt catgttggtg accagattgt tgaaatcaat ggggaaccta cacaaggaat   3300
cacacatact cgagcaattg agctcattca ggctggtgga aataaagttc ttcttctttt   3360
gaggccagga actggcttga tacctgacca tggtttggct ccttccggtc tgtgctccta   3420
cgtgaaaccc gagcaacatt aaggctttca gggctttttct tggtctttcc ttaaaaagac   3480
```

| | |
|---|---|
| ttggtaaatt tgcatgtctt gtaaatcact ttcttctttt | 3520 |

<210> SEQ ID NO 28
<211> LENGTH: 1988
<212> TYPE: DNA
<213> ORGANISM: Homo sapiens
<220> FEATURE:
<221> NAME/KEY: misc_feature
<223> OTHER INFORMATION: Incyte ID No: 55053189CB1

<400> SEQUENCE: 28

| | |
|---|---|
| acagcaatga cttgttcttg gttcaaagca cgatttagca aagctgtaca aactgttgag | 60 |
| tctactccac cactgagtaa aaccaaaact tttgacgtgc ctactctctc tttgatctct | 120 |
| cgaatacact caagttctct gttctgcacg gtgaaggttc cactgcatcc agctatatca | 180 |
| taaaggaaat tcttcagtat tacttttcca ttttctgtaa ggccaacttc agggtggaac | 240 |
| tgtgctccat ataactttt agattcattt gctatgcctg ctggccgcca tgtgcaccgt | 300 |
| agtggaccct cgcattgtcc ggagatacct actcaggcgg cagctcgggc agggggccta | 360 |
| tggcattgtg tggaaggcag tggaccggag gactggtgag gtcgtggcca tcaagaaaat | 420 |
| ctttgatgct tttagggata agacagatgc ccagagaaca ttccgggaaa tcacgctcct | 480 |
| ccaggagttt ggggaccatc ccaacatcat cagcctcctt gacgtgatcc gggcagagaa | 540 |
| cgacagggac atttacctgg tgtttgagtt tatggacact gacctgaacg cagtcatccg | 600 |
| gaagggcggc ctgctgcagg acgtccacgt gcgctccatc ttctaccagc tcctgcgggc | 660 |
| cacccggttc ctccactcgg ggcacgttgt gcaccgggac cagaagccgt ccaatgtgct | 720 |
| cctggatgcc aactgcacag tgaagctgtg tgactttggc ctggcccgct ccctgggcga | 780 |
| cctccctgag gggcctgagg accaggccgt gacagagtac gtggccacac gctggtaccg | 840 |
| agcaccggag gtgctgctct cttcgcaccg atacaccctt ggggtggaca tgtggagtct | 900 |
| gggctgtatc ctgggggaga tgctgcgggg gagacccctg ttccccggca cgtccaccct | 960 |
| ccaccagctg gagctgatcc tggagaccat cccaccgcca tctgaggagg acctcctggc | 1020 |
| tctcggctca ggctgccgtg cctctgtgct gcaccagctg gggtcccggc cacgacagac | 1080 |
| gctggatgcc ctcctaccgc cagacacctc cccagaggcc ttggacctcc ttaggcgact | 1140 |
| cctggtgttc gccccggaca gcggttaag cgcgacccag atgatcctgg agtgtggagg | 1200 |
| cagcagcggc acctcgagag agaagggccc ggagggtgtc tccccaagcc aggcacacct | 1260 |
| gcacaaaccc agagccgacc ctcagctgcc ttctaggaca cctgtgcagg gtcccagacc | 1320 |
| caggccccag agcagcccag gccatgaccc tgccgagcac gagtcccccc gtgcagccaa | 1380 |
| gaacgttccc aggcagaact ccgctcccct gctccaaact gctctcctag ggaatgggga | 1440 |
| aaggcccct ggggcgaagg aagcgccccc cttgacactc tcgctggtga agccaagcgg | 1500 |
| gaggggagct cgcccctccc tgacctccca ggctgcggct caggtggcca accaggccct | 1560 |
| gatccggggt gactggaacc ggggcggtgg ggtgagggtg ccagcgtac aacaggtccc | 1620 |
| tcccggctt cctccggagg cccggccgg cggaggatg ttcagcacct ctgccttgca | 1680 |
| gggtgcccag gggggtgcca gggctttgct tggaggctac tcccaagcct acgggactgt | 1740 |
| ctgccactcg gcactgggcc acctgcccct gctggagggg caccatgtgt gagccgccct | 1800 |
| actcccttca cctggccctc tgttcctgcc ccagcccctt cccagaccc ctctccagtc | 1860 |
| tcctgcaccc cttagccctc cctgctttgc ctggcccgtt gaagttccag ggagcttgcc | 1920 |
| cgggtctcct cggggagca gatgagggcc ctgcccccgc cccactgact tcctccaata | 1980 |

-continued

| | |
|---|---|
| aagtcatc | 1988 |

<210> SEQ ID NO 29
<211> LENGTH: 1822
<212> TYPE: DNA
<213> ORGANISM: Homo sapiens
<220> FEATURE:
<221> NAME/KEY: misc_feature
<223> OTHER INFORMATION: Incyte ID No: 7474797CB1

<400> SEQUENCE: 29

| | |
|---|---|
| caaggtggtg actgagggga acaaaaccaa gaaaggtgga ctaagggagt tacccaacgt | 60 |
| gggagggccc tcggggaaag agagaagttc ccaaggcaac aatgttccgt gtttgttttt | 120 |
| ttttgagagc ggagtctcgc tctggtcgcc caggcctggg agtgcagtgg cgggatctcg | 180 |
| gctcactgca agctctgcct cccaggttca cgccattctc ctgcctcagc ctccccaagt | 240 |
| agctgggac tacaggcgcc cgccactacg cccggctaat ttttgtatt tttagtagag | 300 |
| acggggtttc accgttttag ccgggatggt ctcgatctcc tgacctcgtg atccgcccgc | 360 |
| ctcggcctcc caaagtgctg ggattacagg cgtgagccac cgcgcccggc cgcacttcat | 420 |
| tctcaagttt tgtggccaac gatggatagg aggtggattg tgatgtattc ggaacatggg | 480 |
| accttgagga gttccgtaac caaaaggaga agtaacaac agccagtgga gacaaaaaga | 540 |
| actgcttctc tttctttccc cctccaagtt cctagtggag ggctgagtcc agcatcccag | 600 |
| actcgtgtga ctatataggc aagcatttgg ggacctactt cactttgata ccctagcctt | 660 |
| cagcagctca aggtgttggc cttggatag gaggcttcca agtagtaaag ctccctgctc | 720 |
| tcagcaagcc caacaccatg gggaagggag atgtcttaga ggcagcacca accaccacag | 780 |
| cctaccattc cctcatggat gaatatggtt atgaggtggg caaggccatt ggccatggct | 840 |
| cctatgggtc ggtatatgag gctttctaca caaagcagaa ggttatggtg gcagtcaaga | 900 |
| tcatctcaaa gaagaaggcc tctgatgact atcttaacaa gttcctgccc cgtgaaatac | 960 |
| aggtaatgaa agtcttgcgg cacaagtacc tcatcaactt ctatcgggcc attgagagca | 1020 |
| catctcgagt atacatcatt ctggaactgg ctcagggtgg tgatgtcctt gaatggatcc | 1080 |
| agcgctacgg ggcctgctct gagccccttg ctggcaagtg gttctcccag ctgaccctgg | 1140 |
| gcattgccta cctgcacagc aagagcatcg tgcaccggga cttaaagttg gagaacctgt | 1200 |
| tgctggacaa gtgggagaat gtgaagatat cagactttgg cttgccaag atggtgcctt | 1260 |
| ctaaccagcc tgtgggttgt agcccttctt accgccaagt gaactgcttt tcccacctca | 1320 |
| gccagactta ctgtggcagc tttgcttacg cttgcccaga gatcttacga ggcttgccct | 1380 |
| acaacccttt cctgtctgac acctggagca tgggcgtcat cctttacact ctagtggtcg | 1440 |
| cccatctgcc ctttgatgac accaatctca aaaagctgct aagagagact cagaaggagg | 1500 |
| tcactttccc agctaaccat accatctccc aggagtgcaa gaacctgatc ctccagatgg | 1560 |
| tacgccaagc ccctaagggg gccccccttt tggacatcat caaggatttc tgggggtca | 1620 |
| agttccagcc tgagcaaccc ccccatgaga tcaggctgct tgaggccatg tgccagctcc | 1680 |
| ccaaccccc taaacagccc caatccttgc aaatttcgcc ctgaaaatgg ctgagggagg | 1740 |
| ggggtaaaaa aggagcaaaa caggaggttt tgggctaaaa atcttttta ccaaaaataa | 1800 |
| atttaagttt gatttagttt cc | 1822 |

<210> SEQ ID NO 30
<211> LENGTH: 1814
<212> TYPE: DNA

<213> ORGANISM: Homo sapiens
<220> FEATURE:
<221> NAME/KEY: misc_feature
<223> OTHER INFORMATION: Incyte ID No: 3296272CB1

<400> SEQUENCE: 30

| | | | | | | |
|---|---|---|---|---|---|---|
| ggggcctcgc | cgcgcggcca | gccacctccg | gagtcgccgc | ctctgctctc | agtgccccgg | 60 |
| atcggaggcc | gtccatcgcc | cctcgggccg | acgccatgaa | gatcaaagat | gccaagaaac | 120 |
| cctctttccc | atggtttggc | atggacattg | ggggaactct | agtaaagctc | tcgtactttg | 180 |
| aacctattga | tatcacagca | gaggaagagc | aagaagaagt | tgagagttta | aaaagtattc | 240 |
| ggaaatattt | gacttctaac | gtggcatatg | gatccaccgg | cattcgggat | gtacaccttg | 300 |
| aactgaaaga | tttaacactt | tttggccgaa | gagggaactt | gcactttatc | aggtttccaa | 360 |
| cccaggacct | gcctactttt | atccaaatgg | gaagagataa | aaacttctca | acattgcaga | 420 |
| cggtgctatg | tgctcaggga | ggtggtgctt | acaagtttga | aaaagatttt | cgcacaattg | 480 |
| gaaacctcca | cctgcacaaa | ctggatgaac | ttgactgcct | tgtaaagggc | ttgctgtata | 540 |
| tagactctgt | cagtttcaat | ggacaagccg | agtgctatta | ttttgctaat | gcctcagaac | 600 |
| ctgagcgatg | ccaaaagatg | cctttaacc | tggatgatcc | ctatccactg | cttgtagtga | 660 |
| acattggctc | aggagtcagt | attttagcag | tccattccaa | agacaactat | aaacgagtga | 720 |
| ctgggacaag | tcttggaggg | gtacctata | ctgggtttat | gcagttattg | actggctgtg | 780 |
| aaagttttga | agaggctctt | gaaatggcat | ccaaaggtga | tagcacacaa | gctgacaagc | 840 |
| tggtccgtga | tatttatgga | ggagattatg | aaagatttgg | tttgccaggt | tgggctgtag | 900 |
| catctagttt | tgggaatatg | atttataagg | agaagcgaga | atctgttagt | aaagaagatc | 960 |
| tggcaagagc | tactttagtt | actatcacca | ataacattgg | ttctgtggca | cgaatgtgtg | 1020 |
| ctgttaatga | gaaaataaac | agagttgtct | ttgttggaaa | cttttacgt | gtcaataccc | 1080 |
| tctcaatgaa | acttttggca | tatgcactgg | attactggtc | aaaaggtcaa | ctaaaagcat | 1140 |
| tgtttctaga | acatgagggt | tactttggag | cagttggtgc | acttcttggg | ctgccaaatt | 1200 |
| tcagctaaag | catcaggtct | ctctctctgc | taataaatgt | catccaagag | gaactaaaac | 1260 |
| cagaggcatt | attactgcat | tgttttgtcac | tgggaaccaa | aggataaaag | agtagcataa | 1320 |
| gctgctgaat | gttgccatat | taaggagag | aacttggtaa | cgtgaagtat | ttctcattga | 1380 |
| aatgctttcc | cttttgtata | tagccagtgt | taaatcctta | aatgcaatac | agcctctgat | 1440 |
| tattgagctt | cctcttaaaa | agattttttt | attttatgta | gccaacattg | cagtactgta | 1500 |
| tgctcaaaca | caaatcttaa | agtatcggaa | ctgtttagct | tatgaaaata | atcgactctg | 1560 |
| aatatttgtt | acaagtctgt | tttatgtgtt | ttgattacta | gtgagcagaa | ataacatac | 1620 |
| cctgtattca | aaattactga | aatggcaatc | aaagatgatc | attttttatgt | gattttagaa | 1680 |
| atgttaaggc | aatactacta | attattgtag | gttttttttaa | cgtatcaccc | aaagcatgta | 1740 |
| tgtgatcttt | ccccattagt | atcttttttct | caaatgccat | aattaactga | aatactatta | 1800 |
| ttaaattttg | taga | | | | | 1814 |

<210> SEQ ID NO 31
<211> LENGTH: 4381
<212> TYPE: DNA
<213> ORGANISM: Homo sapiens
<220> FEATURE:
<221> NAME/KEY: misc_feature
<223> OTHER INFORMATION: Incyte ID No: 1989319CB1

<400> SEQUENCE: 31

-continued

```
atggcggcgg cggcggcgag cggagctggc ggggctgccg gggccgggac tgggggagcc      60
gggcccgcgg gccgcctgct gcctccgccc gcgccgggt ccccagccgc cccgctgcc       120
gtgtccctg cggccggcca gccgcgtccc ccagccccgg cctcccgcgg acccatgccc      180
gcccgtatcg gctactacga gatcgaccgc accatcggca agggcaactt cgcggtggtc      240
aagcgggcca cgcacctcgt caccaaggcc aaggttgcta tcaagatcat agataagacc      300
cagctggatg aagaaaactt gaagaagatt ttccgggaag ttcaaattat gaagatgctt      360
tgccaccccc atatcatcag gctctaccag gttatggaga cagaacggat gatttatctg      420
gtgacagaat atgctagtgg agggaaata tttgaccacc tggtggccca tggtagaatg       480
gcagaaaagg aggcacgtcg gaagttcaaa cagatcgtca cagctgtcta ttttgtcac       540
tgtcggaaca ttgttcatcg tgatttaaaa gctgaaaatt tacttctgga tgccaatctg      600
aatatcaaaa tagcagattt tggtttcagt aacctcttca ctcctgggca gctgctgaag      660
acctggtgtg gcagccctcc ctatgctgca cctgaactct tgaaggaaa agaatatgat       720
gggcccaaag tggacatctg gagccttgga gttgtcctct acgtgcttgt gtgcggtgcc      780
ctgccatttg atggaagcac actgcagaat ctgcgggccc gcgtgctgag tggaaagttc      840
cgcatcccat tttttatgtc cacagaatgt gagcatttga tccgccatat gttggtgtta      900
gatcccaata agcgcctctc catggagcag atctgcaagc acaagtggat gaagctaggg      960
gacgccgatc ccaactttga caggttaata gctgaatgcc aacaactaaa ggaagaaaga     1020
caggtggacc ccctgaatga ggatgtcctc ttggccatgg aggacatggg actggacaaa     1080
gaacagacac tgcagtcatt aagatcagat gcctatgatc actatagtgc aatctacagc     1140
ctgctgtgtg atcgacataa agacataaa accctgcgtc tcggagcact tcctagcatg      1200
ccccgagccc tggcctttca agcaccagtc aatatccagg cggagcaggc aggtactgct     1260
atgaacatca gcgttcccca ggtgcagctg atcaacccag agaaccaaat tgtggagccg     1320
gatgggacac tgaatttgga cagtgatgag ggtgaagagc cttcccctga agcattggtg     1380
cgctatttgt caatgaggag gcacacagtg ggtgtggctg acccacgcac ggaagttatg     1440
gaagatctgc agaagctcct acctggcttt cctggagtca accccaggc tccattcctg      1500
caggtggccc ctaatgtgaa cttcatgcac aacctgttgc ctatgcaaaa cttgcaacca     1560
accgggcaac ttgagtacaa ggagcagtct ctcctacagc cgcccacgct acagctgttg     1620
aatggaatgg gccccccttgg ccggagggca tcagatggag gagccaacat ccaactgcat     1680
gcccagcagc tgctgaagcg cccacgggga ccctctccgc ttgtcaccat gacaccagca     1740
gtgcagcag ttaccctgt ggacgaggag agctcagacg gggagccaga ccaggaagct       1800
gtgcagaggt acttggcaaa taggtccaaa agacatacac tggccatgac caaccctaca     1860
gctgagatcc caccggacct acaacggcag ctaggacagc agcctttccg ttcccgggtc     1920
tggcctcctc acctggtacc tgatcagcat cgctctacct acaaggactc caacactctg     1980
cacctcccta cggagcgttt ctcccctgtg cgccggttct cagatggggc tgcgagcatc     2040
caggccttca agctcacct ggaaaaaatg ggcaacaaca gcagcatcaa acagctgcag      2100
caggagtgtg agcagctgca gaagatgtac gggggcaga ttgatgaaag aaccctggag      2160
aagacccagc agcagcatat gttataccag caggagcagc accatcaaat tctccagcaa     2220
caaattcaag actctatctg tcctcctcag ccatctccac ctcttcaggc tgcatgtgaa     2280
aatcagccag ccctccttac ccatcagctc cagaggttaa ggattcagcc ttcaagccca     2340
```

-continued

```
cccccccaacc accccaacaa ccatctcttc aggcagccca gtaatagtcc tcccccatg    2400 agcagtgcca tgatccagcc tcacggggct gcatcttctt cccagtttca aggcttacct    2460
tcccgcagtg caatctttca gcagcaacct gagaactgtt cctctcctcc caacgtggca    2520
ctaacctgct tgggtatgca gcagcctgct cagtcacagc aggtcaccat ccaagtccaa    2580
gagcctgttg acatgctcag caacatgcca ggcacagctg caggctccag tgggcgcggc    2640
atctccatca gccccagtgc tggtcagatg cagatgcagc accgtaccaa cctgatggcc    2700
accctcagct atgggcaccg tcccttgtcc aagcagctga gtgctgacag tgcagaggct    2760
cacagcttga acgtgaatcg gttctcccct gctaactacg accaggcgca tttacacccc    2820
catctgtttt cggaccagtc ccggggttcc cccagcagct acagcccttc aacaggagtg    2880
gggttctctc caacccaagc cctgaaagtc cctccacttg accaattccc caccttccct    2940
cccagtgcac atcagcagcc gccacactat accacgtcgg cactacagca ggccctgctg    3000
tctcccacgc cgccagacta tacaagacac cagcaggtac cccacatcct tcaaggactg    3060
ctttctcccc ggcattcgct caccggccac tcggacatcc ggctgccccc aacagagttt    3120
gcacagctca ttaaaaggca gcagcaacaa cggcagcagc agcagcaaca gcagcaacag    3180
caagaatacc aggaactgtt caggcacatg aaccaagggg atgcggggag tctggctccc    3240
agccttgggg gacagagcat gacagagcgc caggctttat cttatcaaaa tgctgactct    3300
tatcaccatc acaccagccc ccagcatctg ctacaaatca gggcacaaga atgtgtctca    3360
caggcttcct cacccacccc gccccacggg tatgctcacc agccggcact gatgcattca    3420
gagagcatgg aggaggactg ctcgtgtgag ggggccaagg atggcttcca agacagtaag    3480
agttcaagta cattgaccaa aggttgccat gacagccctc tgctcttgag taccggtgga    3540
cctggggacc ctgaatcttt gctaggaact gtgagtcatg cccaagaatt ggggatacat    3600
ccctatggtc atcagccaac tgctgcattc agtaaaaata aggtgcccag cagagagcct    3660
gtcataggga actgcatgga tagaagttct ccaggacaag cagtggagct gccggatcac    3720
aatgggctcg gtacccagc acgcccctcg gtccatgagc accacaggcc ccgggccctc    3780
cagagacacc acacgatcca gaacagcgac gatgcttatg tacagctgga taacttgcca    3840
ggaatgagtc tcgtggctgg gaaagcactt agctctgccc ggatgtcgga tgcagttctc    3900
agtcagtctt cgctcatggg cagccagcag tttcaggatg gggaaaatga ggaatgtggg    3960
gcaagcctgg gaggtcatga gcacccgac ctgagtgatg gcagccagca tttaaactcc    4020
tcttgctatc catctacgtg tattacagac attctgctca gctacaagca ccccgaagtc    4080
tccttcagca tggagcaggc aggcgtgtaa caagaaacag agagttttgt gtacagcttg    4140
ggaatgaaaa ggttgattgt aaacccacag tatctagcag cgttgtgcca aattgccctt    4200
gtgtttctct ccacccaaaa tatcacagct gctttcctca catttggttc atccgtgtgc    4260 tgttctttg ggttctgaga gggttttgcc atgtttgctt gtatgaccaa gtcaccaagg    4320
aaataaacag gaaggaaatc catgttctcc atctttgtg aaagtatatt tgagttggtg    4380
g                                                                   4381
```

<210> SEQ ID NO 32
<211> LENGTH: 7862
<212> TYPE: DNA
<213> ORGANISM: Homo sapiens
<220> FEATURE:
<221> NAME/KEY: misc_feature
<223> OTHER INFORMATION: Incyte ID No: 079284CB1

<400> SEQUENCE: 32

```
atcccacaga cagcgctttg agcagaacgc acggctcaac tcatgtaatt actgtttata      60
gctggccgag cctgactagg agagggcaga cccgagaggg aatcagtttc ccggaccttt     120
gagaggaggc tgtgtgttaa ttaaaggcta ggacgggacg ggtacttctc agacatgctc     180
caagttgttc ttgagatcac agttcccatc acatttctc tggagggagt gagtagataa      240
ttgggatttt ttttttattt ttggccttgt ctttcttcct tttttttacc tctcccatt      300
ttagtcatat ggccttgaac ccacagtgaa ttgaagagag aaagaaatgg gtatgtctga     360
ccccaatttt tggactgtgc tctcaaactt tactttgcct catttgagga gtgggaacag     420
gcttcggcga acacaaagtt gccgaacaag caaccggaaa agcttaatag gcaatgggca     480
gtcaccagca ttgcctcgac cacactcacc tctctctgct catgcaggaa atagccctca     540
agatagtcca agaaatttct cccccagtgc ctcagcccat ttttcatttg cacggaggac     600
tgatggacgc cgctggtcgt tggcttctct cccttcctct ggctatggga caaacacacc     660
cagctctacg gtctcttcat cctgttcctc ccaggagaag ttgcatcagt taccatacca     720
accaacacca gacgagttac acttcttatc aaaacatttc tgtaccaccg aaagcatcgc     780
cactgagaac agatgcagga acacgccgat gcgcccccgt tcccgaagtc tgagccctgg     840
acgttctccc gcctgctgtg accatgaaat aattatgatg aaccatgtct acaaagaaag     900
gttcccaaag gctacagctc agatggaaga acgtctaaag gaaattatca ccagctactc     960
tcctgacaac gttctaccct tagcagatgg agtgcttagt ttcactcacc accagattat    1020
tgaactggct cgagattgct tggataaatc ccaccagggc ctcatcacct cacgatactt    1080
ccttgaatta cagcacaaat tagataagtt gctacaggag gctcatgatc gttcagaaag    1140
tggagaattg gcatttatta acaactagt tcgaaagatc ctaattgtta ttgcccgccc    1200
tgctcggtta ttagagtgcc tggaatttga tccggaagaa ttttactacc tattggaagc    1260
agcagaaggc catgccaaag aaggacaggg tattaaaacc gacattccca ggtacatcat    1320
tagccaactg ggactcaata aggatcccctt ggaagaaatg gctcatttgg gaaactacga    1380
tagtgggaca gcagaaacac cagaaacaga tgaatcagtg agtagctcta atgcctccct    1440
gaaacttcga aggaaacctc gggaaagtga ttttgaaacg attaaattga ttagcaatgg    1500
agcctatggg gcagtctact tgttcggca taaagaatcc cggcagaggt ttgccatgaa    1560
gaagattaat aaacagaacc tcatccttcg aaaccagatc cagcaggcct tgtggagcg    1620
ggatatcctg acttttgcag aaaacccctt tgttgtcagc atgtattgct cctttgaaac    1680
aaggcgccac ttgtgcatgg tcatggaata tgtggaaggg ggagactgtg ctactttaat    1740
gaaaaacatg ggtcctctcc ctgttgatat ggccagaatg tactttgctg agacggtctt    1800
ggccttggaa tatttacata attatggaat tgtacacagg gatttgaaac cagacaactt    1860
gttggttacc tccatgggc acataaagct gacagatttt ggattatcta aggtgggact    1920
aatgagcatg actaccaacc tttacgaggg tcatattgag aaggatgcta gagagttcct    1980
ggataaacag gtctgtggca cacctgaata cattgcacca gaagtgattc tgaggcaggg    2040
ttatggaaag ccggtggact ggtgggccat ggggattatc ctctatgaat ttctggttgg    2100
atgcgtgcca ttctttgggg atactccaga ggagctattt ggacaagtca tcagtgatga    2160
gatcaactgg cctgagaagg atgaggcacc cccacctgat gcccaggatc tgattacctt    2220
actcctcagg cagaatcccc tggagaggct gggaacaggt ggtgcatatg aagtcaaaca    2280
gcatcgattc ttccgttctt tagactggaa cagtttgctg agacagaagg cagaatttat    2340
```

-continued

```
tccccaactg gaatctgagg atgacacaag ttattttgat actcggtctg agaagtatca    2400
tcatatggaa acggaggaag aagatgacac aaatgatgaa gactttaatg tggaaataag    2460
gcagttttct tcatgttcac acaggttttc aaaagttttc agcagtatag atcgaatcac    2520
tcagaattca gcagaagaga aggaagactc tgtggacaaa accaaaagca ccaccttgcc    2580
atccacagaa acactgagct ggagttcaga atattctgaa atgcaacagc tatcaacatc    2640
caactcttca gatactgaaa gcaacagaca taaactcagt tctggcctac ttcccaaact    2700
ggctatttca acagagggag agcaagatga agctgcctcc tgccctggag accccccatga   2760 ggagccagga aagccagccc ttcctcctga agagtgtgcc caggaggagc ctgaggtcac    2820
caccccagcc agcaccatca gcagctccac cctgtcagtt ggcagttttt cagagcactt    2880
ggatcagata aatggacgaa gcgagtgtgt ggacagtaca gataattcct caaagccatc    2940
cagtgaaccc gcttctcaca tggctcggca gcgattagaa agcacagaaa aaagaaaat    3000 ctcggggaaa gtcacaaagt ccctctctgc cagtgctctt tccctcatga tcccaggaga    3060
tatgtttgct gtttccctc tgggaagtcc aatgtctccc cattccctgt cctcggaccc     3120
ttcttcttca cgagattcct ctcccagccg agattcctca gcagcttctg ccagtccaca    3180
tcagccgatt gtgatccaca gttcggggaa gaactacggc tttaccatcc gagccatccg    3240
ggtgtatgtg ggagacagtg acatctatac agtgcaccat atcgtctgga atgtagaaga    3300
aggaagtccg gcatgccagg caggactgaa ggctggagat cttatcactc ccatcaatgg    3360
agaaccagtg catggacttg tccacacaga agttatagaa ctcctactga agagtgggaa    3420
taaggtgtca atcactacta ccccatttga aaacacatca atcaaaactg accagccag    3480 gagaaacagc tataagagcc ggatggtgag gcggagcaag aaatccaaga agaaagaaag    3540
tctcgaaagg aggagatctc ttttcaaaaa gctagccaag cagccttctc ctttactcca    3600
caccagccga agtttctcct gcttgaacag atccctgtca tcgggtgaga gcctcccagg    3660
ttcccccact catagcttgt ctccccggtc tccaacacca agctaccgct ccacccctga    3720
cttcccatct ggtactaatt cctcccagag cagctcccct agttctagtg cccccaattc    3780
cccagcaggg tccgggcaca tccggcccag cactctccac ggtcttgcac ccaaactcgg    3840
cgggcagcgg taccggtccg gaaggcgaaa gtccgccggc aacatcccac tgtcccgct    3900 ggcccggacg ccctctccaa ccccgcaacc cacctccccg cagcggtcac catcccctct    3960
tctgggacac tcactgggca attccaagat cgcgcaagcc tttcccagca agatgcactc    4020
cccgcccacc atcgtcagac acatcgtgag gcccaagagt gcggagcccc ccaggtcccc    4080
gctgctcaag cgcgtgcagt ccgaggagaa gctgtcgccc tcttacggca gtgacaagaa    4140
gcacctgtgc tcccgcaagc acagcctgga ggtgacccaa gaggaggtgc agcgggagca    4200
gtcccagcgg gaggcgccgc tgcagagcct ggatgagaac gtgtgcgacg tgccgccgct    4260
cagccgcgcc cggccagtgg agcaaggctg cctgaaacgc ccagtctccc ggaaggtggg    4320
ccgccaggag tctgtggacg acctggaccg cgacaagctg aaggccaagg tggtggtgaa    4380
gaaagcagac ggcttcccag agaaacagga atcccaccag aaatcccatg acccgggag    4440 tgatttggaa aactttgctc tgtttaagct ggaagagaga gagaagaaag tctatccgaa    4500
ggctgtggaa aggtcaagta cttttgaaaa caaagcgtct atgcaggagg cgccaccgct    4560
gggcagcctg ctgaaggatg ctcttcacaa gcaggccagc gtgcgcgcca gcagggtgc    4620 gatgtcggat ggcccggtgc ctgcggagca ccgccagggt ggcggggact tcagacgggc    4680
```

```
ccccgctcct ggcaccctcc aggatggtct ctgccactcc ctcgacaggg gcatctctgg    4740 gaaggggaa ggcacggaga agtcctccca ggccaaggag cttctccgat gtgaaaagtt    4800
agacagcaag ctggccaaca tcgattacct ccgaaagaaa atgtcacttg aggacaaaga    4860
ggacaacctc tgccctgtgc tgaagcccaa gatgacagct ggctcccacg aatgcctgcc    4920
agggaaccca gtccgaccca cgggtgggca gcaggagccc ccgccggctt ctgagagccg    4980
agcttttgtc agcagcaccc atgcagctca gatgagtgcc gtctcttttg ttcccctcaa    5040
ggccttaaca ggccgggtgg acagtggaac ggagaagcct ggcttggttg ctcctgagtc    5100
ccctgttagg aagagcccct ccgagtataa gctggaaggt aggtctgtct catgcctgaa    5160
gccgatcgag ggcactctgg acattgctct cctgtccgga cctcaggcct ccaagacaga    5220
actgccttcc ccagagtctg cacagagccc cagcccaagt ggtgacgtga gggcctctgt    5280
gccaccagtt ctccccagca gcagtgggaa aaagaacgat accaccagtg caagagagct    5340
ttctccttcc agcttaaaga tgaataaatc ctacctgctg gagccttggt tcctgccccc    5400
cagccgaggt ctccagaatt caccagcagt ttccctgcct gacccagagt tcaagaggga    5460
caggaaaggt ccccatccta ctgccaggag ccctggaaca gtcatggaaa gcaatcccca    5520
acagagagag ggcagctccc ctaaacacca agaccacacc actgacccca gcttctgac     5580 ctgcctgggg cagaacctcc acagcccctga cctggccagg ccacgctgcc cgctcccacc    5640
tgaagcttcc ccctcaaggg agaagccagg cctgagggaa tcgtctgaaa gaggccctcc    5700
cacagccaga agcgagcgct ctgctgcgag ggctgacaca tgcagagagc cctccatgga    5760
actgtgcttt ccagaaactg cgaaaaccag tgacaactcc aaaaatctcc tctctgtggg    5820
aaggacccac ccagatttct atacacagac ccaggccatg gagaaagcat gggcgccggg    5880
tgggaaaacg aaccacaaag atggcccagg tgaggcgagg cccccgccca gagacaactc    5940
ctctctgcac tcagctggaa ttccctgtga gaaggagctg ggcaaggtga ggcgtggcgt    6000
ggaacccaag cccgaagcgc ttcttgccag gcggtctctg cagccacctg gaattgagag    6060
tgagaagagt gaaaagctct ccagtttccc atctttgcag aaagatggtg ccaaggaacc    6120
tgaaaggaag gagcagcctc tacaaaggca tcccagcagc atccctccgc cccctctgac    6180
ggccaaagac ctgtccagcc cggctgccag gcagcattgc agttccccaa gccacgcttc    6240
tggcagagag ccgggggcca agcccagcac tgcagagccc agctcgagcc cccaggaccc    6300
tcccaagcct gttgctgcgc acagtgaaag cagcagccac aagccccggc ctggccctga    6360
cccgggccct ccaaagacta agcaccccga ccggtccctc tcctctcaga aaccaagtgt    6420
cggggccaca aagggcaaag agcctgccac tcaatccctc ggtggctcta gcagagaggg    6480
gaagggccac agtaagagtg ggccggatgt gtttcctgct accccaggct cccagaacaa    6540
agccagcgat gggattggcc agggagaagg tgggccctct gtcccactgc acactgacag    6600
ggctcctcta gacgccaagc cacaacccac cagtggtggg cggcccctgg aggtgctgga    6660
gaagcctgtg catttgccaa ggccgggaca cccagggcct agtgagccag cggaccagaa    6720
actgtccgct gttggtgaaa gcaaaccct gtctccaaag caccccaaac catccactgt     6780
gaaagattgc cccaccctgt gcaaacagac agacaacaga cagacagaca aaagcccgag    6840
tcagccggcc gccaacaccg acagaagggc ggaagggaag aaatgcactg aagcacttta    6900
tgctccagca gagggcgaca agctcgaggc cggccttttcc tttgtgcata gcgagaaccg    6960
gttgaaaggc gcggagcggc cagccgcggg ggtgggggaag gcttccctg aggccagagg    7020 gaaagggccc ggtccccaga agccaccgac ggaggcagac aagcccaatg gcatgaaacg    7080
```

-continued

```
gtcccctca gccactgggc agagttcttt ccgatccacg gccctcccgg aaaagtctct    7140
gagctgctcc tccagcttcc ctgaaaccag ggccggagtt agagaggcct ctgcagccag    7200
cagcgacacc tcttctgcca aggccgccgg gggcatgctg gagcttccag cccccagcaa    7260
cagggaccat aggaaggctc agcctgccgg ggagggccga acccacatga caaagagtga    7320
ctccctgccc tccttccggg tctccaccct gcctctggag tcacaccacc ccgacccaaa    7380
caccatgggc ggggccagcc accgggacag ggctctctcg gtgactgcca ccgtagggga    7440
aaccaaaggg aaggaccctg ccccagccca gcctcccca gctaggaaac agaacgtggg     7500
cagagacgtg accaagccat ccccagcccc aaacactgac cgccccatct ctctttctaa    7560
tgagaaggac tttgtggtac ggcagaggcg ggggaaagag agtttgcgta gcagccctca    7620
caaaaaggcc ttgtaacggg gagggcccag ggcaggact gtggagaccc gtcctgaacg     7680
ggcgactgtg tcttgactac cttcaaaac cagcactgtg tgggaatgtc cgccaggcag     7740
agctcggagc ctcattgaga caggggagag agaaagacaa agagggggacc ttcttccaga   7800 tgccttccca gttgtaaccg gtaaaactgt taccagatag tgtttgtaca aaaaaaaaaa    7860
aa                                                                    7862

<210> SEQ ID NO 33
<211> LENGTH: 7280
<212> TYPE: DNA
<213> ORGANISM: Homo sapiens
<220> FEATURE:
<221> NAME/KEY: misc_feature
<223> OTHER INFORMATION: Incyte ID No: 5502218CB1

<400> SEQUENCE: 33
tcggcgagcg gcggcagtgg gagccgcgtc cgccgcatcc gcctcgactc ggtgccggcc     60
        cctggccctc ccctcatgac tgcggcgcct ctgctgccac cgcccgcccg gccgccgctc   120
        gccgcaggat ggatgcggac cgtgcggcgc taaccccgt ggctcagctc ccgaatcgcc    180
        cgccttcgag ccctcctcgt gagccgcagc agcctcggtg ccagccccg ccgcagctgg    240
        gcccagcggt ccgcctgtcc ctcgttgcgg cttgtcggtg ctgagtgagg cgtcgtccgg    300
        gtcggcgcga acccgcccgg ccgcggttcc ctgcagacct ctgcgcgggc ggctcggccc   360
        ttcacgccct tttcgttcac gaatccgagc ccgctcgcct ctctccagcg aaccgaccat    420
        gtctgcggc gccgcagaga agcagagcag cactcccggt tccctgttcc tctcgccgcc    480
        ggctcctgcc cccaagaatg gctccagctc cgattcctcc gtgggggaga aactgggagc    540
        cgcggccgcc gacgctgtga ccggcaggac cgaggagtac aggcgccgcc gccacactat    600
        ggacaaggac agccgtgggg cggccgcgac cactaccacc actgagcacc gcttcttccg    660
        ccggagcgtc atctgcgact ccaatgccac tgcactggag cttcccggcc ttcctctttc    720
        cctgccccag cccagcatcc ccgcggctgt cccgcagagt gctccaccgg agccccaccg    780
        ggaagagacc gtgaccgcca ccgccacttc ccaggtagcc cagcagcctc cagccgctgc    840
        cgcccctggg gaacaggccg tcgcgggccc tgcccctcg actgtcccca gcagtaccag    900
        caaagaccgc ccagtgtccc agcctagcct tgtggggagc aaagaggagc cgccgccggc    960
        gagaagtggc agcggcggcg gcagcgccaa ggaccacag gaggaacgga gccagcagca   1020
        ggatgatatc gaagagctgg agaccaaggc cgtgggaatg tctaacgatg gccgctttct   1080
        caagtttgac atcgaaatcg cagaggctc ctttaagacg gtctacaaag gtctggacac   1140
        tgaaaccacc gtggaagtcg cctggtgtga actgcaggat cgaaaattaa caaagtctga   1200
        gaggcagaga tttaagaag aagctgaaat gttaaaaggt cttcagcatc ccaatattgt    1260
        tagatttttat gattcctggg aatccacagt aaaagagaaa aagtgcattg ttttggtgac    1320
        tgaacttatg acgtctggaa cacttaaaac gtatctgaaa aggttaaag tgatgaagat    1380
        caaagttcta agaagctggt gccgtcagat ccttaaaggt cttcagttc ttcatactcg     1440
        aactccacct atcattcacc gcgatcttaa atgtgacaac atctttatca ccggccctac   1500
        tggctcagtc aagattggag acctcggtct ggcaaccatg aagcgggctt cttttgccaa   1560
        gagtgtgata ggtacccag agttcatggc ccctgactg tatgaggaga aatatgatga   1620
        atccgttgac gtttatgctt ttgggatgtg catgcttgag atggctacat ctgaatatcc    1680
        ttactcggag tgccaaaatg ctgcgcagat ctaccgtcgc gtgaccagtg ggtgaagcc    1740
        agccagtttt gacaaagtag caattcctga agtgaaggaa attattgaag atgcatacg    1800
        acaaaacaaa gatgaaagat attccatcaa agccttttg aacatgcct tcttccaaga   1860
        ggaaacagga gtacgggtag aattagcaga agaagatgat ggagaaaaaa tagccataaa    1920
        attatggcta cgtattgaag atattaagaa attaaaggga aaatacaaag ataatgaagc   1980
        tattgagttt tcttttgatt tagagagaga tgtcccagaa gatgttcac aagaaatggt    2040
        agagtctggg tatgtctgtg aagtgatca caagaccatg tcaaagcta tcaaagacag    2100
        agtatcatta attaagagga aacgagagca gcggcagttg gtacgggagg agcaagaaaa    2160
        aaaaagcag gaagagagca gtctccaaca gcaggtagaa caatccagtg cttcccagac    2220
        aggaatcaag cagctcccctt ctgctagcac cggcatacct actgcttcta ccacttcagc    2280
        ttcagttttct acacaagtag aacctgaaga acctgaggca gatcaacatc aacaactaca    2340
```

```
gtaccagcaa cccagtatat ctgtgttatc tgatgggacg gttgacagtg gtcagggatc 2400
ctctgtcttc acagaatctc gagtgagcag ccaacagaca gtttcatatg gttcccaaca 2460
tgaacaggca cattctacag gcacagtccc agggcatata ccttctactg tccaagcaca 2520
gtctcagccc catggggtat atccaccctc aagtgtggca caggggcaga gccagggtca 2580
gccatcctca agtagcttaa caggggtttc atcttcccaa cccatacaac atcctcagca 2640
gcagggaata cagcagacag cccctcctca acagacagtg cagtattcac tttcacagac 2700
atcaacctcc agtgaggcca ctactgcaca gccagtgagt caacctcaag ctccacaagt 2760
cttgcctcaa gtatcagctg gaaaacagag tactcaggga gtctctcagg ttgctcctgc 2820
agagccagtt gcagtagcac agccccaagc tacccagccg accactttgg cttcctctgt 2880
agacagtgca cattcagatg ttgcttcagg tatgagtgat ggcaatgaga acgtcccatc 2940
ttccagtgga aggcatgaag gaagaactac aaaacggcat taccgaaaat ctgtaaggag 3000
tcgctctcga catgaaaaaa cttcacgccc aaaattaaga attttgaatg tttcaaataa 3060
aggagaccga gtagtagaat gtcaattaga gactcataat aggaaaatgg ttacattcaa 3120
atttgaccta gatggtgaca accccgagga gatagcaaca attatggtga acaatgactt 3180
tattctagca atagagagag agtcgtttgt ggatcaagtg cgagaaatta ttgaaaaagc 3240
tgatgaaatg ctcagtgagg atgtcagtgt ggaaccagag ggtgatcagg gattggagag 3300
tctacaagga aaggatgact atggcttttc aggttctcag aaattggaag gagagttcaa 3360
acaaccaatt cctgcgtctt ccatgccaca gcaaataggc attcctacca gttctttaac 3420
tcaagttgtt cattctgcgg gaaggcggtt tatagtgagt cctgtgccag aaagccgatt 3480
acgagaatca aaagttttcc ccagtgaaat aacagataca gttgctgcct ctacagctca 3540
gagccctgga atgaacttgt ctcactctgc atcatccctt agtctacaac aggcctttc 3600
tgaacttaga cgtgcccaaa tgacagaagg acccaataca gcacctccaa actttagtca 3660
tacaggacca acatttccag tagtacctcc tttcttaagt agcattgctg gagtcccaac 3720
cacagcagca gccacagcac cagtccctgc aacaagcagc cctcctaatg acatttccac 3780
atcagtaatt cagtctgagg ttacagtgcc cactgaagag gggattgctg gagttgccac 3840
cagcacaggt gtggtaactt caggtggtct ccccatacca cctgtgtctg aatcaccagt 3900
actttccagc gtagtttcaa gtatcacaat acctgcagtt gtctcaatat ctactacatc 3960
cccgtcactt caagtcccca catcccacat tgatatcgtt gttctagta cagcactgta 4020
tccttcagta acagtttcag caacttcagc ctctgcaggg gcagtactg ctaccccagg 4080
tcctaagcct ccagctgtag tatctcagca ggcagcaggc agcactactg tgggagccac 4140
attaacatca gtttctacca ccacttcatt cccaagcaca gcttcacagc tgtccattca 4200
gcttagcagc agtacttcta ctcctacttt agctgaaacc gtggtagtta gcgcacactc 4260
actagataag acatctcata gcagtacaac tggattggcg ttctccctct ctgcaccatc 4320
ttcctcttcc tctcctggag caggagtgtc tagttatatt tctcagcctg gtgggctgca 4380
tcctttggtc attccatcag tgatagcttc tactcctatt cttccccaag cagcaggacc 4440
tacttctaca cctttattac cccaagtacc tagtatccca cccttggtac agcctgttgc 4500
caatgtgcct gctgtacagc agacactaat tcatagtcag cctcaaccag ctttgcttcc 4560
caaccagccc catactcatt gtcctgaagt agattctgat acacaaccca aagctcctgg 4620
aattgatgac ataaagactc tagaagaaaa gctgcggtct ctgttcagtg aacacagctc 4680
atctggagct cagcatgcct ctgtctcact ggagacctca ctagtcatag agagcactgt 4740
cacaccaggc atcccaacta ctgctgttgc accaagcaga ctcctgactt ctaccacaag 4800
tacttgctta ccaccaacca atttaccact aggaacagtt gctttgccag ttacaccagt 4860
ggtcacacct gggcaagttt ctaccccagt cagcactact acatcaggag tgaaacctgg 4920
aactgctccc tccaagccac ctctaactaa ggctccggtg ctgccagtgg gtactgaact 4980
tccagcaggt actctaccca gcgagcagct gccaccttt ccaggacctt ctctaaccca 5040
gtcccagcca cctctagagg atcttgatgc tcaattgaga agaacactta gtccagagat 5100
gatcacagtg acttctgcgg ttggtcctgt gtccatgcg gctccaacag caatcacaga 5160
agcaggaaca cagcctcaga agggtgtttc tcaagtcaaa gaaggccctg tcctagcaac 5220
tagttcagga gctggtgttt ttaagatggg acgatttcag gtttctgttg cagcagacgg 5280
tgcccagaaa gagggtaaaa ataagtcaga agatgcaaag tctgttcatt ttgaatccag 5340
cacctcagag tcctcagtgc tatcaagtag tagtccagag agtaccttgg tgaaaccaga 5400
gccgaatggc ataaccatcc ctggtatctc ttcagatgtg ccagagagtg cccacaaaac 5460
tactgcctca gaggcaaagt cagacactgg gcagcctacc aaggttggac gttttcaggt 5520
gacaactaca gcaaacaaag tgggtcgttt ctctgtatca aaaactgagg acaagatcac 5580
tgcacaaaag aaagaaggac cagtggcatc tcctcctttt atggatttgg aacaagctgt 5640
tcttcctgct gtgataccaa agaaagagaa gcctgaactg tcagagcctt cacatctaaa 5700
tgggccgtct tctgacccgg aggccgcttc tttaagtagg gatgtggatg atggttccgg 5760
tagtccacac tcgcccccatc agctgagctc aaagagcctt cctagccaga atctaagtca 5820
aagccttagt aattcattta actcctctta catgagtagc gacaatgagt cagatatcga 5880
agatgaagac ttaaagttag agctgcgacg actacgagat aaacatctca aagagattca 5940
ggacctgcag agtcgccaga agcatgaaat tgaatctttg tataccaaac tgggcaaggt 6000
gccccctgct gttattattc ccccagctgc tccccttta gggagaagac gacgacccac 6060
taaaagcaaa ggcagcaaat ctagtcgaag cagttccttg gggaataaaa gccccccagct 6120
ttcaggtaac ctgtctggtc agagtcagc ttcagtcttg caccccagc agaccctcca 6180
ccctcctggc aacatcccag agtccgggca gaatcagctg ttacagcccc ttaagccatc 6240
tccctccagt gacaacctct attcagcctt caccagtagt ggtgccattt cagtaccaag 6300
cctttctgct ccaggtcaag gaaccagcag cacaaacact gttggggcaa cagtgaacag 6360
ccaagccgcc caagctcagc ctcctgccat gacgtccagc aggaagggca cattcacaga 6420
tgacttgcac aagttggtag acaattgggc ccgagatgcc atgaatctct caggcaggag 6480
aggaagcaaa gggcacatga attatgaggg ccctggaatg gcaaggaagt tctctgcacc 6540
tgggcaactg tgcatctcca tgacctcgaa cctggctgc tctgcccca tctctgcagc 6600
atcagctacc tctctaggtc acttcaccaa gtctatgtgc ccccacagc agtatggctt 6660
tccagctacc ccatttggcg ctcaatggaa tgggacgggt ggcccagcac cacagccact 6720
tggccagttc aacctgctgg gaactgcctc cttgcagaat ttcaacatca gcaatttgca 6780
gaaatccatc agcaaccccc caggctccaa cctgacctt acttagacct agagacatta 6840
actgaataga tctgggggca ggagatggaa tgctgagggg gtgggtgggg gtgggaagta 6900
gcctatatac taactactag tgctgcattt aactggttat ttcttgccag aggggaatgt 6960
ttttaatact gcattgagcc ctcagaatgg agagtctccc ccgctccagt tattggaatg 7020
ggagaggaag gaaagaacag ctttttttgtc aaggggcagc ttcagaccat gctttcctgt 7080
```

```
ttatctatac tcagtaatga ggatgagggc taggaaagtc ttgttcataa ggaagctgga   7140
gaactcaatg taaaatcaaa cccatctgta atttcgagtg ggtggagctc ttgcttttgg   7200
tacatgccct gaatccctca ctccctcaag aatccgaacc acaggacaaa aaccacctac   7260
tgggctctct cctaccctgc                                               7280
```

<210> SEQ ID NO 34
<211> LENGTH: 1260
<212> TYPE: DNA
<213> ORGANISM: Homo sapiens
<220> FEATURE:
<221> NAME/KEY: misc_feature
<223> OTHER INFORMATION: Incyte ID No: 55056054CB1

<400> SEQUENCE: 34

```
gaagttgtga gctccttctg gaaacatttg cagttacatt aagtaaagtg taaatgcaca     60
tgaatggcag cttatagaga accaccttgt aaccagtata caggtacaac tacagctctt    120
cagaaattgg aaggttttgc tagccggtta tttcatagac actctaaagg tactgcacat    180
gatcagaaaa cagctctgga aaatgacagc cttcatttct ctgaacatac tgccttatgg    240
gacagatcaa tgaaagagtt tctagccaaa gccaaagaag acttttttgaa aaaatgggag   300
aatccaactc agaataatgc cggacttgaa gattttgaaa ggaaaaaaac ccttggaaca    360
ggttcatttg gaagagtcat gttggtaaaa cacaaagcca ctgaacagta ttatgccatg    420
aagatcttag ataagcagaa ggttgttaaa ctgaagcaac tagagctac   tttgaatgag   480
aaaagaatat tacaggcagt gaattttcct ttccttgttc gactggagta tgcttttaag    540
gataattcta atttatacat ggttatggaa tatgtccctg ggggtgaaat gttttcacat    600
ctaagaagaa ttggaaggtt cagtgagccc catgcacggt tctatgcagc tcagatagtg    660
ctaacattcg agtacctcca ttcactagac ctcatctaca gagatctaaa acctgaaaat    720
ctcttaattg accatcaagg ctatatccag gtcacagact ttgggtttgc caaaagagtt    780
aaaggcagaa cttggacatt atgtgaact  ccagagtatt tggctccaga aataattctc    840
agcaagggct acaataaggc agtggattgg tggcattag gagtgctaat ctatgaaatg    900
gcagctggct atcccccatt ctttgcagac caaccaattc agatttatga aagattgtt    960
tctgaaaagg tccgattccc atcccacttc agttcagatc tcaaggacct tctacggaac   1020
ctgctgcagg tggatttgac caagagattt ggaaatcaa agaatggtgt cagtgatata   1080
aaaactcaca agtggtttgc cacgacagat tggattgcta tttaccagag gaaggttgaa   1140
gctccattca taccaaagtt tagaggctct ggagatacca gcaactttga tgactatgaa   1200
gaagaagata tccgtgtctc tataacagaa aaatgtgcaa agaatttggg tgaattttaa   1260
```

<210> SEQ ID NO 35
<211> LENGTH: 3161
<212> TYPE: DNA
<213> ORGANISM: Homo sapiens
<220> FEATURE:
<221> NAME/KEY: misc_feature
<223> OTHER INFORMATION: Incyte ID No: 7481989CB1

<400> SEQUENCE: 35

```
gcggccgggg accgagccgc aaagacagag cgggcagagg cgatggaggg cgacggggtg      60
ccatggggca gcgagcccgt ctcgggtccc ggccccggcg gcggcggaat gatccgcgag     120
ctgtgccggg gcttcggccg ctaccgccgc tacctgggac ggctgcgaca gaacctgcgc     180
gagacccaga agttcttccg cgacatcaag tgctcccaca ccacacttg tctctcctcc      240 ctcacgggcg gcggcggggc cgagcgcggc cctgcaggcg atgtcgccga aaccgggctg     300
caggcgggcc aactgagctg catttccttc ccacctaagg aagagaagta cctccagcag     360
attgtggact gcctcccttg catactgatc ctcggccagg attgtaacgt caagtgccag     420
ctgttgaatc tgctgttggg ggtgcaggtg cttcccacca ccaagctggg cagtgaggag     480
agctgtaagc ttcggcgcct ccgcttcacc tatgggactc agactcgggt cagcctggcg     540
ctccctggac agtatgaact agtgcacacg ctggttgctc atcagggcaa ctgggagacc     600
atccctgagg aggatctgga ggtccaagag aacaatgagg atgctgctca tgttttagcg     660
gaactggagg taacgatgca ccatgctctc ttacaggaag tggacgttgt ggtagcacca     720
tgccaaggcc tccggcccac agtggatgtt ctgggtgact tggtgaatga tttcttgcct     780
gtgataacct atgcactcca caaagatgaa ctctctgaga gggatgagca agagcttcag     840
gaaatccgaa agtatttctc ctttcctgta ttctttttca aagtgccgaa actgggctcg     900
```

```
gagataatag actcctcaac caggagaatg gagagcgaaa gatcaccgct ttatcgccag    960
ctaattgacc tgggctatct gagcagcagt cactggaact gtgggctcc tggccaggat   1020
actaaagctc agagcatgtt ggtggaacag agtgaaaagc tgagacactt gagcacattt   1080
tctcaccagg tgttacagac tcgcctggtg gatgcagcca aggccctgaa cctggtgcac   1140
tgccactgcc ttgacatctt tattaaccag gcatttgaca tgcagcggga cctgcagatc   1200
actcccaaac gtctggaata tactcgaaaa aaggagaatg agttgtatga atcattgatg   1260
aatattgcca accgaaagca ggaggaaatg aaggatatga ttgttgagac acttaatacc   1320
atgaaggagg aacttctgga tgatgctact aacatggagt ttaaagacgt cattgtccct   1380
gagaatggag aaccagtagg caccagagag atcaaatgct gcatccgaca gatccaggaa   1440
ctcatcatct cccgacttaa tcaggcagtg gctaataagc tgatcagctc agtggattac   1500
ctgagggaaa gcttcgtcgg aaccctggaa cgatgtctgc agagcctgga gaagtctcag   1560
gatgtctcag ttcacatcac cagtaattat ctcaaacaga tcttaaatgc tgcctatcat   1620
gttgaagtca cgtttcactc agggtcgtca gttacaagga tgctatggga gcaaatcaaa   1680
cagatcatcc agcgcatcac atgggtgagc ccacctgcca tcactctgga atggaagagg   1740
aaggtggccc aggaagccat tgagagcctc agcgcctcca aattggctaa gagcatttgc   1800
agccaattcc ggactcggct caatagttcc cacgaggctt ttgcagcctc cttgcggcag   1860
ctggaagctg ccactcagg ccggttagag aaaacggaag atctatggct gagggttcgg   1920
aaagatcatg ctccccgcct ggcccgcctt tctctggaaa gccgttcttt acaggatgtc   1980
ttgcttcatc gtaaacctaa actgggacag gaactgggcc ggggccagta tggtgtggta   2040
tacctgtgtg acaactgggg aggacacttt ccttgtgccc tcaaatcagt tgtccctcca   2100
gatgagaagc actggaatga tctggctttg gaatttcact atatgaggtc tctgccgaag   2160
catgagcgat tggtggatct ccatggttca gtcattgact acaactatgg tggtggctcc   2220
agcattgctg tgctcctcat tatggagcgg ctacaccggg atctctacac agggctgaag   2280
gctgggctga ccctggagac acgtttgcag atagcactag atgtggtgga gggaatccgc   2340
ttcctgcaca gccagggact tgtccatcgt gatatcaaac tgaaaaatgt gctgctggat   2400
aagcagaacc gtgccaagat cactgactta ggattctgca agccagaggc catgatgtca   2460
ggcagcattg tggggacacc aatccatatg gcccctgaac ttttcacagg gaagtacgat   2520
aattccgtgg atgtctacgc ttttggaatt cttttctgg tatatctgct caggctctgtc   2580
aagctccctg aggcatttga gaggtgtgct agcaaagacc atctctggaa caatgtgcgg   2640
agggggggctc gcccagaacg tcttcctgtg tttgatgagg agtgctggca gttgatggaa   2700
gcctgttggg atggcgaccc cttgaagagg cctctcttgg gcattgtcca gcccatgctc   2760
cagggcatca tgaatcggct ctgcaagtcc aattctgagc agccaaacag aggactagat   2820
gattctactt gaaagccaag acctttctct ttcactctct agttatttcc ttcccctca   2880
cctttggcc atgggagaa tttgacattt attcactata ggacacactc ccaagggaac   2940
tggtgcttgc tggaaaactt ggaaccctc ccaggcaggg atgactcctg gacagtgaag   3000
agttgaatga ctgagcatat tcagcagctc actgaagcgc ccagctatcc ctttagcaaa   3060
aaagtgtctc agatgtgtaa aagctgagga atgtggtgtt ctggcttcac aaatgaaaag   3120
gaggcagatg ttaccattgt cttttcactg tatatacttc t                      3161
```

<210> SEQ ID NO 36
<211> LENGTH: 3538

-continued

<212> TYPE: DNA
<213> ORGANISM: Homo sapiens
<220> FEATURE:
<221> NAME/KEY: misc_feature
<223> OTHER INFORMATION: Incyte ID No: 55052990CB1

<400> SEQUENCE: 36

| | | | | | |
|---|---|---|---|---|---|
| atggagccct | ccagagcgct | tctcggctgc | ctagcgagcg | ccgccgctgc | cgccccgccg | 60 |
| ggggaggatg | gagcaggggc | cggggccgag | gaggaggagg | aggaggagga | ggaggcggcg | 120 |
| gcggcggtgg | gccccgggga | gctgggctgc | gacgcgccgc | tgccctactg | gacggccgtg | 180 |
| ttcgagtacg | aggcggcggg | cgaggacgag | ctgaccctgc | ggctgggcga | cgtggtggag | 240 |
| gtgctgtcca | aggactcgca | ggtgtccggc | gacgagggct | ggtggaccgg | gcagctgaac | 300 |
| cagcgggtgg | gcatcttccc | cagcaactac | gtgaccccgc | gcagcgcctt | ctccagccgc | 360 |
| tgccagcccg | gcggcgagga | ccccagttgc | tacccgccca | ttcagttgtt | agaaattgat | 420 |
| tttgcggagc | tcaccttgga | agagattatt | ggcatcgggg | gctttgggaa | ggtctatcgt | 480 |
| gctttctgga | tagggatga | ggttgctgtg | aaagcagctc | gccacgaccc | tgatgaggac | 540 |
| atcagccaga | ccatagagaa | tgttcgccaa | gaggccaagc | tcttcgccat | gctgaagcac | 600 |
| cccaacatca | ttgccctaag | aggggtatgt | ctgaaggagc | ccaacctctg | cttggtcatg | 660 |
| gagtttgctc | gtggaggacc | tttgaataga | gtgttatctg | ggaaaaggat | tcccccagac | 720 |
| atcctggtga | attgggctgt | gcagattgcc | agagggatga | actacttact | tgatgaggca | 780 |
| attgttccca | tcatccaccg | cgaccttaag | tccagcaaca | tattgatcct | ccagaaggtg | 840 |
| gagaatggag | acctgagcaa | caagattctg | aagatcactg | attttggcct | ggctcgggaa | 900 |
| tggcaccgaa | ccaccaagat | gagtgcggca | gggacgtatg | cttggatggc | acccgaagtc | 960 |
| atccgggcct | ccatgttttc | caaaggcagt | gatgtgtgga | gctatggggt | gctactttgg | 1020 |
| gagttgctga | ctggtgaggt | gccctttcga | ggcattgatg | gcttagcagt | cgcttatgga | 1080 |
| gtggccatga | acaaactcgc | ccttcctatt | ccttctacgt | gcccagaacc | ttttgccaaa | 1140 |
| ctcatggaag | actgctggaa | tcctgatccc | cactcacgac | catctttcac | gaatatcctg | 1200 |
| gaccagctaa | ccaccataga | ggagtctggt | ttctttgaaa | tgcccaagga | ctccttccac | 1260 |
| tgcctgcagg | acaactggaa | acacgagatt | caggagatgt | ttgaccaact | cagggccaaa | 1320 |
| gaaaaggaac | ttcgcacctg | ggaggaggag | ctgacgcggg | ctgcactgca | gcagaagaac | 1380 |
| caggaggaac | tgctgcggcg | tcgggagcag | gagctggccg | agcggagat | tgacatcctg | 1440 |
| gaacgggagc | tcaacatcat | catccaccag | ctgtgccagg | agaagccccg | ggtgaagaaa | 1500 |
| cgcaagggca | agttcaggaa | gagccggctg | aagctcaagg | atggcaaccg | catcagcctc | 1560 |
| ccttctgatt | tccagcacaa | gttcacggtg | caggcctccc | ctaccatgga | taaaaggaag | 1620 |
| agtcttatca | acagccgctc | cagtcctcct | gcaagcccca | ccatcattcc | tcgccttcga | 1680 |
| gccatccagt | tgcacaccag | gtgaaagcag | caaaacctggg | gcaggagctc | agtcgtccca | 1740 |
| aaggaggaag | gggaggagga | ggagaagagg | gcccaaaga | agaagggacg | gacgtggggg | 1800 |
| ccagggacgc | ttggtcagaa | ggagcttgcc | tcgggagatg | aaggcctcaa | gtccctggta | 1860 |
| gatggatata | agcagtggtc | gtccagtgcc | cccaacctgg | tgaagggccc | aaggagtagc | 1920 |
| ccggccctgc | cagggttcac | cagccttatg | gagatggagg | atgaggacag | tgaaggccca | 1980 |
| gggagtggag | agagtcgcct | acagcattca | cccagccagt | cctacctctg | tatcccattc | 2040 |
| cctcgtggag | aggatggcga | tgcccctcc | agtgatggaa | tccatgagga | gcccacccca | 2100 |
| gtcaactcgg | ccacgagtac | ccctcagctg | acgccaacca | acagcctcaa | gcggggcggt | 2160 |

```
gcccaccacc gccgctgcga ggtggctctg ctcggctgtg gggctgttct ggcagccaca   2220
ggcctagggt ttgacttgct ggaagctggc aagtgccagc tgcttcccct ggaggagcct   2280
gagccaccag cccggagga gaagaaaaga cgggagggtc tttttcagag gtccagccgt   2340
cctcgtcgga gcaccagccc cccatcccga aagcttttca agaaggagga gcccatgctg   2400
ttgctaggag acccctctgc ctccctgacg ctgctctccc tctcctccat ctccgagtgc   2460
aactccacac gctccctgct gcgctccgac agcgatgaaa ttgtcgtgta tgagatgcca   2520
gtcagcccga tcgaggcccc tcccctgagt ccatgtaccc acaaccccct ggtcaatgtc   2580
cgagtagagc gcttcaaacg agatcctaac caatctctga ctcccaccca tgtcaccctc   2640
accaccccct cgcagcccag cagtcaccgg cggactcctt ctgatgggc ccttaagcca    2700 gagactctcc tagccagcag gagcccctcc agcaatgggt tgagcccag tcctggagca    2760 ggtgagtctt cttcctcttt tctctttcct ttctttgtgc ctcctcaggg aatgttgaaa   2820 accccccagtc ccagccgaga cccaggtgaa ttccccgtc tccctgaccc caatgtggtc    2880
ttccccccaa ccccaaggcg ctggaacact cagcaggact ctaccttgga gagacccaag   2940
actctggagt ttctgcctcg gccgcgtcct tctgccaacc ggcaacggct ggaccttgg    3000 tggtttgtgt cccccagcca tgcccgcagc acctccccag ccaacagctc cagcacagag   3060
acgcccagca acctggactc ctgctttgct agcagtagca gcactgtaga ggagcggcct   3120
ggacttccag ccctgctccc gttccaggca gggccgctgc ccccgactga gcggacgctc   3180
ctggacctgg atgcagaggg gcagagtcag gacagcaccg tgccgctgtg cagagcggaa   3240
ctgaacacac acaggcctgc cccttatgag atccagcagg agttctggtc ttagcacgaa   3300
aaggattggg gcgggcaagg gggacagcca gcggagatga ggggagctgg cgggcacagc   3360
cctttctcag ggttggaccc cctgagatcc agccctactt cttgcactga taatgcactt   3420
tgaagatgga agggatggaa acagggccac ttcagagggt ctcctgccct gcagggcctt   3480
tctacccgtg tccactggag gggctgtggc catcagctct ggctgtgtag gggaggag    3538
```

<210> SEQ ID NO 37
<211> LENGTH: 3047
<212> TYPE: DNA
<213> ORGANISM: Homo sapiens
<220> FEATURE:
<221> NAME/KEY: misc_feature
<223> OTHER INFORMATION: Incyte ID No: 7482377CB1

<400> SEQUENCE: 37

```
aagcccgctg tgactctcct cagccactcc cccagcccgg ggtgggggcc gattgactgt     60
ttccaggacc ccctcgggta ggggggctgg agagccccca ggtgaccat ggcggtgaga    120
ttccaggtgg ctgacatgga ggagctgacc atctgggaac agcacacggc cacactgtcc    180
aaggaccccc gccgggctt tggcattgcg atctctggag gccgagaccg gcccggtgga    240
tccatggttg tatctgacgt ggtacctgga gggccggcgg agggcaggct acagacaggc    300
gaccacattg tcatggtgaa cgggggtttcc atggagaatg ccacctccgc gtttgccatt    360
cagatactca agacctgcac caagatggcc aacatcacag tgaaacgtcc ccggaggatc    420
cacctgcccg ccaccaaagc cagccccctc agcccagggc gccaggatcc ggatgaagac    480
gatgggcccc agcgggtgga ggaggtggac cagggccggg gctatgacgg cgactcatcc    540
agtggctccg gccgctcctg ggacgagcgc tcccgccggc cgaggcctgg tcgccgggc    600
cgggccggca gccatgggcg taggagccca ggtggtggct ctgaggccaa cgggctggcc    660
ctggtgtccg gctttaagcg gctgccacgg caggacgtgc agatgaagcc tgtgaagtca    720
gtgctggtga agaggagaga cagcgaagag tttggcgtga agtgggcag tcagatcttc    780
atcaagcaca ttacagattc gggcctggct gccggcacc gtgggctgca ggaaggagat    840
ctcattctac agatcaacg ggtgtctagc cagaacctgt cactgaacga caccggcga    900
ctgattgaga agtcagaagg gaagctaagc ctgctggtgc tgagagatcg tgggcagttc    960
ctggtgaaca ttccgcctgc tgtcagtgac agcacagct cgctcattgga ggacatctcg   1020
gacctcgcct cggagctatc gcaggcacca ccatcccaca tccaccacc accccggcat   1080
gctcagcgga gccccgaggc cagccagacc gactctcccg tggagagtcc ccggcttcgg   1140
cgggaaagtt cagtagattc cagaaccatc tcggaaccag atgagcaacg gtcagagttg   1200
cccagggaaa gcagctatga catctacaga gtgcccagca gtcagagcat ggaggatcgt   1260
```

-continued

```
gggtacagcc cgacacgcg tgtggtccgc ttcctcaagg gcaagagcat cgggctgcgg   1320
ctggcagggg gcaatgacgt gggcatcttc gtgtccgggg tgcaggcggg cagcccggcc   1380
gacgggcagg gcatccagga gggagatcag attctgcagg tgaatgacgt gccattccag   1440
aacctgacac gggaggagcg agtgcagttc ctgctgcagg tgccaccagg cgaggagatg   1500
gagctggtga cgcagccgaa gcaggacatt ttctggaaaa tggtgcagtc ccgcgtgggt   1560
gactccttct acatccgcac tcactttgag ctggagccca gtccgccgtc tggcctgggc   1620
ttcacccgtg gcgacgtctt ccacgtgctg gacacgctgc accccggccc cgggcagagc   1680
cacgcacgag gaggccactg gctggcggtg cgcatgggtc gtgacctgcg ggagcaagag   1740
cggggcatca ttcccaacca gagcagggcg gagcagctgg ccagcctgga agctgcccag   1800
agggccgtgg gagtcgggcc cggctcctcc gcgggctcca atgctcgggc cgagttctgg   1860
cggctgcggg gtctgcgtcg aggagccaag aagaccactc agcggagccg tgaggacctc   1920
tcagctctga cccgacaggg ccgctacccg ccctacgaac gagtggtgtt gcagaagcc    1980
agtttcaagc gcccggtagt gatcctggga cccgtggccg acattgctat gcagaagttg   2040
actgctgaga tgcctgacca gtttgaaatc gcagagactg tgtccaggac cgacagcccc   2100
tccaagatca tcaaactaga caccgtgcgg gtgattgcag aaaaagacaa gcatgcgctc   2160
ctggatgtga ccccctccgc catcgagcgc ctcaactatg tgcagtacta ccccattgtg   2220
gtcttcttca tccccgagag ccggccgggc ctcaaggcac tgccagtg gctggcgcct    2280
gcctcccgcc gcagcacccg tcgcctctac gcacaagccc agaagctgcg aaaacacagc   2340
agccacctct tcacagccac catccctctg aatggcacga gtgacacctg gtaccaggag   2400
ctcaaggcca tcattcgaga gcagacacg cggcccatct ggacggcgga agatcagctg   2460
gatggctcct tggaggacaa cctagacctc cctccaccacg gcctggccga cagctccgct   2520
gacctcagct gcgacagccg cgttaacagc gactacgaga cggacgtgcga gggcggcgcg   2580
tacacggatg gcgagggcta cacagacggc gaggggggcc cctacacgga tgtggatgat   2640
gagcccccgg ctccagccct ggcccggtcc tcggagcccg tgcaggcaga tgagtcccag   2700
agcccgaggg atcgtgggag aatctcggct catcagggga ccaggtgga cagccgccac   2760
ccccagggac agtgcgcaca ggacagcatg cgaacctatg aacgggaagc cctgaagaaa   2820
aagtttatgc gagtacatga tgcggagtcc tccgatgaag acggctatga ctgggtccgg   2880
gccactgacc tgtgacctct cgaaggctgc cagctggtcc gtcctccttc tccctccctg   2940
gggctgggac tcagtttccc atacagaacc cacaacccta cctccctccg cctggtcttt   3000
aataaacaga gtattttcac agcaaaaaaa aaaaaaaaa aaaaaaa                  3047
```

<210> SEQ ID NO 38
<211> LENGTH: 2667
<212> TYPE: DNA
<213> ORGANISM: Homo sapiens
<220> FEATURE:
<221> NAME/KEY: misc_feature
<223> OTHER INFORMATION: Incyte ID No: 7758364CB1

<400> SEQUENCE: 38

```
tttagctgag ggcgcgggcg ggtcggctcc tccgcggctc ctcggcccca cctgcgcgga     60
gagggcggga tgccagagcc aggtgtcccg gcgcgttaag ggccctcgca gtcagacgtc    120
cctgcaccgg cgctcgcacc cttagtcggc ccggaacgtc ttttgcgga cgccctcgga    180 gcagccgcga tggccagcac caggagtatc gagctggagc actttgagga acgggacaaa    240
aggccgcggc cggggtcgcg gagagggcc cccagctcct ccgggggcag cagcagctcg    300
ggccccaagg ggaacgggct catccccagt ccggcgcaca gtgccactg cagcttctac    360 cgcacgcgga ccctgcaggc cctcagctcg gagaagaagg ccaagaaggc gcgcttctac    420
cggaacgggg accgctactt caagggcctg gtgtttgcca tctccagcga ccgcttccgg    480
tccttcgatg cgctcctcat agagctcacc cgctccctgt cggacaacgt gaacctgccc    540
cagggtgtcc gcactatcta caccatcgac ggcagccgga aggtcaccag cctggacgag    600
ctgctggaag gtgagagtta cgtgtgtgca tccaatgaac catttcgtaa agtcgattac    660
accaaaaata ttaatccaaa ctggtctgtg aacatcaagg gtgggacatc ccgagcgctg    720
gctgctgcct cctctgtgaa aagtgaagta aagaaagta aagatttcat caaacccaag    780
ttagtgactg tgattcgaag tggagtgaag cctagaaaag ccgtgcggat ccttctgaat    840
aaaaagactg ctcattcctt tgaacaagtc ttaacagata tcaccgaagc cattaaacta    900
gactcaggag tcgtcaagag gctctgcacc tggatggaa agcaggttac ttgtctgcaa    960
gacttttttg gtgatgacga tgtttttatt gcatgtggac cagaaaaatt tcgttatgcc   1020
caagatgact ttgtcctgga tcatagtgaa tgtcgtgtcc tgaagtcatc ttattctcga   1080
tcctcagctg ttaagtattc tggatccaaa agccctgggc cctctcgacg cagcaaatca   1140
```

-continued

```
ccagcttcag ttaatggaac tcccagcagc caactttcta ctcctaaatc tacgaaatcc   1200
tccagttcct ctccaactag tccaggaagt ttcagaggat taaagcagat ttctgctcat   1260
ggcagatctt cttccaatgt aaacggtgga cctgagcttg accgttgcat aagtcctgaa   1320
ggtgtgaatg gaaacagatg ctctgaatca tcaactcttc ttgagaaata caaaattgga   1380
aaggtcattg gtgatggcaa ttttgcagta gtcaaagagt gtatagacag gtccactgga   1440
aaggagtttg ccctaaagat tatagacaaa gccaaatgtt gtggaaagga acacctgatt   1500
gagaatgaag tgtcaatact cgccgagtg aaacatccca atatcattat gctggtcgag   1560
gagatggaaa cagcaactga gctctttctg gtgatggaat tggtcaaagg tggagatctc   1620
tttgatgcaa ttacttcgtc gaccaagtac actgagagag atggcagtgc catggtgtac   1680
aacttagcca atgccctcag gtatctccat ggcctcagca tcgtgcacag agacatcaaa   1740
ccagagaatc tcttggtgtg tgaatatcct gatggaacca agtctttgaa actgggagac   1800
tttgggcttg cgactgtggt agaaggccct ttatacacag tctgtggcac acccacttat   1860
gtggctccag aaatcattgc tgaaactggc tatggcctga aggtggacat ttgggcagct   1920
ggtgtgatca catacatact ctctgtgga ttcccaccat tccgaagtga aacaatctc    1980 caggaagatc tcttcgacca gatcttggct gggaagctgg agtttccggc cccctactgg   2040
gataacatca cggactctgc caaggaatta atcagtcaaa tgcttcaggt aaatgttgaa   2100
gctcggtgta ccgcgggaca atcctgagt caccectggg tgtcagatga tgcctcccag   2160
gagaataaca tgcaagctga ggtgacaggt aaactaaaac agcactttaa taatgcgctc   2220
cccaaacaga acagcactac caccgggggtc tccgtcatca tgaacacggc tctagataag   2280
gaggggcaga ttttctgcag caagcactgt caagacagcg gcaggcctgg gatggagccc   2340
atctctccag ttcctccctc agtggaggag atccctgtgc ctggggaagc agtcccggcc   2400
cccacccctc cggaatctcc caccccccac tgtcctcccg ctgccccggg tggtgagcgg   2460
gcaggaacct ggcgccgcca ccgagactga gcctcctgca gacgggcgaa gccgcctgct   2520
gcagcccagg aagccagccc tctgctcggc ctcgccggcc tccctgctgc aggcctccct   2580
ctcttcaccg cctgcgcctg agttcgcggg tcctccgcag gccgcctggg aaccggagcc   2640
tggcgtgccg gagcctggcc tggtgct                                       2667
```

<210> SEQ ID NO 39
<211> LENGTH: 1719
<212> TYPE: DNA
<213> ORGANISM: Homo sapiens
<220> FEATURE:
<221> NAME/KEY: misc_feature
<223> OTHER INFORMATION: Incyte ID No: 5850001CB1

<400> SEQUENCE: 39

```
gcggaggagg cgagaaggaa tccgacgctg gggggcttgc tcgggcggca gcgactgctg    60
ctgcggatgg gagcgggccg gctcggcgcg cccatggagc gccacggcag ggcttccgcc   120
acctccgtct cgtcggctgg ggagcaggcg gccggggacc ccgaagggcg gcggcaggag   180
ccactgcggc gccgggcgag cagcgcgtcg gtgcccgcgg tcgggccctc ggctgagggc   240
acgaggcggg atcgactggg ctcttacagc ggccccacct cggtctcccg ccagcgcgtc   300
gaaagcctga ggaaaaagcg gccgcttttt ccatggtttg gactggatat cggtggaact   360
ctggtcaagc tggtatattt tgaacccaaa gacatcactg ctgaagaaga gaggaagaa    420 gtggaaagtc ttaaaagcat tcggaagtac ctgacctcca atgtggctta tgggtctaca   480
```

```
ggcattcggg acgtgcacct cgagctgaag gacctgactc tgtgtggacg caaaggcaat    540
ctgcacttta tacgctttcc cactcatgac atgcctgctt ttattcaaat gggcagagat    600
aaaaacttct cgagtctcca cactgtcttt tgtgccactg gaggtggagc gtacaaattt    660
gagcaggatt ttctcacaat aggtgatctt cagctttgca aactggatga actagattgc    720
ttgatcaaag gaattttata cattgactca gtcggattca atggacggtc acagtgctat    780
tactttgaaa accctgctga ttctgaaaag tgtcagaagt taccatttga tttgaaaaat    840
ccgtatcctc tgcttctggt gaacattggc tcagggggtta gcatcttagc agtatattcc    900
aaagataatt acaaacgggt cacaggtact agtcttggag gaggaactttt ttttggtctc    960 tgctgtcttc ttactggctg taccactttt gaagaagctc ttgaaatggc atctcgtgga   1020
gatagcacca aagtggataa actagtacga gatatttatg gaggggacta tgagaggttt   1080
ggactgccag gctgggctgt ggcttcaagc tttggaaaca tgatgagcaa ggagaagcga   1140
gaggctgtca gtaaagagga cctggccaga gcgactttga tcaccatcac caacaacatt   1200
ggctcaatag caagaatgtg tgcccttaat gaaaacatta accaggtggt atttgttgga   1260
aatttcttga gaattaatac gatcgccatg cggcttttgg catatgcttt ggattattgg   1320 tccaagggc agttgaaagc acttttttcg gaacacgagg gttatttgg agctgttgga   1380 gcactccttg agctgttgaa gatcccgtga tcattacctg ggagggggtt cctgaaacct   1440
tccacaatgg gatctgtgga cttttcattt tttaagagac ttactcaatt tcatgactgt   1500
actacctgaa acaaagtgag aaaggacagg tgtattttc taagtcatca agataaatcc   1560
ttaagaattc agtctaaatt agcaaccagg aaggaaaaat atattaaaaa caacaaaaaa   1620
gtggcacatg tccaggcagt gtgaggattt gctgtatata agttgcctgc tttgtatttt   1680
tgaaatctct gcatcactca ttggaagtgc ttctgaagt                         1719
```

<210> SEQ ID NO 40
<211> LENGTH: 1156
<212> TYPE: DNA
<213> ORGANISM: Homo sapiens
<220> FEATURE:
<221> NAME/KEY: misc_feature
<223> OTHER INFORMATION: Incyte ID No: 7477062CB1

<400> SEQUENCE: 40

```
agtcggggcg gggtcttgct cctaggcagg cctctgctgg catgagccct aagtgccggg     60
cactgaccac agccggcagc cggagggtca ggagggcctt ggaggagaga tgcccggcaa    120
acagtctgag gaagggccgg cggaggcagg ggcttcggag gacagcgagg aggagggtct    180
gggcggcctg acattagagg agctccagca gggccaggag gctgcccgcg cgctggagga    240
catgatgacg ctgagtgctc agaccctggt ccgagccgag gtggacgagc tctacgagga    300
agtgcgtccc ctgggccagg gtcgctatgg ccgcgtcctt ctggtcaccc atcgtcagaa    360
aggcacaccc ctggcactga agcagctccc gaaaccccgc acgtccctcc gtggcttcct    420
gtacgagttc tgtgtgggc tctcgctggg cgcgcactca gccatcgtga cggcctacgg    480
cattggcatc gagtcggcac actcctacag cttcctgacg gagcccgtcc tgcacgggga    540
cctcatggcc ttcatccagc ccaaggtggg cctcccgcag cccgcggtgc accgctgcgc    600
cgcccagctg gcctccgccc tggagtacat ccacgcccgc ggcctggtgt accgggacct    660
gaagccggag aacgtcctgg tgtgcgaccc ggcctgccgg cgcttcaagc tgaccgactt    720
cggccacacg aggcctcgcg ggacgctgct gcgcctggcc gggccgccca tcccctacac    780
```

```
ggcccccgag ctctgcgcgc ccccgccgct ccccgagggc ctgcccattc agcccgccct      840
ggacgcctgg gcgctgggcg tcctgctctt ctgcctcctc acgggctact tccctggga       900 ccggcccctg gccgaggccg acccttcta cgaggacttc ctcatctggc aggcgtcggg       960
ccagccccgg gaccgccctc agccctggtt cggcctggcc gccgcggccg acgcgcttct     1020 gcggggggctg ctggaccctc accccgaag gaggagcgct gtgatcgcca tcagggagca     1080 cctgggggcgc ccctggaggc agcgggaggg cgaggcggag gcagtgggag cggtggaaga   1140
ggaggctggg cagtga                                                     1156
```

<210> SEQ ID NO 41
<211> LENGTH: 1096
<212> TYPE: DNA
<213> ORGANISM: Homo sapiens
<220> FEATURE:
<221> NAME/KEY: misc_feature
<223> OTHER INFORMATION: Incyte ID No: 7477207CB1

<400> SEQUENCE: 41

```
ggcctgcaga gcccatgaga gggagaagcg gcagcgtcta ccctgagaaa cctcgacctt       60
gaagatggtg agtagccagc caaagtacga tctaatacgg gaggtaggcc gaggtagtta      120
cggtgttgtg tatgaagcag tcatcagaaa gacctctgca cgggtggcag tgaagaaaat     180
tcgatgtcac gcacctgaaa atgttgaact agcccttcgt gagttctggg cactaagcag     240
tatcaagagc caacatccaa atgtgattca cttggaggaa tgcatcctac aaaaggatgg     300
gatggtgcaa aagatgtccc acggctctaa ttcttccctt tatttacagc ttgtagaaac     360
ttcattaaaa ggagaaattg cctttgatcc cagaagcgcc tattatttgt ggtttgtgat     420 ggattttgt gacggaggag atatgaatga gtatctgttg tccaggaaac ccaatcgtaa      480
aactaacacc agcttcatgc ttcagctgag cagtgccctg gctttcttgc ataaaaacca    540
gatcatccac cgagatctta agcctgataa catcctgatt tctcaaacca ggttggatac    600
cagtgacttg gaacctaccc tcaaagtggc tgattttggt ctaagtaaag tttgttcagc    660
ctctgggcag aacccagaag aacctgtcag tgtaaacaag tgttttccttt ccacagcatg   720 tggaacagat ttttacatgg ctcctgaagt ttgggaagga cattacacag caaaagctga    780
catctttgct ctggggatta tcatctggggc aatgctggaa aggatcacat tcatagacac    840
agagacaaag aaggaactct tggggagtta tgtaaaacaa ggaactgaga ttgtgcctgt   900
tggggaggca cttctggaaa atcccaaaat ggaacttctc attcctgtga agaaaaaatc   960
tatgaatggg cgaatgaaac aactgattaa ggaaatgctg gctgcaaacc ctcaggatcg  1020
tccagatgct tttgaactag aactcagatt agtacaaatt gcatttaaag atagcagctg  1080
ggaaacgtga cacata                                                  1096
```

<210> SEQ ID NO 42
<211> LENGTH: 2647
<212> TYPE: DNA
<213> ORGANISM: Homo sapiens
<220> FEATURE:
<221> NAME/KEY: misc_feature
<223> OTHER INFORMATION: Incyte ID No: 4022651CB1

<400> SEQUENCE: 42

```
atggcctcag ccgagacccc aggccaatgg tatgttgggc cctaccggct ggagaagacg       60
ctgggcaagg ggcagacagg tctggtgaag ctggggggttc actgcgtcac ctgccagaag    120
gtggccatca agatcgtcaa ccgtgagaag ctcagcgagt cggtgctgat gaaggtggag     180
```

```
cgggagatcg cgatcctgaa gctcattgag cacccccacg tcctaaagct gcacgacgtt    240
tatgaaaaca aaaatatttt gtacctggtg ctagaacacg tgtcaggtgg tgagctcttc    300
gactacctgg tgaagaaggg gaggctgacg cctaaggagg ctcggaagtt cttccggcag    360
atcatctctg cgctggactt ctgccacagc cactccatat gccacaggga tctgaaacct    420
gaaaacctcc tgctggacga gaagaacaac atccgcatcg cagactttgg catggcgtcc    480
ctgcaggttg gcgacagcct gttggagacc agctgtgggt ccccccacta cgcctgcccc    540
gaggtgatcc ggggggagaa gtatgacggc cggaaggcgg acgtgtggag ctgcggcgtc    600
atcctgttcg ccttgctggt gggggctctg cccttcgacg atgacaactt gcgacagctg    660
ctggagaagt gaagcggggc gtgttccac atgccgcact ttatcccgcc cgactgccag    720
agtctgctac ggggcatgat cgaggtggac gccgcacgcc gcctcacgct agagcacatt    780
cagaaacaca tatggtatat agggggcaag aatgagcccg aaccagagca gcccattcct    840
cgcaaggtgc agatccgctc gctgcccagc ctggaggaca tcgaccccga cgtgctggac    900
agcatgcact cactgggctg cttccgagac cgcaacaagc tgctgcagga cctgctgtcc    960
gaggaggaga accaggagaa gatgatttac ttcctcctcc tggaccggaa agaaaggtac   1020
ccgagccagg aggatgagga cctgccccc cggaacgaga tagaccctcc ccggaagcgt   1080
gtggactccc cgatgctgaa ccggcacggc aagcggcggc cagaacgcaa atccatggag   1140
gtgctcagcg tgacggacgg cggctccccg gtgcctgcgc ggcgggccat tgagatggcc   1200
cagcacggcc agaggtctcg gtccatcagc ggtgcctcct caggcctttc caccagccca   1260
ctcagcagcc cccgggtgac ccctcacccc tcaccaaggg gcagtcccct ccccacccc   1320 aaggggacac ctgtccacac gccaaaggag agcccggctg gcacgcccaa ccccacgccc   1380
ccgtccagcc ccagcgtcgg aggggtgccc tggagggcgc ggctcaactc catcaagaac   1440
agctttctgg gctcaccccg cttccaccgc cggaaactgc aagttccgac gccggaggag   1500
atgtccaacc tgacaccaga gtcgtcccca gagctggcga agaagtcctg gtttgggaac   1560
ttcatcagcc tggagaagga ggagcagatc ttcgtggtca tcaaagacaa acctctgagc   1620
tccatcaagg ctgacatcgt gcacgccttc ctgtcgattc ccagtctcag ccacagcgtc   1680
atctcccaaa cgagcttccg ggccgagtac aaggccacgg gggggccagc cgtgttccag   1740
aagccggtca agttccaggt tgatatcacc tacacggagg gtggggaggc gcagaaggag   1800
aacggcatct actccgtcac cttcacccctg ctctcaggcc ccagccgtcg cttcaagagg   1860
gtggtggaga ccatccaggc ccagctgctg agcacacacg acccgcctgc ggcccagcac   1920
ttgtcagaca ccactaactg tatggaaatg atgacgggc ggctttccaa atgtggaatt   1980
atcccgaaaa gttaacatgt cacctccacg aggccatcct ctgtgaccga aggcagctgc   2040
tgcggacccg ccctccctcc gctcctgctg ttgctgccgg gcagtgaggc ccagcccagc   2100
gccccgtcca ccccgcggca gctcctcgcc tcagctccgc acggcccgtg ggaggaaggc   2160
caggctcggg ggagcctcct ccagcccggc cgacccggac tccggtcac ctgaccctc    2220 agcaagaaca gcctgcctgg tggccttctg gggccaggac ccccggtggg caacgtagcc   2280
acaggaacag gccccgtcca ccgctccac gccgcacctg aggcctcct cgcaggcccg   2340 tgccccgccc tccctggccg cgccggcctc cgtgtagtct tggcctcctc aggctgcctc   2400
ccgtcctctc gtctcacccg cgcctccctt gcctcatctg gggcggctgt gggctctggc   2460
gctcctctct ggctgaggtg gaaacagaga caccctgcgg caccagagcc ttcccagcag   2520
```

```
gccaggccgc tgggctggga tcagtgttat ttatttgccg ttttaattta tggattctcc    2580
gcacctctgt tcagggaagg gcggcggcca catcccctgc cgtctgcgcg tctcaggcag    2640
tgggggg                                                              2647
```

<210> SEQ ID NO 43
<211> LENGTH: 864
<212> TYPE: DNA
<213> ORGANISM: Homo sapiens
<220> FEATURE:
<221> NAME/KEY: misc_feature
<223> OTHER INFORMATION: Incyte ID No: 7274927CB1

<400> SEQUENCE: 43

```
ggcgcgtttc gggtgctggc ggctgcagcc ggagttcaaa cctaagcagc tggaagggcc     60
ctgtggctag gtaccataga gtctctacac aggactaaat cagcctggtg tgcaggggag    120
gcagacacac aaacagaaaa ttggactaca gtgctaagat gctgtaagaa gaggttaact    180
aaaggacagg aagatggggc caagagatgg tgctactgtc tactttaggg atcgtctttc    240
aaggcgaggg gcctcctatc tcaagctgtg atacaggaac catggccaac tgtgagcgta    300
ccttcattgc gatcaaacca gatggggtcc agcgggtct tgtgggagag attatcaagc     360
gttttgagca gaaaggattc cgccttgttg gtctgaaatt catgcaagct tccgaagatc    420
ttctcaagga acactacgtt gacctgaagg accgtccatt ctttgccggc ctggtgaaat    480
acatgcactc agggccggta gttgccatgt ctgggagggg gctgaatgtg gtgaagacgg    540
gccgagtcat gctcggggag accaaccctg cagactccaa gctgggacc atccgtggag     600 acttctgcat acaagttggc aggaacatta tacatggcag tgattctgtg gagagtgcag    660
agaaggagat cggcttgtgg tttcaccctg aggaactggt agattacacg agctgtgctc    720
agaactggat ctatgaatga caggagggca gaccacattg cttttcacat ccatttcccc    780
tccttcccat gggcagagga ccaggctgta ggaaatctag ttatttacag gaagggatc     840 cactagttct aagcgccgca cccc                                           864
```

<210> SEQ ID NO 44
<211> LENGTH: 1594
<212> TYPE: DNA
<213> ORGANISM: Homo sapiens
<220> FEATURE:
<221> NAME/KEY: misc_feature
<223> OTHER INFORMATION: Incyte ID No: 7946584CB1

<400> SEQUENCE: 44

```
gcggagacgc ccgctggcaa gcagatcctg cctccttccc tggccaagga gccgcccctc     60
cggggtagct gtgcgctggg cggcgctcgg accccttggc agccgcaggt gcctcccag     120 cccagcccag ctcagtccag cgcagcccag cccagcccag cccggcgctc gcagcctccg    180
ccgcttccgg gcagataggt gccttttctt gctccttgct cttggagttc ttctcttagt    240
ccctgttccc tggatgaaag catcgctccg agcctcatgg gaggaatgaa ggaagaatcg    300
agactagata tccaactaag gcttcgggac atgttttgag cgaagatggg tgtttctgcc    360
cggatagtat aaatcgagga tccaggtctg ggcagattca accatgggag ccaacacttc    420 aagaaaaccca ccagtgtttg atgaaaatga agatgtcaac tttgaccact ttgaaatttt    480
gcgagccatt gggaaaggca gttttgggaa ggtctgcatt gtacagaaga atgataccaa    540
gaagatgtac gcaatgaagt acatgaataa acaaaagtgc gtggagcgca atgaagtgag    600
aaatgtcttc aaggaactcc agatcatgca gggtctggag caccctttcc tggttaattt    660
```

```
gtggtattcc ttccaagatg aggaagacat gttcatggtg gtggacctcc tgctgggtgg      720
agacctgcgt tatcacctgc aacagaacgt ccacttcaag gaagaaacag tgaagctctt      780
catctgtgag ctggtcatgg ccctggacta cctgcagaac cagcgcatca ttcacaggga      840
tatgaagcct gacaatattt tacttgacga acatgggcac gtgcacatca cagatttcaa      900
cattgctgcg atgctgccca gggagacaca gattaccacc atggctggca ccaagcctta      960
catggcacct gagatgttca gctccagaaa aggagcaggc tattcctttg ctgttgactg     1020
gtggtccctg ggagtgacgg catatgaact gctgagaggc cggagaccgt atcatattcg     1080
ctccagtact tccagcaagg aaattgtaca cacgtttgag acgactgttg taacttaccc     1140
ttctgcctgg tcacaggaaa tggtgtcact tcttaaaaag ctactcgaac ctaatccaga     1200
ccaacgattt tctcagttat ctgatgtcca gaacttcccg tatatgaatg atataaactg     1260
ggatgcagtt tttcagaaga ggctcattcc aggtttcatt cctaataaag gcaggctgaa     1320
ttgtgatcct acctttgaac ttgaggaaat gattttggag tccaaacctc tacataagaa     1380
aaaaaagcgt ctggcaaaga aggagaagga tatgaggaaa tgcgattctt ctcagacatg     1440
tcttcttcaa gagcaccttg actctgtcca gaaggagttc ataattttca acagagaaaa     1500
agtaaacagg gactttaaca aaagacaacc aaatctagcc ttggaacaaa ccaaagaccc     1560
acaaggtgag gatggtcaga ataacaactt gtaa                                 1594
```

<210> SEQ ID NO 45
<211> LENGTH: 1845
<212> TYPE: DNA
<213> ORGANISM: Homo sapiens
<220> FEATURE:
<221> NAME/KEY: misc_feature
<223> OTHER INFORMATION: Incyte ID No: 8088078CB1

<400> SEQUENCE: 45

```
atggagtggc taagccctga tatcgctctg cccagaagag atgagtggac tcaaacttct       60
ccagccagga agaggatcac gcatgccaaa gtccagggtg caggtaagtc catcggtcag      120
ctgaggctgt ccattgatgc ccaggaccgg gttctgctgc ttcacattat agaaggtaaa      180
ggcctgatca gcaaacagcc tggcaccctgt gatccgtatg tgaagatttc tttgatccct      240
gaagatagta gactacgcca ccagaagacg cagaccgttc cagactgcag agacccggct      300
ttccacgagc acttcttctt tcctgtccaa gaggaggatg atcagaagcg tctcttggtt      360
actgtgtgga acagggccag ccagtccaga cagagtggac tcattggctg catgagcttt      420
ggggtgaagt ctctcctgac tccagacaag gagatcagtg gttggtacta cctcctaggg      480
gagcacctgg gccggaccaa gcacttgaag gtggccaggg ggcgactgcg gccgctgaga      540
gacccgctgc tgagaatgcc aggaggtggg gacactgaga atgggaagaa actacagatc      600
accatcccga ggggaaagga cggctttggc ttcaccatct gctgcgactc tccagttcga      660
gtccaggccg tggattccgg gggtccggcg gaacgggcag gctgcagca gctggacacg      720 gtgctgcagc tgaatgagag gcctgtggag cactggaaat gtgtggagct ggcccacgag      780
atccggagct gccccagtga gatcatccta ctcgtgtggc gcatggtccc ccaggtcaag      840
ccaggaccag atggcgggt cctgcggcgg gcctcctgca gtcgacaca tgacctccag      900 tcaccccca acaaacggga agaactgc acccatgggg tccaggcacg gcctgagcag      960
cgccacagct gccacctggt atgtgacagc tctgatgggc tgctgctcgg cggctgggag     1020
cgctacaccg aggtggccaa gcgcgggggc cagcacaccc tgcctgcact gtcccgtgcc     1080
```

-continued

| | |
|---|---|
| actgccccca ccgaccccaa ctacatcatc ctggccccgc tgaatcctgg gagccagctg | 1140 |
| ctccggcctg tgtaccagga ggataccatc cccgaagaat cagggagtcc cagtaaaggg | 1200 |
| aagtcctaca caggcctggg gaagaagtcc cggctgatga agacagtgca gaccatgaag | 1260 |
| ggccacggga actaccaaaa ctgcccggtt gtgaggccgc atgccacgca ctcaagctat | 1320 |
| ggcacctacg tcaccctggc ccccaaagtc ctggtgttcc ctgtctttgt tcagcctcta | 1380 |
| gatctctgta atcctgcccg gaccctcctg ctgtcagagg agctgctgct gtatgaaggg | 1440 |
| aggaacaagg ctgccgaggt gacactgttt gcctattcgg acctgctgct cttcaccaag | 1500 |
| gaggacgagc ctggccgctg cgacgtcctg aggaaccccc tctacctcca gagtgtgaag | 1560 |
| ctgcaggaag gttcttcaga agacctgaaa ttctgcgtgc tctatctagc agagaaggca | 1620 |
| gagtgcttat tcactttgga agcgcactcg caggagcaga agaagagagt gtgctggtgc | 1680 |
| ctgtcggaga acatcgccaa gcagcaacag ctggcagcat cacccccgga cagcaagaaa | 1740 |
| ctccacccct tcggctctct ccagcaggag atggggccgg tcaactcaac caatgccacc | 1800 |
| caggatagaa gctttacctc accaggacag actctgattg ctga | 1845 |

<210> SEQ ID NO 46
<211> LENGTH: 1680
<212> TYPE: DNA
<213> ORGANISM: Homo sapiens
<220> FEATURE:
<221> NAME/KEY: misc_feature
<223> OTHER INFORMATION: Incyte ID No: 2674269CB1

<400> SEQUENCE: 46

| | |
|---|---|
| gctcatttcg gcgaaaccgc ggtctttcct tctcccttg atgctttcag gtactgaccc | 60 |
| actaccgccc ccatcttccc ccatgggaag atgagcactg agggcagatt accctcctgc | 120 |
| agcgcgtgtg tgaaagggga gttgagagtc ctgacgagcg cggcgctcac tagtcgggac | 180 |
| ggcccgagac cgtgtcatgt cctcttcagg attgtgcacc tgtgcctgcg aaaggctgac | 240 |
| cagaagctgg tgatcatcaa gcagattcca gtggaacaga tgaccaagga agagcggcag | 300 |
| gcagcccaga atgagtgcca ggtcctcaag ctgctcaacc accccaatgt cattgagtac | 360 |
| tacgagaact tcctggaaga caaagcccct atgatcgcca tggaatatgc caccaggcgc | 420 |
| actctggctg agttcatcca aaagcgctgt aattccctgc tggaggagga gaccatcctg | 480 |
| cacttcttcg tgcagatcct gcttgcactg catcatgtgc acaccccacct catcctgcac | 540 |
| cgagacctca agacccagaa catcctgctt gacaaacacc gcatggtcgt caagatcggt | 600 |
| gatttcggca ctccaagat ccttagcagc aagagcaagg cctacacggt ggtgggtacc | 660 |
| ccatgctata tctcccctga gctgtgtgag ggcaagccct acaaccagaa gagtgacatc | 720 |
| tgggccctgg gctgtgtcct ctacgagctg ccagcctca agagggcttt cgaggctgcg | 780 |
| aacttgccag cactggtgct gaagatcatg agtggcacct ttgcacctat ctctgaccgg | 840 |
| tacagccctg agcttcgcca gctggtcctg agtctactca gcctggagcc tgcccagcgg | 900 |
| ccaccactca gccacatcat ggcacagccc tctgcatcc gtgccctcct caacctccac | 960 |
| accgacgtgg gcagtgtccg catgcggagg cctgtgcagg acagcgagc ggtcctgggc | 1020 |
| ggcagggtgt gggcacccag tgggagcaca ggaggtctga gcagaggga acctggggc | 1080 |
| aagtcctccc ttcctgcatg taggaatgtc aggagggtct ttgtccttag gccccatct | 1140 |
| gtcctgcagg gcagagaagt ccgtggcccc cagcaacaca gggagcagga ccaccagtgt | 1200 |
| ccgctgcaga ggtatccccc ggggacctgt gaggccagcc atcccaccac cactgtcgtc | 1260 |

```
agtgtatgcc tggggtggtg ggctgggcac cccctgcgg ctgccaatgc tcaacacaga    1320
ggtggtccag gtggcagctg ggcgcacgca gaaagccggc gtcacgcgct ctgggcgtct    1380
catcctgtgg gaggccccac ccctaggtgc aggcggaggc agtctccttc ctggggcagt    1440
ggagcagcca cagccccagt tcatctcgcg tttcctggag ggccagtcgg gtgtgaccat    1500
caagcacgtg gcctgtgggg acttcttcac tgcctgcctg actgacagag gcatcatcat    1560
gacattcggc agcggcagca atgggtgcct aggccatggc agcctcactg acatcagcca    1620
gcccaccatt gtggaggctt tgctgggcta tgaaatggtg caggtggcct gtggggcctc    1680
```

<210> SEQ ID NO 47
<211> LENGTH: 1528
<212> TYPE: DNA
<213> ORGANISM: Homo sapiens
<220> FEATURE:
<221> NAME/KEY: misc_feature
<223> OTHER INFORMATION: Incyte ID No: 7472409CB1

<400> SEQUENCE: 47

```
gtgaaactct aagaaatgag atggagaagt acgagcggat ccgagtggtg gggagaggtg      60
ccttcgggat tgtgcacctg tgcctgcgaa aggctgacca gaagctggtg atcatcaagc     120
agattccagt ggaacagatg accaaggaag agcggcaggc agcccagaat gagtgccagg     180
tcctcaagct gctcaaccac cccaatgtca ttgagtacta cgagaacttc ctggaagaca     240
aagcccttat gatcgccatg gaatatgcac aggcggcac tctggctgag ttcatccaaa      300
agcgctgtaa ttcccctgctg gaggaggaga ccatcctgca cttcttcgtg cagatcctgc    360
ttgcactgca tcatgtgcac acccacctca tcctgcaccg agacctcaag acccagaaca    420
tcctgcttga caaacaccgc atggtcgtca agatcggtga tttcggcatc tccaagatcc    480
ttagcagcaa gagcaaggcc tacacggtgg tgggtacccc atgctatatc tcccctgagc    540
tgtgtgaggg caagccctac aaccagaaga gtgacatctg ggcctgggc tgtgtcctct     600 acgagctggc cagcctcaag agggctttcg aggctgcgaa cttgccagca ctggtgctga    660
agatcatgag tggcaccttt gcacctatct ctgaccggta cagccctgag cttcgccagc    720
tggtcctgag tctactcagc ctggagcctg cccagcggcc accactcagc acatcatgg     780 cacagcccct ctgcatccgt gccctcctca acctccacac cgacgtgggc agtgtccgca    840
tgcggaggcc tgtgcaggga cagcgagcgg tcctgggcgg cagggtgtgg gcacccagtg    900
ggagcacagg aggtctgagg cagagggaaa cctggggcaa gtcctcccctt cctgcatgta   960 ggaatgtcag gagggtcttt gtccttaggc ccccatctgt cctgcagggc agagaagtcc   1020
gtggccccca gcaacacagg gagcaggacc accagtgtcc gctgcagagg tatccccgg    1080 ggacctgtga ggccagccat cccaccacca ctgtcgtcag tgtatgcctg ggtggtggg    1140 ctgggcaccc cctgcgggct gccaatgctc aacacagagg tggtccaggt ggcagctggg   1200
cgcacgcaga aagccggcgt cacgcgctct gggcgtctca tcctgtggga ggccccaccc   1260
ctaggtgcag gcggaggcag tctccttcct ggggcagtgg agcagccaca gccccagttc   1320
atctcgcgtt tcctggaggg ccagtcgggt gtgaccatca gcacgtggc ctgtggggac    1380 ttcttcactg cctgcctgac tgacagaggc atcatcatga cattcggcag cggcagcaat   1440
gggtgcctag gccatggcag cctcactgac atcagccagc ccaccattgt ggaggctttg    1500
ctgggctatg aaatggtgca ggtggcct                                         1528
```

<210> SEQ ID NO 48
<211> LENGTH: 4988
<212> TYPE: DNA
<213> ORGANISM: Homo sapiens
<220> FEATURE:
<221> NAME/KEY: misc_feature
<223> OTHER INFORMATION: Incyte ID No: 7477484CB1

<400> SEQUENCE: 48

| | | | | | |
|---|---|---|---|---|---|
| ccggctcccc | agcatctctc | ctctgtccgc | ctctccatcc | cttcatccgt | ctgtcccttc | 60 |
| aaagaggggg | aggggggtac | ctgagccagc | aagcagcccc | tccctccccc | tgtcctgcgt | 120 |
| ctcctgcccc | tctcctgggc | cgggaggagg | ccaggtcgcg | cgggtcccca | tggctggggg | 180 |
| ctgagggccc | gccccccccct | cctccccagc | cgccaccacc | tccacctccc | tgccatcctc | 240 |
| gacaagatgc | ctgcccccgg | cgccctcatc | ctccttgcgg | ccgtctccgc | ctccggctgc | 300 |
| ctggcgtccc | cggcccaccc | cgatggattc | gccctgggcc | gggctcctct | ggctcctccc | 360 |
| tacgctgtgg | tcctcatttc | ctgctccggc | ctgctggcct | tcatcttcct | cctcctcacc | 420 |
| tgtctgtgct | gcaaacgggg | cgatgtcggc | ttcaaggaat | ttgagaaccc | tgaaggggag | 480 |
| gactgctccg | gggagtacac | tcccctgcg | gaggagacct | cctcctcaca | gtcgctgcct | 540 |
| gatgtctaca | ttctcccgct | ggctgaggtc | tccctgccaa | tgcctgcccc | gcagccttca | 600 |
| cactcagaca | tgaccacccc | cctgggcctt | agccggcagc | acctgagcta | cctgcaggag | 660 |
| attgggagtg | gctggtttgg | gaaggtgatc | ctgggagaga | ttttctccga | ctacaccccc | 720 |
| gcccaggtgg | tggtgaagga | gctccgagcc | agcgcgggc | ccctggagca | acgcaagttc | 780 |
| atctcggaag | cacagccgta | caggagcctg | cagcacccca | atgtcctcca | gtgcctgggt | 840 |
| ctgtgcgtgg | agacgctgcc | gtttctgctg | attatggagt | tctgtcaact | ggggacctg | 900 |
| aagcgttacc | tccgagccca | gcggcccccc | gagggcctgt | cccctgagct | accccctcga | 960 |
| gacctgcgga | cgctgcagag | gatgggcctg | gagatcgccc | gcgggctggc | gcacctgcat | 1020 |
| tcccacaact | acgtgcacag | cgacctggcc | ctgcgcaact | gcctgctgac | ctctgacctg | 1080 |
| accgtgcgca | tcggagacta | cgggctggcc | cacagcaact | acaaggagga | ctactacctg | 1140 |
| accccagagc | gcctgtggat | cccactgcgc | tgggcggcgc | cgagctcct | cggggagctc | 1200 |
| cacgggacct | tcatggtggt | ggaccagagc | cgcgagagca | acatctggtc | cctgggggtg | 1260 |
| accctgtggg | agctgtttga | gtttgggggcc | cagccctacc | gccacctgtc | agacgaggag | 1320 |
| gtcctcgcct | tcgtggtccg | ccagcagcat | gtgaagctgg | cccggccgag | gctcaagctg | 1380 |
| ccttacgcgg | actactggta | tgacattctt | cagtcctgct | ggcggccacc | tgcccagcgc | 1440 |
| ccttcagcct | ctgatctcca | attgcagctc | acctacttgc | tctccgagcg | gcctccccgg | 1500 |
| cccccaccgc | cgccaccccc | accccgagac | ggtcccttcc | cctggccctg | gccccctgca | 1560 |
| cacagtgcgc | cccgcccggg | gaccctctcc | tcaccgttcc | ccctactgga | tggcttccct | 1620 |
| ggagccgacc | ccgacgatgt | gctcacggtc | accgagagta | gccgcggcct | caacctcgag | 1680 |
| tgcctgtggg | agaaggcccg | gcgtggggcc | ggccggggtg | gggggcacc | tgcctggcag | 1740 |
| ccggcgtcgg | ccccccggc | ccccacgcc | aaccctcca | accctttcta | cgaggcgctg | 1800 |
| tccacgccca | gcgtgctgcc | tgtcatcagc | gcccgcagcc | cctccgtgag | cagcgagtac | 1860 |
| tacatccgct | tggaggagca | cggctccct | cctgagcccc | tcttcccaa | cgactgggac | 1920 |
| ccctggacc | aggagtgcc | cgcccctcag | gccccccagg | cccctccga | ggtcccccag | 1980 |
| ctggtgtccg | agacctgggc | ctcccccctc | ttccctgcgc | cccggccctt | ccagcccag | 2040 |
| tcctcagcgt | caggcagctt | cctgctgagc | ggctgggacc | ccgagggccg | gggcgccggg | 2100 |

```
gagaccctgg cgggagaccc tgccgaggtc ttgggggagc gggggaccgc cccgtggggtg    2160 gaagaagaag aggaggagga ggagggcagc tccccagggg aagacagcag cagccttgga    2220
ggacgactcc tcgctgcggg cagagcgggg ctccctggcc gacttgccca tggcccccccc    2280 gcctcggccc cccccgagtt tctggacccc ctcatggggg cggcggcgcc ccagtacccc    2340
gggcgggggc cacctcccgc tccccccccc ccgccgccac ctcctcgggc ccccgcggac    2400
ccggccgcgt ccccccgaccc cccttcggcc gtggccagtc ccggttcagg cctctcgtcg    2460 ccgggccccca gccgggggga cagcggctac gagaccgaga ccccttttttc cccagagggga    2520 gccttcccag gtgggggggc ggccgaggag aaggggtccc ctcggccgcg ggctccccccc    2580 gagccacccg acccaggagc gcccggggcca cctccagacc cgggtccgct cccactcccg    2640
ggcccccggg agaagccgac cttcgtggtt caagtgagca cggaacagct gctgatgtcc    2700
ctgcgggagg atgtgacaag gaacctcctg ggggagaagg gggcgacagc ccggagaca    2760 ggacccagga aggcggggag aggcccccggg aacagagaga aagtcccggg cctgaacagg    2820
gacccgacag tcctgggcaa cgggaaacaa gccccaagcc tgagcctccc agtgaacggg    2880
gtgacagtgc tggagaacgg ggaccagaga gccccaggca tcgaggagaa ggcggcggag    2940 aatgggggccc tggggtcccc cgagagagaa gagaaagtgc tggagaatgg ggagctgaca    3000 ccccccaagga gggaggagaa agcgctggag aatgggggagc tgaggtcccc agaggccggg    3060
gagaaggtgc tggtgaatgg gggcctgaca cccccaaaga gcgaggacaa ggtgtcagag    3120 aatggggggcc tgagattccc caggaacacg gagaggccac cagagactgg gccttggaga    3180
gccccagggc cctgggagaa gacgcccgag agttggggtc cagcccccac gatcggggag    3240
ccagccccag agacctctct ggagagagcc cctgcaccca gcgcagtggt ctcctcccgg    3300
aacggcgggg agacagcccc tggccccctt ggcccagccc ccaagaacgg gacgctggaa    3360
cccgggaccg agaggagagc ccccgagact ggggggggcgc cgagagcccc aggggctggg    3420
aggctggacc tcgggagtgg gggccgagcc ccagtgggca cgggggacggc cccccggcggc    3480 ggccccggaa gcggcgtgga cgcaaaggcc ggatgggtag acaacacgag gccgcagcca    3540
ccgccgccac cgctgccacc gccaccggag gcacagccga ggaggctgga gccagcgccc    3600
ccgagagcca ggccggaggt ggccccccgag ggagagcccg gggccccaga cagcagggcc    3660
ggcggagaca cggcactcag cggagacggg gaccccccca gcccgagag aagggcccc    3720 gagatgccac gactattctt ggacttggga cccctcaggg gaacagcga gcagatcaaa    3780 gccaggctct cccggctctc gctggcgctg ccgccgctca cgctcacgcc attcccgggg    3840 ccgggccccgc ggcggccccc gtgggagggc cggacgccg gggcggctgg cggggaggcc    3900
ggcggggcgg gagcgccggg gccggcggag gaggacgggg aggacgagga cgaggacgag    3960
gaggaggacg aggaggcggc ggccgccggc cggcggcgcgg ggccgcgggg ccccgggagg    4020
gcgcgagcag ccccggtgcc cgtcgtggtg agcagcgccg acgcggacgc ggcccgcccg    4080 ctgcggggggc tgctcaagtc tccgcgcggg gccgacgagc cagaggacag cgagctggag    4140
aggaagcgca agatggtctc cttccacggg gacgtgaccg tctacctctt cgaccaggag    4200
acgccaacca acgagctgag cgtccaggcc ccccccgagg gggacacgga cccgtcaacg    4260
cctccagcgc ccccgacacc tccccacccc gccaccccccg gagatgggtt tcccagcaac    4320
gacagcggct ttggaggcag tttcgagtgg gcggaggatt tccccctcct cccccctcca    4380
ggccccccgc tgtgcttctc ccgcttctcc gtctcgcctg cgctggagac cccgggggcca    4440
```

```
                                          -continued
cccgcccggg cccccgacgc ccggcccgca ggccccgtgg agaattgatt ccccgaagac    4500 ccgacccgc tgcaccctca gaagagggt tgagaatgga atcctctgtg gatgacggcg     4560
ccactgccac caccgcagac gccgcctctg gggaggcccc cgaggctggg ccctccccct   4620
cccactcccc taccatgtgc caaacgggag gccccggcc cccgcccccc agcccccag     4680 atggctcccc tgacccccct gacccctcg gagccaaatg aggcaggaat cccccgccc    4740 ctccatagag agccgccttt ctcggaactg aactgaactc ttttgggcct ggagcccctc   4800
gacacagcgg aggtccctcc tcacccactc ctggcccaag acaggggccg caggcttcgg   4860
ggacccggac cccccatttc gcgtctcccc tttccctccc cagcccggcc cctggagggg   4920
cctctggttc aaaccttcgc gtggcatttt cacattattt aaaaaagaca aaaacaactt   4980
tttggagg                                                           4988
```